US012773154B2

(12) United States Patent
Duffy et al.

(10) Patent No.: US 12,773,154 B2
(45) Date of Patent: Oct. 27, 2026

(54) MACHINE LEARNING TECHNIQUES FOR ELECTROCARDIOGRAM (ECG) ANALYSIS

(71) Applicant: NeuralCloud Solutions Inc., Toronto (CA)

(72) Inventors: John Paul Duffy, Toronto (CA); Michael Feist, St. Albert (CA); Esmatullah Naikyar, Edmonton (CA)

(73) Assignee: NeuralCloud Solutions Inc., Toronto (CA)

( * ) Notice: Subject to any disclaimer, the term of this patent is extended or adjusted under 35 U.S.C. 154(b) by 0 days.

(21) Appl. No.: 19/301,762

(22) Filed: Aug. 15, 2025

(65) Prior Publication Data

US 2026/0047793 A1 Feb. 19, 2026

Related U.S. Application Data

(60) Provisional application No. 63/819,451, filed on Jun. 6, 2025, provisional application No. 63/684,432, filed on Aug. 18, 2024.

(51) Int. Cl.
*A61B 5/346* (2021.01)
*A61B 5/00* (2006.01)
(Continued)

(52) U.S. Cl.
CPC .............. *A61B 5/346* (2021.01); *A61B 5/332* (2021.01); *A61B 5/333* (2021.01); *A61B 5/339* (2021.01);
(Continued)

(58) Field of Classification Search
CPC .. G06F 1/163; G06F 2218/04; G06F 2218/10; G06F 2218/12; G16H 50/20;
(Continued)

(56) References Cited

U.S. PATENT DOCUMENTS

| | | | |
|---|---|---|---|
| 12,465,266 B1 | 11/2025 | Duffy et al. | |
| 2008/0001735 A1 | 1/2008 | Tran | |

(Continued)

FOREIGN PATENT DOCUMENTS

| | | |
|---|---|---|
| CN | 112603328 A | 4/2021 |
| CN | 116153320 A | 5/2023 |

OTHER PUBLICATIONS

International Search Report and Written Opinion, mailed Dec. 3, 2025 for International Application No. PCT/CA2025/051082.

(Continued)

*Primary Examiner* — Deborah L Malamud
(74) *Attorney, Agent, or Firm* — Wolf, Greenfield & Sacks, P.C.

(57) ABSTRACT

Described herein are techniques for analyzing at least one electrocardiogram (ECG) signal. In some embodiments, the techniques include: receiving at least one ECG signal; encoding the at least one ECG signal using the encoder to obtain a numeric encoding of the at least one ECG signal; and processing the numeric encoding of the at least one ECG signal using at least one trained machine learning model to obtain: (i) at least one denoised ECG signal corresponding to the at least one ECG signal, and/or (ii) characteristics of the at least one ECG signal, the characteristics comprising: (i) rhythm types including a respective rhythm type for each of at least some segments of the at least one ECG signal, and/or (ii) sample-level ECG labels including a respective sample-level ECG label for each of at least some of the plurality of samples.

20 Claims, 56 Drawing Sheets

(51) Int. Cl.

| | |
|---|---|
| ***A61B 5/332*** | (2021.01) |
| ***A61B 5/333*** | (2021.01) |
| ***A61B 5/339*** | (2021.01) |
| ***G16H 50/70*** | (2018.01) |

(52) U.S. Cl.
CPC .......... *A61B 5/7203* (2013.01); *A61B 5/7267* (2013.01); *G16H 50/70* (2018.01)

(58) Field of Classification Search
CPC .... G16H 50/70; A61B 5/7282; A61B 5/7275; A61B 5/02405; A61B 5/7246; A61B 5/7264; A61B 5/024; A61B 5/0006; A61B 5/318; A61B 5/361; A61B 5/366; A61B 5/346; A61B 5/05; A61B 5/308; A61B 5/363; A61B 5/364
See application file for complete search history.

(56) References Cited

U.S. PATENT DOCUMENTS

| | | | | |
|---|---|---|---|---|
| 2017/0112401 | A1 | 4/2017 | Rapin et al. | |
| 2019/0231207 | A1 | 8/2019 | Perschbacher et al. | |
| 2021/0106281 | A1* | 4/2021 | Tran ...................... | A61B 5/486 |
| 2025/0032030 | A1 | 1/2025 | Duffy et al. | |
| 2025/0311956 | A1 | 10/2025 | Ellinor et al. | |
| 2026/0047791 | A1 | 2/2026 | Duffy et al. | |
| 2026/0047792 | A1 | 2/2026 | Duffy et al. | |
| 2026/0047794 | A1 | 2/2026 | Duffy et al. | |

OTHER PUBLICATIONS

Aziz et al., ECG-based machine-learning algorithms for heartbeat classification. Sci Rep. Sep. 21, 2021;11(1):18738. doi: 10.1038/s41598-021-97118-5.

Brown et al., Language models are few-shot learners. Proc 34th Intl Conf Neural Info Proc Sys. Dec. 6, 2020;159:1877-1901.

Devlin et al., BERT: Pre-training of Deep Bidirectional Transformers for Language Understanding. Proceedings of the 2019 Conference of the North American Chapter of the Association for Computational Linguistics: Human Language Technologies, vol. 1 (Long and Short Papers). Jun. 2, 2019;4171-4186. doi: 10.18653/v1/N19-1423.

Hassaballah et al., ECG Heartbeat Classification Using Machine Learning and Metaheuristic Optimization for Smart Healthcare Systems. Bioengineering (Basel). Mar. 28, 2023;10(4):429. doi: 10.3390/bioengineering10040429.

Jambukia et al., Classification of ECG signals using machine learning techniques: A survey. Computer Engineering and Applications (ICACEA), 2015 International Conference on Advances at Ghaziabad, India. 2015;714-721. doi: 10.1109/ICACEA.2015.7164783.

Joung et al., Deep learning based ECG segmentation for delineation of diverse arrhythmias. PLoS One. Jun. 13, 2024;19(6):e0303178. doi: 10.1371/journal.pone.0303178.

Kalyakulina et al., Lobachevsky University Electrocardiogramatabase (version 1.0.1). PhysioNet. Jan. 19, 2021. 6 pages. doi: 10.13026/eegm-h675.

Kalyakulina et al., LUDB: a new open-access validation tool for electrocardiogram delineation algorithms. IEEE Access. Sep. 16, 2020;8:186181-186190. doi: 10.1109/ACCESS.2020.3029211.

Kingma et al., Adam: A Method for Stochastic Optimization. Proceedings of the 3rd International Conference for Learning Representations. Jul. 23, 2015. 15 pages. doi: 10.48550/arXiv.1412.6980v8.

Kolhar et al., Deep learning hybrid model ECG classification using AlexNet and parallel dual branch fusion network model. Sci Rep. Nov. 6, 2024;14(1):26919. doi: 10.1038/s41598-024-78028-8.

Makowski et al., NeuroKit2: A Python toolbox for neurophysiological signal processing. Behav Res Methods. Aug. 2021;53(4):1689-1696. doi: 10.3758/s13428-020-01516-y. Epub Feb. 2, 2021.

Narotamo et al., Deep learning for ECG classification: A comparative study of 1D and 2D representations and multimodal fusion approaches. Biomed Signal Process Control. Jul. 2024;93:106141. doi: 10.1016/j.bspc.2024.106141.

Nemcova et al., Brno University of Technology ECG Quality Database (BUT QDB) version 1.0.0. PhysioNet. Jul. 22, 2020. 4 pages. doi: 10.13026/kah4-0w24.

Peimankar et al., DENS-ECG: A Deep Learning Approach for ECG Signal Delineation. arXiv. May 18, 2020. 15 pages. https://arxiv.org/pdf/2005.08689.

Radford et al., Language Models Are Unsupervised Multitask Learners. OpenAI Blog 1.8. 2019:9. 24 pages.

Ribeiro et al. Code-15%: a large scale annotated dataset of 12-lead ECGs. Zenodo. Jun. 9, 2021. 11 pages. doi.org/10.5281/zenodo.4916206.

Staszak et al., From Data to Diagnosis: How Machine Learning Is Changing Heart Health Monitoring. Int J Environ Res Public Health. Mar. 5, 2023;20(5):4605. doi: 10.3390/ijerph20054605.

Tan et al., Icentiallk Single Lead Continuous Raw Electrocardiogram Dataset (version 1.0). PhysioNet. Apr. 12, 2022. 5 pages. doi.org/10.13026/kk0v-r952.

Tan et al., Icentia11K: An Unsupervised Representation Learning Dataset for Arrhythmia Subtype Discovery. arXiv. Oct. 21, 2019. 10 pages. doi: 10.48550/arXiv.1910.09570.

Yang et al., HiFi-Codec: Group-residual vector quantization for high fidelity audio codec. arXiv. May 7, 2023. 6 pages. doi.org/10.48550/arXiv.2305.02765.

Zeghidour et al., SoundStream: An End-to-End Neural Audio Codec. IEEE/ACM Transactions on Audio, Speech, and Language Processing. Nov. 23, 2021;30:495-507. doi: 10.1109/TASLP.2021.3129994.

* cited by examiner

FIG. 7B
Edit patient's profile
07.edf
Add info manually
Please enter all the information for your new report
Device
Referring Physician
Patient Name
Patient ID
Date of Birth
MMMM DD, YYYY
Patient Sex
Downloaded Date
Jun 12, 2025
Medications
Hookup Technician
Scanning Technician
Test Indication
Comments

MACHINE LEARNING TECHNIQUES FOR ELECTROCARDIOGRAM (ECG) ANALYSIS

CROSS-REFERENCE TO RELATED APPLICATIONS

The present application claims the benefit of and priority under 35 U.S.C. § 119(e) of U.S. Provisional Patent Application No. 63/684,432 filed Aug. 18, 2024, entitled "METHODS AND SYSTEMS FOR ANALYZING ECG SIGNALS USING NEURAL NETWORKS," and U.S. Provisional Patent Application No. 63/819,451 filed Jun. 6, 2025, entitled "MACHINE LEARNING TECHNIQUES FOR ELECTROCARDIOGRAM (ECG) ANALYSIS," each of which is incorporated by reference herein in its entirety.

BACKGROUND

Heartbeats are triggered by electrical impulses that travel through conduction pathways in the heart, causing coordinated contractions of the atria and ventricles. An electrocardiogram (ECG) is a tool that measures signals ("ECG signals") representing the electrical activity of the heart over time. An ECG signal typically includes at least one waveform representing at least one measured heartbeat. In a healthy subject, an ECG waveform is expected to have several different portions, each of which represents a particular function that contributes to the heartbeat. ECG waveform portions may include the P-wave, the QRS complex, and the T-wave. The P-wave represents the depolarization of the atria, which precedes atrial contraction. The QRS complex typically includes three waves (e.g., the Q-wave, the R-wave, and the S-wave) and represents the rapid depolarization of the ventricles, leading to ventricular contraction. The T-wave represents the repolarization of the ventricles, which allows the ventricles to reset for the next cycle of depolarization. ECG waveforms can be analyzed and interpreted to diagnose and treat cardiac issues.

An ECG system measures ECG signals using one or more leads. A "lead" refers to the electrical viewpoint of the heart's activity. A lead measures the voltage difference between two or more points on the body. For example, the voltage difference may be measured between two or more ECG sensors (e.g., electrodes) placed in direct or indirect contact with the body. Different ECG systems may use different numbers of leads. For example, some ECG systems may use 1, 3, 6, or 12 leads.

SUMMARY

Some embodiments provide for a method for denoising at least one electrocardiogram (ECG) signal, the method comprising: using at least one processor to perform: obtaining the at least one ECG signal, the at least one ECG signal having been previously measured using ECG sensors; processing the at least one ECG signal using a trained denoising model to obtain at least one denoised ECG signal, the trained denoising model comprising an encoder, a residual vector quantizer, and a decoder, the processing comprising: encoding the at least one ECG signal using the encoder to obtain a numeric encoding of the at least one ECG signal; quantizing the numeric encoding of the at least one ECG signal using the residual vector quantizer to obtain a quantized numeric encoding of the at least one ECG signal; and decoding the quantized numeric encoding of the at least one ECG signal using the decoder to obtain the at least one denoised ECG signal; and outputting the at least one denoised ECG signal. The trained denoising model may be a denoising model that has been trained using a method of training a denoising model to denoise at least one electrocardiogram (ECG) signal as described herein. Methods according to the present embodiments may further comprise obtaining the trained denoising model using a method of training a denoising model to denoise at least one electrocardiogram (ECG) signal as described herein.

Some embodiments provide for at least one non-transitory computer-readable storage medium storing processor-executable instructions that, when executed by at least one processor, cause the at least one processor to perform a method for denoising at least one electrocardiogram (ECG) signal, the method comprising: obtaining the at least one ECG signal, the at least one ECG signal having been previously measured using ECG sensors; processing the at least one ECG signal using a trained denoising model to obtain at least one denoised ECG signal, the trained denoising model comprising an encoder, a residual vector quantizer, and a decoder, the processing comprising: encoding the at least one ECG signal using the encoder to obtain a numeric encoding of the at least one ECG signal; quantizing the numeric encoding of the at least one ECG signal using the residual vector quantizer to obtain a quantized numeric encoding of the at least one ECG signal; and decoding the quantized numeric encoding of the at least one ECG signal using the decoder to obtain the at least one denoised ECG signal; and outputting the at least one denoised ECG signal.

Some embodiments provide for a system comprising: at least one processor; and at least one non-transitory computer-readable storage medium storing processor-executable instructions that, when executed by the at least one processor, cause the at least one processor to perform a method for denoising at least one electrocardiogram (ECG) signal, the method comprising: obtaining the at least one ECG signal, the at least one ECG signal having been previously measured using ECG sensors; processing the at least one ECG signal using a trained denoising model to obtain at least one denoised ECG signal, the trained denoising model comprising an encoder, a residual vector quantizer, and a decoder, the processing comprising: encoding the at least one ECG signal using the encoder to obtain a numeric encoding of the at least one ECG signal; quantizing the numeric encoding of the at least one ECG signal using the residual vector quantizer to obtain a quantized numeric encoding of the at least one ECG signal; and decoding the quantized numeric encoding of the at least one ECG signal using the decoder to obtain the at least one denoised ECG signal; and outputting the at least one denoised ECG signal.

Some embodiments provide for a method for labelling at least one electrocardiogram (ECG) signal comprising a plurality of samples, wherein a sample is an ECG measurement corresponding to a single time point, the method comprising: using at least one processor to perform: obtaining the at least one ECG signal, the at least one ECG signal having been previously measured using ECG sensors; encoding the at least one ECG signal using a trained encoder to obtain a numeric encoding of the at least one ECG signal; quantizing the numeric encoding of the at least one ECG signal using a trained residual vector quantizer to obtain a quantized numeric encoding of the at least one ECG signal; and processing the quantized numeric encoding of the at least one ECG signal using a trained sample-level ECG classifier to obtain sample-level ECG labels for at least some of the plurality of samples of the at least one ECG signal, wherein a sample-level ECG label for a particular sample of the at least some of the plurality of samples is indicative of a respective portion of an ECG waveform to which the particular sample corresponds; and outputting the sample-level ECG labels.

In embodiments, encoding the at least one ECG signal to obtain a numeric encoding of the at least one ECG signal and quantizing the numeric encoding of the at least one ECG signal using a trained residual vector quantizer to obtain a quantized numeric encoding of the at least one ECG signal comprise using an encoder and a residual vector quantizer as described herein in relation to methods for denoising at least one ECG signal. Thus, in embodiments, encoding the at least one ECG signal to obtain a numeric encoding of the at least one ECG signal and quantizing the numeric encoding of the at least one ECG signal using a trained residual vector quantizer to obtain a quantized numeric encoding of the at least one ECG signal comprise using the encoder and the residual vector quantizer as described herein in relation to methods for denoising at least one ECG signal, wherein the encoder and residual vector quantizer have been trained as part of a denoising model as described herein. The denoising model may have been trained using a method of training a denoising model to denoise at least one electrocardiogram (ECG) signal as described herein. Methods according to the present embodiments may further comprise obtaining the trained denoising model using a method of training a denoising model to denoise at least one electrocardiogram (ECG) signal as described herein.

Some embodiments provide for at least one non-transitory computer-readable storage medium storing processor-executable instructions that, when executed by at least one processor, cause the at least one processor to perform a method for labelling at least one electrocardiogram (ECG) signal comprising a plurality of samples, wherein a sample is an ECG measurement corresponding to a single time point, the method comprising: obtaining the at least one ECG signal, the at least one ECG signal having been previously measured using ECG sensors; encoding the at least one ECG signal using a trained encoder to obtain a numeric encoding of the at least one ECG signal; quantizing the numeric encoding of the at least one ECG signal using a trained residual vector quantizer to obtain a quantized numeric encoding of the at least one ECG signal; and processing the quantized numeric encoding of the at least one ECG signal using a trained sample-level ECG classifier to obtain sample-level ECG labels for at least some of the plurality of samples of the at least one ECG signal, wherein a sample-level ECG label for a particular sample of the at least some of the plurality of samples is indicative of a respective portion of an ECG waveform to which the particular sample corresponds; and outputting the sample-level ECG labels.

Some embodiments provide for a system comprising: at least one processor; and at least one non-transitory computer-readable storage medium storing processor-executable instructions that, when executed by the at least one processor, causes the at least one processor to perform a method for labelling at least one electrocardiogram (ECG) signal comprising a plurality of samples, wherein a sample is an ECG measurement corresponding to a single time point, the method comprising: obtaining the at least one ECG signal, the at least one ECG signal having been previously measured using ECG sensors; encoding the at least one ECG signal using a trained encoder to obtain a numeric encoding of the at least one ECG signal; quantizing the numeric encoding of the at least one ECG signal using a trained residual vector quantizer to obtain a quantized numeric encoding of the at least one ECG signal; and processing the quantized numeric encoding of the at least one ECG signal using a trained sample-level ECG classifier to obtain sample-level ECG labels for at least some of the plurality of samples of the at least one ECG signal, wherein a sample-level ECG label for a particular sample of the at least some of the plurality of samples is indicative of a respective portion of an ECG waveform to which the particular sample corresponds; and outputting the sample-level ECG labels.

Some embodiments provide for a method for labelling at least one electrocardiogram (ECG) signal comprising a plurality of samples, wherein a sample is an ECG measurement at a single time point, the method comprising: using at least one processor to perform: obtaining the at least one ECG signal, the at least one ECG signal having been previously measured using ECG sensors; encoding the at least one ECG signal to obtain a numeric encoding of the at least one ECG signal; processing the numeric encoding of the at least one ECG signal using a trained sample-level ECG classifier to obtain sample-level ECG labels for at least some of the plurality of samples, wherein a sample-level ECG label for a particular sample of the at least some of the plurality of samples is indicative of a respective portion of an ECG waveform to which the particular sample corresponds; generating an interactive graphical user interface (GUI) indicating the sample-level ECG labels for the at least some of the plurality of samples; and receiving user input via the interactive GUI, wherein the user input is indicative of a verification or a modification of a sample-level ECG label of the sample-level ECG labels.

In embodiments, encoding the at least one ECG signal to obtain a numeric encoding of the at least one ECG signal comprises using an encoder and a residual vector quantizer as described herein in relation to methods for denoising at least one ECG signal. Thus, in embodiments, encoding the at least one ECG signal to obtain a numeric encoding of the at least one ECG signal comprises encoding the at least one ECG signal using the encoder to obtain a numeric encoding of the at least one ECG signal; quantizing the numeric encoding of the at least one ECG signal using the residual vector quantizer to obtain a quantized numeric encoding of the at least one ECG signal, as described herein in relation to methods for denoising at least one ECG signal, wherein the encoder and residual vector quantizer having been trained as part of a denoising model as described herein. In embodiments, encoding the at least one ECG signal to obtain a numeric encoding of the at least one ECG signal comprises using an encoder as described herein in relation to methods for denoising at least one ECG signal. Thus, in embodiments, encoding the at least one ECG signal to obtain a numeric encoding of the at least one ECG signal comprises encoding the at least one ECG signal using the encoder to obtain a numeric encoding of the at least one ECG signal, as described herein in relation to methods for denoising at least one ECG signal, wherein the encoder has been trained as part of a denoising model as described herein. The denoising model may have been trained using a method of training a denoising model to denoise at least one electrocardiogram (ECG) signal as described herein. Methods according to the present embodiments may further comprise obtaining the trained denoising model using a method of training a denoising model to denoise at least one electrocardiogram (ECG) signal as described herein.

The methods according to the present embodiments may have any of the features described in relation to methods for labelling at least one ECG signal using a trained encoder, trained residual vector quantizer and trained sample-level ECG classifier. Specifically, the trained sample-level ECG classifier according to present embodiments may have any of the properties described in relation to the trained sample-level ECG classifier in embodiments of such methods. Further, the encoding of the at least one ECG signal may be performed using a trained encoder that has any of the properties described in relation to a trained encoder in such methods.

Some embodiments provide for at least one non-transitory computer-readable storage medium storing processor-executable instructions that, when executed by at least one processor, cause the at least one processor to perform a method for labelling at least one electrocardiogram (ECG) signal comprising a plurality of samples, wherein a sample is an ECG measurement at a single time point, the method comprising: obtaining the at least one ECG signal, the at least one ECG signal having been previously measured using ECG sensors; encoding the at least one ECG signal to obtain a numeric encoding of the at least one ECG signal; processing the numeric encoding of the at least one ECG signal using a trained sample-level ECG classifier to obtain sample-level ECG labels for at least some of the plurality of samples, wherein a sample-level ECG label for a particular sample of the at least some of the plurality of samples is indicative of a respective portion of an ECG waveform to which the particular sample corresponds; generating an interactive graphical user interface (GUI) indicating the sample-level ECG labels for the at least some of the plurality of samples; and receiving user input via the interactive GUI, wherein the user input is indicative of a verification or a modification of a sample-level ECG label of the sample-level ECG labels.

Some embodiments provide for a system comprising: at least one processor; and at least one non-transitory computer-readable storage medium storing processor-executable instructions that, when executed by the at least one processor, cause the at least one processor to perform a method for labelling at least one electrocardiogram (ECG) signal comprising a plurality of samples, wherein a sample is an ECG measurement at a single time point, the method comprising: obtaining the at least one ECG signal, the at least one ECG signal having been previously measured using ECG sensors; encoding the at least one ECG signal to obtain a numeric encoding of the at least one ECG signal; processing the numeric encoding of the at least one ECG signal using a trained sample-level ECG classifier to obtain sample-level ECG labels for at least some of the plurality of samples, wherein a sample-level ECG label for a particular sample of the at least some of the plurality of samples is indicative of a respective portion of an ECG waveform to which the particular sample corresponds; generating an interactive graphical user interface (GUI) indicating the sample-level ECG labels for the at least some of the plurality of samples; and receiving user input via the interactive GUI, wherein the user input is indicative of a verification or a modification of a sample-level ECG label of the sample-level ECG labels.

Some embodiments provide for a method for classifying rhythms of segments of at least one ECG signal, the method comprising: using at least one processor to perform: obtaining the at least one ECG signal, the at least one ECG signal comprising segments and having been previously measured using ECG sensors; encoding the at least one ECG signal to obtain a numeric encoding of the at least one ECG signal; positionally encoding the numeric encoding of the at least one ECG signal to obtain a positionally encoded numeric encoding of the at least one ECG signal; and classifying a respective rhythm of each of at least some of the segments between a plurality of classes to obtain a plurality of rhythm classifications, the classifying comprising: processing the positionally encoded numeric encoding of the at least one ECG signal using a trained rhythm classifier to obtain, for each of the at least some of the segments, a respective output indicative of a respective class of the plurality of classes; and outputting the plurality of rhythm classifications.

In embodiments, encoding the at least one ECG signal to obtain a numeric encoding of the at least one ECG signal comprises using an encoder and a residual vector quantizer as described herein in relation to methods for denoising at least one ECG signal. Thus, in embodiments, encoding the at least one ECG signal to obtain a numeric encoding of the at least one ECG signal comprises encoding the at least one ECG signal using the encoder to obtain a numeric encoding of the at least one ECG signal; quantizing the numeric encoding of the at least one ECG signal using the residual vector quantizer to obtain a quantized numeric encoding of the at least one ECG signal, as described herein in relation to methods for denoising at least one ECG signal, wherein the encoder and residual vector quantizer having been trained as part of a denoising model as described herein. In embodiments, encoding the at least one ECG signal to obtain a numeric encoding of the at least one ECG signal comprises using an encoder as described herein in relation to methods for denoising at least one ECG signal. Thus, in embodiments, encoding the at least one ECG signal to obtain a numeric encoding of the at least one ECG signal comprises encoding the at least one ECG signal using the encoder to obtain a numeric encoding of the at least one ECG signal, as described herein in relation to methods for denoising at least one ECG signal, wherein the encoder has been trained as part of a denoising model as described herein. The denoising model may have been trained using a method of training a denoising model to denoise at least one electrocardiogram (ECG) signal as described herein. Methods according to the present embodiments may further comprise obtaining the trained denoising model using a method of training a denoising model to denoise at least one electrocardiogram (ECG) signal as described herein. Some embodiments provide for at least one non-transitory computer-readable storage medium storing processor-executable instructions that, when executed by at least one processor, cause the at least one processor to perform a method for classifying rhythms of segments of at least one ECG signal, the method comprising: obtaining the at least one ECG signal, the at least one ECG signal comprising segments and having been previously measured using ECG sensors; encoding the at least one ECG signal to obtain a numeric encoding of the at least one ECG signal; positionally encoding the numeric encoding of the at least one ECG signal to obtain a positionally encoded numeric encoding of the at least one ECG signal; and classifying a respective rhythm of each of at least some of the segments between a plurality of classes to obtain a plurality of rhythm classifications, the classifying comprising: processing the positionally encoded numeric encoding of the at least one ECG signal using a trained rhythm classifier to obtain, for each of the at least some of the segments, a respective output indicative of a respective class of the plurality of classes; and outputting the plurality of rhythm classifications.

Some embodiments provide for a system comprising: at least one processor; and at least one non-transitory computer-readable storage medium storing processor-executable instructions that, when executed by the at least one processor, cause the at least one processor to perform a method for classifying rhythms of segments of at least one ECG signal, the method comprising: obtaining the at least one ECG signal, the at least one ECG signal comprising segments and having been previously measured using ECG sensors; encoding the at least one ECG signal to obtain a numeric encoding of the at least one ECG signal; positionally encoding the numeric encoding of the at least one ECG signal to obtain a positionally encoded numeric encoding of the at least one ECG signal; and classifying a respective rhythm of each of at least some of the segments between a plurality of classes to obtain a plurality of rhythm classifications, the classifying comprising: processing the positionally encoded numeric encoding of the at least one ECG signal using a trained rhythm classifier to obtain, for each of the at least some of the segments, a respective output indicative of a respective class of the plurality of classes; and outputting the plurality of rhythm classifications.

Some embodiments provide for a method of training a denoising model to denoise at least one electrocardiogram (ECG) signal, the method comprising: using at least one processor to perform: obtaining training data comprising a plurality of pairs of ECG signals, wherein a pair of ECG signals of the plurality of pairs of ECG signals comprises a clean ECG signal and a noisy ECG signal; training the denoising model, using the training data, to generate denoised ECG signals, the denoising model comprising an encoder, a residual vector quantizer, and a decoder, the training comprising: processing the noisy ECG signal using the denoising model to generate a denoised ECG signal corresponding to the noisy ECG signal; processing the denoised ECG signal using at least one discriminator model to obtain at least one classification indicative of whether the denoised ECG signal is a real ECG signal or an artificial ECG signal; and updating parameters of the denoising model based on (i) a loss that is a function of the denoised ECG signal and the clean ECG signal and (ii) a loss that is a function of the at least one classification.

Some embodiments provide for at least one non-transitory computer-readable storage medium storing processor-executable instructions that, when executed by at least one processor, cause the at least one processor to perform a method of training a denoising model to denoise at least one electrocardiogram (ECG) signal, the method comprising: using at least one processor to perform: obtaining training data comprising a plurality of pairs of ECG signals, wherein a pair of ECG signals of the plurality of pairs of ECG signals comprises a clean ECG signal and a noisy ECG signal; training the denoising model, using the training data, to generate denoised ECG signals, the denoising model comprising an encoder, a residual vector quantizer, and a decoder, the training comprising: processing the noisy ECG signal using the denoising model to generate a denoised ECG signal corresponding to the noisy ECG signal; processing the denoised ECG signal using at least one discriminator model to obtain at least one classification indicative of whether the denoised ECG signal is a real ECG signal or an artificial ECG signal; and updating parameters of the denoising model based on (i) a loss that is a function of the denoised ECG signal and the clean ECG signal and (ii) a loss that is a function of the at least one classification.

Some embodiments provide for a system comprising: at least one processor; and at least one non-transitory computer-readable storage medium storing processor-executable instructions that, when executed by the at least one processor, cause the at least one processor to perform a method of training a denoising model to denoise at least one electrocardiogram (ECG) signal, the method comprising: using at least one processor to perform: obtaining training data comprising a plurality of pairs of ECG signals, wherein a pair of ECG signals of the plurality of pairs of ECG signals comprises a clean ECG signal and a noisy ECG signal; training the denoising model, using the training data, to generate denoised ECG signals, the denoising model comprising an encoder, a residual vector quantizer, and a decoder, the training comprising: processing the noisy ECG signal using the denoising model to generate a denoised ECG signal corresponding to the noisy ECG signal; processing the denoised ECG signal using at least one discriminator model to obtain at least one classification indicative of whether the denoised ECG signal is a real ECG signal or an artificial ECG signal; and updating parameters of the denoising model based on (i) a loss that is a function of the denoised ECG signal and the clean ECG signal and (ii) a loss that is a function of the at least one classification.

Some embodiments provide for a Holter monitor, comprising: electrocardiogram (ECG) leads comprising at least three ECG leads; at least one processor; and at least one non-transitory computer-readable storage medium storing processor-executable instructions that, when executed by the at least one processor, cause the at least one processor to perform a method comprising: measuring at least one ECG signal using the ECG leads at a sampling rate of between 128 Hz and 256 Hz and for a duration of between one and fourteen days, the at least one ECG signal comprising a plurality of segments and a plurality of samples, wherein a sample is an ECG measurement corresponding to a single time point, and wherein a segment comprises at least some samples of the plurality of samples; encoding the at least one ECG signal to obtain a numeric encoding of the at least one ECG signal; processing the numeric encoding of the at least one ECG signal using at least one trained machine learning model to obtain one or more characteristics of the at least one ECG signal, the one or more characteristics comprising: (i) rhythm types including a respective rhythm type for each of at least some of the plurality of segments, wherein the rhythm types are selected from among a normal sinus type, an atrial fibrillation type, an atrial flutter type, a premature atrial contraction (PAC) type, or a premature ventricular contraction (PVC) type, and/or (ii) sample-level ECG labels including a respective sample-level ECG label for each of at least some of the plurality of samples, each sample-level ECG label being indicative of a respective portion of an ECG waveform to which a respective sample corresponds; and outputting the one or more characteristics of the at least one ECG signal.

In embodiments, encoding the at least one ECG signal to obtain a numeric encoding of the at least one ECG signal comprises using an encoder and a residual vector quantizer as described herein in relation to methods for denoising at least one ECG signal. Thus, in embodiments, encoding the at least one ECG signal to obtain a numeric encoding of the at least one ECG signal comprises encoding the at least one ECG signal using the encoder to obtain a numeric encoding of the at least one ECG signal; quantizing the numeric encoding of the at least one ECG signal using the residual vector quantizer to obtain a quantized numeric encoding of the at least one ECG signal, as described herein in relation to methods for denoising at least one ECG signal, wherein the encoder and residual vector quantizer having been trained as part of a denoising model as described herein. In embodiments, encoding the at least one ECG signal to obtain a numeric encoding of the at least one ECG signal comprises using an encoder as described herein in relation to methods for denoising at least one ECG signal. Thus, in embodiments, encoding the at least one ECG signal to obtain a numeric encoding of the at least one ECG signal comprises encoding the at least one ECG signal using the encoder to obtain a numeric encoding of the at least one ECG signal, as described herein in relation to methods for denoising at least one ECG signal, wherein the encoder has been trained as part of a denoising model as described herein.

In embodiments, the at least one trained machine learning model comprises a machine learning model as described herein in relation to methods for classifying rhythms of segments of at least one ECG signal described herein. For example, the at least one trained machine learning model may comprise a trained rhythm classifier as described herein in relation to such methods. In embodiments, the at least one trained machine learning model comprises a machine learning model as described herein in relation to methods for labelling at least one electrocardiogram (ECG) signal comprising a plurality of samples. For example, the at least one trained machine learning model may comprise a trained residual vector quantizer and a trained sample-level ECG classifier as described herein in relation to methods for labelling at least one electrocardiogram (ECG) signal comprising a plurality of samples. In embodiments, the encoding may be performed using a trained encoder as described herein in relation to methods for denoising at least one electrocardiogram (ECG) signal. The trained encoder may have been trained as described herein in relation to methods of training a denoising model to denoise at least one electrocardiogram (ECG) signal.

Thus, also described herein is a Holter monitor, comprising: electrocardiogram (ECG) leads comprising at least three ECG leads; at least one processor; and at least one non-transitory computer-readable storage medium storing processor-executable instructions that, when executed by the at least one processor, cause the at least one processor to perform a method for classifying rhythms of segments of at least one ECG signal as described herein and/or a method for labelling at least one ECG signal comprising a plurality of samples, wherein the at least one ECG signal processed in said methods is obtained by said processor from the ECG leads.

Some embodiments provide for a smartwatch, comprising: an electrocardiogram (ECG) lead; at least one processor; and at least one non-transitory computer-readable storage medium storing processor-executable instructions that, when executed by the at least one processor, cause the at least one processor to perform a method, comprising: measuring the at least one ECG signal using the ECG lead at a sampling rate of between 128 Hz and 256 Hz and for a duration of between 10 seconds and 24 hours, the at least one ECG signal comprising a plurality of segments and a plurality of samples, wherein a sample is an ECG measurement at a single time point, and wherein a segment comprises at least some samples of the plurality of samples; encoding the at least one ECG signal to obtain a numeric encoding of the at least one ECG signal; processing the numeric encoding of the at least one ECG signal using at least one trained machine learning model to obtain one or more characteristics of the at least one ECG signal, the characteristics comprising: (i) rhythm types including a respective rhythm type for each of at least some of the plurality of segments, wherein the rhythm types are selected from among a normal sinus type, an atrial fibrillation type, an atrial flutter type, a premature atrial contraction (PAC) type, or a premature ventricular contraction (PVC) type, and/or (ii) sample-level ECG labels including a respective sample-level ECG label for each of at least some of the plurality of samples, each sample-level ECG label being indicative of a respective portion of an ECG waveform to which a respective sample corresponds; and outputting the one or more characteristics of the at least one ECG signal via a graphical user interface (GUI) of the smartwatch.

In embodiments, encoding the at least one ECG signal to obtain a numeric encoding of the at least one ECG signal comprises using an encoder and a residual vector quantizer as described herein in relation to methods for denoising at least one ECG signal. Thus, in embodiments, encoding the at least one ECG signal to obtain a numeric encoding of the at least one ECG signal comprises encoding the at least one ECG signal using the encoder to obtain a numeric encoding of the at least one ECG signal; quantizing the numeric encoding of the at least one ECG signal using the residual vector quantizer to obtain a quantized numeric encoding of the at least one ECG signal, as described herein in relation to methods for denoising at least one ECG signal, wherein the encoder and residual vector quantizer having been trained as part of a denoising model as described herein. In embodiments, encoding the at least one ECG signal to obtain a numeric encoding of the at least one ECG signal comprises using an encoder as described herein in relation to methods for denoising at least one ECG signal. Thus, in embodiments, encoding the at least one ECG signal to obtain a numeric encoding of the at least one ECG signal comprises encoding the at least one ECG signal using the encoder to obtain a numeric encoding of the at least one ECG signal, as described herein in relation to methods for denoising at least one ECG signal, wherein the encoder has been trained as part of a denoising model as described herein.

In embodiments, the at least one trained machine learning model comprises a machine learning model as described herein in relation to methods for classifying rhythms of segments of at least one ECG signal described herein. For example, the at least one trained machine learning model may comprise a trained rhythm classifier as described herein in relation to such methods. In embodiments, the at least one trained machine learning model comprises a machine learning model as described herein in relation to methods for labelling at least one electrocardiogram (ECG) signal comprising a plurality of samples. For example, the at least one trained machine learning model may comprise a trained residual vector quantizer and a trained sample-level ECG classifier as described herein in relation to methods for labelling at least one electrocardiogram (ECG) signal comprising a plurality of samples. In embodiments, the encoding may be performed using a trained encoder as described herein in relation to methods for denoising at least one electrocardiogram (ECG) signal. The trained encoder may have been trained as described herein in relation to methods of training a denoising model to denoise at least one electrocardiogram (ECG) signal.

Thus, also described herein is smartwatch, comprising: an electrocardiogram (ECG) lead; at least one processor; and at least one non-transitory computer-readable storage medium storing processor-executable instructions that, when executed by the at least one processor, cause the at least one processor to perform a method for classifying rhythms of segments of at least one ECG signal as described herein and/or a method for labelling at least one ECG signal comprising a plurality of samples, wherein the at least one ECG signal processed in said methods is obtained by said processor from the ECG lead.

Some embodiments provide for a method, comprising: using at least one processor to perform: receiving, from at least one wearable device, at least one electrocardiogram (ECG) signal comprising a plurality of samples, wherein a sample is an ECG measurement corresponding to a single time point, and comprising segments; encoding the at least one ECG signal using an encoder to obtain a numeric encoding of the at least one ECG signal; processing the numeric encoding of the at least one ECG signal using at least one trained machine learning model to obtain: (i) at least one denoised ECG signal corresponding to the at least one ECG signal, and/or (ii) characteristics of the at least one ECG signal, the characteristics comprising: (i) rhythm types including a respective rhythm type for each of at least some of the segments, wherein the rhythm types are selected from among a normal sinus type, an atrial fibrillation type, an atrial flutter type, a premature atrial contraction (PAC) type, or a premature ventricular contraction (PVC) type, and/or (ii) sample-level ECG labels including a respective sample-level ECG label for each of at least some of the plurality of samples, each sample-level ECG label being indicative of a respective portion of an ECG waveform to which a respective sample corresponds; and transmitting the denoised ECG signal and/or the characteristics of the at least one ECG signal to a remote device.

In embodiments, the at least one trained machine learning model comprises a machine learning model as described herein in relation to methods for denoising at least one electrocardiogram (ECG) signal as described herein. For example, the at least one trained machine learning model may comprise a trained denoising model comprising an encoder, a residual vector quantizer, and a decoder. In embodiments, the at least one trained machine learning model comprises a machine learning model as described herein in relation to methods for classifying rhythms of heartbeats described herein. For example, the at least one trained machine learning model may comprise a trained rhythm classifier as described herein in relation to such methods. In embodiments, the at least one trained machine learning model comprises a machine learning model as described herein in relation to methods for labelling at least one electrocardiogram (ECG) signal comprising a plurality of samples. For example, the at least one trained machine learning model may comprise a trained residual vector quantizer and a trained sample-level ECG classifier as described herein in relation to methods for labelling at least one electrocardiogram (ECG) signal comprising a plurality of samples. In embodiments, the encoding may be performed using a trained encoder as described herein in relation to methods for denoising at least one electrocardiogram (ECG) signal. The trained encoder may have been trained as described herein in relation to methods of training a denoising model to denoise at least one electrocardiogram (ECG) signal.

Thus, also described herein is a method, comprising: using at least one processor to: perform a method for denoising at least one electrocardiogram (ECG) signal and/or perform a method for classifying rhythms of heartbeats as described herein and/or a method for labelling at least one electrocardiogram (ECG) signal comprising a plurality of samples, thereby obtaining a denoised signal and/or characteristics of the at least one ECG signal, wherein the at least one ECG signal processed in said methods is received by said processor from a wearable device, and transmitting the denoised ECG signal and/or the characteristics of the at least one ECG signal to a remote device.

Some embodiments provide for a distributed electrocardiogram (ECG) system comprising: at least one wearable device configured to: measure at least one ECG signal at a sampling rate of between 128 Hz and 256 Hz and for a duration of between one and fourteen days, the at least one ECG signal comprising a plurality of samples, wherein a sample is an ECG measurement at a single time point; encode the at least one ECG signal using an encoder to obtain a numeric encoding of the at least one ECG signal; and quantize the numeric encoding of the at least one ECG signal using a residual vector quantizer to obtain a quantized numeric encoding of the at least one ECG signal; and at least one processor coupled to the at least one wearable device and configured to: receive the quantized numeric encoding of the at least one ECG signal from the at least one wearable device; and process the quantized numeric encoding of the at least one ECG signal using at least one trained machine learning model to obtain: (i) at least one denoised ECG signal corresponding to the at least one ECG signal, and/or (ii) at least one characteristic of the at least one ECG signal, the at least one characteristic comprising: (i) rhythm types including a respective rhythm type for each of at least some segments of the at least one ECG signal, wherein the rhythm types are selected from among a normal sinus type, an atrial fibrillation type, an atrial flutter type, a premature atrial contraction (PAC) type, or a premature ventricular contraction (PVC) type, and/or (ii) sample-level ECG labels including a respective sample-level ECG label for each of at least some of the plurality of samples, each sample-level ECG label being indicative of a respective portion of an ECG waveform to which a respective sample corresponds.

Some embodiments provide for a distributed electrocardiogram (ECG) system, comprising: at least one wearable device configured to: measure at least one ECG signal at a sampling rate of between 128 Hz and 256 Hz and for a duration of between one and fourteen days, the at least one ECG signal comprising a plurality of samples, wherein a sample is an ECG measurement at a single time point; and segment the at least one ECG signal to obtain a plurality of ECG segments; and at least one processor coupled to the at least one wearable device and configured to: receive at least one ECG segment of the plurality of ECG segments from the at least one wearable device; encode the at least one ECG segment using an encoder to obtain a numeric encoding of the at least one ECG segment; quantize the numeric encoding of the at least one ECG segment using a residual vector quantizer to obtain a quantized numeric encoding of the at least one ECG segment; and process the quantized numeric encoding of the at least one ECG segment using at least one trained machine learning model to obtain: (i) at least one denoised ECG segment corresponding to the at least one ECG segment, and/or (ii) at least one characteristic of the at least one ECG segment, the at least one characteristic comprising: (i) at least one rhythm type for the at least one ECG segment, wherein the at least one rhythm type is selected from among a normal sinus type, an atrial fibrillation type, an atrial flutter type, a premature atrial contraction (PAC) type, or a premature ventricular contraction (PVC) type, and/or (ii) sample-level ECG labels including a respective sample-level ECG label for each of at least some of the plurality of samples, each sample-level ECG label being indicative of a respective portion of an ECG waveform to which a respective sample corresponds.

Some embodiments provide for a distributed electrocardiogram (ECG) system, comprising: at least one wearable device configured to: measure at least one ECG signal at a sampling rate of between 128 Hz and 256 Hz and for a duration of between one and fourteen days, the at least one ECG signal comprising a plurality of samples, wherein a sample is an ECG measurement at a single time point; and at least one processor coupled to the at least one wearable device and configured to: receive the at least one ECG signal from the at least one wearable device; encode the at least one ECG signal using an encoder to obtain a numeric encoding of the at least one ECG signal; quantize the numeric encoding of the at least one ECG signal using a residual vector quantizer to obtain a quantized numeric encoding of the at least one ECG signal; and process the quantized numeric encoding of the at least one ECG signal using at least one trained machine learning model to obtain: (i) at least one denoised ECG signal corresponding to the at least one ECG signal, and/or (ii) at least one characteristic of the at least one ECG signal, the at least one characteristic comprising: (i) rhythm types including a respective rhythm type for each of at least some segments of the at least one ECG signal, wherein the rhythm types are selected from among a normal sinus type, an atrial fibrillation type, an atrial flutter type, a premature atrial contraction (PAC) type, or a premature ventricular contraction (PVC) type, and/or (ii) sample-level ECG labels including a respective sample-level ECG label for each of at least some of the plurality of samples, each sample-level ECG label being indicative of a respective portion of an ECG waveform to which a respective sample corresponds.

Also described herein is at least one non-transitory computer-readable storage medium storing processor-executable instructions that, when executed by at least one processor, cause the at least one processor to perform any method described herein.

Also described herein is a system comprising: at least one processor; and at least one non-transitory computer-readable storage medium storing processor-executable instructions that, when executed by the at least one processor, cause the at least one processor to perform any method described herein.

BRIEF DESCRIPTION OF DRAWINGS

Various aspects and embodiments of the disclosure provided herein are described below with reference to the following figures. The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 5I-1 and FIG. 5I-2 show an example architecture of a discriminator (e.g., discriminator 222 shown in FIG. 2) used to train a denoising model, according to some embodiments of the technology described herein.

DETAILED DESCRIPTION

Figure 1A:
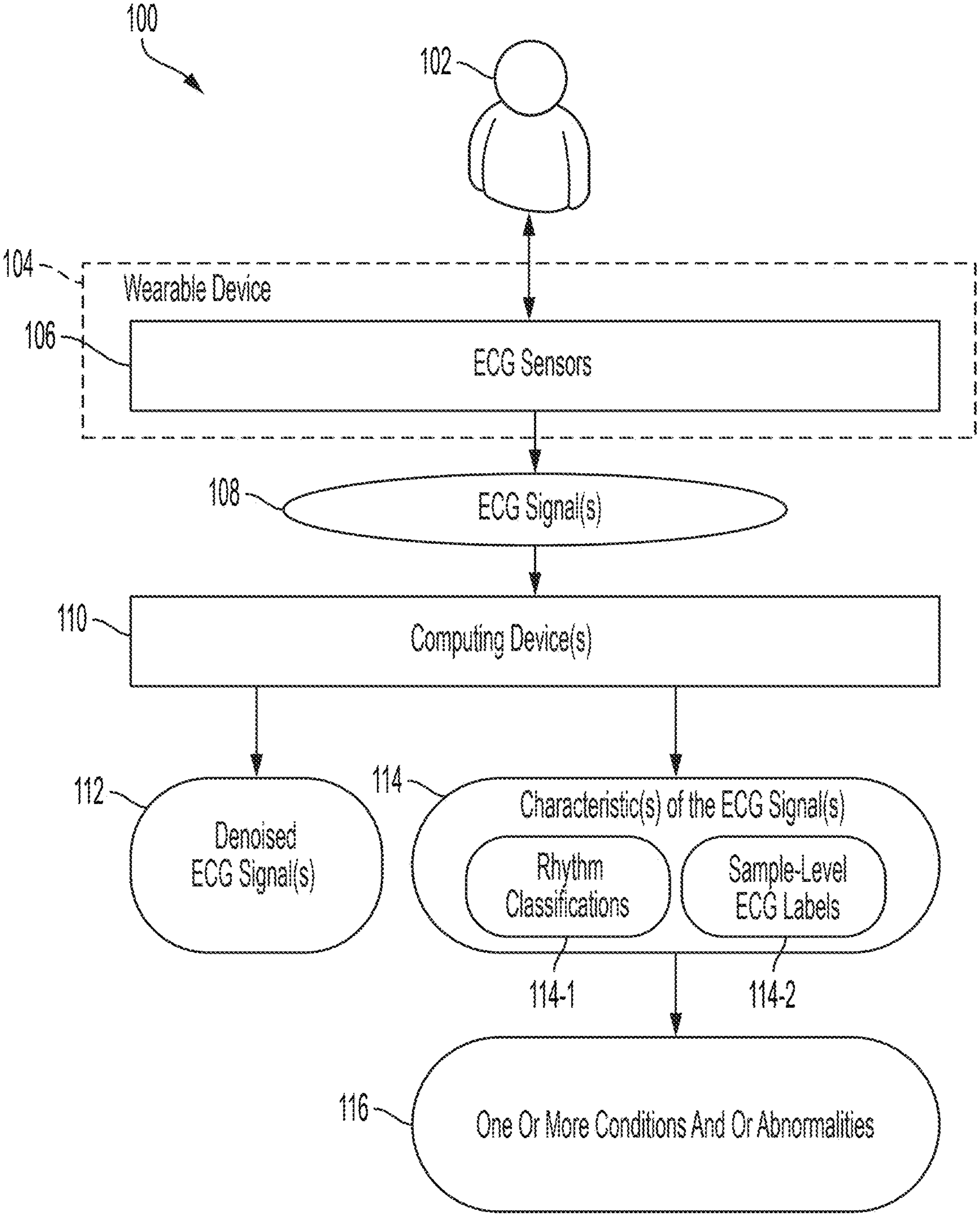
FIG. 1A and FIG. 1B are diagrams of illustrative techniques for analyzing at least one electrocardiogram (ECG) signal, according to some embodiments of the technology described herein.

The present application describes machine learning (ML) techniques for analyzing at least one electrocardiogram (ECG) signal having been measured using ECG sensors. In some embodiments, the machine learning techniques involve encoding the at least one ECG signal using an encoder to obtain a numeric encoding of the at least one ECG signal, and processing the numeric encoding of the at least one ECG signal using at least one trained machine learning model to obtain: (i) at least one denoised ECG signal corresponding to the at least one ECG signal, and/or (ii) one or more characteristics of the at least one ECG signal. For example, the one or more characteristics may include rhythm types for segments of the at least one ECG signal. Additionally or alternatively, the one or more characteristics may include sample-level ECG labels for samples of the at least one ECG signal. The label for a sample may indicate a portion of an ECG waveform (e.g., P, Q, R, S, or T-wave) containing the sample. In some embodiments, the denoised ECG signal(s) and/or characteristic(s) of the at least one ECG signal can be used to accurately and efficiently interpret the at least one ECG signal and detect various conditions such as, for example, arrhythmias, atrioventricular (AV) block, prolonged QT, congenital short QT syndrome, and Wolf-Parkison-White syndrome.

An ECG is a tool used for measuring ECG signals representing the electrical activity of the heart over time. The ECG signals are measured using ECG sensors placed in contact with a subject's body. For example, the ECG sensors may be implemented as two or more electrodes adhered to the subject's skin. Additionally or alternatively, the ECG sensors may be included in a wearable device such as a Holter monitor, smartwatch, chest strap, and/or patch. It should be appreciated, however, that the technology described herein is not limited to processing ECG signals collected by wearable sensors and may be applied to ECG signals collected in any suitable way including non-wearable equipment (e.g., using an ECG system in a healthcare facility). The ECG signals can be measured for a duration ranging from seconds to multiple weeks. For example, during an in-patient visit, to obtain a quick snapshot of heart rhythm and electrical activity, a standard 12-lead ECG may be used to obtain ECG signals having a duration on the order of seconds or minutes. By contrast, a wearable device such as a Holter monitor or smartwatch may be worn by a patient for day(s) or week(s) and used to measure ECG signals to catch abnormalities that are unlikely to be detected during a short-term, in-patient ECG given their frequency of occurrence.

After ECG signals have been measured, they are typically analyzed and interpreted to obtain insights into the subject's cardiac activity and/or health. Conventional techniques for analyzing and labelling ECG signals can involve manual review by a technician, who meticulously labels the peaks of individual waves and measures intervals between said peaks. This analysis is both inefficient and imprecise for several reasons. First, manual review by a technician is time consuming, especially when reviewing ECG data from multiple leads that were measured over long periods of time. Consider, for example, ECG data measured using a 3-lead Holter monitor over a period of 14 days, at a sampling rate of 250 Hz, for a subject having an average heart rate of 70 beats per minute (bpm). The resulting ECG data would include three ECG signals, each representing over a million heartbeats, resulting in over three million waveforms to be labelled and analyzed by the technician. Such an analysis is extremely time-consuming and labor intensive and can delay diagnosing medical conditions that should be detected and treated as early as possible. Moreover, the resulting ECG data would include 907,200,000 samples. Thus, to the extent that clinicians label, they would never label on a sample-by-sample basis due to the sheer number of samples that would need to be labeled for a single patient, never mind multiple (e.g., tens to thousands) patients. Rather, they label only some portions of the ECG signals and, even then, just the peaks of certain waves. Much of the ECG signals go without being analyzed, resulting in a loss of information that is helpful in detecting nuances important for the diagnosis and treatment of heart conditions.

While there are conventional automated techniques for working with ECG signals that attempt to address the above-described inefficiencies associated with the manual techniques, they too suffer from numerous drawbacks.

First, the conventional automated techniques cannot effectively handle the various different types of noise typically present in ECG signals. Examples of such noise include powerline interference, muscle artifacts (e.g., caused by voluntary and/or involuntary muscle contractions), motion artifacts (e.g., caused by shifting of ECG sensors), electrode contact noise, white noise (e.g., intense sectional white noise), wander, and random jumps in baseline. Moreover, while noise poses a challenge in all environments, that challenge is exacerbated in wearable environments. The clinical setting is controlled, but wearable devices (e.g., Holter monitors, smartwatches, chest straps, patches, etc.) are managed and worn by the patient, as they move about their days, in a variety of environments. As a result, the devices may shift, may not be ideally positioned, and may be used in environments with substantial radio frequency (RF) and other electromagnetic interference, all of which would be less of an issue in a controlled environment of a hospital or clinic. Thus, ECG signals measured by wearable devices may include various different types of noise that depend on the environment and the actions of the wearer, making such noise difficult to predict and account for ahead of time.

The conventional automated denoising techniques attempt to address the presence of noise in an ECG signal using various pre-processing and post-processing techniques. The pre-processing techniques include filtering the ECG signal (e.g., using bandpass filtering) to remove certain frequency components from the ECG signal. However, because the different types of noise are present at various different frequencies, many of which overlap with frequencies of the ECG signal itself, the filtering techniques are limited to filtering out only a subset of the noise present in the ECG signal (otherwise ECG signal itself would be removed). The post-processing techniques include initially labelling the ECG signal (e.g., labeling waves in the ECG signal), then identifying potential regions of noise based on labeling discrepancies. However, by failing to distinguish between noise and the ECG signal at or prior to the labeling stage, and due to the similarities between ECG signals and certain types of noise, the resulting labels may be inaccurate and thus unreliable for use in extracting meaningful insights from the ECG signal about the subject's cardiac activity and/or health.

Second, the conventional automated techniques for analyzing and labeling ECG signals have poor accuracy and cannot be used to reliably detect features of the ECG signal. The conventional automated labelling techniques involve performing peak detection to identify peaks of the P-wave, QRS-complex, and T-wave. Such techniques are not accurate or reliable because they do not enable the precise identification of the onsets and offsets of different waves (e.g., the onsets and offsets of the P-wave, Q-wave, R-wave, S-wave, T-wave, etc.). Rather, such techniques merely estimate the onsets and offsets by using a predetermined time/distance on each side of a detected peak. Thus, metrics that are determined based on inaccurate and imprecise estimates of the onsets and offsets (e.g., RR interval, PR segment, PR interval, QRS interval, QT duration, ST segment, P-wave duration, T-wave duration, etc.) are also inaccurate, which can result in the misdiagnosis and/or mistreatment of abnormalities and conditions detected using such metrics. Moreover, because P-waves and T-waves have amplitudes that are comparable to that of noise and flutter, and due to their inability to effectively address noise in ECG signals, the conventional automated techniques (e.g., the peak detection techniques) often confuse P-waves and T-waves with noise, and vice versa. Without the ability to accurately and consistently distinguish P-waves from noise, it is challenging to accurately identify the presence of abnormalities and/or conditions that are detectable based on P-wave characteristics (e.g., duration, amplitude, morphology, PR segment, a PR interval, etc.). Such abnormalities and conditions include, for example, P mitrale, P pulmonale, ectopic atrial rhythms, junctional rhythms, multifocal tachycardia (MAT), AV block, Wolff-Parkinson-White syndrome, atrial fibrillation, and atrial flutter.

Third, the conventional automated techniques are constructed in an ad hoc manner for use in specific environments, resulting in a set of rigid and ungeneralizable tools that cannot be widely adopted. A technique or model developed for one environment may not work well in another environment because such a technique or model may require a certain type, number, and format of inputs that can depend on the number of ECG sensors, leads, signal duration, and sampling rate, among other environment-specific factors. For example, a technique or model developed for handling ECG signals obtained in a clinic may not work well for handling ECG signals obtained using a Holter monitor. Similarly, a technique or model developed for handling ECG signals obtained using a Holter monitor may not work well for handling ECG signals obtained using a smartwatch.

The conventional automated labelling techniques are also limited in that they provide only a high-level analysis of ECG signals, leaving out important details that make it challenging to efficiently validate the results and derive further insights. Specifically, the conventional automated techniques fail to provide sample-based labels indicating parts of the ECG waveform containing the label. Rather, the conventional automated techniques often limit the analysis to peak identification and determination of other high-level metrics such as ECG intervals (e.g., RR interval, PR interval, QRS interval, etc.) and segments (e.g., QT segment, ST segment, etc.). Without accompanying sample-based labels, and thus without precise boundaries (e.g., onsets and offsets) of the individual ECG waves, it is challenging, if not impossible, to confirm the accuracy of the results of the high-level analysis. Moreover, it limits further low-level, high-resolution analysis to gain insights that may not be revealed using a high-level analysis.

Finally, the conventional automated techniques for denoising ECG signals are computationally expensive and inefficient making them unscalable to ECG signals that are obtained over relatively long durations. Specifically, as described above, the conventional automated denoising techniques rely on applying a series of different pre-processing and post-processing techniques that are complex and computationally inefficient. Consequently, it is unrealistic to rely on such techniques for the real-time analysis of ECG signals to alert a user (e.g., a wearer of a wearable ECG device) to a condition that requires urgent medical attention. Moreover, such techniques are inefficient for analysis of ECG signals measured over relatively long durations of time, such as ECG signals measured using Holter monitors, which are often used to continuously measure ECG signals for up to two weeks.

Accordingly, the inventors have developed techniques that address the above-described drawbacks associated with the conventional automated techniques for analyzing ECG signals. In some embodiments, the techniques developed by the inventors involve: (a) obtaining at least one ECG signal comprising a plurality of samples; (b) encoding the at least one ECG signal to obtain a numeric encoding of the at least one ECG signal; and (c) processing the numeric encoding of the at least one ECG signal using at least one trained machine learning model to obtain: (i) at least one denoised ECG signal corresponding to the at least one ECG signal, and/or (ii) one or more characteristics of the at least one ECG signal. For example, characteristics of the at least one ECG signal may include (i) rhythm type(s) and/or (ii) sample-level ECG labels, each of which is indicative of a respective portion of an ECG waveform to which a respective sample corresponds.

The techniques developed by the inventors are an improvement over conventional automated techniques for analyzing ECG signals for multiple reasons. First, the techniques developed by the inventors effectively address noise in the ECG signal(s) using a trained denoising model, rather than merely filtering out obvious noise components in a pre- or post-processing step. In particular, the techniques developed by the inventors for denoising ECG signal(s) involve (a) processing the numeric encoding of the ECG signal(s) using a residual vector quantizer (RVQ) to obtain a quantized numeric encoding and (b) decoding the quantized numeric encoding to obtain the denoised ECG signal(s). The inventors have recognized that using an RVQ enables effective denoising of ECG signals. In particular, quantizing numeric encodings using an RVQ helps the denoising model to become less sensitive and more robust to environmental differences, such as the introduction of various, unexpected types of noise in uncontrolled environments (e.g., wearable device environments). As such, the trained denoising model can be used to effectively remove various different types of noise from the input ECG signals, regardless of whether or not the trained denoising model was previously trained on similar ECG samples. Further, the output of the RVQ can also be used directly as input to models for determining the one or more characteristics of the ECG signals (e.g. a classification model trained to determine rhythm types and/or sample-level ECG labels for the ECG signals).

Second, the techniques developed by the inventors are more accurate than the conventional automated techniques for analyzing ECG signals. Specifically, the techniques developed by the inventors can be used to more accurately determine the one or more characteristics (e.g., rhythm type(s) and/or sample-level ECG labels) of the ECG signal(s) because they account for the noise in the ECG signal(s), rather than filtering out the noise in a pre-processing step or ignoring the noise until reaching a post-processing step. For example, one or more outputs of the trained denoising model (e.g., a numeric encoding, a quantized numeric encoding, etc.) may be provided as input to at least one trained machine learning model (e.g., a trained rhythm classifier and/or a trained sample-level ECG classifier) to obtain the characteristic(s) of the ECG signal(s). By accounting for the noise (e.g., using the output(s) of the trained denoising model or the output(s) of a component thereof, such as the encoder or RVQ), the techniques developed by the inventors can make intelligent and nuanced distinctions between the noise and the ECG signal that would otherwise go undetected had information (e.g., noise and/or signal information) been filtered out or simply treated as part of the ECG signal. This approach to managing noise enables more accurate downstream classifications (e.g., by the rhythm classifier and/or sample-level ECG classifier) because such predictions are made using complete and comprehensive information about the ECG signal(s). For example, compared to the conventional techniques, the techniques developed by the inventors more accurately and consistently detect P-waves. Specifically, as described in the section entitled "Example 2: Sample-Level ECG Classifier," the techniques developed by the inventors were used to correctly identify 94.3% of P-waves present in a set of ECG signals and 85.7% of P-waves that were missing from the set of ECG signals.

The one or more characteristics of the ECG signal(s) can further be used to determine (e.g., automatically determine) whether the subject has or is at risk of having one or more abnormalities and/or conditions. Examples of abnormalities and conditions include P mitrale, P pulmonale, ectopic atrial rhythms, junctional rhythms, multifocal tachycardia (MAT), bradycardia, AV block, Wolff-Parkinson-White syndrome, ventricular arrhythmias, premature ventricular complex (PVC) burden, paroxysmal atrial fibrillation, and sudden cardiac death. Thus, by enabling a more accurate determination of the one or more characteristics of the ECG signal(s), the techniques developed by the inventors can be used to more accurately determine whether the subject has or is at risk of having one or more conditions and/or abnormalities. This, in turn, enables a more accurate identification of treatments that can be used to effectively treat the subject.

Third, the techniques developed by the inventors are an improvement over the conventional automated techniques for analyzing ECG signals because they are applicable to a wide variety of environments. Specifically, the techniques developed by the inventors can be adapted to multiple different environments because the techniques utilize an RVQ. As described herein, by quantizing numeric encodings of ECG signals, the RVQ enables the denoising and classification techniques to become less sensitive and more robust to environmental differences, such as the introduction of various, unexpected types of noise in uncontrolled environments (e.g., wearable device environments). By contrast, as described herein, the conventional automated techniques are not equipped to handle the various types of noise present in different environments, and they lack flexibility in handling inputs of different sizes, formats, and types.

Figure 8A:
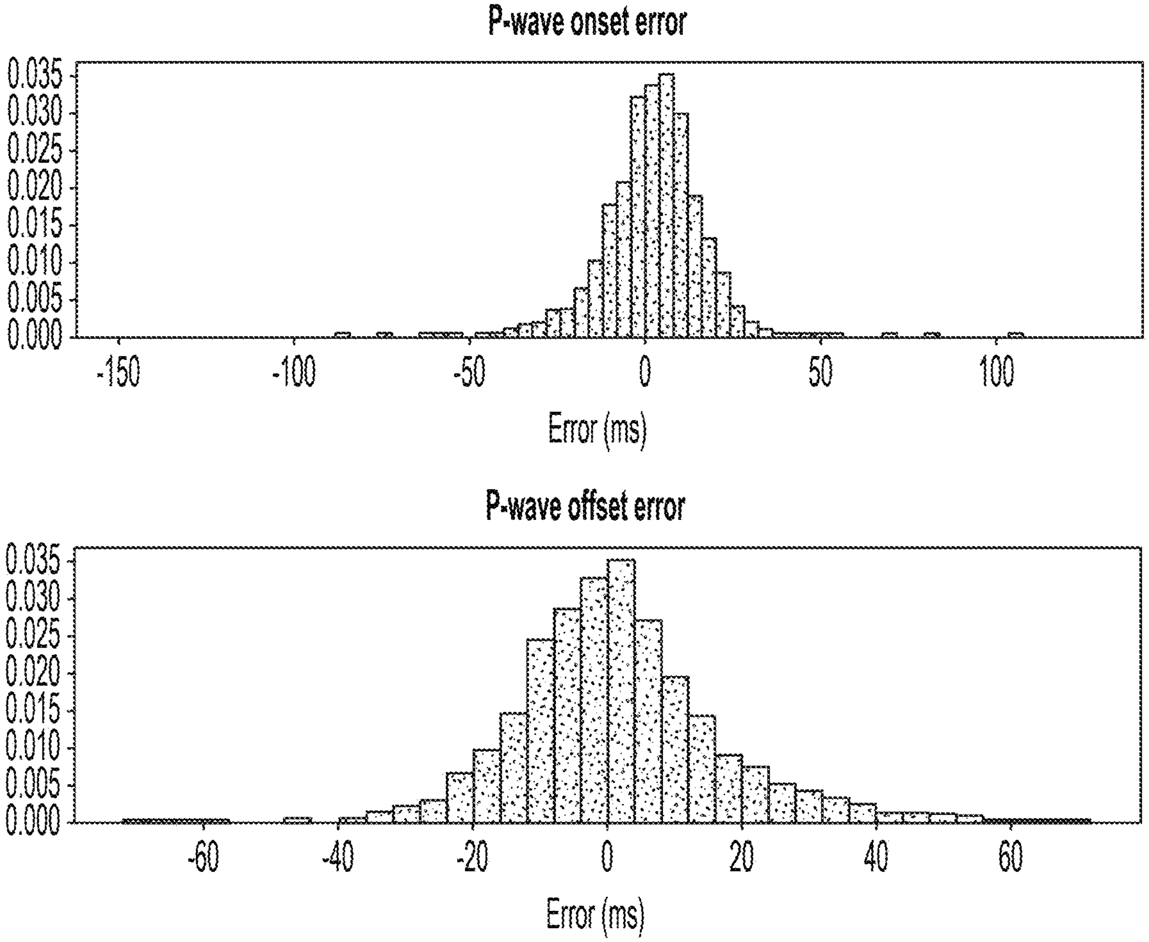
FIG. 8A illustrates accuracy with which P-waves may be identified in accordance with embodiments of the technology described herein.
Figure 8B:
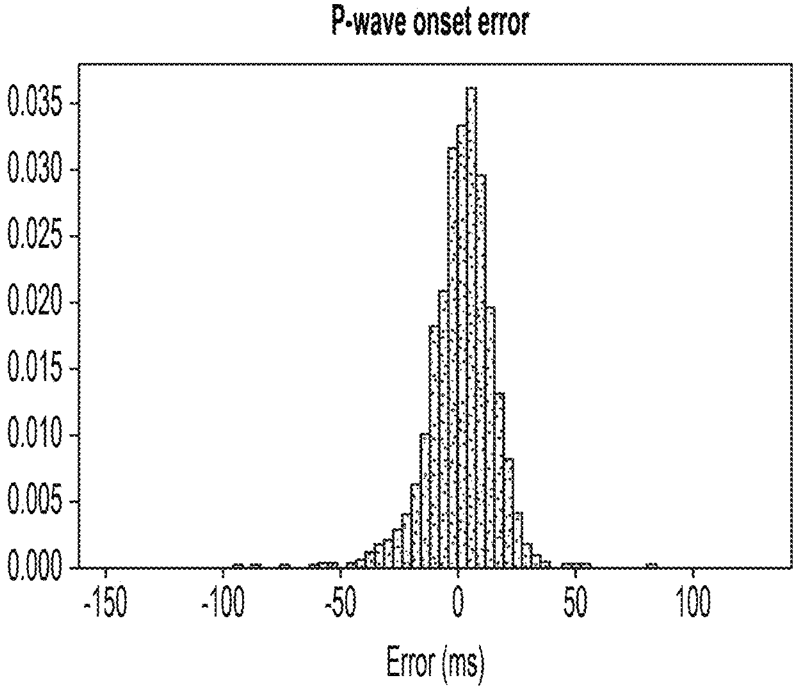
FIGS. 8B and 8C illustrate accuracy with which embodiments of the technology described herein can be used to determine PR intervals by identifying onsets of P-waves and onsets of QRS complexes.
Figure 8C:
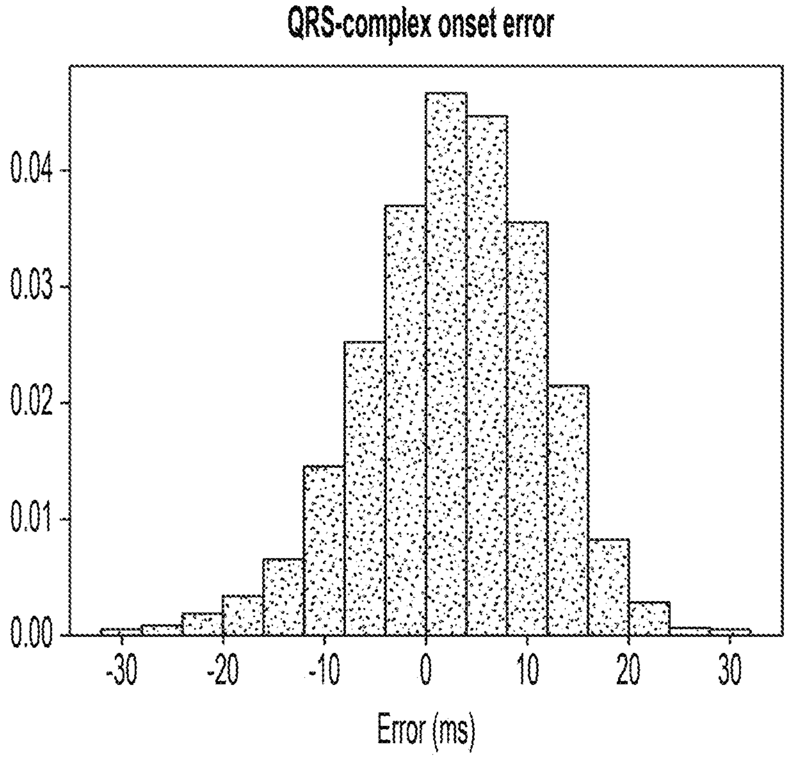

Fourth, the techniques developed by the inventors are an improvement over the conventional automated techniques for analyzing ECG signals because they enable high resolution, sample-level analysis of ECG signals, rather than low resolution, high-level analysis of ECG signals. As described above, the conventional automated techniques for analyzing and labeling ECG signals involve detecting peaks of ECG waveforms and estimating onsets and offsets based on the detected peaks, which is imprecise and can be inaccurate. By contrast, in some embodiments, the techniques developed by the inventors involve processing a numeric encoding of at least one ECG signal using a trained sample-level ECG classifier to obtain sample-level ECG labels for at least some of the plurality of samples, wherein a sample-level ECG label for a particular sample of the at least some of the plurality of samples is indicative of a respective portion of an ECG waveform to which the particular sample corresponds. As described herein, sample-based labels enable the identification of precise boundaries (e.g., onsets and offsets) of individual ECG waves, which can be used to derive various different ECG metrics and information about the subject's health. Moreover, the sample-based labels enable a user to easily and efficiently validate results (e.g., metrics, conditions, abnormalities, etc.) of analyzing ECG signals. For example, as shown in FIGS. 8A-8C and as described in the section entitled "Example 2: Sample-Level ECG Classifier," the techniques developed by the inventors were used to precisely identify the onsets and offsets of P-waves and QRS-complexes in ECG signals with limited error.

Figure 8D:
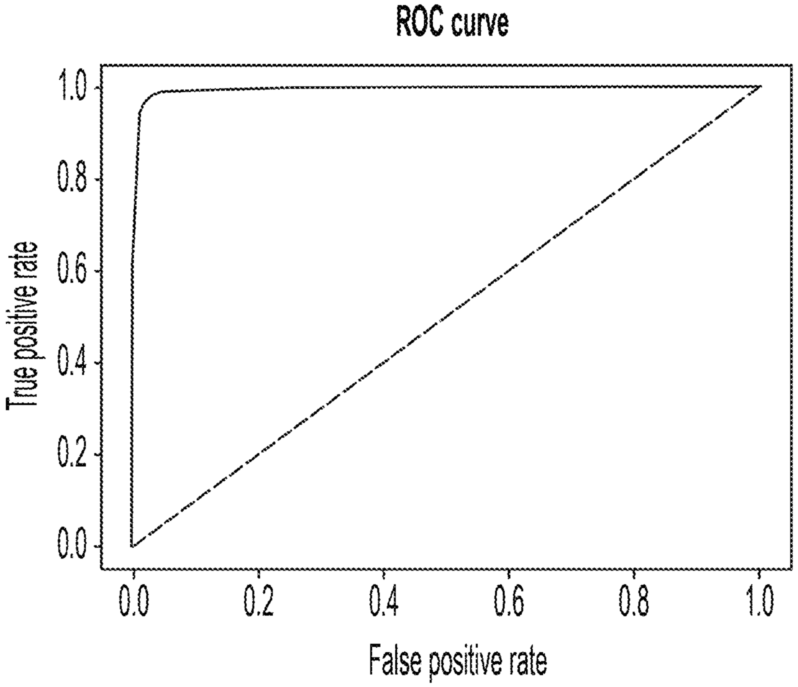
FIG. 8D is a receiver operating characteristic (ROC) curve showing that embodiments of the technology described herein can be used to accurately predict arrhythmias.
Figure 8E:
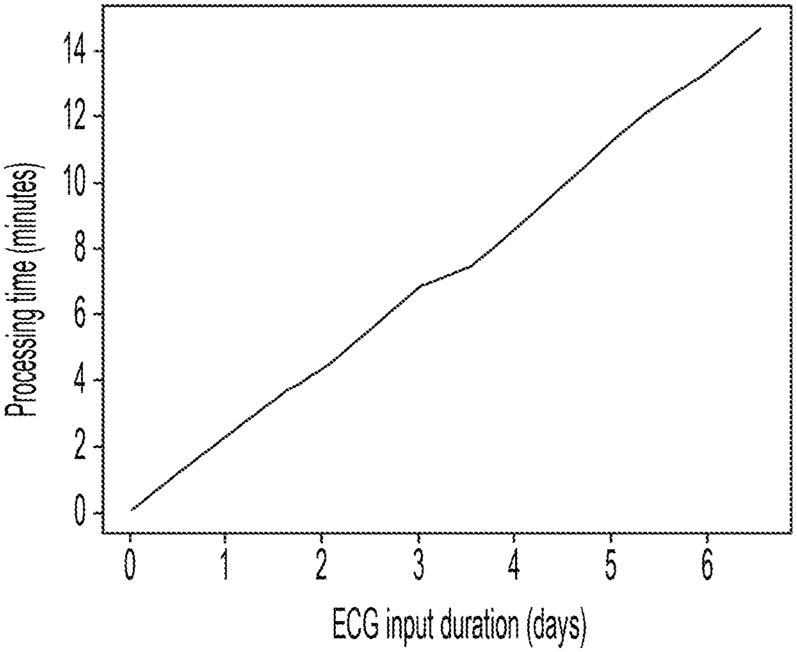
FIG. 8E is a graph showing how long it takes for a trained denoising model to denoise ECG signals, according to some embodiments of the technology described herein.

Fifth, the techniques developed by the inventors are an improvement over the conventional automated techniques for denoising and analyzing ECG signals because they are more computationally efficient than the conventional automated techniques. For example, as shown in FIG. 8E, the techniques developed by the inventors can be used to denoise an ECG signal spanning multiple days in a matter of minutes, enabling near-real-time analysis of ECG signals, even when they span relatively long durations. Moreover, in embodiments utilizing an RVQ, the RVQ serves to compress the numeric encodings (e.g., high-dimensional numeric encodings), which helps to reduce storage requirements and increase data transmission efficiency, thereby contributing to improved computational efficiency. For example, if at least the quantizing is performed on a device with limited storage capacity (e.g., a smartwatch), then the resulting quantized numeric encodings may (i) be stored on said device without exceeding the storage capacity and/or (ii) efficiently transmitted to another device for further processing.

In addition to offering several improvements over the conventional automated techniques for analyzing ECG signals, the techniques developed by the inventors may further include presenting the denoised ECG signal(s) via an interactive graphical user interface (GUI). The denoised ECG signal(s) may be presented together with one or more characteristics determined for the ECG signal(s) and/or the original ECG signal(s) (e.g., the ECG signal(s) prior to denoising). For example, the denoised ECG signal(s) may include annotations such as sample-level ECG labels and/or rhythm types determined for the denoised ECG signal(s). A user may interact with the interactive GUI to validate the characteristic(s) of the ECG signal(s). For example, the GUI may allow a user to select an annotation and provide input validating or editing the annotation. Additionally or alternatively, the interactive GUI may allow the user to view and compare the denoised ECG signal(s) and the corresponding original ECG signal(s), to validate the accuracy of the denoising. The interactive GUI may collate several different functions and types of information together on the same screen, allowing for simple and efficient use by the user.

Following below are descriptions of various concepts related to, and embodiments of, techniques for analyzing at least one ECG signal. It should be appreciated that various aspects described herein may be implemented in any of numerous ways, as the techniques are not limited in any particular manner of implementation. Example details of implementations are provided herein solely for illustrative purposes. Furthermore, the techniques disclosed herein may be used individually or in any suitable combination, as aspects of the technology described herein are not limited to the use of any particular technique or combination of techniques.

FIG. 1A is a diagram of an illustrative technique 100 for analyzing at least one ECG signal, according to some embodiments of the technology described herein. Illustrative technique 100 includes (a) obtaining at least one ECG signals 108 having been previously measured by ECG sensors 106, and (b) processing the ECG signal(s) 108 using at least one computing device 110 to obtain (i) at least one denoised ECG signal 112 and/or (ii) at least one characteristic 114 of the ECG signal(s) 108.

As shown in FIG. 1A, the ECG signal(s) 108 may be measured, or may have previously been measured, using at least two ECG sensors 106. An ECG sensor may include, for example, an ECG electrode. The ECG electrode may include a silver/silver chloride electrode, a capacitive electrode, a textile-based electrode, or any other suitable type of electrode used for measuring ECG signals, as aspects of the technology described herein are not limited in this respect. An ECG sensor may be disposable or reusable. An ECG sensor may be a wet-contact sensor, a dry-contact sensor, or a no-contact sensor. For example, the metal conductor of a wet-contact sensor may be coated in an electrolyte gel and/or solution used for coupling the ECG sensor to the skin.

In some embodiments, the ECG sensors 106 are configured to be placed in direct or indirect contact with the subject's skin. For example, the ECG sensors 106 may be adhered to the subject's skin using an adhesive, such as ECG tape. In some embodiments, the ECG sensors 106 are included in (e.g., embedded in) a wearable device 104 worn by subject 102. The wearable device 104 may include a Holter monitor, a smartwatch, a chest strap, and/or any other suitable wearable device configured to support ECG sensors, as aspects of the technology described herein are not limited in this respect.

The ECG sensors 106 are used to measure the ECG signal(s) 108. Specifically, an ECG signal represents the potential difference between a pair of the ECG sensors 106 placed in contact with the subject's skin. The potential difference measured by the pair of ECG sensors 106 is considered to be a "lead," which refers to an electrical viewpoint of the heart's activity. Other "leads" may be formed by different pairs of ECG sensors 106 placed in contact with the subject's skin. Multiple ECG signals can be obtained from multiple leads in parallel, thereby enabling analysis of different viewpoints of the heart's activity over the same period of time. As described herein. different ECG systems may use different numbers of leads. For example, some ECG systems may use 1, 3, 6, or 12 leads.

The number of ECG sensors may vary depending on how they are used to measure the ECG signal(s) 108 and/or the wearable device in which they are embedded. For example, the number of ECG sensors 106 may be at least two, at least three, at least four, at least five, at least six, at least seven, at least eight, at least nine, at least ten, at least eleven, at least twelve, at least thirteen, at least fourteen, at least fifteen, at least sixteen, or at least any other suitable number of ECG sensors, as aspects of the technology described herein are not limited in this respect. The number of ECG sensors 106 may be at most two, at most three, at most four, at most five, at most six, at most seven, at most eight, at most nine, at most ten, at most eleven, at most twelve, at most thirteen, at most fourteen, at most fifteen, at most sixteen, or at most any other suitable number of ECG sensors, as aspects of the technology described herein are not limited in this respect. It should be appreciated that any of the above-listed upper bounds may be coupled to any of the above-listed lower bounds. For example, the number of ECG sensors 106 may be between two and twelve. The number of ECG sensors 106 may be two, three, four, five, six, seven, eight, nine, ten, eleven or twelve. The number of ECG sensors 106 may be two. For example, smartwatches typically include two ECG sensors. The number of ECG sensors 106 may be between three and eight. For example, Holter monitors typically include between three and eight ECG sensors. A lead may be produced by measuring a voltage difference between two or more of the ECG sensors. Thus, the number of ECG leads may depend on the number of ECG sensors. For example the number of leads may be at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, or at least any other suitable number of ECG leads, as aspects of the technology described herein are not limited in this respect. The number of leads may be at most one, at most two, at most three, at most four, at most five, at most six, at most seven, at most eight, at most nine, at most ten, at most eleven, at most twelve, at most thirteen, at most fourteen, at most fifteen, at most sixteen, at most seventeen, at most eighteen, at most nineteen, at most twenty, or at most any other suitable number of ECG leads, as aspects of the technology described herein are not limited in this respect. It should be appreciated that any of the above-listed upper bounds may be coupled to any of the above-listed lower bounds. For example, the number of leads may be between one and twelve. The number of leads may be one, two, three, four, five, six, seven, eight, nine, ten, eleven or twelve. The number of leads may be one. For example, smartwatches typically have one lead. The number of leads may be between three and five. For example, Holter monitors typically include three, five, or twelve leads.

In some embodiments, a lead (e.g., each lead) formed by ECG sensors 106 is configured to measure an ECG signal. The ECG signal may be measured, by the lead, at a particular sampling rate over a particular duration of time. Thus, the measured ECG signal may comprise a plurality of samples (e.g., individual data points), each of which represents a measurement for the lead at a respective time point.

Regardless of whether the ECG sensors 106 are placed directly in contact with the subject's skin or included in a wearable device 104, the ECG sensors 106 may be connected (e.g., via a wired or wireless connection) to a processor (e.g., computing device(s) 110) used to digitize the measured ECG signal(s). For example, the processor may digitize the measured ECG signal(s) 108 by sampling the analog signal(s) measured using the ECG sensors 106. The sampling may be performed at any suitable sampling rate such as, for example, at a sampling rate between 250 Hz and 1,000 Hz. Thus, each of the ECG signal(s) 108 may include multiple samples representing the heart's electrical activity (e.g., heartbeats) over a respective period of time.

As described herein, in some embodiments, the ECG sensors 106 are included in (e.g., embedded in) a wearable device 104 such as a Holter monitor, a smartwatch, and/or a chest strap.

A Holter monitor is a portable device that can be worn by the subject 102 and used to monitor the subject 102 as they go about their day (e.g., remote from a clinical setting). The Holter monitor may be configured to measure ECG signals (optionally, continuously) for relatively long durations of time. For example, the Holter monitor may be configured to measure ECG signals for a duration between 12 hours and 15 days. Thus, a Holter monitor may be used to monitor a patient's cardiac activity to detect issues that might not show up during a short in-patient ECG. The sampling rate of a Holter monitor may be between 128 and 2,000 Hz, though it should be appreciated that the Holter monitor sampling rate is not limited to these sampling rates and may include other suitable sampling rates. As such, ECG signal(s) measured using a Holter monitor may include at least 5,529,600 samples, at least 10,800,000, at least 12,960,000 samples, at least 21,600,000 samples, at least 43,200,000 samples, at least 64,800,000 samples, at least 86,400,000, at least 129,600,000, at least 172,800,000, or at least any other suitable number of samples as aspects of the technology described herein are not limited in this respect. Additionally or alternatively the ECG signal(s) measured using a Holter monitor may include at most 165,888,000 samples, at most 324,000,000 samples, at most 388,800,000 samples, at most 648,000,000 samples, at most 972,000,000 samples, at most 1,296,000,000 samples, at most 1,944,000,000 samples, at most 2,592,000,000 samples, or at most any other suitable number of samples as aspects of the technology described herein are not limited in this respect. It should be appreciated that any of the above-listed upper bounds may be coupled with any of the above-listed lower bounds. For example, the number of samples may be any number of samples between 5,529,600 samples and 2,592,000,000 samples. The Holter monitor may be a wireless patch that is adhered to the subject's skin or a device connected to electrodes adhered to the subject's skin. Examples of Holter monitors include the DR400 patch style Holter recorder and the DR200 Holter recorder from NorthEast Monitoring, Inc. and the CardioSTAT® device from Icentia.

A smartwatch is a wearable electronic device worn on the wrist of the subject 102. The smartwatch may be configured to measure ECG signals for relatively short durations of time. For example, the smartwatch may be configured to measure ECG signals for a duration between five seconds and two minutes. The sampling rate of a smartwatch may be between 100 and 250 Hz, though it should be appreciated that the smartwatch sampling rate is not limited to these sampling rates and may include other suitable sampling rates. As such, ECG signal(s) measured using a smartwatch may include at least 500 samples, at least 625 samples, at least 750 samples, at least 875 samples, at least 1,000 samples, at least 1,125 samples, at least 1,250 samples, or at least any other suitable number of samples, as aspects of the technology described herein are not limited in this respect. Additionally or alternatively, ECG signal(s) measured using a smartwatch may include at most 12,000 samples, at most 15,000 samples, at most 18,000 samples, at most 21,000 samples, at most 24,000 samples, at most 27,000 samples, at most 30,000 samples, or at most any other suitable number of samples, as aspects of the technology described herein are not limited in this respect. It should be appreciated that any of the above-listed upper bounds may be coupled with any of the above-listed lower bounds. For example, the number of samples may be any number of samples between 500 samples and 30,000 samples. Because smartwatches include other functionalities and are discreet and comfortable wear, they can be used to easily and conveniently measure ECG signal(s) outside of the clinical setting. Examples of smartwatches include smartwatches with ECG capabilities made by manufacturers such as Apple®, Samsung®, Withings®, Garmin®, and Fitbit®.

A chest strap is a wearable electronic device that includes a device secured to the subject's chest using a strap worn around the torso. Chest straps may be worn to measure ECG signal(s) during exercise and/or sports. Chest straps may be configured to measure ECG signal(s) of varying durations, which may depend on the duration of exercise and/or participating in a sport. For example, a chest strap may be configured to measure ECG signal(s) for a duration between 10 minutes and 24 hours. The sampling rate of a chest strap may be between 128 Hz and 1,000 Hz, though it should be appreciated that the chest strap sampling rate is not limited to these sampling rates and may include other suitable sampling rates. As such, ECG signal(s) measured using a chest strap may include at least 76,800 samples, at least 90,000 samples, at least 120,000 samples, at least 150,000 samples, at least 180,000 samples, at least 240,000 samples, at least 300,000 samples, at least 360,000 samples, at least 420,000 samples, at least 450,000 samples, at least 480,000 samples, at least 510,000 samples, at least 540,000 samples, at least 570,000 samples, at least 600,000 samples, or at least any other suitable number of samples, as aspects of the technology described herein are not limited in this respect. Additionally or alternatively, ECG signal(s) measured using a chest strap may include at most 11,059,200 samples, at most 12,960,000 samples, at most 17,280,000 samples, at most 21,600,000 samples, at most 25,920,000 samples, at most 25,920,000 samples, at most 43,200,000 samples, at most 51,840,000 samples, at most 60,480,000 samples, at most 64,800,000 samples, at most 69,120,000 samples, at most 73,440,000 samples, at most 77,760,000 samples, at most 82,080,000 samples, at most 86,400,000, or at most any other suitable number of samples, as aspects of the technology described herein are not limited in this respect. It should be appreciated that any of the above-listed upper bounds may be coupled with any of the above-listed lower bounds. For example, the number of samples may be between 76,800 samples and 86,400,000 samples. The Polar H10® heart rate sensor is an example of a chest strap configured to measure ECG signals.

The ECG signal(s) 108 include one or more ECG signals measured using ECG sensors 106. When the ECG signal(s) 108 include multiple ECG signals, the multiple ECG signals may represent ECG signals measured using different ECG leads. For example, each of the ECG signals may have been measured using a different ECG lead over the same period of time. Additionally or alternatively, when the ECG signal(s) 108 include multiple ECG signals, at least some of the ECG signals may have been measured using the same lead over different periods of time. For example, a first ECG signal may have been measured using a lead between 8:00 AM and 8:30 AM, while a second ECG signal may have measured using the same lead between 9:00 AM and 9:30 AM.

In some embodiments, the ECG signal(s) 108 are contained in one or more files. Each of the files may have a format suitable for storing time series data. For example, a file may be a European Data Format (EDF) file, an Extensible Markup Language (XML)-ECG file, an HL7-XML file, an mPCG-XML file, a Phillips-XML file, an ecgML file, an mECGML file, a JavaScript Object Notation (JSON) file, an SaECG file, an HL7 aECG file, a CDA R2 file, a PDF-ECG file, an (Medical Waveform Format Encoding Rules (MFER) file, a comma-separated values (CSV) file, an ECGWARE file, or a file of any other format suitable for storing ECG signals, as aspects of the technology described herein are not limited in this respect.

In some embodiments, the ECG signal(s) 108 are processed using computing device(s) 110 to obtain (i) denoised signal(s) 112 and/or (ii) characteristic(s) 114 of the ECG signal(s) 108. The computing device(s) 110 may be separate from the wearable device 104 and/or co-located with the wearable device 104 (not shown). For example, a computing device that is co-located with the wearable device 104 may include a computing device that is part of (e.g., on-board) the wearable device. A computing device that is separate from the wearable device 104 may include one or more servers, laptops, desktops, smartphones, tablets, cloud instances, virtual machines, and/or any other suitable type of computing device, as aspects of the technology described herein are not limited in this respect. When the computing device(s) 110 include multiple computing devices, the multiple computing devices may be configured to communicate via at least one communication network such as the Internet or any other suitable communication network(s), as aspects of the technology described herein are not limited in this respect. For example, the multiple computing devices may be part of a cloud computing environment. The cloud computing environment may be a public cloud computing environment, a private computing environment, or a hybrid computing environment operating using a combination of publicly accessible and private infrastructure.

Software (e.g., software 320 shown in FIG. 3A) on the computing device(s) 110 may be configured to process the ECG signal(s) 108. In some embodiments, the processing includes encoding the ECG signal(s) 108 using an encoder to obtain a numeric encoding of the ECG signal(s) 108, and processing the numeric using one or more trained machine learning models to obtain: (i) denoised ECG signal(s) 112 corresponding to the ECG signal(s) 108, and/or (ii) one or more characteristics 114 of the ECG signal(s) 108. Additionally or alternatively, the processing may include training the machine learning model(s) to (i) denoise an ECG signal and/or (ii) determine one or more characteristics of an ECG signal. Example techniques for processing one or more ECG signal(s) are described herein including at least with respect to FIGS. 1B-1D and FIGS. 4A-4D. Example techniques for training one or more machine learning models are described herein including at least with respect to FIG. 2 and FIG. 4D.

The ECG signal(s) 108 may be processed using computing device(s) 110 on a per signal base or in batches of multiple ECG signals. For batch processing, the computing device(s) 110 may be configured to obtain a batch of multiple ECG signals and process the multiple ECG signals together. For example, the multiple ECG signals may be stored in one or more data store(s) (e.g., ECG data store(s) 328 shown in FIG. 3A). Batch processing multiple ECG signals may include processing the multiple ECG signals in parallel or sequentially. The computing device(s) 110 may be configured to access the data store(s) and batch process the ECG signals stored thereon. In some embodiments, batch processing multiple ECG signals includes batch processing at least 5, at least 10, at least 20, at least 25, at least 50, at least 75, at least 100, at least 125, at least 150, at least 175, at least 200, at least 250, at least 300, at least 400, at least 500, at least 750, at least 1,000, at least 1,500, at least 2,000, at least 2,500, at least 5,000, at least 10,000, at least 25,000, at least 50,000, at least 75,000, or at least any other suitable number of ECG signals as aspects of the technology described herein are not limited in this respect. In some embodiments, batch processing multiple ECG signals includes batch processing at most 5, at most 10, at most 20, at most 25, at most 50, at most 75, at most 100, at most 125, at most 150, at most 175, at most 200, at most 250, at most 300, at most 400, at most 500, at most 750, at most 1,000, at most 1,500, at most 2,000, at most 2,500, at most 5,000, at most 10,000, at most 25,000, at most 50,000, at most 75,000, or at most any other suitable number of ECG signals as aspects of the technology described herein are not limited in this respect. It should be appreciated that any of the above-listed upper bounds may be coupled with any of the above-listed lower bounds.

The output of the computing device(s) 110 includes the denoised ECG signal(s) 112, characteristic(s) 114 of the ECG signal(s) 108, and/or one or more conditions and/or abnormalities 116. The denoised ECG signal(s) 112 represent version(s) of the initially measured ECG signal(s) 108 from which noise has been removed to reveal underlying, meaningful information. As described herein, examples of types of noise that may be removed to obtain the denoised ECG signal(s) 108 include powerline interference, muscle artifacts (e.g., caused by voluntary and/or involuntary muscle contractions), motion artifacts (e.g., caused by shifting of ECG sensors), electrode contact noise, white noise (e.g., intense sectional white noise), wander, and random jumps in baseline. In some embodiments, outputting the denoised ECG signal(s) 112 includes displaying the denoised ECG signal(s) 112 via a graphical user interface (GUI) (e.g., an interactive GUI), including the denoised ECG signal(s) 112 in a report, storing the denoised ECG signal(s) 112 (e.g., in memory), transmitting the denoised ECG signal(s) 112 to one or more devices or servers, and/or outputting the denoised ECG signal(s) 112 using any other suitable techniques, as aspects of the technology described herein are not limited in this respect. In some embodiments, when displaying the denoised ECG signal(s) 112 via a GUI and/or in a report, the denoised ECG signal(s) 112 may be presented together with the original ECG signal(s) 108. For example, the denoised ECG signal(s) 112 may overlay the original ECG signal(s) 108 to facilitate efficient visual comparison between the signals.

The characteristic(s) 114 of the ECG signal(s) may include rhythm classifications 114-1 and/or sample-level ECG labels 114-2. The rhythm classifications 114-1 may indicate a respective rhythm type determined for each of at least some (e.g., all) segments of ECG signal(s) 108. For example, as shown in FIG. 1C, the rhythm types may include a normal sinus type 152-1, an atrial fibrillation type 152-2, an atrial flutter type 152-3, a premature atrial contraction (PAC) type 152-4, or a premature ventricular contraction (PVC) type 152-5. The sample-level ECG labels 114-2 may include labels for each of at least some (e.g., all) of the samples of the ECG signal(s) 108. A sample-level ECG label for a particular sample may be indicative of a respective portion of the ECG waveform to which the particular sample corresponds. For example, as shown in FIG. 1D, a sample-level ECG label may include a P-wave label 172-1 indicating that a particular sample corresponds to a P-wave, a QRS complex label 172-2 indicating that the particular sample corresponds to a QRS complex, a T-wave label 172-3 indicating that the particular sample corresponds to a T-wave, and/or a label 172-4 indicating that the particular sample does not correspond to a P-wave, QRS complex, or T-wave. While not shown, the sample-level ECG labels may additionally or alternatively include respective labels for the individual Q, R, and S waves. For example, the labels may include a Q-label indicating that the particular sample corresponds to a Q-wave, an R-label indicating that the particular sample corresponds to an R-wave, and/or an S-wave label indicating that the particular sample corresponds to an S-wave.

In some embodiments, outputting the characteristic(s) 114 of the ECG signal(s) 108 includes displaying the characteristic(s) 114 via a graphical user interface (GUI), including the characteristic(s) 114 in a report, storing the characteristic(s) 114 (e.g., in memory), transmitting the characteristic(s) 114 to one or more devices or servers, and/or outputting the denoised ECG signal(s) 112 using any other suitable techniques, as aspects of the technology described herein are not limited in this respect. In some embodiments, the characteristic(s) 114 may be presented together with the denoised ECG signal(s) 112. For example, the characteristic(s) 114 may be used to annotate the denoised ECG signal(s) 112. Annotating the denoised ECG signal(s) 112 may include labelling the samples of the denoised ECG signal(s) 112 using the sample-level ECG labels 114-2. Additionally or alternatively, annotating the denoised ECG signal(s) 112 may include providing an indication of the respective rhythm classifications 114-1 determined for segments of the ECG signal(s) 108. When presented via an interactive GUI, one or more users may interact with the GUI to validate and/or edit the characteristic(s) 114.

The one or more characteristics 114 may be used to determine whether the subject 102 has one or more conditions and/or abnormalities 116. The one or more conditions and/or abnormalities 116 may include irregular rhythm classifications included in rhythm classifications 114-1. With reference to FIG. 1C, examples of irregular rhythm classifications include the atrial fibrillation type 152-2, the atrial flutter type 152-3, the PAC type 152-4, and/or the PVC type 152-5.

Additionally or alternatively, the one or more conditions and/or abnormalities 116 may include those derived from the sample-level ECG labels 114-2. For example, with reference to FIG. 1D, the sample-level ECG labels 114-2 may be used, at act 174, to determine boundaries 176 of the ECG waves (e.g., the P, Q, R, S, and T-waves) represented by the ECG signal(s) 108. The boundaries may include, for example, the onset (e.g., start) and/or offset (e.g., end) of a particular wave. For example, the boundaries may indicate the onset(s) and offset(s) of P-waves, Q-waves, R-waves, S-waves, QRS complex, and/or T-waves represented by the ECG signal(s) 108.

In some embodiments, prior to determining the onsets and offsets, the sample-level ECG labels are pre-processed. First, the sample-level ECG labels are used to identify short (e.g., less than or equal to a threshold) segments of the ECG signal. In this context, a segment of the ECG signal refers to one or more consecutive samples sharing the same label. For examples, one or more consecutive samples labeled as a corresponding to a P-wave (e.g., a P-wave segment), one or more consecutive samples labeled as corresponding to a QRS-complex (e.g., a QRS-complex segment), one or more samples labeled as corresponding to a T-wave (e.g., a T-wave segment). The ECG segments may be compared to one or more thresholds to determine whether further preprocessing should be applied. For example, P-wave segments may be compared to first threshold, QRS-complex segments may be compared to second threshold, and T-wave segments may be compared to a third threshold. The first threshold may be at least 14 milliseconds (ms), at least 15 ms, at least 16 ms, at least 17 ms, at least 18 ms, or at least any other suitable threshold, as aspects of the technology described herein are not limited in this respect. For example, the first threshold may be 16 ms. The second threshold may be at least 10 ms, at least 11 ms, at least 12 ms, at least 13 ms, at least 14 ms, at least 15 ms, or at least any other suitable threshold, as aspects of the technology described herein are not limited in this respect. The third threshold may be at least 20 ms, at least 21 ms, at least 22 ms, at least 23 ms, at least 24 ms, at least 25 ms, at least 26 ms, at least 27 ms, at least 28 ms, or at least any other suitable threshold, as aspects of the technology are not limited in this respect. For example, the third threshold may be 24 ms. In some embodiments, if a segment is shorter than its respective threshold, then the segment is (i) removed, or (ii) relabeled. For example, if the short segment occurs immediately before or after another longer wave segment (e.g., P-wave segment, QRS-wave segment, or T-wave segment), then the short segment is relabeled to match the labels of the longer segment. Otherwise, the short segment may be removed. Additionally, if two segments sharing the same label are separated by a gap that is shorter than a threshold, then the gap is labelled with the shared label (e.g., to connect the two segments). For example, the threshold may be at least 25 ms, at least 26 ms, at least 27 ms, at least 28 ms, at least 29 ms, at least 30 ms, at least 31 ms, at least 32 ms, at least 33 ms, at least 34 ms, at least 35 ms, at least 36 ms, or at least any other suitable threshold, as aspects of the technology described herein are not limited in this respect.

In some embodiments, the onsets and offsets of the different waves (e.g., P-waves, QRS-complex (Q-waves, R-waves, S-waves), and T-waves) are determined by identifying changes in the sample-level ECG labels. For example, this may include identifying a segment of consecutive samples sharing the same sample-level ECG label, and identifying the ends (e.g., first and last sample) of the segment. The first and last sample may be considered the onset and offset, respectively.

Additionally or alternatively, the sample-level ECG labels 114-2 and/or the boundaries 176 may be used to determine one or more ECG wave metrics 180 at act 178. Examples of ECG wave metrics are listed in Table 1. Techniques for determining the onset and offset of a wave are described above. The peak of a wave may be determined for a wave by identifying the sample(s) of an ECG wave segment corresponding to the largest amplitude relative to other samples in the segment, by using a peak finding algorithm, or using any other suitable peak detection techniques, as aspects of the technology described herein are not limited in this respect.

TABLE 1

| Example ECG wave metrics. | |
|---|---|
| ECG Wave Metric | Description |
| P-Wave Peak | Peak of the P-wave. |
| Q-Wave Peak | Peak of the Q-wave. |
| R-Wave Peak | Peak of the R-wave. |
| S-Wave Peak | Peak of the S-wave. |
| T-Wave Peak | Peak of the T-wave. |
| RR Interval | Time between successive R peaks. |
| PR Segment | Time from P-wave offset to Q onset. |
| PR Interval | Time from P-wave onset to Q onset. |
| QRS Interval | Time from Q onset to S offset. |
| QT Interval | Time from Q onset to T offset. |
| Corrected QT Interval | QT interval that accounts for heart rate variability. $\left(\text{e.g., } \frac{QT \text{ interval}}{\sqrt{RR \text{ interval}}}.\right)$ |

TABLE 1-continued

| Example ECG wave metrics. | |
|---|---|
| ST Segment | Time from S offset to T onset. |
| P-wave Duration | Time from P onset to P offset. |
| P-Wave Amplitude | Amplitude of the P-wave. |
| P-Wave Absence | No discernible P-wave. |
| T-Wave Duration | Time from T onset to T offset. |
| T-Wave Amplitude | Amplitude of the T-wave. |
| T-Wave Absence | No discernible T-wave. |

In some embodiments, the ECG wave metric(s) 180 may be used to determine whether the subject 102 has one or more conditions and/or abnormalities 116. For example, values of the ECG wave metric(s) 180 may be compared to predetermined criteria to determine whether the subject 102 has the one or more conditions and/or abnormalities. Additionally or alternatively, values of ECG wave metric(s) 180 may be compared to baseline (e.g., expected normal) to determine whether the subject 102 has the one or more conditions and/or abnormalities. For example, to determine whether an ECG metric is elevated, depressed, and/or inverted, the metric may be compared to a respective baseline to determine whether it is elevated, depressed, and/or inverted. Examples of conditions and abnormalities that may be determined using ECG metrics, and associated predetermined criteria, are listed in Table 2-1.

TABLE 2-1

Examples of conditions and abnormalities that may be determined using ECG metrics.

| ECG Wave Metric | Description | Condition and/or Abnormality |
|---|---|---|
| PR Interval | Prolonged (e.g., greater than or equal to a predetermined threshold e.g., 0.20 seconds). | First-degree atrioventricular (AV) block. |
| PR Interval | Short (e.g., less than or equal to a predetermined threshold e.g., 0.12 seconds). | Wolff-Parkinson-White syndrome. |
| QRS Duration | Prolonged (e.g., greater than or equal to a predetermined threshold e.g., 0.12 seconds). | Bundle branch block; Ventricular hypertrophy. |
| ST Segment | Elevated. | Myocardial infarction; Pericarditis. |
| ST Segment | Depressed. | Myocardial ischemia; Digoxin effect. |
| QT Interval | Prolonged (e.g., greater than or equal to a predetermined threshold e.g., 0.44 seconds). | Ventricular arrhythmias (e.g., Torsades de Pointes). |
| QT Interval | Shortened | Congenital short QT syndrome. |
| T-Wave Amplitude | Elevated. | Hyperkalemia; Myocardial ischemia; Electrolyte imbalances. |
| T-Wave Amplitude | Depressed. | Hypokalemia; Myocardial hypoxia; Pericarditis. |
| T-Wave Amplitude | Inverted. | Myocardial ischemia; Myocardial infarction; Hypertrophy; Strain; Pulmonary embolism; Cerebrovascular events |
| T-Wave Absence | T-wave absence. | Pericardial effusion; Hyperkalemia; Severe myocardial ischemia |
| P-Wave Absence | P-wave absence. | Atrial fibrillation; Atrial flutter |
| P-Wave Amplitude | Elevated. | P pulmonale; Chronic obstructive pulmonary disease (COPD); Pulmonary hypertension. |
| P-Wave Amplitude | Inverted. | Ectopic atrial rhythms; Junctional rhythms |
| P-Wave Duration | Prolonged (e.g., greater than or equal to a threshold). | P mitrale; Mitral stenosis. |

In some embodiments, an indication of the one or more conditions and/or abnormalities 116 is output by computing device(s) 110. For example, the outputting may include displaying the indication via a GUI, including the indication in a report, storing the indication (e.g., in memory), transmitting the indication to one or more devices or servers, and/or outputting the indication using any other suitable techniques, as aspects of the technology described herein are not limited in this respect. The indication may include a recommendation to conduct one or more additional diagnostic tests. Additionally or alternatively, the indication may include a recommendation to administer a treatment for treating the one or more abnormalities and/or conditions 116.

In some embodiments, a user (e.g., an interpreting clinician) may use results of processing the ECG signal(s) 108 to administer a treatment to the subject. For example, the user may use a recommendation output by computing device(s) 110 and/or review the results of processing the ECG signal(s) 108 to determine how to treat the subject. For example, when using a Holter monitor, (i) a technician may process the Holter monitor, (ii) ECG data from the Holter monitor may be uploaded to an electronic repository, (iii) a doctor may receive a message (e.g., text, email, EMR, etc.) that the ECG data is waiting for interpretation, and (iv) the doctor may interpret the ECG data (e.g., using techniques described herein). In some embodiments, a doctor (e.g., the interpreting doctor or the ordering doctor) may review the interpretation, which may include a recommendation output by computing device(s) 110, and make a treatment decision.

Treatment decisions may be individualized and may depend on the severity of the abnormality, the patient's symptoms (e.g., dizziness, fainting, etc.), and the patient's overall health, age, co-morbidities, and wishes. Example actions for specific cardiac conditions are listed in Table 2-2.

TABLE 2-2

Example actions for specific cardiac conditions.

| Condition | Action |
|---|---|
| Atrial Fibrillation/ Atrial Flutter | Potential Actions:<br>Starting anticoagulant<br>Starting other medication<br>Ordering a procedure<br>Actions Depend On:<br>Amount of atrial fibrillation/atrial flutter<br>Heart rate<br>Patient Knowledge |
| Premature Atrial Contractions/Premature Ventricular Contractions | Potential Actions<br>Discuss with patient during next routine appointment.<br>Discuss with patient via a telephone call. |
| Pauses (e.g., Sinus Pause, Atrioventricular (AV) Node-Related Pauses, Conversion Pauses, Post-Pause Rhythms) | Potential Actions<br>Discuss with the patient<br>Start or stop medication<br>Recommend a pacemaker<br>Insert a pacemaker |
| Second-Degree AV Block | Potential Actions<br>Type A: Discuss with patient.<br>Type B:<br>Discuss with the patient<br>Conduct a physical exam of the patient<br>Recommend a pacemaker<br>Insert a pacemaker |
| Third-Degree AV Block | Potential Actions<br>Type A: Discuss with patient.<br>Type B:<br>Discuss with the patient<br>Conduct a physical exam of the patient<br>Recommend a pacemaker<br>Insert a pacemaker |
| General Care Path Decisions | Potential Actions<br>No Action: If the test is normal, or the abnormality is not clinically significant for that patient, the doctor may simply sign off, and no further action is taken.<br>Inform Patient: Call the patient to inform them the test is normal or discuss abnormal results.<br>Accelerate Appointment: Call the patient to schedule an urgent follow-up appointment.<br>Hospitalization/Intervention: Call the patient to come to the hospital immediately if the problem is serious (e.g., needs a pacemaker). |

Figure 1B:
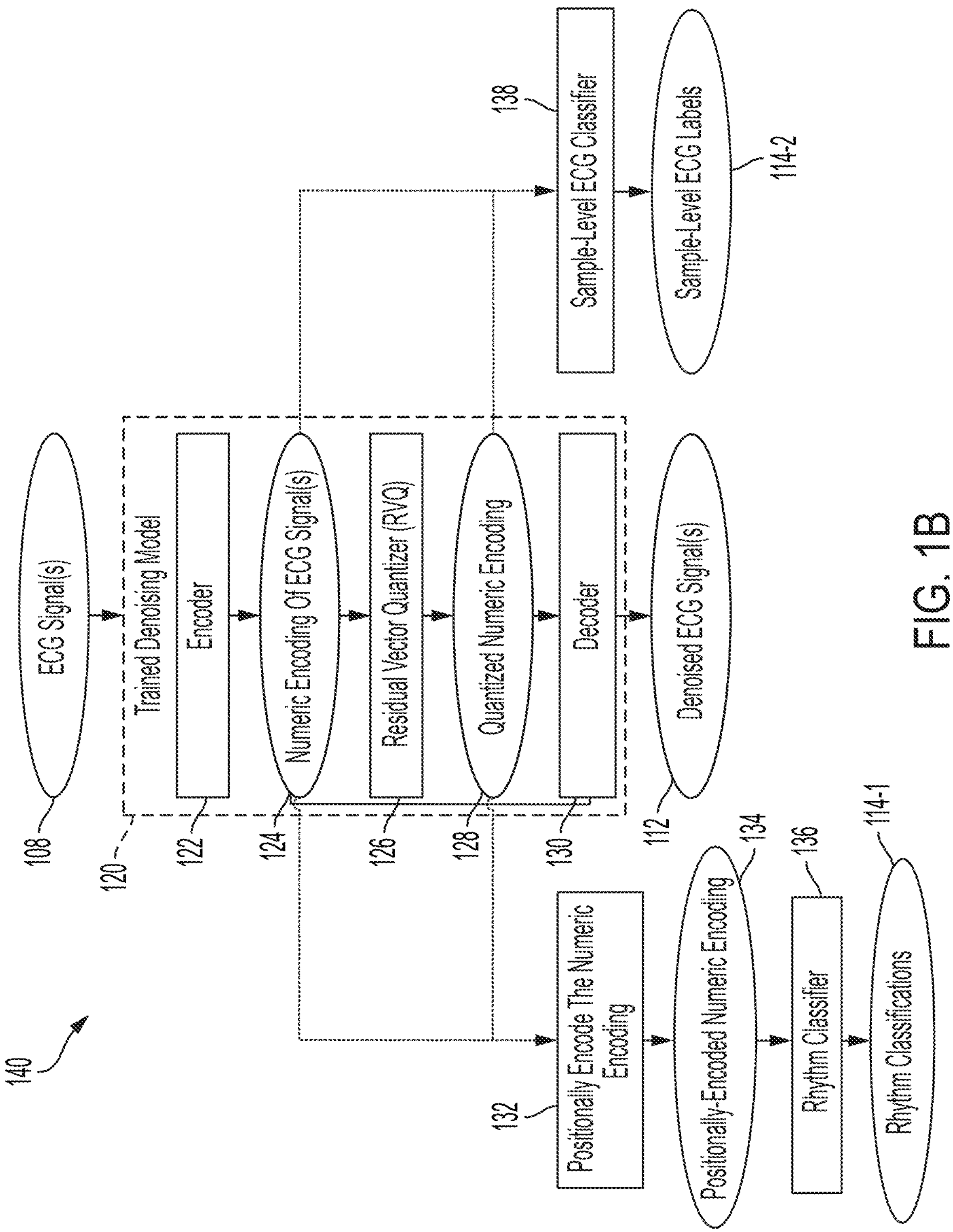
Figure 1C:
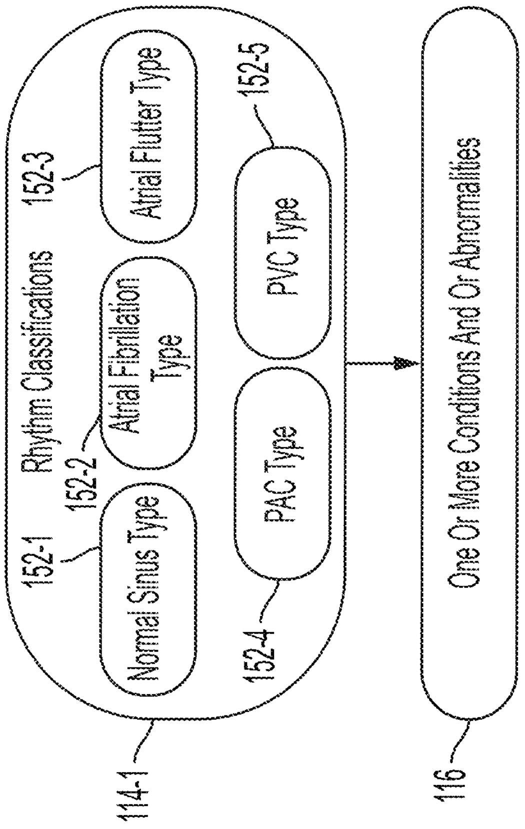
FIG. 1C is a diagram of example rhythm classifications determined according to some embodiments of the technology described herein.
Figure 1D:
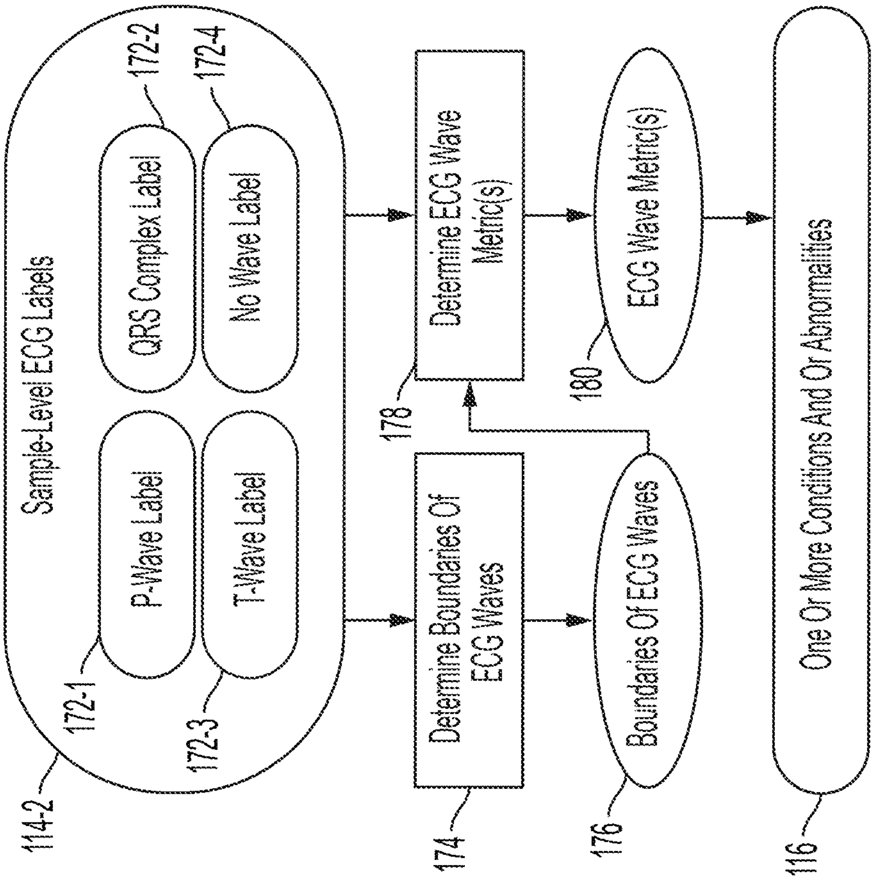
FIG. 1D is a diagram of an illustrative technique for determining ECG wave metrics and boundaries of ECG waves using sample-level ECG labels, according to some embodiments of the technology described herein.

FIG. 1B is a diagram of an illustrative technique 140 for denoising ECG signal(s) 108 and determining the characteristic(s) 114 of the ECG signal(s) 108, according to some embodiments of the technology described herein. The illustrative technique 140 may be performed by software (e.g., software 320 shown in FIG. 3A) on the computing device(s) 110.

In some embodiments, when the ECG signal(s) 108 include multiple ECG signals (e.g., obtained using different leads), each of at least some (e.g., all) of the ECG signals may be separately processed using the illustrative technique 140. For example, each ECG signal may be separately denoised and/or processed to determine respective characteristic(s) of the particular ECG signal.

Additionally or alternatively, an individual ECG signal may be divided up into shorter segments, and the shorter segments may be separately processed using illustrative technique 140. The ECG signal may be divided up into segments of multiple seconds, multiple minutes, or multiple hours. For example, the ECG signal may be divided up into segments of at least one second, at least five seconds, at least ten seconds, at least thirty seconds, at least forty-five seconds, at least one minute, at least five minutes, at least eight minutes, at least ten minutes, at least twelve minutes, at least fifteen minutes, at least twenty minutes, at least thirty minutes, at least forty-five minutes, at least one hour, at least twelve hours, at least one day, or at least any other suitable duration of time, as aspects of the technology described herein are not limited in this respect. The ECG signal may be divided up into segments of at most 10 seconds, at most thirty seconds, at most forty-five seconds, at most one minute, at most five minutes, at most eight minutes, at most ten minutes, at most twelve minutes, at most fifteen minutes, at most twenty minutes, at most thirty minutes, at most forty-five minutes, at most one hour, at most twelve hours, at most one day, or at most any other suitable duration of time, as aspects of the technology described herein are not limited in this respect. It should be appreciated that any of the above-listed upper bounds may be coupled with any of the above-listed lower bounds. For example, a segment may be between one second and one hour. A segment may be between ten seconds and ten minutes. A segment may be one second. At segment may be ten seconds. A segment may be thirty seconds. A segment may be one minute. A segment may be five minutes. A segment may be ten minutes. A second may be thirty minutes. A segment may be one hour. A segment may be one day. Dividing the ECG signal into shorter segments may help to prevent system limitations, such as limited random-access memory (RAM), which may in turn enable longer monitoring times and real-time or near-real-time analysis of ECG data. For example, some Holter monitors periodically or continuously offload ECG data (e.g., segments of ECG signal(s)) during the monitoring period, thereby freeing up onboard memory, allowing the device to record longer without hitting storage limits. By contrast, other Holter monitors store data locally until the end of the recording period, which is often limited by the onboard storage capacity.

Additionally or alternatively, an ECG signal may be divided up into segments using a beat segmenter. The beat segmenter may be a machine learning model trained to utilize Shannon's entropy for ECG beat segmentation. In some embodiments, beat segmentation involve determining the entropy across an ECG signal in sliding windows, then using those entropy values to locate features of the ECG waveform, which can be used to identify and segment the ECG signal into segments comprising individual heartbeats. For example, the entropy values may be used to identify peaks of ECG waveforms, and a sample may be taken between the peaks (e.g., the ECG signal may be segmented between the peaks). Alternatively, a sample may be taken based on a time distance (e.g., one second) on either side of a respective peak. Accordingly, in some embodiments, a beat segmenter segments an ECG signal into multiple individual heartbeats, which when concatenated allow for the reconstruction of the ECG signal. In some embodiments, segmented individual heartbeats are used in training of the machine learning models described herein.

In some embodiments, prior to processing the ECG signal(s) 108 using illustrative technique 140, the ECG signal(s) 108 are resampled. The ECG signal(s) 108 may be resampled to any suitable sampling rate, as aspects of the technology described herein are not limited in this respect. For example, the ECG signal(s) 108 may be resampled to a sampling rate between 100 Hz and 500 Hz, such as a sampling rate of 250 Hz. The ECG signal(s) 108 may be resampled using NeuroKit2. For example, the resampling may be performed using the neurokit2.signal_resample function using the 'FFT' method. NeuroKit2 is described by Makowski, D., et al. (NeuroKit2: A Python toolbox for neurophysiological signal processing. *Behavior Research Methods,* 53(4), 1689-1696. doi.org/10.3758/s13428-020-01516-y), which is incorporated by reference herein in its entirety. Regardless of whether or not the ECG signal(s) 108 are resampled, one or more of the machine learning models described herein may be trained to take as input, ECG signal(s) (or segment(s) thereof) having a particular sampling rate (e.g., between 100 Hz and 500 Hz, such as 250 Hz).

As shown in FIG. 1B, the techniques for denoising the ECG signal(s) 108 include processing the ECG signal(s) 108 using a trained denoising model 120 to obtain the denoised ECG signal(s) 112. The trained denoising model 120 includes a trained encoder 122, a trained residual vector quantizer (RVQ) 126, and a trained decoder 130. Processing the ECG signal(s) 108 using the trained denoising model 120 includes: (a) encoding the ECG signal(s) 108 using the encoder 122 to obtain a numeric encoding 124 of the ECG signal(s) 108, (b) quantizing the numeric encoding 124 using the RVQ 126 to obtain a quantized numeric encoding 128 of the ECG signal(s) 108, and (c) decoding the quantized numeric encoding 128 using the decoder 130 to obtain the denoised ECG signal(s) 112. Example techniques for training the denoising model 120 are described herein including at least with respect to FIGS. 2 and 4E.

The encoder 122 is trained to encode the ECG signal(s) 108 to obtain a numeric encoding 124 of the ECG signal(s) 108. The numeric encoding 124 is a representation (e.g., a latent representation) of the ECG signal(s) 108. For example, the numeric encoding 124 may be a vector representation of the ECG signal(s) 108. The numeric encoding 124 may have fewer dimensions than the ECG signal(s) 108. The encoder 122 may be a deep neural network. The encoder 122 may be a convolutional neural network (CNN)-based encoder, a recurrent neural network (RNN)-based encoder, a transformer-based encoder, and/or any other suitable type of encoder that can be used to encode ECG signal(s), as aspects of the technology described herein are not limited in this respect. An example of an encoder that may be used to encode ECG signal(s) is described herein including at least with respect to FIGS. 5A-5C. Another example of an encoder is described by Z., Neil, et al. ("Soundstream: An end-to-end neural audio codec." *IEEE/ACM Transactions on Audio, Speech, and Language Processing* 30 (2021): 495-507.), which is incorporated by reference herein in its entirety. The architecture of the encoder 502 described with respect to FIGS. 5A-5C differs from the encoder described by Z., Neil, et al. at least because the encoder 502 includes fewer encoder blocks and excludes the FiLM conditioning layer. Z., Neil, et al. relates only to sound compression and enhancement, and makes no teaching or suggestion about ECG signal processing (e.g., ECG signal analysis, ECG signal denoising). The purposes, field of application and training data are therefore completely different. For example, with respect to training data, the type of data (e.g., audio data) used in sound compression and enhancement is completely different than ECG signal data (ECG signals and audio signals have different wave types). Similarly, the types of noise present in audio signals are very different than the types of noise present in ECG signals, and even more so in the context of wearable devices, which produce ECG signals that are particularly hard to denoise and process.

The RVQ 126 is trained to quantize the numeric encoding 124 to obtain quantized numeric encoding 128. Specifically, the codebooks of the RVQ are trained. The quantized numeric encoding 128 is an approximation of the numeric encoding 124. The quantized numeric encoding 128 may have a fixed dimensionality, regardless of the dimensionality of the numeric encoding 124, thereby enabling the flexible processing of ECG signal(s) 108 having variable lengths. The RVQ 126 may be a multi-stage quantizer that first quantizes the input numeric encoding 124, then quantizes the residuals (e.g., the difference between the input and the quantized output). For example, a first vector quantizer may quantize the input numeric encoding by mapping the input to the closest vector (the "first quantized vector") in a first codebook of vectors. A first residual may be computed by determining the difference between the input numeric encoding and the first quantized vector. A second vector quantizer may quantize the first residual by mapping the first residual to the closest vector (the "second quantized vector") in a second codebook of vectors. This may be repeated for multiple stages. For example, a second residual may be computed based on the difference between the first residual and the second quantized vector, then a third vector quantizer may quantize the second residual by mapping the second residual to the closest vector in a third codebook of vectors. The RVQ 126 may then approximate the quantized numeric encoding 128 by summing the quantized vectors. In some embodiments, the RVQ 126 is a grouped RVQ configured to split the numeric encoding 124 into multiple groups, then quantize each group separately (e.g., in parallel or sequentially). For example, the numeric encoding may be split evenly according to the number of groups (e.g., using 64 dimensional vectors and 2 groups, the size of each of the groups is 64/2=32). An example of a grouped RVQ is described herein including at least with respect to FIG. 5D. Alternatively, the grouped RVQ 506 may be modified such that it is not grouped. This would mean that the entire vector is quantized using a single codebook. Thus, the architecture shown in FIG. 5D would omit the step of splitting the vector into groups, and there would be a single residual vector quantizer layer that uses a single codebook (instead of a first and second residual vector quantizer layer and a group 1 and group 2 codebook). Using a grouped RVQ allows the denoising model to represent a much larger number of vectors without significantly increasing the size of the codebook. This improves the efficiency of the RVQ without sacrificing the quality of the reconstruction during inference, thus representing an improvement over machine learning techniques that do not use a grouped RVQ such as, for example, the RVQ described by Z., Neil, et al. ("Soundstream: An end-to-end neural audio codec." *IEEE/ACM Transactions on Audio, Speech, and Language Processing* 30 (2021): 495-507.).

The decoder 130 is trained to decode the quantized numeric encoding 128 to obtain the denoised ECG signal(s) 112. In some embodiments, the denoised ECG signal(s) 112 have the same dimensions as the input ECG signal(s) 108. The decoder may be a deep neural network. The decoder may be a convolutional neural network (CNN)-based decoder, a recurrent neural network (RNN)-based decoder, a transformer-based decoder, and/or any other suitable type of decoder that can be used to decode quantized numeric encodings of ECG signal(s), as aspects of the technology described herein are not limited in this respect. An example of a decoder that may be used to decode quantized numeric encodings of ECG signal(s) is described herein including at least with respect to FIG. 5E, FIG. 5F, and FIG. 5B. Another example of a decoder is described by Z., Neil, et al. ("Soundstream: An end-to-end neural audio codec." *IEEE/ACM Transactions on Audio, Speech, and Language Processing* 30 (2021): 495-507.). The architecture of the decoder 513 described with respect to FIGS. 5E, 5F, and 5B differs from the decoder described by Z., Neil, et al. at least because the decoder 513 includes fewer decoder blocks, excludes the FiLM conditioning layer, and includes an encoder block.

Technique 140 may additionally or alternatively include processing the ECG signal(s) 108 to determine rhythm classifications 114-1. As shown in FIG. 1B, the processing includes: (a) encoding the ECG signal(s) 108 using the encoder 122 to obtain the numeric encoding 124 of the ECG signal(s) 108, (b) positionally encoding the numeric encoding 124, at act 132, to obtain a positionally-encoded numeric encoding 134, and (c) processing the positionally-encoded numeric encoding 134 using a rhythm classifier 136 to obtain the rhythm classifications 114-1. Optionally, the processing additionally includes quantizing the numeric encoding 124 using an RVQ 126 to obtain the quantized numeric encoding 128, then positionally encoding the quantized numeric encoding 128 (e.g., instead of the numeric encoding 124) to obtain a positionally-encoded numeric encoding 134.

At act 132, the (optionally, quantized) numeric encoding is positionally encoded to obtain positionally-encoded numeric encoding 134. The positionally-encoded numeric encoding 134 may be a vector that encodes the position of each element within the numeric encoding. In some embodiments, the numeric encoding is positionally encoded using absolute positional encoding. For example, the numeric encoding may be positionally encoded using sinusoidal functions. For example, the numeric encoding may be positionally encoded using Equations 1 and 2:

$$PE_{(pos,2i)} = \sin\left(\frac{pos}{10000^{\frac{2i}{d_{model}}}}\right) \quad \text{(Equation 1)}$$

$$PE_{(pos,2i+1)} = \cos\left(\frac{pos}{10000^{\frac{2i}{d_{model}}}}\right) \quad \text{(Equation 2)}$$

where pos is the position in the signal, i is the index of the encoding vector, and $d_{model}$ is the size of the encoding vector. Positional encodings are added to the encoding output from the model by taking the sum of both. Additionally, or alternatively, the numeric encoding may be positionally encoded using a model trained (e.g., pre-trained) to generate positional encodings. For example, the numeric encoding may be positionally encoded using a transformer-based model (e.g., a pre-trained transformer-based model). Examples of models trained to generate positional encodings include Bidirectional Encoder Representations from Transformers (BERT) and the Generative Pre-Trained Transformer (GPT) models. BERT is described by Devlin, J., et al. ("Bert: Pre-training of deep bidirectional transformers for language understanding." *Proceedings of NAACL-HLT* Vol. 1. No. 2. 2019.), which is incorporated by reference herein in its entirety. GPT-2 is described by Radford, A., et al. ("Language models are unsupervised multitask learners." *OpenAI blog* 1.8 (2019): 9.), which is incorporated by reference herein in its entirety. GPT-3 is described by Brown, T., et al. ("Language models are few-shot learners." *Advances in neural information processing systems* 33 (2020): 1877-1901.), which is incorporated by reference herein in its entirety. It should be appreciated that the positional encoding may be performed using any other suitable positional encoding technique(s), as aspects of the technology described herein are not limited in this respect.

The positionally-encoded numeric encoding 134 is processed using the trained rhythm classifier 136 to obtain the rhythm classifications 114-1. The rhythm classifier 136 may be trained to predict a respective rhythm type for each of at least some (e.g., all) segment(s) of the ECG signal(s) 108.

For example, the rhythm types may include a normal sinus type, an atrial fibrillation type, an atrial flutter type, a premature atrial contraction (PAC) type, and/or a premature ventricular contraction (PVC) type.

In some embodiments, the output of the rhythm classifier 136 is indicative of the predicted rhythm types for the respective segments of the ECG signal. For example, the output may indicate a class, of a plurality of classes, into which the segment was classified. In some embodiments, the plurality of classes includes a respective class for each rhythm type (e.g., selected from a normal sinus type, an atrial fibrillation type, an atrial flutter type, a premature atrial contraction (PAC) type, and/or a premature ventricular contraction (PVC) type). In some embodiments, the plurality of classes includes a first class corresponding to a normal sinus rhythm type and second class corresponding to an arrhythmia of any type (e.g., an atrial fibrillation type, an atrial flutter type, a premature atrial contraction (PAC) type, and/or a premature ventricular contraction (PVC) type). In some embodiments, the plurality of classes includes a first class corresponding to a first rhythm type, and a second class corresponding to any rhythm type that is not the first rhythm type. The output may include one or more values indicating the likelihood (e.g., the probability) that the segment belongs to the different classes (e.g., the likelihood that the segment represents a particular rhythm type). Alternatively, the output may include one or more binary values indicating whether or not the segment belongs to the different classes. It should be appreciated that the rhythm classifier output may be any suitable type of classifier output, as aspects of the technology described herein are not limited in this respect.

As described herein, rhythm types may be predicted for segments of the ECG signal(s) 108. In some embodiments, the segments of the ECG signal(s) 108 are segments of equal length (e.g., equal duration and/or an equal number of samples). For example, the ECG signal(s) 108 may be split into time intervals (e.g., one second time intervals, two second time intervals, etc.), and the segments of the ECG signal(s) 108 may correspond respectively to the time intervals. In some embodiments, a segment represents at least a portion of a heartbeat (e.g., a portion of an ECG signal that represents a heartbeat may include a portion comprising an ECG waveform (e.g., P, Q, R, S, T-waves)).

In some embodiments, the rhythm classifier 136 is implemented as a deep neural network. In some embodiments, the rhythm classifier 136 is implemented as a convolutional neural network (CNN) trained to predict rhythm types for segments of ECG signals. For example, the rhythm classifier 136 may be implemented as rhythm classifier 516 shown in FIG. 5G, which includes a plurality of 1D convolutional layers, activation layers, and an encoder block (e.g., encoder block 504 shown in FIG. 5B). However, it should be appreciated that the rhythm classifier 136 is not limited to the implementation shown in FIG. 5G and that other implementations are possible. For example, the rhythm classifier 136 may be implemented as any suitable type of classification or regression model. For example, the rhythm classifier 136 may be implemented as a non-linear regression model (e.g., a logistic regression model), a support vector machine, a Gaussian mixture model, a random forest model, a decision tree classifier, a gradient boosted decision tree classifier, a neural network model, and/or any other suitable type of machine learning model, as aspects of the technology described herein are not limited in this respect.

Illustrative technique 140 may additionally or alternatively include processing the ECG signal(s) 108 to determine sample-level ECG labels 114-2. As shown in FIG. 1B, the processing includes: (a) encoding the ECG signal(s) 108 using the encoder 122 to obtain the numeric encoding 124 of the ECG signal(s) 108, and (b) processing the numeric encoding 124 using a sample-level ECG classifier 138 to obtain the sample-level ECG labels 114-2. Optionally, the processing additionally includes quantizing the numeric encoding 124 using an RVQ 126 to obtain the quantized numeric encoding 128, then processing the quantized numeric encoding 128 (e.g., instead of the numeric encoding 124) using the sample-level ECG classifier 138 to obtain the sample-level ECG labels 114-2.

The (optionally, quantized) numeric encoding is processed using the trained sample-level ECG classifier 138 to obtain the sample-level ECG labels 114-2. The sample-level ECG classifier 138 may be trained to predict a respective sample-level ECG label for each of at least some (e.g., all) of the samples of ECG signal(s) 108. For example, a sample-level ECG label may indicate a respective portion of the ECG waveform (e.g., P-wave, QRS complex, T-wave, etc.) to which the sample corresponds.

In some embodiments, the output of the sample-level ECG classifier 138 is indicative of the predicted sample-level ECG labels for the respective samples of the ECG signal(s). For example, the output may indicate a class, of a plurality of classes, into which the sample was classified. In some embodiments, the plurality of classes includes a respective class for each ECG waveform portion selected from: the P-wave, the QRS-complex, the Q-wave, the R-wave, the S-wave, the T-wave, and/or no wave. In some embodiments, the plurality of classes includes a respective class for each of the ECG waveform portions. In some embodiments, the output indicating the class into which the sample is classified includes a class label for a particular sample that indicates the predicted (e.g., the most probable) ECG label for the particular sample. Additionally or alternatively, the output may include one or more class probabilities for a particular sample of the ECG signal. A class probability may represent the probability that the particular sample of the ECG signal represents a particular portion of an ECG waveform. For example, the class probabilities may include a probability that the sample represents a P-wave, a probability that the sample represents a QRS-complex, a probability that the sample represents a Q-wave, a probability that the sample represents an R-wave, a probability that the sample represents an S-wave, and/or a probability that the sample represents a T-wave. Additionally or alternatively, the output may include one or more binary classifications. For example, the binary classification may indicate whether or not a particular sample of the ECG signal represents a particular part of the ECG waveform (e.g., a particular wave). For example, the binary classifications may indicate, for each of multiple portions of the ECG waveform (e.g., the P-wave, the QRS-complex, the Q-wave, the R-wave, the S-wave, the T-wave, no wave, etc.), whether or not the sample represents the particular portion of the ECG waveform. It should be appreciated that the sample-level ECG classifier output may be any suitable type of classifier output, as aspects of the technology described herein are not limited in this respect.

In some embodiments, the sample-level ECG classifier 138 is implemented as a deep neural network. In some embodiments, the sample-level ECG classifier 138 is implemented as a convolutional neural network (CNN) trained to predict sample-level ECG labels for samples of ECG signals. For example, the sample-level ECG classifier 138 may be implemented as sample-level ECG classifier 518 shown in FIG. 5H, which includes 1D convolutional layers, decoder blocks (e.g., decoder block 515 shown in FIG. 5F), an encoder block (e.g., encoder block 504 shown in FIG. 5B), and an activation layer. However, it should be appreciated that the sample-level ECG classifier 138 is not limited to the implementation shown in FIG. 5H and that other implementations are possible. For example, the sample-level ECG classifier 138 may be implemented as any suitable type of classification or regression model. For example, the sample-level may include a non-linear regression model (e.g., a logistic regression model), a support vector machine, a Gaussian mixture model, a random forest model, a decision tree classifier, a gradient boosted decision tree classifier, a neural network model, and/or any other suitable type of machine learning model, as aspects of the technology described herein are not limited in this respect.

Figure 2:
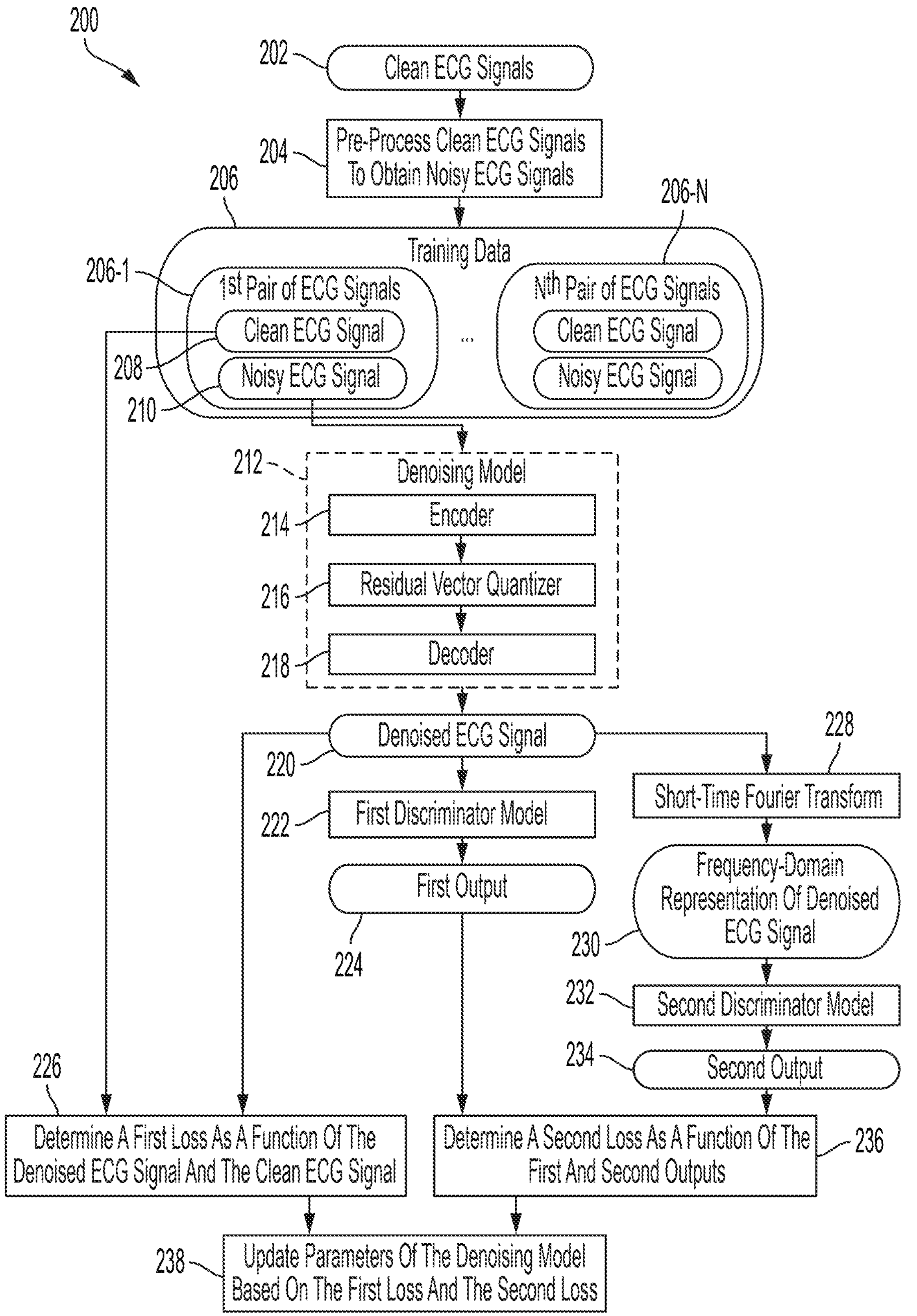
FIG. 2 is a diagram of an illustrative technique for training a denoising model to denoise at least one ECG signal, according to some embodiments of the technology described herein.

FIG. 2 is a diagram of an illustrative technique 200 for training a denoising model to denoise at least one ECG signal, according to some embodiments of the technology described herein. As shown in FIG. 2, the illustrative technique 200 includes obtaining training data 206, and training the denoising model 212, using the training data 206, to generate denoised ECG signals. Training the denoising model 212 includes: (a) processing a noisy ECG signal 210 using the denoising model 212 to generate a denoised ECG signal 220 corresponding to the noisy ECG signal 210, and (b) updating parameters of the denoising model based on a loss that is a function of the denoised ECG signal and the clean ECG signal (e.g., the loss determined at act 226). Additionally or alternatively, the parameters of the denoising model may be updated based on a loss that is a function of the outputs of one or more discriminator models (e.g., the loss determined at act 236.

As shown in FIG. 2, the training data 206 includes a plurality of pairs of ECG signals including a first pair of ECG signals 206-1 through an Nth pair of ECG signals 206-N. A pair of ECG signals includes a clean ECG signal and a corresponding noisy ECG signal. For example, the first pair of ECG signals 206-1 includes a clean ECG signal 208 and a corresponding noisy ECG signal 210.

The noisy ECG signals may be obtained by pre-processing a plurality of clean ECG signals 202 at act 204. In some embodiments, one or more noisy ECC signals may be generated from the same clean ECG signal. For example, multiple noisy ECG signals may be generated from each clean ECG signal by adding different kinds of noise to the same signal. This helps to reduce the need for obtaining a very large dataset of clean ECG signals and results in computational improvements as less memory and processing power has to be devoted to managing the clean ECG dataset.

The plurality of clean ECG signals 202 may include at least 50,000, at least 75,000, at least 100,000, at least 125,000, at least 150,000, at least 175,000, at least 200,000, at least 225,000, at least 250,000, at least 275,000, at least 300,000, at least 325,000, at least 350,000, at least 375,000, at least 400,000, at least 450,000, at least 500,000, or at least any other suitable number of ECG signals, as aspects of the technology described herein are not limited in this respect. Additionally or alternatively, the plurality of clean ECG signals 202 may include at most 50,000, at most 75,000, at most 100,000, at most 125,000, at most 150,000, at most 175,000, at most 200,000, at most 225,000, at most 250,000, at most 275,000, at most 300,000, at most 325,000, at most 350,000, at most 375,000, at most 400,000, at most 450,000, at most 500,000, or at most any other suitable number of ECG signals, as aspects of the technology described herein are not limited in this respect. It should be appreciated that any of the above-listed upper bounds may be coupled with any of the above-listed lower bounds. The plurality of clean ECG signals 202 may be obtained from any suitable source such as one or more public or private datasets. For example, the plurality of clean ECG signals 202 may be obtained from one or more of the following public datasets: the Icentia11k Single Lead Continuous Raw Electrocardiogram Dataset (Tan, S., et al. (2022). Icentia11k Single Lead Continuous Raw Electrocardiogram Dataset (version 1.0). PhysioNet. doi.org/10.13026/kk0v-r952.), CODE-15% (Ribeiro, A. H., et al. (2021). CODE-15%: a large scale annotated dataset of 12-lead ECGs (1.0.0) [Data set]. Zenodo. doi.org/10.5281/zenodo.4916206), Brno University of Technology ECG Quality Database (Nemcova, A., et al. (2020). Brno University of Technology ECG Quality Database (BUT QDB) (version 1.0.0). PhysioNet. doi.org/10.13026/kah4-0w24.), and the Lobachevsky University Electrocardiography Database (Kalyakulina, A., et al. (2021). Lobachevsky University Electrocardiography Database (version 1.0.1). PhysioNet. https://doi.org/10.13026/eegm-h675.).

In some embodiments, pre-processing the clean ECG signals includes resampling the clean ECG signals 202. The clean ECG signals 202 may be resampled to a sampling rate between 150 Hz and 500 Hz. In some embodiments, all clean ECG signals 202 are resampled to the same sampling rate. For example, the resampling rate may be selected from the range of 150 Hz-500 Hz. The resampling rate may be selected from the range at random. In some embodiments, different ECG signals of the clean ECG signals 202 are resampled to different resampling rates. For example, the different resampling rates may be selected from the range of 150 Hz-500 Hz. The different resampling rates may be selected from the range at random. The ECG signals 202 may be resampled using NeuroKit2. For example, the resampling may be performed using the neurokit2.signal_ resample function using the 'FFT' method. The sampling rate may be generated using: 250+random.randint(−80,80). NeuroKit2 is described by Makowski, D., et al. (NeuroKit2: A Python toolbox for neurophysiological signal processing. *Behavior Research Methods,* 53(4), 1689-1696. doi.org/10.3758/s13428-020-01516-y), which is incorporated by reference herein in its entirety.

Pre-processing the clean ECG signals 202, at act 204, may additionally or alternatively include adding amplitude noise to at least some (e.g., all) of the ECG signals, such that at least some of the final, noisy ECG signals include amplitude noise. In some embodiments, amplitude noise may be added to an ECG signal by multiplying the ECG signal by a respective factor. In some embodiments, the factor is a number between 0.5 and 2. In some embodiments, the factor may be randomly generated for a respective ECG signal. For example, the factor may be randomly generated based on a random number, between 0.0 and 1.0, output by a random number generator (e.g., the Python random.random( ) function). For example, the factor may be determined using Equation 3:

$$\text{factor} = \text{random.random}(\,) + 0.5 \quad \text{(Equation 3)}$$

Pre-processing the clean ECG signals 202, at act 204, may additionally or alternatively include padding ECG signal(s) that have length(s) less than or equal to a threshold length. For example, the ECG signal(s) may be padded with zeros at the beginning and/or at the end. The threshold may be a threshold of at least 10 seconds, at least 25 seconds, at least 30 seconds, at least 40 seconds, at least 50 seconds, at least 60 seconds, at least 70 seconds, at least 75 seconds, at least 80 seconds, at least 90 seconds, or at least any other suitable threshold value, as aspects of the technology described herein are not limited in this respect. The threshold may be a threshold of at most 10 seconds, at most 25 seconds, at most 30 seconds, at most 40 seconds, at most 50 seconds, at most 60 seconds, at most 70 seconds, at most 75 seconds, at most 80 seconds, at most 90 seconds, or at most any other suitable threshold value, as aspects of the technology described herein are not limited in this respect. It should be appreciated that any of the above-listed upper bounds may be coupled with any of the above-listed lower bounds. In an example, the threshold may be 60 seconds.

Pre-processing the clean ECG signals 202, at act 204, may additionally or alternatively include filtering at least some (e.g., all, 4/5, 3/4, 2/3, 1/2, 1/3, 1/4, 1/5, 1/10, etc.) of the ECG signals. For example, one in three of the ECG signals may be filtered, such that one in three of the final, noisy ECG signals have been filtered. The ECG signals may be filtered using a high-pass Butterworth filter. Additionally or alternatively, the ECG signals may be filtered to reduce powerline noise. In some embodiments, the filtering is performed using NeuroKit2. For example, the filtering may be performed using the neurokit2.ecg_clean using the "neurokit" method. NeuroKit2 is described by Makowski, D., et al. (NeuroKit2: A Python toolbox for neurophysiological signal processing. *Behavior Research Methods,* 53(4), 1689-1696. doi.org/10.3758/s13428-020-01516-y). While more extensive filtering may result in the removal of the ECG signal itself, the filtering techniques that may be applied at act 204 are limited such that they do not disturb the underlying ECG signal.

Pre-processing the clean ECG signals 202, at act 204, may additionally or alternatively include adding noise to at least some (e.g., all, 4/5, 3/4, 2/3, 1/2, 1/3, 1/4, 1/5, 1/10, etc.) of the ECG signals, such that at least some of the final, noisy ECG signals include the added noise. For example, noise may be added to four in five ECG signals, such that four in five of the final, noisy ECG signals include the added noise. In some embodiments, adding noise to an ECG signal includes adding one or more types of noise selected from: white noise, intense sectional white noise, artifacts with random amplitude, linear drift, random jumps in the baseline, wander, and powerline noise.

In some embodiments, white noise may be added to an ECG signal during act 204 when generating noisy ECG signals from clean ECG signals 202. White noise may be generated from a random normal distribution with a mean of zero and a standard deviation equal to the standard deviation of the clean ECG signal, multiplied by a number chosen from a random uniform distribution (e.g., a random uniform distribution from 0.001 to 1.001). In some embodiments, the white noise is added to the whole ECG signal. In some embodiments, the white noise is added to one or more segments of the ECG signal ("intense sectional white noise"). When the white noise is added to a segment of the ECG signal, a start point of the segment may be chosen from a distribution (e.g., a uniform distribution) from 0 to the length of the signal. The length of the segment may also be chosen from a distribution, such as a uniform distribution from 10 to 500 samples, for example. The number of segments to which to add white noise may be a random number. For example, the number of segments may be a random number, such as a random number chosen from a uniform distribution from 0 to 3. In some embodiments, white noise is added to the ECG signal using NeuroKit2. For example, noise may be added using the function neurokit2.signal_distort. The neurokit2.signal_distort function uses the parameters noise_amplitude and noise_frequency. The parameter noise_amplitude may be based on a random integer between 0 and 4 and/or a random floating number between 0.0 and 1.0. For example, noise_amplitude may be determined using Equation 4:

$$\text{noise\_amplitude} = \text{random.}\mathit{randint}(0, 4) * 0.5 * \text{random.random}(\,) \quad \text{(Equation 4)}$$

The parameter noise_frequency may include one or more frequencies. For example, the parameter noise_frequency may include four frequences. The frequencies may be randomly generated. For example, the frequencies may be randomly generated using Equation 5:

$$\text{frequency} = \text{int}(10.0 * \text{random.random}(\,) + 5) \quad \text{(Equation 5)}$$

In some embodiments, artifacts with random amplitude may be added to a clean ECG signal. In some embodiments, the artifacts may be added to the ECG signal using NeuroKit2. For example, the artifacts may be added using the function neurokit2.signal_distort. The neurokit2.signal_distort function uses the parameters artifacts_amplitude, artifacts_frequency, and artifacts_number. The parameter artifacts_amplitude may be based on a number ('artifacts') and/or a random number between 0.0 and 1.0. The number 'artifacts' may be a random number between 0 and 2. The random number may be generated by a random number generator, such as the random.randint( ) Python function. The parameter artifacts_amplitude may be determined using Equation 6:

$$\text{artifacts\_amplitude} = \text{artifacts} * 2.0 * \text{random.random}(\,) \quad \text{(Equation 6)}$$

The parameter artifacts_frequency may be a random integer, such as a random integer between 5 and 25. For example, the random integer may be generated using the random.randint( ) Python function. The parameter artifacts_number may be based on the number of artifacts ('artifacts') and/or a random integer (e.g., between 1 and 20). For example, the parameter artifacts_number may be determined using Equation 7:

$$\text{artifacts\_number} = \text{artifacts} * \text{random} \cdot \mathit{randomint}\,(1, 20) \quad \text{(Equation 7)}$$

In some embodiments, linear drift may be added to the ECG signal. For example, linear drift may be added to 1 in 4 of the ECG signals, such that 1 in 4 of the final, noisy ECG signals include linear drift. In some embodiments, linear drift ("distorted") is generated using the algorithm of Equations 8-12:

$$\text{drift\_start} = 2.0 * \text{random}\cdot\text{random}\ (\ ) - 1.0 \quad \text{(Equation 8)}$$

$$\text{drift\_end} = 2.0 * \text{random}\cdot\text{random}\ (\ ) - 1.0 \quad \text{(Equation 9)}$$

$$\text{drift} = \mathit{linspace}\,(\text{drift\_start, drift\_end, } \mathit{len}\,(\text{signal})) \quad \text{(Equation 10)}$$

$$\text{baseline} = 10.0 * \text{random}\cdot\text{random}\ (\ ) - 5.0 \quad \text{(Equation 11)}$$

$$\text{distorted} = \text{distorted} + \text{drift} + \text{baseline} \quad \text{(Equation 12)}$$

where linspace is a function that returns an array of evenly spaced numbers over a specified range, random.random( ) is a function that generates a random floating-point number between 0.0 and 1.0, and len(signal) is the length of the clean ECG signal.

In some embodiments, a random baseline jump is added to the ECG signal. For example, a random baseline jump may be added to 1 in 6 ECG signals, such that 1 in 6 of the final, noisy ECG signals include random baseline jump. In some embodiments, the random baseline jump is generated using the algorithm of Equations 13-16:

$$\text{baseline} = 2.0 * \text{random}\cdot\text{random}\ (\ ) - 1.0 \quad \text{(Equation 13)}$$

$$s = \text{random}\cdot\text{randint}\ (0, \mathit{len}\,(\text{signal}) - 1) \quad \text{(Equation 14)}$$

$$e = \text{random}\cdot\text{randint}\ (s, \mathit{len}\,(\text{signal}) - 1) \quad \text{(Equation 15)}$$

$$\text{signal}[s{:}e] \mathrel{+}= \text{baseline} \quad \text{(Equation 16)}$$

where random.randint( ) is a function used to generate a random integer within a specified inclusive range.

In some embodiments, wander may be added to the ECG signals. For example, wander may be added to 1 in 4 ECG signals, such that 1 in 4 of the final, noisy ECG signals include wander. In some embodiments, the wander is added by repeating the algorithm of Equations 17-20 one or more times. For example, the algorithm may be repeated four times.

$$fs = 1.0 * \text{random}\cdot\text{random}\ (\ ) + 0.001 \quad \text{(Equation 17)}$$

$$\text{time} = \mathit{linspace}\,(0, \mathit{len}\,(\text{signal}) * \text{sampling\_rate}, \mathit{len}\,(\text{signal})) + fs * \text{random}\cdot\text{random}\ (\ ) \quad \text{(Equation 18)}$$

$$\text{wave} = (3 * \text{random}\cdot\text{random}\ (\ ) + 0.2) * \sin(\text{time} * 2 * \pi * fs) \quad \text{(Equation 19)}$$

$$\text{distorted} = \text{distorted} + \text{wave} \quad \text{(Equation 20)}$$

In some embodiments, powerline noise may be added to the ECG signals. For example, powerline noise may be added to 1 in 6 ECG signals, such that 1 in 6 of the final noisy ECG signals include powerline noise. In some embodiments, the powerline noise is added using the algorithm of Equations 21-23:

$$fs = 5 * \text{random}\cdot\text{random}(\ ) + 60 \quad \text{(Equation 21)}$$

$$\mathit{time} = \mathit{linspace}(0, \mathit{len}(\text{signal}) * \text{sampling\_rate}, \mathit{len}(\text{signal}) + fs * \text{random}\cdot\text{random}(\ )$$

$$\text{wave} = (0.5 * \text{random}\cdot\text{random}(\ ) + 0.02) * \sin(\text{time} * 2 * \pi * fs) \quad \text{(Equation 22)}$$

$$\text{distorted} = \text{distorted} + \text{wave} \quad \text{(Equation 23)}$$

As shown in FIG. 2, after pre-processing the clean ECG signals 202 to obtain training data 206, the training data 206 is used to train the denoising model 212. In some embodiments, the denoising model 212 is trained by (a) processing the noisy ECG signal 210 using the denoising model 212, and (b) updating parameters of the denoising model 212. The denoising model 212 may include an encoder 214, a residual vector quantizer (RVQ) 216, and a decoder 218. For example, the denoising model 212 may be trained to obtain the trained denoising model 120 described herein including at least with respect to FIG. 1B.

In some embodiments, the parameters of the denoising model 212 are updated based on (a) a first loss that is determined, at act 226, as a function of the denoised ECG signal 220 and the clean ECG signal 208, and (b) a second loss that is determined, at act 236, as a function of at least one of the first output 224 and the second outputs 234 of the first and second discriminator models 222, 232, respectively. For example, the second loss may be determined as a function of both of the first and second outputs 224, 234.

As described herein, the first loss may be determined, at act 226, as a function of the denoised ECG signal 220 and the clean ECG signal 208. For example, the first loss may be a reconstruction loss that measures how well the denoising model 212 can reproduce or reconstruct the clean ECG signal 208. For example, the first loss may be a reconstruction loss that measures the similarity between the clean ECG signal 208 and a corresponding denoised ECG signal output by the denoising model. Examples of types of loss functions that may be used to approximate the similarity of ECG signals include L1 loss, L2 loss, spectral loss (e.g., multi-resolution spectral loss, power loss, Mel spectrogram loss, etc.), perceptual loss, or any other suitable type of loss function used for or suitable for approximating the similarity of ECG signals, as aspects of the technology described herein are not limited in this respect. In some embodiments, the first loss is computed based on Mel spectrogram loss. The mel function takes as input a signal, frame size, and frame step and outputs a mel spectrogram. For example, the first loss may be computed using Equations 24 and 25:

$$\text{loss} = \text{spectrogram loss} + \sum_{s=1}^{10} \frac{1}{N_{frames_s}} \left( \sum_{f=1}^{N_{frames_s}} \left| y_{pred\_splits_s} \right| + \text{z\_norm}\left(y_{pred\_splits_s}\right) - \text{z\_norm}\left(y_{real\_splits_s}\right) \right)^2 \Bigg) \quad \text{(Equation 24)}$$

To calculate the loss, the original ECG signal and denoised ECG signal were split into evenly sized splits (segments) (e.g., 10 evenly sized splits). In Equation 24, the z_norm function performs z-score normalization along the frames axis, $N_{frames_s}$ is the number of frames used when calculating the spectrogram, $y_{pred\_splits_s}$ refers to the denoised ECG signal values for a split, $y_{real\_splits_s}$ refers to the original ECG values for a split, s is the index of the split, and where:

$$\text{spectrogram loss} = \frac{1}{6} \sum_{w=7}^{10} \left( \sum_{i=1}^{N} \left| mel\left(y_{real}, 2^w, 2^{w-2}\right) - \right.\right. \quad \text{(Equation 25)}$$

-continued $$mel\left(y_{pred}, 2^{w}, 2^{w-2}\right)\|\Big) + \sqrt{2^{w-1}}\left(\sum_{i=1}^{N}\left\|\log\_mel\left(y_{real}, 2^{w}, 2^{w-2}\right) - \log\_mel\left(y_{pred}, 2^{w}, 2^{w-2}\right)\right\|\right)$$

In Equation 25, $y_{real}$ refers to the original ECG signal values, i is the index of a frequency in the mel spectrogram (all values of i are iterated over to get all values in the spectrogram), and N is the number of frequencies in the mel spectrogram. Different values of w are used to calculate the mel spectrogram using frames of differing lengths. The frame length is equal to $2^{w}$.

As described herein, the second loss may be determined, at act 236, as a function of the first output 224 of the first discriminator model and/or a second output 234 of the second discriminator model 232. For example, the first output 224 may be obtained by processing the denoised ECG signal 220 using the first discriminator model 222. The second output 234 may be obtained by processing a frequency-domain representation 230 of the denoised ECG signal 220 using the second discriminator model 232. For example, the frequency-domain representation 230 of the denoised ECG signal 220 may be obtained by determining the short-time Fourier transform (STFT) of the denoised ECG signal 220, at act 228. The first and/or second outputs 224, 234 may then be used to compute the second loss at act 236. Thus, in some embodiments only the first discriminator model 222 is present and the second loss is calculated at act 236 using the first output 224. In other embodiments, only the second discriminator model 232 is present and the second loss is calculated at act 236 using the second output 234. In yet other embodiments both the first and second discriminator models 222 and 232 are present, and the second loss is calculated at act 236 using both the first output 224 and the second output 234. In some embodiments, the first discriminator model 222 is a machine learning model trained to distinguish between real ECG signals (e.g., the clean ECG signals 202) and artificial ECG signals. For example, the first discriminator model 222 may be trained to predict whether the denoised ECG signal 220 is a real ECG signal or an artificial ECG signal. The first discriminator model 222 may have a neural network architecture having a plurality of layers (i.e., a deep neural network). In some embodiments, the first discriminator model 222 is made up of two smaller discriminator models. An example architecture of a first discriminator model is shown in FIG. 5I-1 and FIG. 5I-2. In some embodiments, the first output 224 of the first discriminator model 222 includes a classification indicative of whether or not the denoised ECG signal 220 is real or artificial. Additionally or alternatively, the first output 224 may include outputs of one or more layers of the first discriminator model 222. For example, with reference to FIG. 5I-1 and FIG. 5I-2, the first output 224 may include the output of each of the layers except the layers 523-1, 523-10, 522-1, and 522-6.

In some embodiments, at act 236, the second loss is determined based on the first output 224 of the first discriminator model 222. For example, the second loss may include generator loss. Generator loss may represent how well the denoising model 212 is fooling the first discriminator model 222 into classifying denoised ECG signals as real ECG signals. For example, the generator loss may be computed using Equation 26:

$$\text{generator loss} = \sum_{k=1}^{N_{discriminators}}\left(\left(\sum_{f=1}^{N_{features_{k-1}}} ReLU\left(1-y_{pred_{k-1}}\right)\right) + \frac{1}{N_{discriminators}N_{layers_k}\sum_{l=1}^{N_{layers_k}} N_{features_{k,l}}}\sum_{l=1}^{N_{layers_k}}\sum_{f=1}^{l}\left|y_{real_{k,l}}-y_{pred_{k,l}}\right|\right) \quad \text{(Equation 26)}$$

where $N_{discriminators}$ is the number of discriminators, $N_{layers_k}$ is the number of layers in a given discriminator k, k is the index of the discriminator, l is the index of a layer in a discriminator k, $N_{features}$ is the number of features in a given discriminator k or in a given layer l of a given discriminator k, f is the index of a feature in a layer, $y_{pred}$ refers to the values of the denoised ECG signal, and $y_{real}$ refers to the values of the original ECG signal. $N_{layers_k}$ and $N_{features}$ may be used so that larger discriminators don't have outsized influence just because they have more features.

In some embodiments, the second discriminator model 232 is a machine learning model trained to distinguish between frequency-domain representations of real ECG signals (e.g., the clean ECG signals 202) and frequency-domain representations artificial ECG signals. For example, the second discriminator model 232 may be trained to predict whether a frequency-domain representation 230 of denoised ECG signal 220 is real or artificial. The frequency-domain representation 230 may be generated, at act 228, by determining the short-time Fourier transform (STFT) of the denoised ECG signal 220. The second discriminator model 232 may have a neural network architecture having a plurality of layers (i.e., a deep neural network). An example architecture of a second discriminator model is shown in FIG. 5J and FIG. 5K. In some embodiments, the second output 234 of the second discriminator model 232 includes a classification indicative of whether or not the frequency-domain representation 230 of the denoised ECG signal 220 is real or artificial. Additionally or alternatively, the second output 234 may include outputs of one or more layers of the second discriminator model 232. For example, with reference to FIG. 5J, the second output 234 may include the output of each of the layers except the layer 525-1.

In some embodiments, at act 236, the second loss is determined based on the second output 234 of the second discriminator model 232. For example, the second loss may include STFT generator loss. The STFT generator loss may represent how well the denoising model 212 is fooling the second discriminator model 232 into classifying the frequency-domain representation of denoised ECG signals as real ECG signals. For example, the STFT generator loss may be computed using Equation 27:

$$STFT\ \text{generator loss} = \left(\sum_{f=1}^{N_{frames}} ReLU\left(1 - y_{pred_{-1,f}}\right)\right) + \frac{10.0}{N_{layers}\sum_{l=1}^{N_{layers}} N_{frames}}\sum_{l=1}^{N_{layers}}\sum_{f=1}^{N_{frames}}\left|y_{real_{l,f}} - y_{pred_{l,f}}\right| \quad \text{(Equation 27)}$$

where $N_{frames}$ is the number of frames, $N_{layers}$ is the number of layers in the STFT discriminator, f refers to the index of the frame, l refers to the index of the layer, $y_{pred}$ refers to the values of the denoised ECG signal, and $y_{real}$ refers to the values of the original ECG signal.

In some embodiments, determining the second loss, at act 236, includes determining one or both of the generator loss (Equation 26) and the STFT generator loss (Equation 27). For example, the second loss may be the sum of the generator loss and the STFT generator loss.

As shown in FIG. 2, at act 238, the parameters of the denoising model are updated based on the first loss and the second loss. The parameters of the denoising model may be updated using any suitable neural network optimization software. The optimization software may be configured to update the parameters by gradient descent, stochastic gradient descent, or in any other suitable way. In some embodiments, the Adam optimizer (Kingma, D. and Ba, J. (2015) Adam: A Method for Stochastic Optimization. Proceedings of the 3rd International Conference on Learning Representations (ICLR 2015)) may be used.

Illustrative technique 200 may additionally include training the first discriminator model 222 to classify input ECG signals as real or artificial. The first discriminator model 222 may be trained using a set of the clean ECG signals 202 and a corresponding set of artificial ECG signals. The set of artificial ECG signals may include denoised ECG signals generated by processing the set of clean ECG signals 202 using denoising model 212.

In some embodiments, training the first discriminator model 222 includes (a) processing the clean and artificial ECG signals using the first discriminator model 222 to obtain the first output 224, (b) determining a loss based on the first output 224, and (c) updating the parameters of the first discriminator model 222 based on the loss. For example, the loss may be determined using Equations 28-30:

$$\text{real loss} = \frac{1}{ecg\ \text{length}}\sum_{k=1}^{N}\sum_{i=1}^{ecg\ length} ReLU\left(1-y_{real_{k,i}}\right) \quad \text{(Equation 28)}$$

$$\text{generated loss} = \frac{1}{ecg\ \text{length}}\sum_{k=1}^{N}\sum_{i=1}^{ecg\ length} ReLU\left(1-y_{pred_{k,i}}\right) \quad \text{(Equation 29)}$$

$$\text{loss} = \text{real loss} + \text{generated loss} \quad \text{(Equation 30)}$$

where ecg length is the length of the ECG signal, $y_{pred}$ refers to the values of the denoised ECG signal, and $y_{real}$ refers to the values of the original ECG signal.

Illustrative technique 200 may additionally or alternatively include training the second discriminator model 232 to classify input frequency-domain representations of ECG signals as real or artificial. The second discriminator model 232 may be trained using a set of the frequency-domain representations of clean ECG signals 202 and a corresponding set of frequency-domain representations of artificial ECG signals. The set of frequency-domain representations of artificial ECG signals may be generated by processing the set of clean ECG signals 202 using denoising model 212 to obtain denoised ECG signals, then determining the STFT of the denoised ECG signals.

In some embodiments, training the second discriminator model 232 includes: (a) processing the frequency-domain representations of the clean and artificial ECG signals using the second discriminator model 232 to obtain the second output 234, (b) determining a loss based on the second output 234, and (c) updating the parameters of the second discriminator model 232 based on the loss. For example, the loss may be determined using Equations 31-33:

$$\text{generated loss} = \frac{1}{N_{pred}}\sum_{n=1}^{N_{pred}} ReLU\left(1-y_{pred_n}\right) \quad \text{(Equation 32)}$$

$$\text{real loss} = \frac{1}{N_{real}}\sum_{n=1}^{N_{real}} ReLU\left(1-y_{real_n}\right) \quad \text{(Equation 32)}$$

$$\text{loss} = \text{real loss} + \text{generated loss} \quad \text{(Equation 33)}$$

where $y_{pred}$ refers to the values of the denoised ECG signal, $y_{real}$ refers to the values of the original ECG signal, $N_{pred}$ is the number of samples in the predicted ECG signal, and $N_{real}$ is equal to $N_{pred}$.

In some embodiments, a rhythm classifier (e.g., rhythm classifier 136 shown in FIG. 1B) is trained to predict a respective rhythm type for each of at least some segments of an ECG signal. As described herein, the rhythm classifier may take, as input, a positionally encoded version of a numeric encoding output by an encoder that is part of the denoising model or a quantized numeric encoding output by an RVQ that is part of the denoising model. In some embodiments, the rhythm classifier is trained using any suitable supervised learning techniques, as aspects of the technology described herein are not limited in this respect. For example, the training data may include a plurality of ECG signals and corresponding ground truth labels. Each of the plurality of ECG signals may comprise a plurality of segments, and the ground truth labels may include a respective ground truth label for each segment. A ground truth label may indicate the class to which the segment belongs. As described herein, the class may include a rhythm type or set of rhythm types. During training, parameters of the rhythm classifier may be initialized using randomly generated weights. The output of the rhythm classifier and the ground truth labels may be used to compute a loss, which is used to update the weights of the rhythm classifier.

In some embodiments, the rhythm classifier is trained jointly with the denoising model as described herein with respect to FIG. 2. For example, the rhythm classifier may be trained using training data 206, where training data 206 additionally includes ground truth labels for the segments of the clean ECG signals in the training data. During the training of the denoising model 212, a clean ECG signal is provided as input to encoder 214 and optionally to the RVQ 216. The output of the encoder 214 or the RVQ 216 is positionally encoded and provided as input to the rhythm classifier. The output of the rhythm classifier is compared to the ground truth label(s) included in the training data 206. For example, the output of the rhythm classifier and the ground truth label(s) may be used to compute a loss that is used to update the weights of the rhythm classifier.

In alternative embodiments, the rhythm classifier is trained using a pre-trained denoising model. That is, a denoising model is trained first and the trained denoising model is used to train the rhythm classifier, unlike the preceding embodiment in which both the denoising model and the rhythm classifier are jointly trained. For example, the rhythm classifier may obtain the numeric encoding from a pre-trained encoder of the denoising model or a quantized numeric encoding from a pre-trained RVQ of the denoising model. Thus, in some embodiments, all of the weights of the pre-trained denoising model may be frozen during training of the rhythm classifier. In alternative embodiments, at least some of the weights may be updated, while others are frozen, to allow for finetuning of the pre-trained denoising model, thereby allowing it to denoise ECG signals in a way that improves rhythm classification.

In some embodiments, a sample-level ECG classifier (e.g., sample-level ECG classifier 138) is trained to predict sample-level ECG labels for the respective samples of the ECG signal(s). As described herein, the sample-level ECG classifier may take, as input, a numeric encoding output by an encoder that is part of the denoising model or a quantized numeric encoding output by an RVQ that is part of the denoising model. In some embodiments, the sample-level ECG classifier is trained using any suitable supervised learning techniques, as aspects of the technology described herein are not limited in this respect. For example, the training data may include a plurality of ECG signals and corresponding ground truth labels. Each of the plurality of ECG signals comprises a plurality of samples, and the ground truth labels may include a respective ground truth label for each sample. A ground truth label may indicate the class to which the sample belongs. As described herein, the class may indicate the portion of the ECG waveform to which the sample corresponds. During training, the rhythm classifier may be initialized using randomly generated weights. The output of the sample-level ECG classifier and the ground truth labels may be used to compute a loss, which is used to update the weights of the sample-level ECG classifier.

In some embodiments, the sample-level ECG classifier is trained together with the denoising model as described herein with respect to FIG. 2. For example, the sample-level ECG classifier may be trained using training data 206, where training data 206 additionally includes ground truth labels for the samples of the clean ECG signals in the training data. During the training of the denoising model 212, a clean ECG signal is provided as input to encoder 214 and optionally to the RVQ 216. The output of the encoder 214 or the RVQ 216 is provided as input to the sample-level ECG classifier. The output of the sample-level ECG classifier is compared to the ground truth label(s) included in the training data 206. For example, the output of the sample-level ECG classifier and the ground truth label(s) may be used to compute a loss that is used to update the weights of the sample-level ECG classifier.

In alternative embodiments, the sample-level ECG classifier is trained using a pre-trained denoising model. For example, the sample-level ECG classifier may obtain the numeric encoding from a pre-trained encoder of the denoising model or a quantized numeric encoding from a pre-trained RVQ of the denoising model. Thus, in some embodiments, all of the weights of the pre-trained denoising model may be frozen during training of the sample-level ECG classifier. In alternative embodiments, at least some of the weights may be updated, while others are frozen, to allow for finetuning of the pre-trained denoising model, thereby allowing it to denoise ECG signals in a way that improves sample-level ECG classification.

Figure 3A:
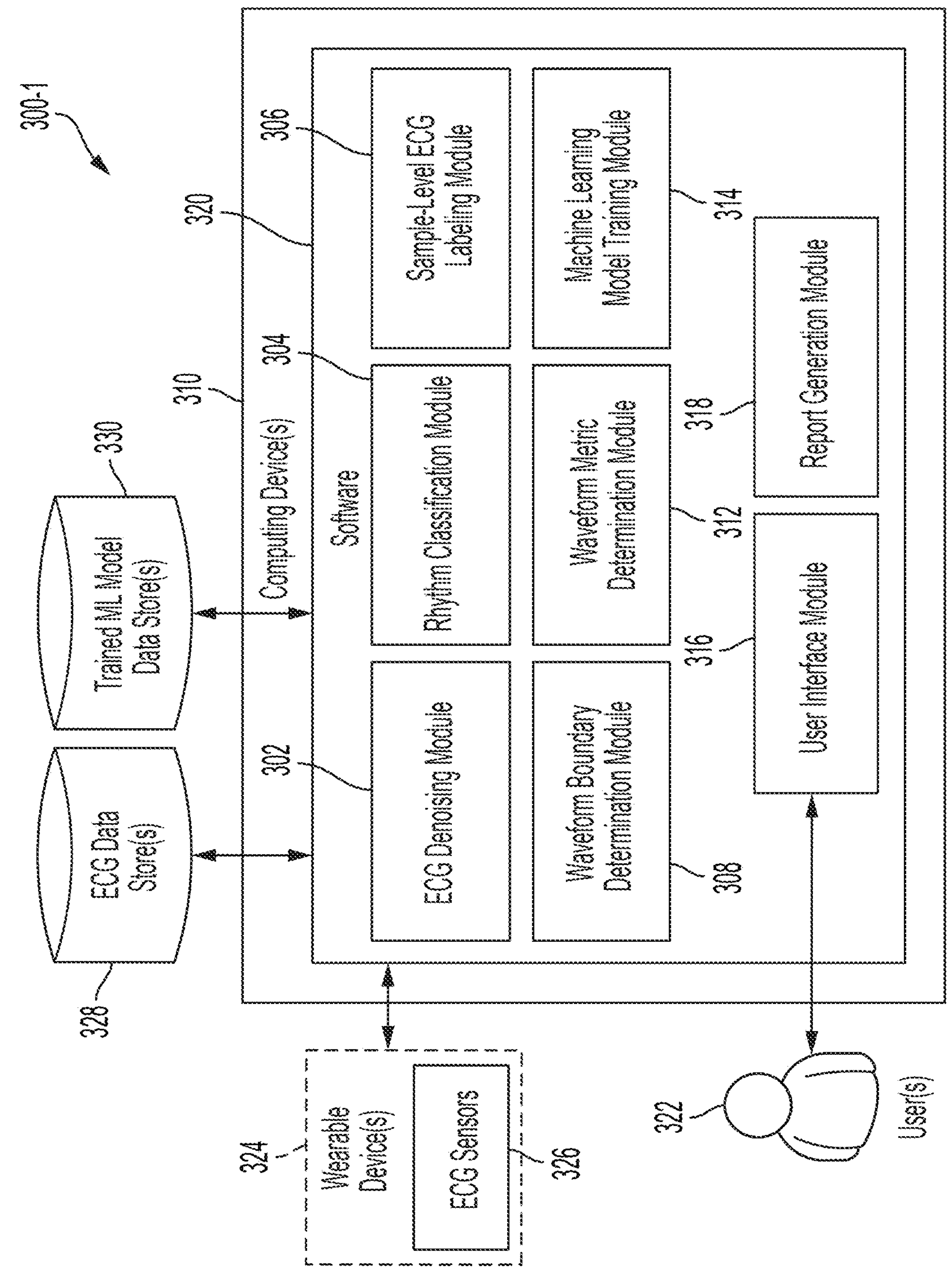
FIG. 3A is a block diagram of an example system for analyzing at least one ECG signal, according to some embodiments of the technology described herein.

FIG. 3A is a block diagram of an example system for analyzing at least one ECG signal, according to some embodiments of the technology described herein. System 300-1 includes computing device(s) 310 configured to have software 320 execute thereon to perform various functions in connection with analyzing at least one ECG signal. In some embodiments, software 320 includes a plurality of modules. A module may include processor-executable instructions that, when executed by at least one computer hardware processor, cause the at least one computer hardware processor to perform function(s) of the module. Such modules are sometimes referred to herein as "software modules," each of which includes processor-executable instructions configured to perform one or more acts of one or more processes, such as process 400 shown in FIG. 4A, process 410 shown in FIG. 4B, process 420 shown in FIG. 4C, process 430 shown in FIG. 4D, and process 440 shown in FIG. 4E.

The computing device(s) 310 may be operated by one or more user(s) 322. The user(s) 322 may provide input specifying processing or other methods to be performed by the computing device(s) 310. For example, the user(s) 322 may provide input specifying processing (e.g., denoising, rhythm classification, sample-level ECG classification, training, etc.) to be performed on one or more ECG signals. Additionally or alternatively, the user(s) 322 may provide input validating and/or editing results of the processing performed using computing device(s) 310. User(s) 322 may provide input by uploading one or more files, interacting with a user interface module 316, and/or using any other suitable technique for providing input, as aspects of the technology described herein are not limited in this respect.

Software 320 may include one or more modules configured to perform functions in connection with analyzing at least one ECG signal. As shown in FIG. 3A, such modules include the ECG denoising module 302, the rhythm classification module 304, the sample-level ECG labeling module 306, the waveform boundary determination module 308, and the waveform metric determination module 312.

The ECG denoising module 302, the rhythm classification module 304, and the sample-level ECG labeling module 306 may each be configured to obtain ECG signal(s) from ECG sensors 326, wearable device(s) 324, ECG data store(s) 328, and/or user(s) 322 (e.g., by the user(s) uploading one or more files). Additionally or alternatively, the ECG denoising module 302, the rhythm classification module 304, and the sample-level ECG labeling module 306 may each be configured to obtain one or more trained machine learning models from the trained machine learning model data store(s) 330 and/or the machine learning model training module 314.

The ECG denoising module 302 is configured to denoise at least one ECG signal. The denoising module 302 may be configured to denoise the at least one ECG signal by processing the at least one ECG signal using a denoising model trained to denoise the at least one ECG signal. For example, the trained denoising model may include the trained denoising model 120 shown in FIG. 1B. In some embodiments, processing the ECG signal using the trained denoising model includes: (a) encoding the at least one ECG signal using an encoder (e.g., encoder 122 shown in FIG. 1B) to obtain a numeric encoding of the at least one ECG signal, (b) quantizing the numeric encoding of the at least one ECG signal using an RVQ (e.g., RVQ 126 shown in FIG. 1B) to obtain a quantized numeric encoding of the at least one ECG signal, and (c) decoding the quantized numeric encoding of the at least one ECG signal using a decoder (e.g., decoder 130 shown in FIG. 1B) to obtain at least one denoised ECG signal. Example techniques for denoising at least one ECG signal are described herein including at least with respect to FIGS. 1A-1B and 4A.

The rhythm classification module 304 is configured to classify rhythms of segments of the at least one ECG signal. In some embodiments, the rhythm classification module 304 is configured to classify rhythms of the segments by: (a) encoding the at least one ECG signal to obtain a numeric encoding of the at least one ECG signal, (b) positionally encoding the numeric encoding of the at least one ECG signal to obtain a positionally encoded numeric encoding of the at least one ECG signal, and (c) classifying a respective rhythm of each of at least some of the segments between a plurality of classes to obtain a plurality of rhythm classifications. For example, the encoding may be performed using an encoder (e.g., the encoder 122 shown in FIG. 1B) and/or an RVQ (e.g., the RVQ 126 shown in FIG. 1B). The classifying may be performed using a rhythm classifier (e.g., rhythm classifier 136 shown in FIG. 1B). Example techniques for classifying rhythms of segments of at least one ECG signal are described herein including at least with respect to FIGS. 1A-1C and 4C.

The sample-level ECG labeling module 306 is configured to label at least one ECG signal comprising a plurality of samples. In some embodiments, the sample-level ECG labeling module 306 is configured to generate sample-level ECG labels for at least one ECG signal by: (a) encoding the at least one ECG signal to obtain a numeric encoding of the at least one ECG signal, and (b) processing the numeric encoding of the at least one ECG signal using a trained sample-level ECG classifier (e.g., sample-level ECG classifier 138 shown in FIG. 1B) to obtain sample-level ECG labels for at least some of a plurality of samples of the at least ECG signal. For example, the encoding may be performed using an encoder (e.g., the encoder 122 shown in FIG. 1B) and optionally an RVQ (e.g., the RVQ 126 shown in FIG. 1B). Example techniques for generating sample-level ECG labels for at least one ECG signal are described herein including at least with respect to FIGS. 1A-1B, 1D, and 4B.

The waveform boundary determination module 308 is configured to determine boundaries of ECG waves (e.g., P, Q, R, S, and T-waves) in at least one ECG signal. Determining the boundaries may include, for example, determining the onset (e.g., start) and/or offset (e.g., end) of a particular wave. In some embodiments, the waveform boundary determination module 308 is configured to determine the boundaries based on sample-level ECG labels generated for the at least one ECG signal. For example, the waveform boundary determination module 308 may obtain the sample-level ECG labels from the sample-level ECG labeling module 306, the ECG data store(s) 328, and/or user(s) 322. Example techniques for determining waveform boundaries are described herein including at least with respect to FIG. 1A and FIG. 1D.

The waveform metric determination module 312 is configured to determine one or more metrics of ECG waveforms in at least one ECG signal. The metrics may be determined based on sample-level ECG labels generated for the at least one ECG signal and/or boundaries determined for ECG waves in the at least one ECG signal. For example, the waveform metric determination module 312 may be configured to obtain sample-level ECG labels from the sample-level ECG labeling module 306, the ECG data store(s) 328, and/or user(s) 322. Additionally or alternatively, the waveform metric determination module 312 may be configured to obtain waveform boundaries from the waveform boundary determination module 308, the ECG data store(s) 328, and/or user(s) 322. Example techniques for determining waveform metrics are described herein including at least with respect to FIG. 1A and FIG. 1D. For example, the waveform metric determination module 312 may be configured to determine one or more of the metrics listed in Tables 1 and 2.

As shown in FIG. 3A, software 320 also includes machine learning model training module 314, user interface module 316, and report generation module 318.

In some embodiments, the machine learning model training module 314 is configured to train one or more machine learning models. For example, the machine learning model training module 314 may be configured to train a denoising model to denoise at least one ECG signal. Additionally or alternatively, the machine learning model training module 314 may be configured to train a sample-level ECG classifier to generate a respective sample-level ECG label for each of a plurality of samples of at least one ECG signal. Additionally or alternatively, the machine learning model training module 314 may be configured to train a rhythm classifier to classify rhythms of segments of at least one ECG signal. Additionally or alternatively, the machine learning model training module 314 may be configured to train at least one discriminator model to classify an input as real or artificial. The machine learning model training module 314 may obtain training data, for training the one or more machine learning models, from ECG data store(s) 328, wearable device(s) 324, ECG sensors 326, and/or user(s) 322. The machine learning model training module 314 may provide the trained machine learning model(s) to the trained machine learning model data store(s) 330 for storage thereon. For example, the machine learning model training module 314 may provide the values of the parameters of the machine learning model(s) to the trained machine learning model data store(s) 330 for storage thereon. Example techniques for training one or more machine learning models are described herein including at least with respect to FIG. 2.

Report generation module 318 may be configured to generate one or more reports that include results of processing the at least one ECG signal. For example, the report generation module 318 may be configured to generate a report that displays a denoised ECG signal. The denoised ECG signal may be presented together with the original (e.g., noisy) ECG signal. Additionally or alternatively, the report generation module 318 may be configured to generate a report that displays sample-level ECG labels determined for the at least one ECG signal. For example, the report may display a denoised ECG signal having samples annotated with the sample-level ECG labels. Additionally or alternatively, the report generation module 318 may be configured to generate a report that displays rhythms of segments of at least one ECG signal. For example, the report may display a denoised ECG signal having segments annotated with respective rhythm types. Additionally or alternatively, the report generation module 318 may be configured to generate a report that displays waveform boundaries and/or waveform metrics. For example, the report may list the waveform boundaries and/or metrics. Additionally or alternatively, the report may display a denoised ECG signal annotated to include indications of the waveform boundaries and/or metrics. Additionally or alternatively, the report generation module 318 may include an indication of one or more conditions, abnormalities, and/or treatments for the subject. In some embodiments, the report generation module 318 is configured to generate a report that include multiple different types of information (e.g., denoised ECG signal(s), sample-level ECG labels, rhythm types, waveform boundaries, waveform metrics, etc.), thereby simplifying review.

User interface module 316 may be configured to generate an interactive graphical user interface (GUI) through which user(s) 322 may provide input and view information generated by software 320. For example, the user(s) 322 may view reports generated by report generation module 318 and provide input validating and/or editing information presented in said reports. In some embodiments, the user interface module 316 may be a webpage or web application accessible through an Internet browser. In some embodiments, the user interface module 316 may generate a GUI of an app executing on a user's mobile device and/or wearable device. In some embodiments, the user interface module 316 may generate a number of selectable elements through which a user may interact. For example, the user interface module 316 may generate dropdown lists, checkboxes, text fields, or any other suitable element.

System 300-1 also includes data stores including ECG data store(s) 328 and trained machine learning model data store(s) 330. Each of the data stores includes any suitable type of data store (e.g., a flat file, a database system, a multi-file, etc.) and may store data in any suitable format, as aspects of the technology described herein are not limited in this respect. The data stores may be part of software 320 (not shown) or excluded from software 320, as shown in FIG. 3A.

In some embodiments, the ECG data store(s) 328 include one or more data stores configured to store information relating to measuring and/or processing ECG signal(s). For example, the ECG data store(s) 328 may store ECG signal(s) measured using ECG sensors 326 and/or wearable device(s) 324. Additionally or alternatively, the ECG data store(s) 328 may be configured to store output(s) of the ECG denoising module 302, rhythm classification module 304, sample-level ECG labeling module 306, waveform boundary determination module 308, waveform metric determination module 312, and/or report generation module 318. For example, the ECG data store(s) 328 may be configured to store denoised ECG signal(s), rhythm types, sample-level ECG labels, waveform boundaries, waveform metrics, and/or one or more reports.

In some embodiments, the trained machine learning model data store(s) 330 includes one or more data stores configured to store one or more trained machine learning models. For example, the trained machine learning model data store(s) 330 may store a trained denoising model trained to denoise at least one ECG signal. Additionally or alternatively, the trained machine learning model data store(s) 330 may store a trained sample-level ECG classifier trained to determine sample-level ECG labels for samples of at least one ECG signal. Additionally or alternatively, the trained machine learning model data store(s) 330 may store a rhythm classifier trained to determine rhythm types of segments of at least one ECG signal. Additionally or alternatively, the trained machine learning model data store(s) 330 may store one or more discriminators trained to classify input as real or artificial. In some embodiments, the trained machine learning model data store(s) 330 store parameter values for trained machine learning model(s). When the stored trained machine learning model(s) are loaded and used, for example by ECG denoising module 302, rhythm classification module 304, and/or sample-level ECG labeling module 306, the parameter values of the trained machine learning model are loaded and stored in memory using at least one data structure.

As described herein, system 300-1 may be implemented in various different ways. For example, system 300-1 may include multiple computing devices that are communicatively coupled. In some embodiments, one computing device is configured to perform all of the processing. In some embodiments, each of multiple different computing devices is configured to perform all of the processing. In some embodiments, different computing devices may be configured to perform different functions. Data and/or results of processing on one computing device may be transmitted to one or more other computing devices. FIGS. 3B-3J show example implementations of the example system shown in FIG. 3A, according to some embodiments of the technology described herein.

Figure 3B:
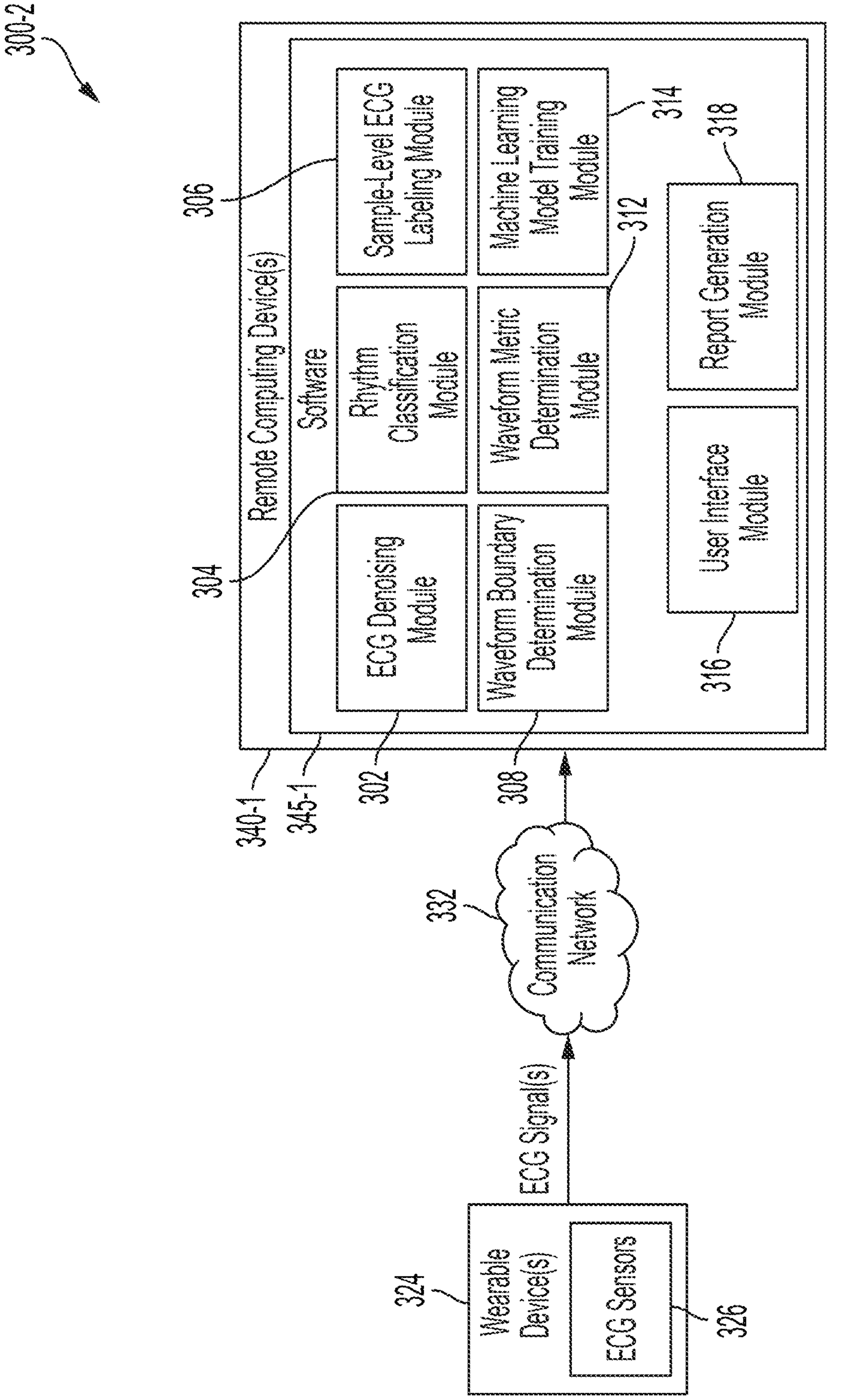
FIGS. 3B-3J show example implementations of the example system shown in FIG. 3A, according to some embodiments of the technology described herein.

As shown in FIG. 3B, the example system 300-2 includes wearable device(s) 324 coupled to one or more remote computing device(s) 340-1 via communication network 332. In this example implementation, the wearable device(s) 324 are configured to transmit ECG signal(s) to the remote computing device(s) 340-1 via the communication network 332. For example, the wearable device(s) 324 may be worn by user(s) and configured to transmit the ECG signal(s) to one or more other computing device(s) (e.g., a server, a personal computer, a portable electronic device, etc.) for processing thereon. For example, with reference to example system 300-3 shown in FIG. 3C, the one or more remote computing device(s) may include one or more server(s) and/or one or more other computing device(s) (e.g., a personal computer, a portable electronic device, etc.).

In some embodiments, the wearable device(s) 324 are configured to pre-process the ECG signal(s) prior to transmitting them to remote computing device(s) 340-1. In some embodiments, pre-processing the ECG signal(s) includes segmenting the ECG signal(s) into a plurality of segments. Example techniques for segmenting an ECG signal are described herein including at least with respect to FIG. 1B. In some embodiments, transmitting the ECG signal(s) includes transmitting one or more (e.g., all) of the segments to the remote computing device(s) 340-1. In some embodiments, the segments are transmitted selectively. For example, after measuring an ECG signal for a threshold duration of time, the ECG signal measured during that time may be segmented and the segments transmitted to the remote computing device(s) 340-1. The one or more remote computing device(s) 340-1 are configured to have software 345-1 execute thereon to process the ECG signal(s). For example, as shown in FIG. 3B, software 345-1 includes all of the software modules: ECG denoising module 302, rhythm classification module 304, sample-level ECG labeling module 306, waveform boundary determination module 308, waveform metric determination module 312, machine learning model training module 314, user interface module 316, and report generation module 318.

In some embodiments, the one or more remote computing device(s) 340-1 are configured to transmit information back to wearable device(s) 324. For example, the remote computing device(s) 340-1 may be configured to transmit notifications to wearable device(s) 324 that may be used to alert the wearer to one or more conditions and/or abnormalities (e.g., arrhythmias) detected as a result of processing the ECG signal(s). Additionally or alternatively, the remote computing device(s) 340-1 may be configured to transmit notifications to wearable device(s) 324 prompting the wearer to seek medical attention and/or treatment by a clinician.

The communication network 332 may include a local area network or a wide area network, such as an enterprise network, an intelligent network (IN) or the Internet. Such networks may be based on any suitable technology and may operate according to any suitable protocol and may include wireless networks, wired networks or fiber optic networks.

Figure 3C:
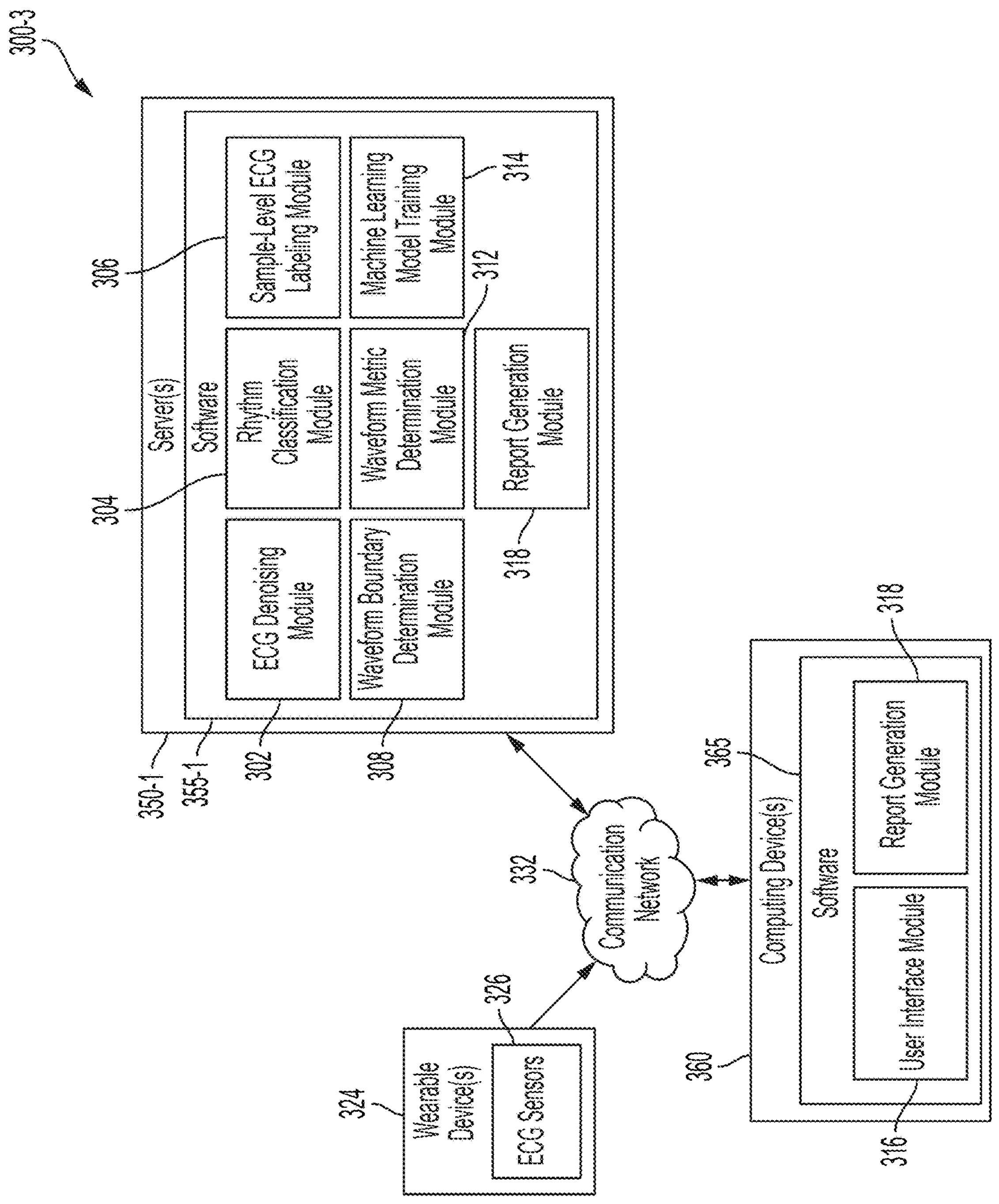

FIG. 3C shows an example system 300-3 having wearable device(s) 324 communicatively coupled with one or more remote computing devices including server(s) 350-1 and computing device(s) 360. In this example, the wearable device(s) 324 are configured to transmit ECG signal(s) to server(s) 350-1 via communication network 332. The server(s) 350-1 are configured to have software 355-1 execute thereon to perform functions relating to processing the ECG signals and generating a report comprising results of processing the ECG signals. For example, software 355-1 includes ECG denoising module 302, rhythm classification module 304, sample-level ECG labeling module 306, waveform boundary determination module 308, waveform metric determination module 312, and machine learning model training module 314. Software 355-1 may also include report generation module 318.

In some embodiments, one or more computing device(s) 360 other than the wearable device(s) 324 and server(s) 350-1 may be used to output information relating to processing the ECG signal(s) and/or to receive input from one or more user(s). For example, the one or more computing device(s) 360 may include computing device(s) located in a clinical setting. Additionally or alternatively, the computing device(s) 360 may be computer(s) (e.g., personal computer(s) such as laptops, portable electronic devices, desktops, tablets, etc.) accessible to user(s) (e.g., wearer(s) of the wearable device(s) 324). Additionally or alternatively, the computing device(s) 360 may be computer(s) accessible to ECG technicians, who may review and/or edit results of processing the ECG signal(s).

As shown in FIG. 3C, the computing device(s) 360 may have software 365 execute thereon to perform functions related to user interaction. For example, software 365 may include user interface module 316. Additionally, software 365 may include report generation module 318. For example, report generation module 318 may be configured to update and/or generate report(s) based on user input. Report generation module 318 may be part of software 365 and/or part of software 355-1.

Figure 3D:
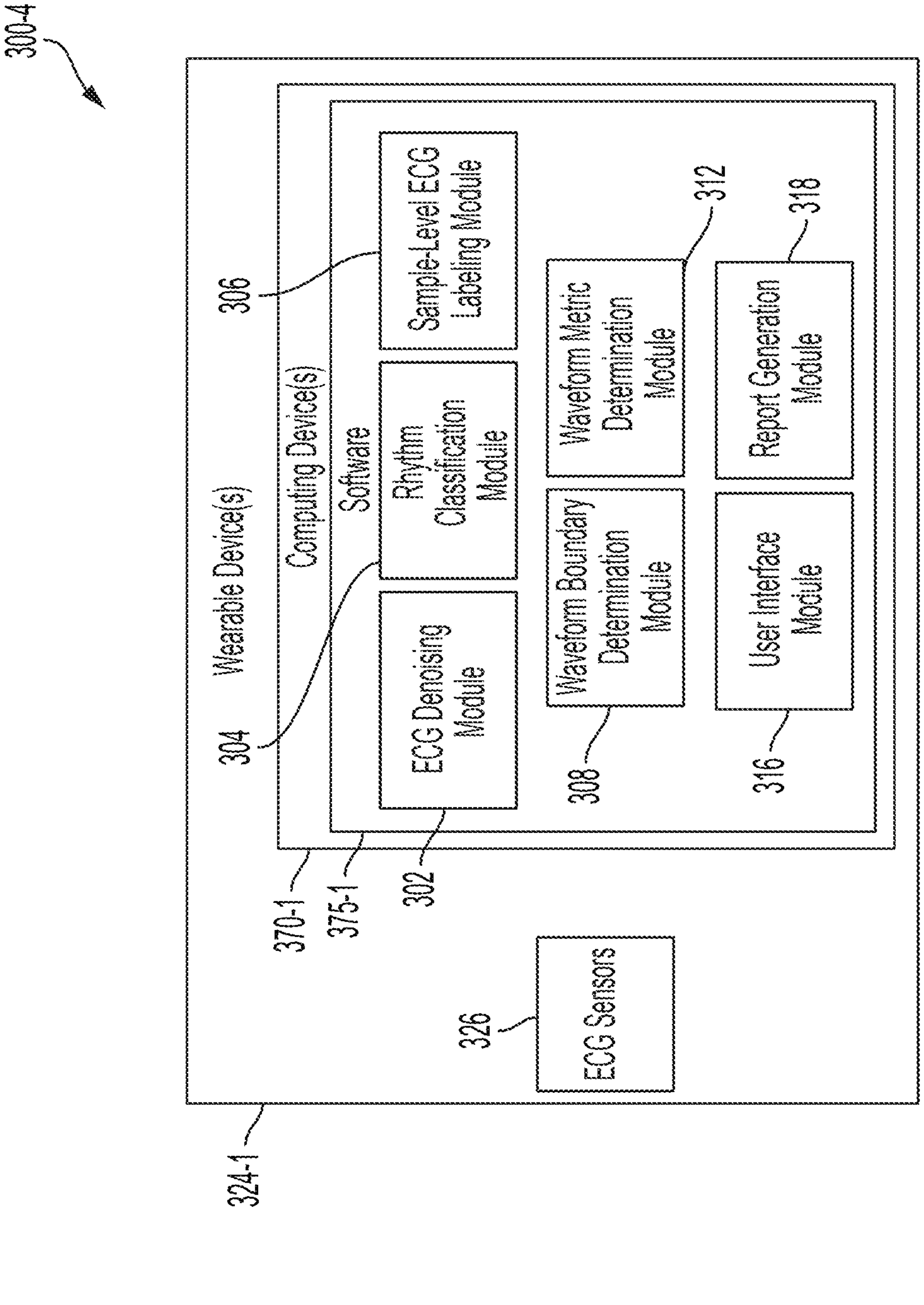

In the example system 300-4 shown in FIG. 3D, all of the processing is performed onboard the wearable device(s) 324-1. For example, the wearable device(s) 324-1 include computing device(s) 370-1 having software 375-1 configured to execute thereon to perform the various functions relating to processing ECG signals (e.g., measured using ECG sensors 326), receiving user input, displaying results of processing to one or more users, and/or transmitting results to remote device(s) (e.g., to the user's clinician). For example, software 375-1 includes all of the software modules: ECG denoising module 302, rhythm classification module 304, sample-level ECG labeling module 306, waveform boundary determination module 308, waveform metric determination module 312, user interface module 316, and report generation module 318. One or more machine learning models may be trained off of the wearable device(s) 324-1 (e.g., on one or more remote devices, such as a server), and the trained machine learning model(s) may be provided to the wearable device(s) 324-1. Thus, the wearable device(s) 324-1 can be used by the wearer(s) to measure ECG signal(s), view results of processing the ECG signal(s) (e.g., the denoised ECG signal(s), sample-level label types, ECG metrics, conditions, and/or abnormalities, etc.), and/or transmit the results of the processing to one or more remote devices.

Figure 3E:
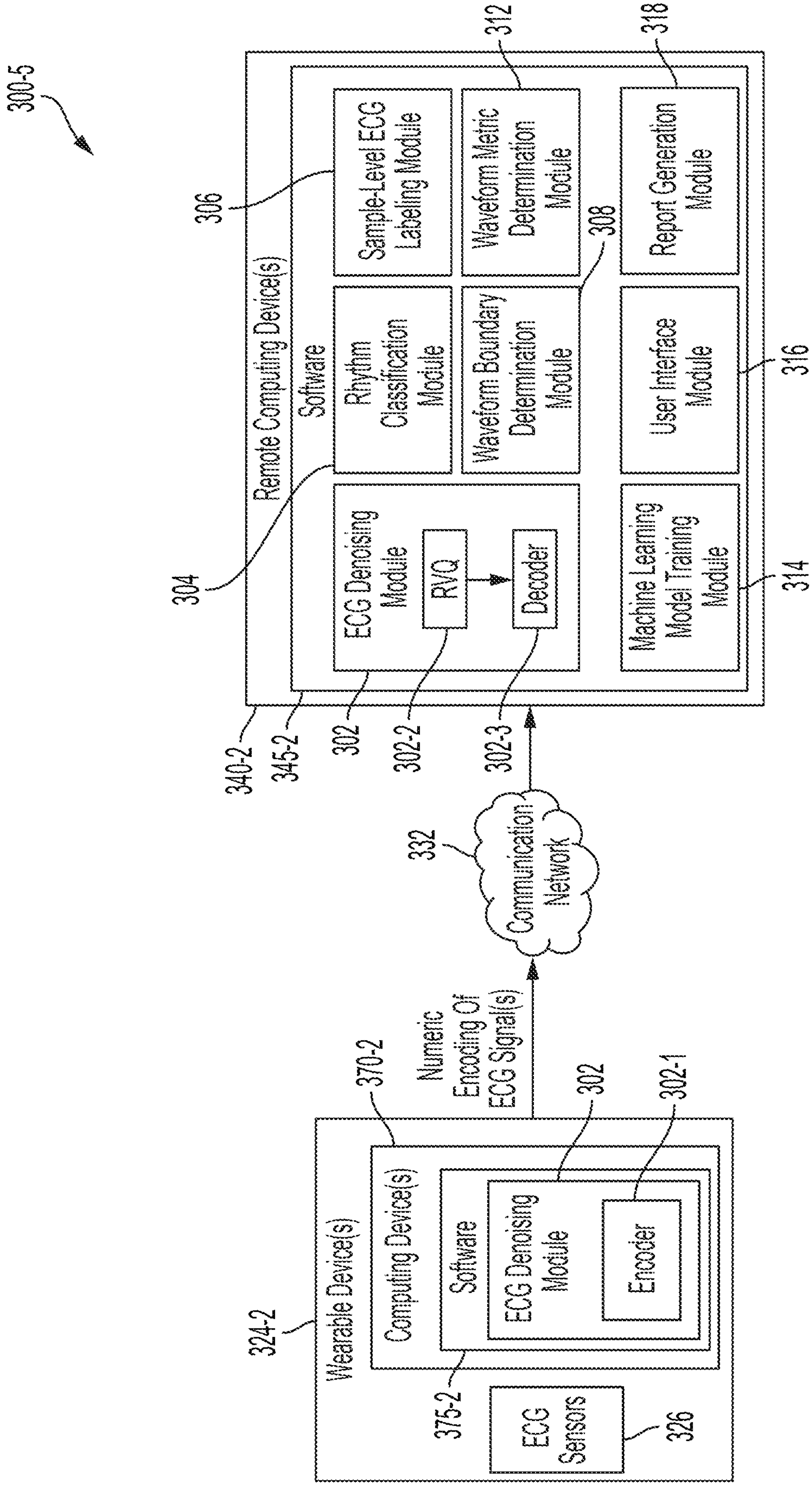

FIG. 3E shows an example system 300-5 where some of the processing is performed on the wearable device(s) 324-2 and some of the processing is performed on the remote computing device(s) 340-2. For example, the computing device(s) 370-2 on wearable device(s) 324-2 may have software 375-2 configured to encode ECG signal(s) measured using wearable device(s) 324-2. For example, software 375-2 may include an ECG denoising module 302 configured to use a trained encoder 302-1 to encode the ECG signal(s). Numeric encoding(s) of the ECG signal(s) may be transmitted to the remote computing device(s) 340-2, via communication network 332, for further processing. For example, an ECG denoising module 302 on software 345-2 may use an (optional) trained residual vector quantizer 302-2 and trained decoder 302-3 to process the numeric encoding(s) to obtain denoised ECG signal(s). Additionally or alternatively, the rhythm classification module 304 may take the numeric encoding(s) as input to classify rhythm types of segments of the ECG signal(s). Additionally or alternatively, the sample-level ECG labeling module 306 may take the numeric encoding(s) as input to generate sample-level ECG labels for the ECG signal(s).

Figure 3F:
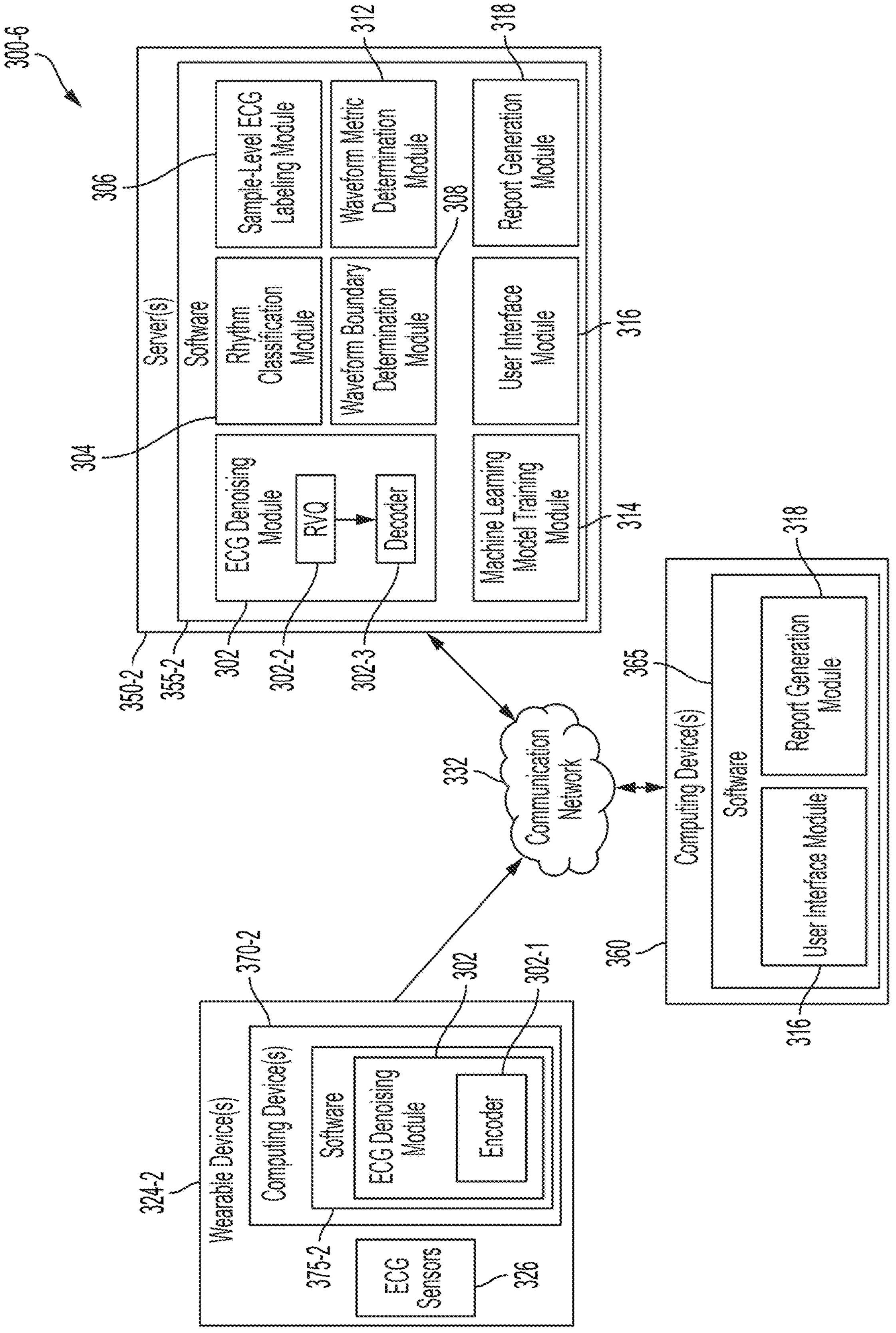

The one or more remote computing devices 340-2 may include one or more servers 350-2 and the one or more computing devices 360, as shown in the example system 300-6 of FIG. 3F. The server(s) 350-2 are configured to have software 355-2 execute thereon to perform functions relating to processing the ECG signals and generating a report comprising results of processing the ECG signals.

Figure 3G:
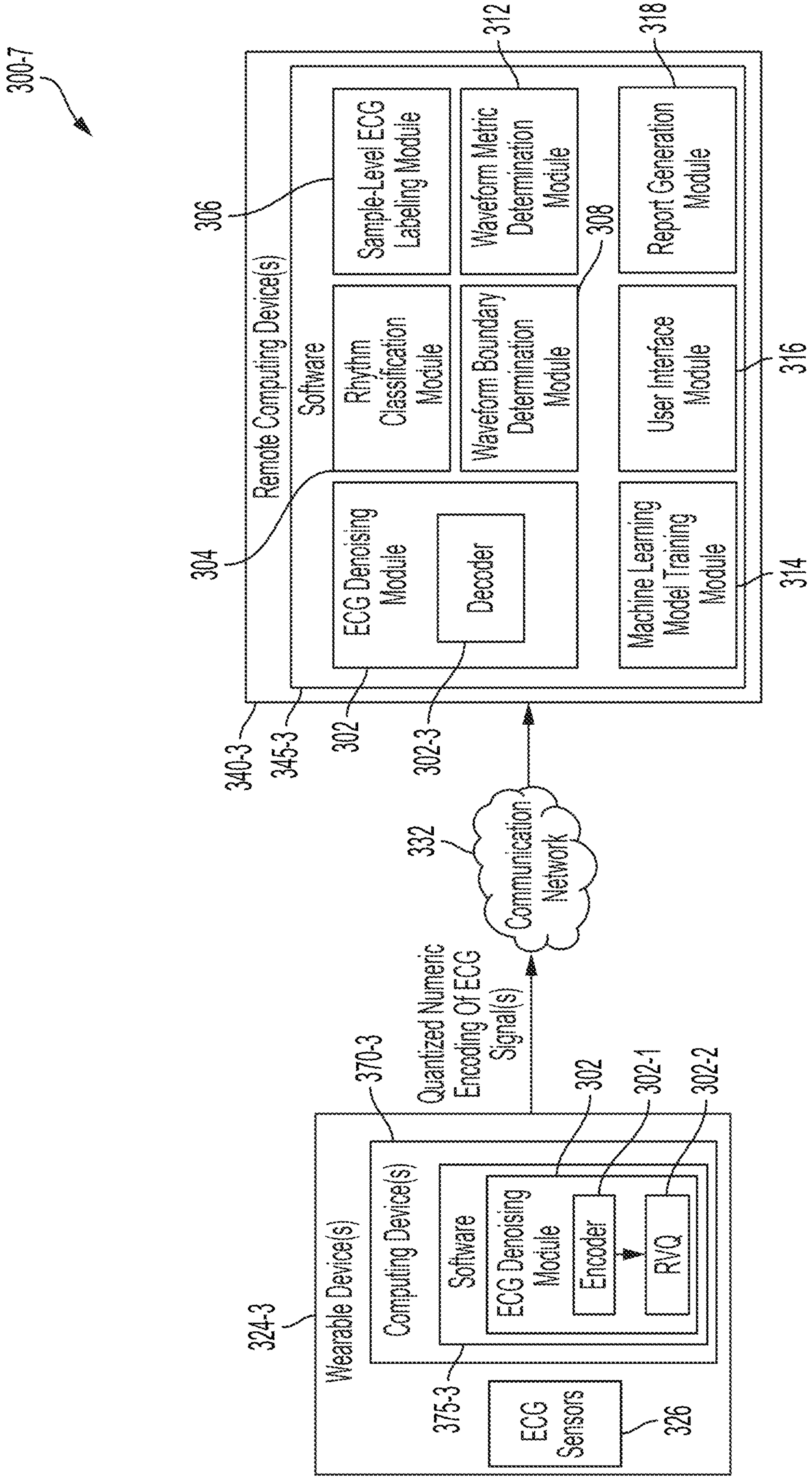

FIG. 3G shows another example system 300-7 where some of the processing is performed on the wearable device(s) 324-3 and some of the processing is performed on the remote computing device(s) 340-3. For example, the computing device(s) 370-3 on wearable device(s) 324-3 may have software 375-3 configured to (i) encode ECG signal(s) measured using wearable device(s) 324-3 to obtain numeric encoding(s) of the ECG signal(s) and (ii) quantize the numeric encoding(s). For example, software 375-3 may include an ECG denoising module 302 configured to use a trained encoder 302-1 to encode the ECG signal(s) and a trained RVQ 302-2 to quantize the numeric encoding(s). Quantizing the numeric encoding(s) has the effect of compressing the numeric encoding(s), thus making transmission and storage of the quantized numeric encodings more computationally efficient. This is important in the context of wearable devices, which have limited storage capacity. The quantized numeric encoding(s) may be transmitted to the remote computing device(s) 340-3, via communication network 332, for further processing. For example, an ECG denoising module 302 on software 345-3 may use a trained decoder 302-3 to process the quantized numeric encoding(s) to obtain denoised ECG signal(s). Additionally or alternatively, the rhythm classification module 304 may take the quantized numeric encoding(s) as input to classify rhythm types of segments of the ECG signal(s). Additionally or alternatively, the sample-level ECG labeling module 306 may take the quantized numeric encoding(s) as input to generate sample-level ECG labels for the ECG signal(s).

Figure 3H:
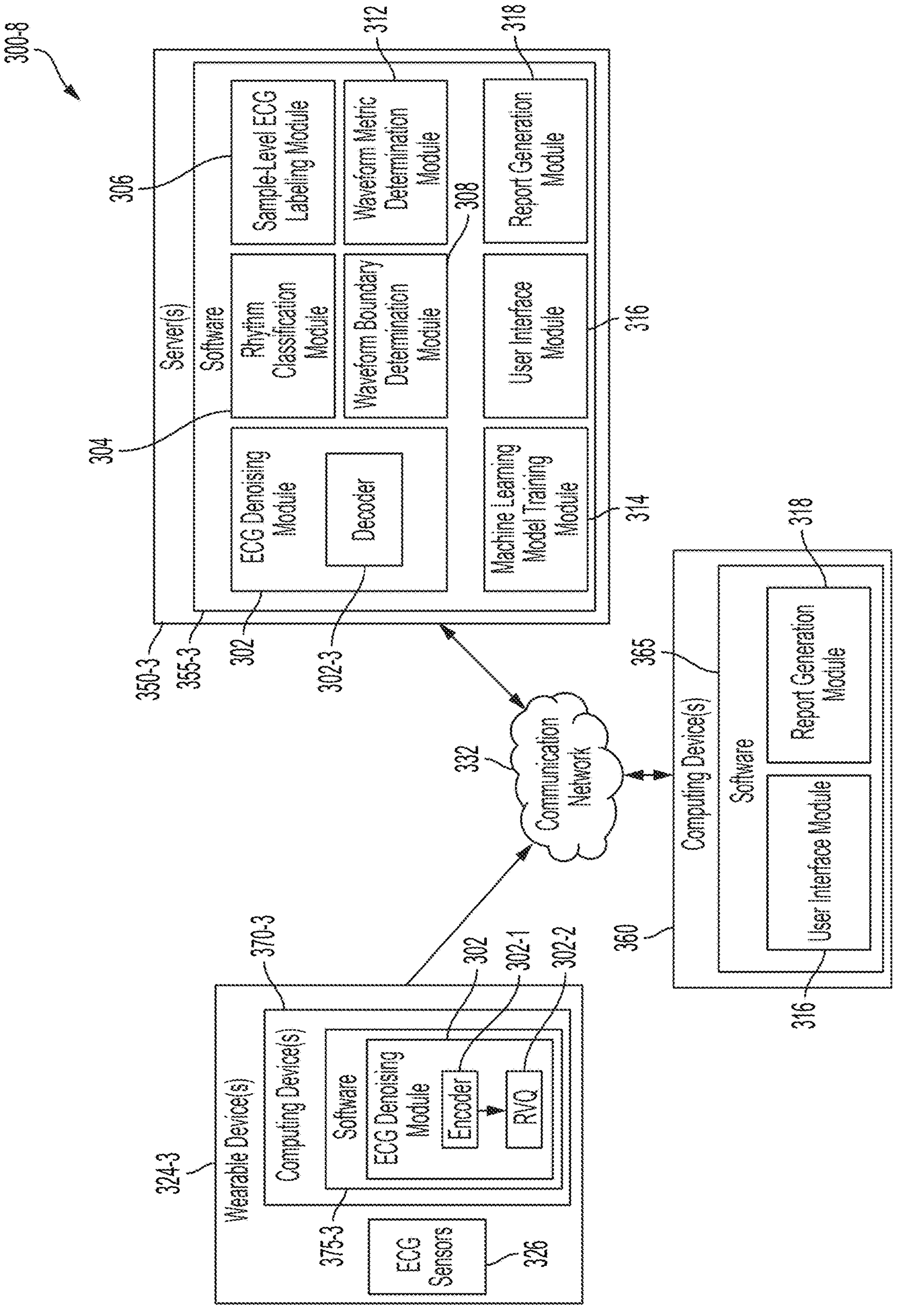

The one or more remote computing devices 340-3 may include one or more servers 350-3 and the one or more computing devices 360, as shown in the example system 300-8 of FIG. 3H. The server(s) 350-3 are configured to have software 355-3 execute thereon to perform functions relating to processing the ECG signals and generating a report comprising results of processing the ECG signals.

Figure 3I:
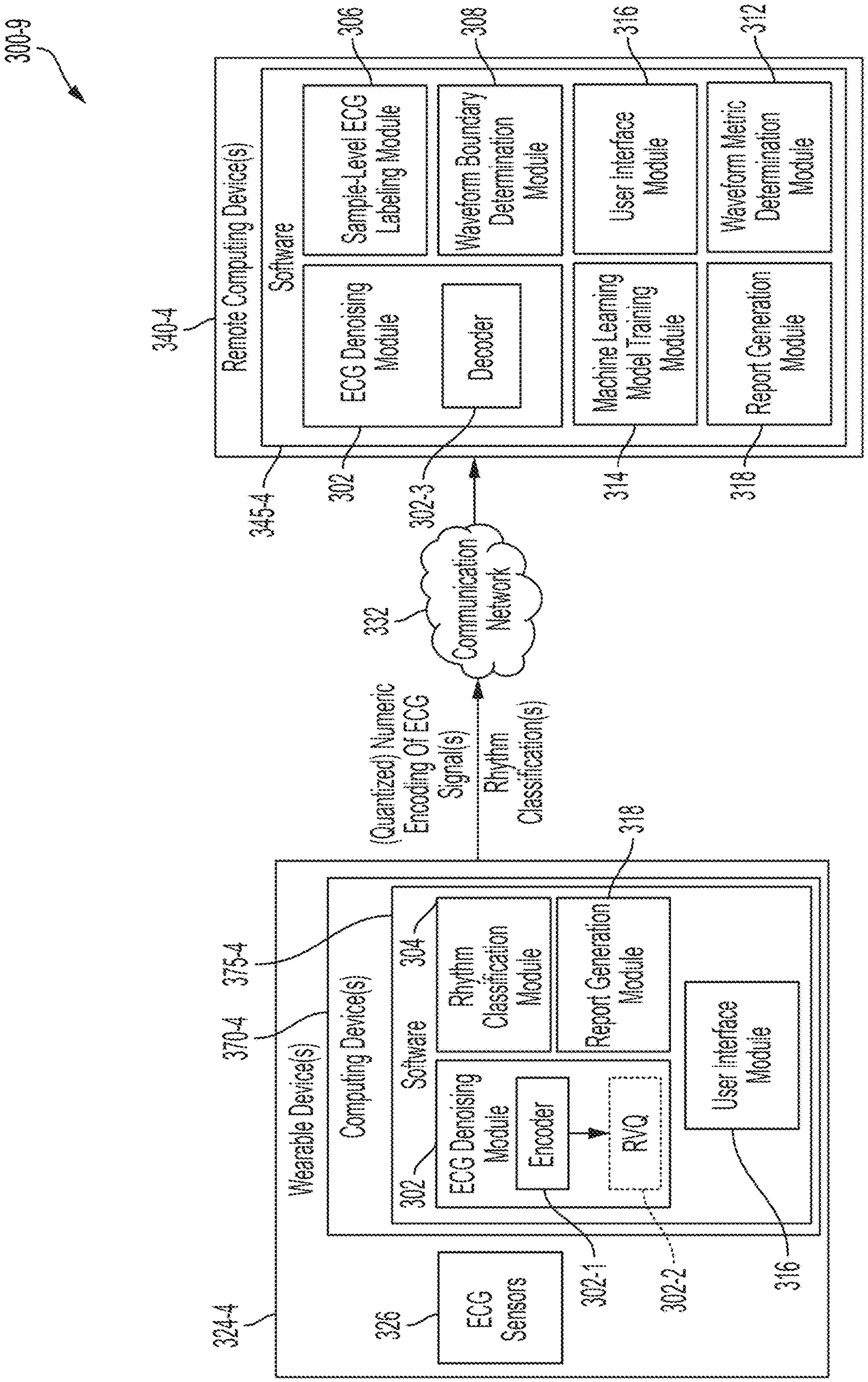

FIG. 3I shows another example system 300-9 where some of the processing is performed on the wearable device(s) 324-4 and some of the processing is performed on the remote computing device(s) 340-4. For example, the wearable device(s) 324-4 may be configured to perform rhythm classification, such that wearer(s) may be efficiently alerted to detected arrhythmias. Early and efficient detection of arrhythmias may prompt wearer(s) to seek medical attention that may be urgent. For example, the wearer may be treated with cardioversion or defibrillation, which are procedures used to put the heart back into a normal rhythm. As another example, the wearer may seek an evaluation from a clinician, who may diagnose the wearer and/or prescribe the wearer with subsequent treatments.

For example, the computing device(s) 370-4 on wearable device(s) 324-4 may have software 375-4 configured to (i) encode ECG signal(s) measured using wearable device(s) 324-4 to obtain numeric encoding(s) of the ECG signal(s) and (ii) optionally quantize the numeric encoding(s). For example, software 375-4 may include an ECG denoising module 302 configured to use a trained encoder 302-1 to encode the ECG signal(s) and optionally use a trained RVQ 302-2 to quantize the numeric encoding(s). The software 375-4 may additionally include rhythm classification module 304, which may process the numeric encoding(s) and/or quantized numeric encodings to classify rhythm types of segments of the ECG signal(s). The software 375-4 may additionally include report generation module 318 and user interface module 316, which may be configured to generate and output reports (e.g., notifications) of the rhythm types. For example, the wearable device(s) 324-4 may be configured to output a visual and/or sensory (e.g., sound, vibration, etc.) notification used to notify the wearer of an arrhythmia.

Additionally or alternatively, the numeric encoding(s) and/or quantized numeric encoding(s) may be transmitted to the remote computing device(s) 340-4, via communication network 332, for further processing. For example, an ECG denoising module 302 on software 345-4 may use a trained decoder 302-3 to process the numeric encoding(s) or quantized numeric encoding(s) to obtain denoised ECG signal(s). Additionally or alternatively, the sample-level ECG labeling module 306 may take the numeric encoding(s) or quantized numeric encoding(s) as input to generate sample-level ECG labels for the ECG signal(s).

Figure 3J:
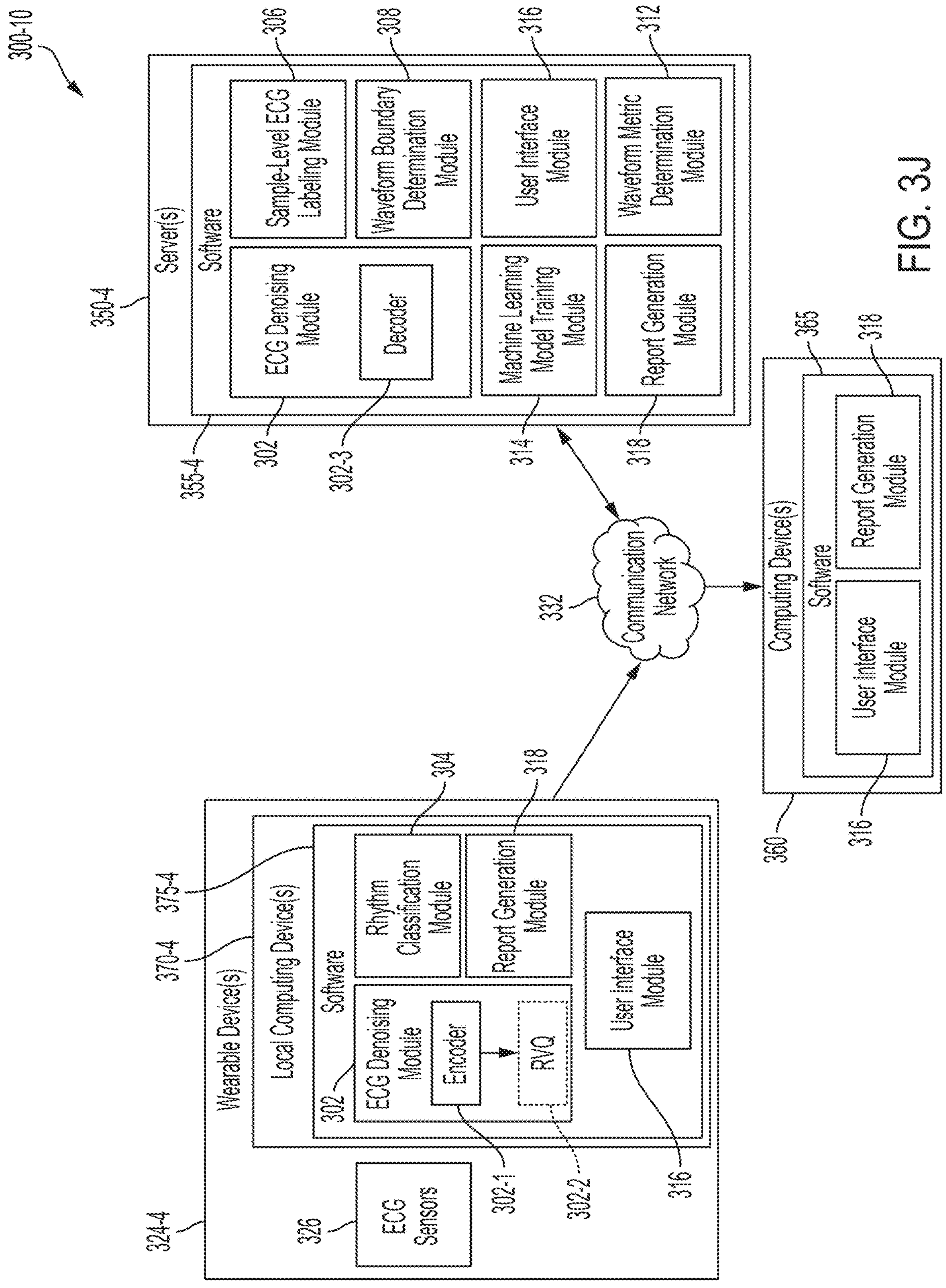

The one or more remote computing devices 340-4 may include one or more servers 350-4 and the one or more computing devices 360, as shown in the example system 300-10 of FIG. 3J. The server(s) 350-4 are configured to have software 355-4 execute thereon to perform functions relating to processing the ECG signals and generating a report comprising results of processing the ECG signals.

Figure 3K:
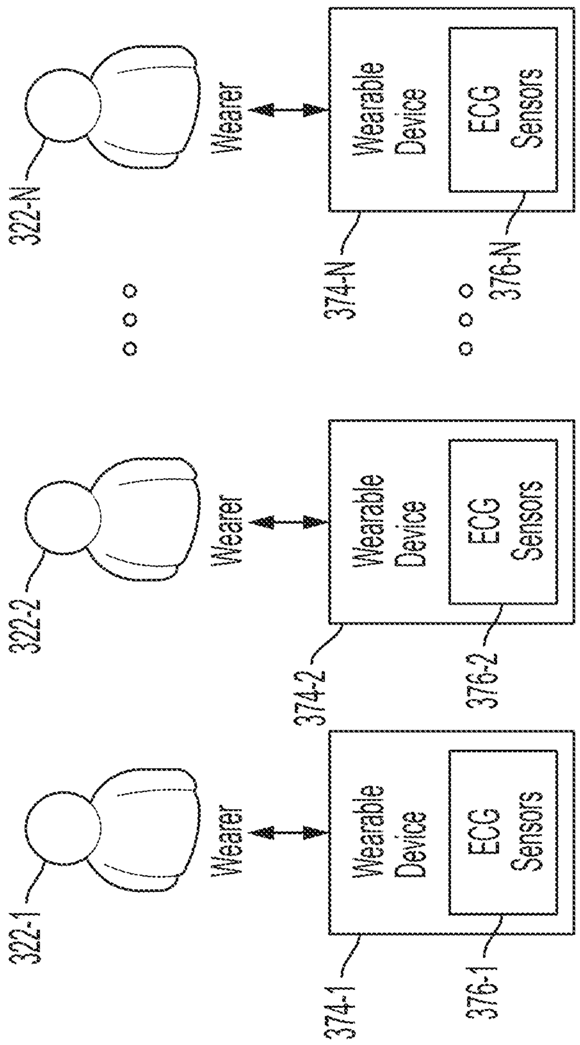
FIG. 3K shows an example of a system comprising multiple wearable devices worn by multiple wearers, according to some embodiments of the technology described herein.

FIG. 3K shows an example of a system comprising multiple wearable devices 374-1-374-N worn by multiple wearers 322-1-322-N, according to some embodiments of the technology described herein. Each wearable device may include respective ECG sensors 376-1-376-N. Each wearable device may be communicatively coupled to a respective one or more computing device. For example, the first wearable device 374-1 may be coupled to a first set of one or more computing devices, the second wearable device 374-2 may be coupled to a second set of one or more computing devices, and the Nth wearable device 374-N may be coupled to an Nth set of one or more computing devices. Additionally or alternatively, each wearable device may be communicatively coupled to the same set of one or more computing devices. For example, all of the wearable devices may be communicatively coupled to the same server.

Figure 4A:
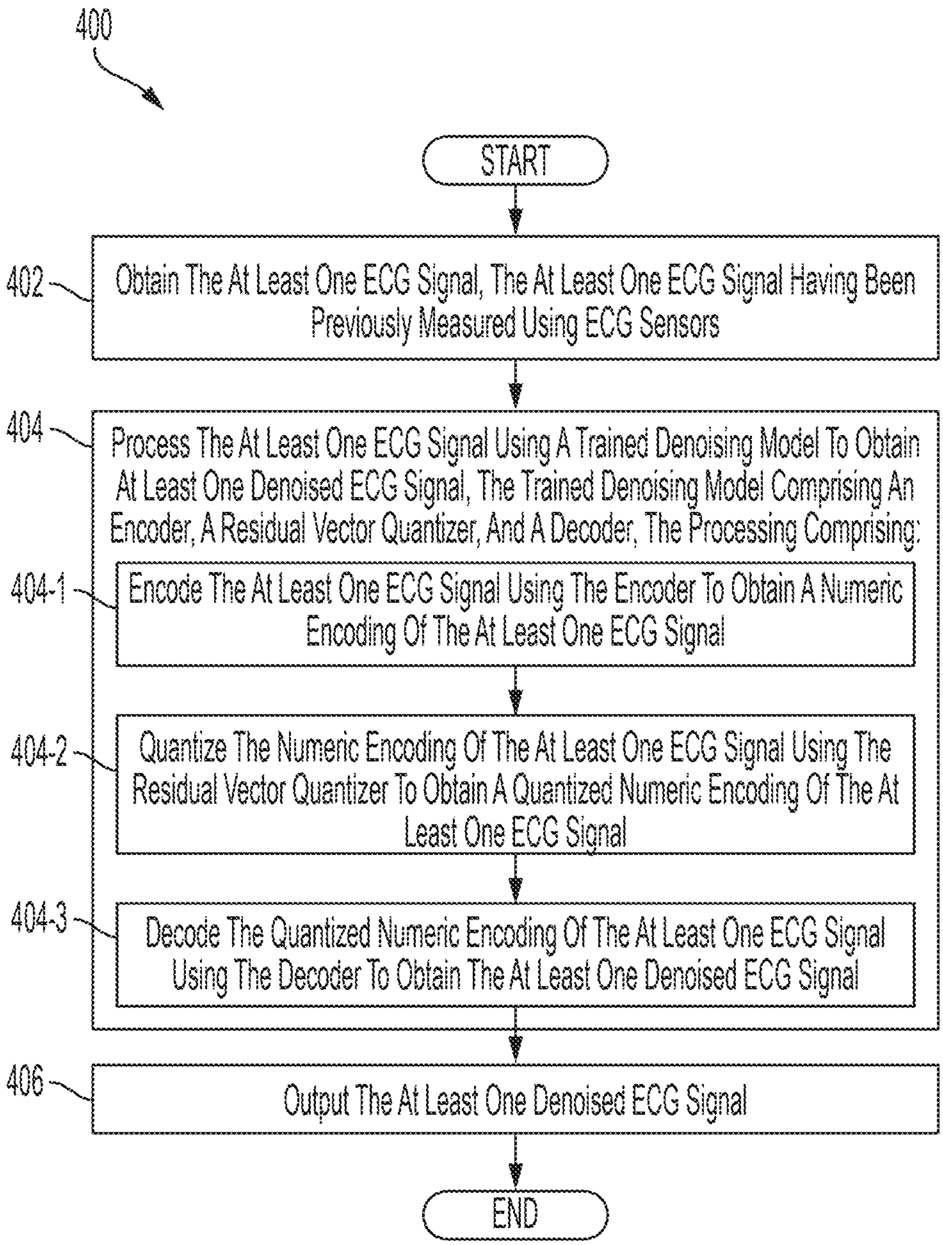
FIG. 4A is a flowchart of an illustrative process for denoising at least one ECG signal, according to some embodiments of the technology described herein.

Aspects of the technology described herein relate to denoising at least one ECG signal. FIG. 4A is a flowchart of an illustrative process 400 for denoising at least one ECG signal, according to some embodiments of the technology described herein. One or more of the acts of process 400 may be performed automatically by at least one wearable device, such as wearable device 104 described herein with respect to FIG. 1A. Additionally or alternatively, one or more of the acts of process 400 may be performed using any suitable computing device(s) such as, for example, a laptop computer, a desktop computer, a server, in a cloud computing environment, computing device(s) 110 described herein with respect to FIG. 1A, computing device(s) 310 described herein with respect to FIG. 3A, computing system 900 described herein with respect to FIG. 9, and/or in any other suitable way, as aspects of the technology described herein are not limited in this respect.

At act 402, at least one ECG signal is obtained. In some embodiments, the at least one ECG signal is measured or was previously measured using ECG sensors. Example techniques for obtaining at least one ECG signal are described herein including at least with respect to FIG. 1A. For example, the at least one ECG signal may include ECG signal(s) 108 shown in FIG. 1A, and the ECG sensors may include ECG sensors 106 shown in FIG. 1A.

At act 404, the at least one ECG signal is processed using a trained denoising model to obtain at least one denoised ECG signal. In some embodiments, the trained denoising model comprises an encoder, a residual vector quantizer (RVQ), and a decoder. For example, the trained denoising model may include the trained denoising model 120, described herein including at least with respect to FIG. 1B. In some embodiments, processing the at least on ECG signal includes performing acts 404-1, 404-2, and 404-3.

At act 404-1, the at least one ECG signal is encoded using the encoder to obtain a numeric encoding of the at least one ECG signal. Example techniques for encoding at least one ECG signal are described herein including at least with respect to FIG. 1B and FIGS. 5A-5C. For example, the at least one ECG signal may be processed using encoder 122 shown in FIG. 1B and/or encoder 502 shown in FIG. 5A.

At act 404-2, the numeric encoding of the at least one ECG signal is quantized using the RVQ to obtain a quantized numeric encoding of the least one ECG signal. Example techniques for quantizing a numeric encoding of at least one ECG signal are described herein including at least with respect to FIG. 1B and FIG. 5D. For example, the numeric encoding may be quantized using the RVQ 126 shown in FIG. 1B and/or the grouped RVQ 506 shown in FIG. 5D.

At act 404-3, the quantized numeric encoding of the at least one ECG signal is decoded using the decoder to obtain the at least one denoised ECG signal. Example techniques for decoding a quantized numeric encoding to obtain at least one denoised ECG signal are described herein including at least with respect to FIG. 1B and FIGS. 5E-5F. For example, the quantized numeric encoding may be decoded using the decoder 130 shown in FIG. 1B and/or the decoder 513 shown in FIG. 5E.

At act 406, the at least one denoised ECG signal is output. Example techniques for outputting at least one denoised ECG signal are described herein including at least with respect to FIG. 1A.

Figure 4B:
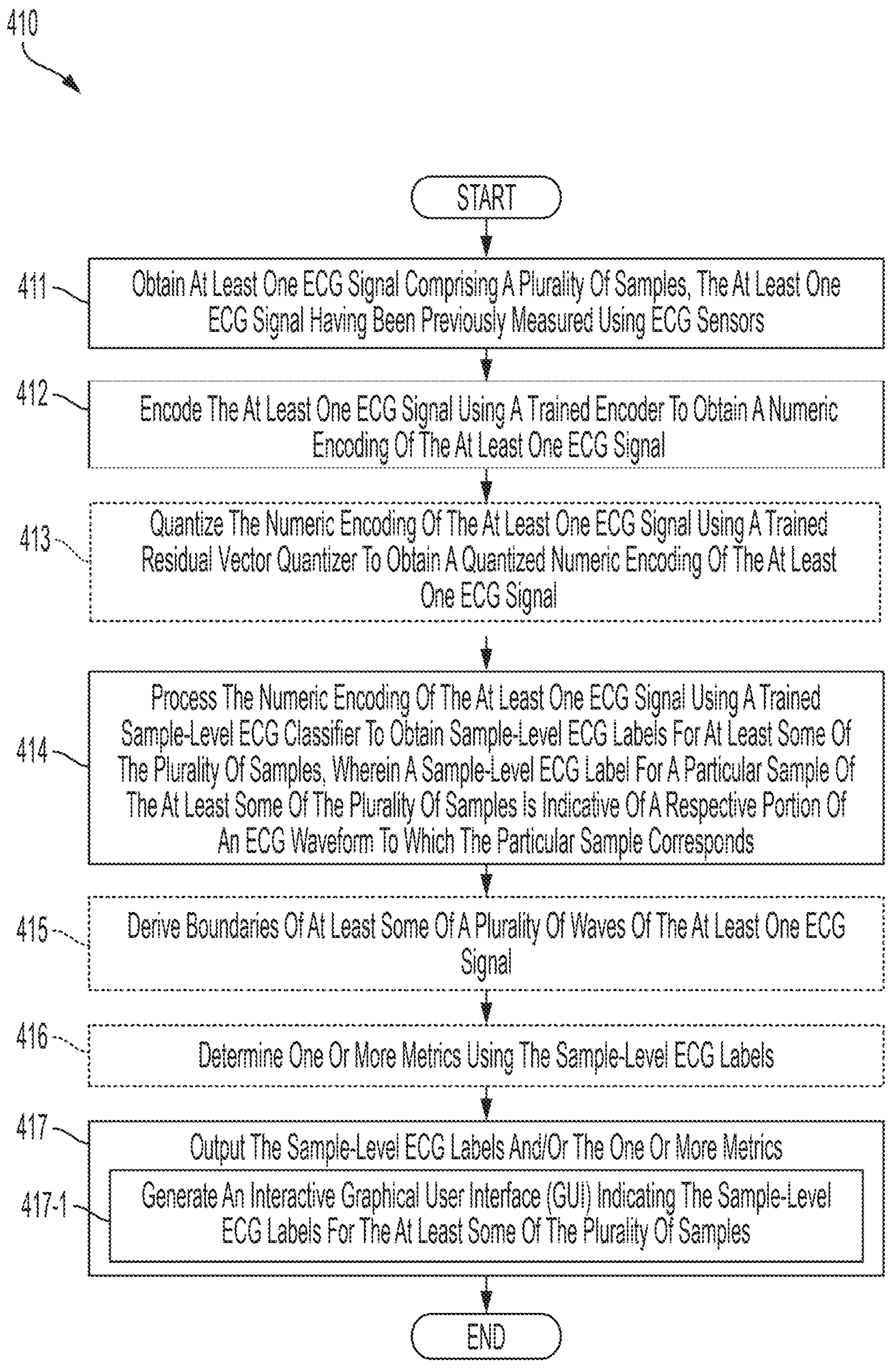
FIG. 4B is a flowchart of an illustrative process for labelling at least one ECG signal comprising a plurality of samples, according to some embodiments of the technology described herein.

Aspects of the technology described herein relate to determining sample-level ECG labels for samples at least one ECG signal. FIG. 4B is a flowchart of an illustrative process 410 for labelling at least one ECG signal comprising a plurality of samples, according to some embodiments of the technology described herein. One or more of the acts of process 410 may be performed automatically by at least one wearable device, such as wearable device 104 described herein with respect to FIG. 1A. Additionally or alternatively, one or more of the acts of process 410 may be performed using any suitable computing device(s) such as, for example, a laptop computer, a desktop computer, a server, in a cloud computing environment, computing device(s) 110 described herein with respect to FIG. 1A, computing device(s) 310 described herein with respect to FIG. 3A, computing system 900 described herein with respect to FIG. 9, and/or in any other suitable way, as aspects of the technology described herein are not limited in this respect.

At act 411, at least one ECG signal comprising a plurality of samples is obtained. In some embodiments, the at least one ECG signal is measured or was previously measured using ECG sensors. Example techniques for obtaining at least one ECG signal are described herein including at least with respect to FIG. 1A. For example, the at least one ECG signal may include ECG signal(s) 108 shown in FIG. 1A, and the ECG sensors may include ECG sensors 106 shown in FIG. 1A.

At act 412, the at least one ECG signal is encoded to obtain a numeric encoding of the at least one ECG signal. The at least one ECG signal is encoded using a trained encoder to obtain a numeric encoding of the at least one ECG signal. Example techniques for encoding at least one ECG signal are described herein including at least with respect to FIG. 1B and FIGS. 5A-5C. For example, the at least one ECG signal may be processed using encoder 122 shown in FIG. 1B and/or encoder 502 shown in FIG. 5A.

At (optional) act 413, the numeric encoding of the at least one ECG signal is quantized using a trained RVQ to obtain a quantized numeric encoding of the at least one ECG signal. Example techniques for quantizing a numeric encoding of at least one ECG signal are described herein including at least with respect to FIG. 1B and FIG. 5D. For example, the numeric encoding may be quantized using the RVQ 126 shown in FIG. 1B and/or the grouped RVQ 506 shown in FIG. 5D.

At act 414, the numeric encoding or the quantized numeric encoding of the at least one ECG signal is processed using a trained sample-level ECG classifier to obtain sample-level ECG labels for at least some of the plurality of samples. In some embodiments, a sample-level ECG label for a particular sample of the at least some of the plurality of samples is indicative of a respective portion of an ECG waveform to which the particular sample corresponds. Example techniques for processing a numeric encoding or quantized numeric encoding using a trained sample-level classifier are described herein including at least with respect to FIG. 1B, FIG. 1D, and FIG. 5H. For example, the numeric encoding or quantized numeric encoding may be processed using the sample-level ECG classifier 138 shown in FIG. 1B and/or the sample-level ECG classifier 518 shown in FIG. 5H. The sample-level ECG labels may include sample-level ECG labels 114-2 shown in FIG. 1D.

At (optional) act 415, boundaries of at least some of a plurality of waves of the at least one ECG signal are derived. Example techniques for deriving boundaries of at least some of a plurality of waves of an ECG signal are described herein including at least with respect to FIG. 1D. For example, the sample-level ECG labels 114-2, shown in FIG. 1D, may be used to derive boundaries 176, shown in FIG. 1D.

At (optional) act 416, one or more metrics are determined using the sample-level ECG labels. Example techniques for determining metrics of ECG waveforms are described herein including at least with respect to FIG. 1D. For example, the sample-level ECG labels 114-2 and/or boundaries 176, shown in FIG. 1D, may be used to determine metrics 180, shown in FIG. 1D. Examples of metrics of ECG waveforms are listed in Table 1.

At act 417, the sample-level ECG labels and/or the one or more metrics are output. Example techniques for outputting sample-level ECG labels and/or one or more metrics are described herein including at least with respect to FIG. 1A. Outputting the sample-level ECG labels and/or one or more metrics may include generating, at act 417-1, an interactive graphical user interface (GUI) indicating the sample-level ECG labels for the at least some of the plurality of samples.

Figure 4C:
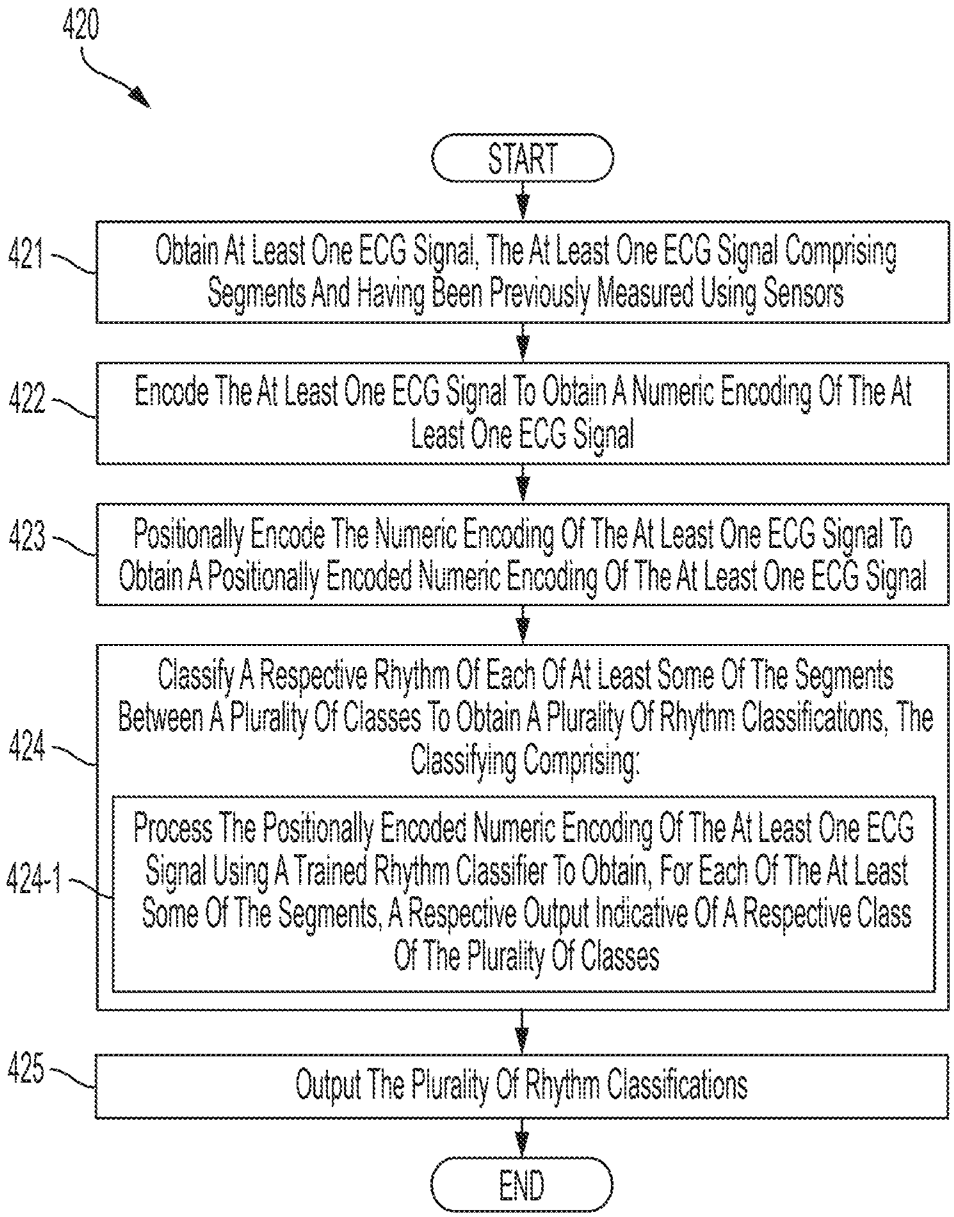
FIG. 4C is a flowchart of an illustrative process for classifying rhythms of segments of at least one ECG signal, according to some embodiments of the technology described herein.

FIG. 4C is a flowchart of an illustrative process 420 for classifying rhythms of segments of at least one ECG signal, according to some embodiments of the technology described herein. One or more of the acts of process 420 may be performed automatically by at least one wearable device, such as wearable device 104 described herein with respect to FIG. 1A. Additionally or alternatively, one or more of the acts of process 420 may be performed using any suitable computing device(s) such as, for example, a laptop computer, a desktop computer, a server, in a cloud computing environment, computing device(s) 110 described herein with respect to FIG. 1A, computing device(s) 310 described herein with respect to FIG. 3A, computing system 900 described herein with respect to FIG. 9, and/or in any other suitable way, as aspects of the technology described herein are not limited in this respect.

At act 421, at least one ECG signal is obtained. In some embodiments, the at least one ECG signal is measured or was previously measured using ECG sensors. Example techniques for obtaining at least one ECG signal are described herein including at least with respect to FIG. 1A. For example, the at least one ECG signal may include ECG signal(s) 108 shown in FIG. 1A, and the ECG sensors may include ECG sensors 106 shown in FIG. 1A.

At act 422, the at least one ECG signal is encoded to obtain a numeric encoding of the at least one ECG signal. Example techniques for encoding the at least one ECG signal are described herein including at least with respect to FIG. 1B and FIGS. 5A-5C. For example, the at least one ECG signal may be processed using encoder 122 shown in FIG. 1B and/or encoder 502 shown in FIG. 5A.

In some embodiments, encoding the at least one ECG signal at act 422 optionally includes quantizing the numeric encoding of the at least one ECG signal to obtain a quantized numeric encoding of the at least one ECG signal. Example techniques for quantizing a numeric encoding of at least one ECG signal are described herein including at least with respect to FIG. 1B and FIG. 5D. For example, the numeric encoding may be quantized using the RVQ 126 shown in FIG. 1B and/or the grouped RVQ 506 shown in FIG. 5D.

At act 423, the numeric encoding of the at least one ECG signal is positionally encoded to obtain a positionally encoded numeric encoding of the at least one ECG signal. For example, the numeric encoding may include the numeric encoding and/or the quantized numeric encoding. Example techniques for positionally encoding a numeric encoding are described herein including at least with respect to FIG. 1B. For example, the numeric encoding may be positionally encoded using act 132 shown in FIG. 1B to obtain positionally-encoded numeric encoding 134 shown in FIG. 1B.

At act 424, a respective rhythm of each of at least some of the segments of the at least one ECG signal is classified between a plurality of classes to obtain a plurality of rhythm classifications. In some embodiments, the plurality of classes includes a respective class for each rhythm type (e.g., selected from a normal sinus type, an atrial fibrillation type, an atrial flutter type, a premature atrial contraction (PAC) type, and/or a premature ventricular contraction (PVC) type). In some embodiments, the plurality of classes includes a first class corresponding to a normal sinus rhythm type and second class corresponding to an arrhythmia of any type (e.g., an atrial fibrillation type, an atrial flutter type, a premature atrial contraction (PAC) type, and/or a premature ventricular contraction (PVC) type). In some embodiments, the plurality of classes include a first class corresponding to a first rhythm type, and a second class corresponding to any rhythm type that is not the first rhythm type. In some embodiments, the plurality of rhythm types include a normal sinus type, an atrial fibrillation type, an atrial flutter type, a premature atrial contraction (PAC) type, or a premature ventricular contraction (PVC) type, or combinations thereof. In some embodiments, classifying the rhythms at act 424 includes performing act 424-1.

At act 424-1, the positionally encoded numeric encoding of the at least one ECG signal is processed using a trained rhythm classifier to obtain, for each of the at least some of the segments, a respective output indicative of a class of the plurality of classes. Example techniques for classifying rhythms using a rhythm classifier are described herein including at least with respect to FIG. 1B, FIG. 1C, and FIG. 5G. For example, the rhythms may be classified using rhythm classifier 136 shown in FIG. 1B and/or rhythm classifier 516 shown in FIG. 5G.

At act 425, the plurality of rhythm classifications is output. Example techniques for outputting a plurality of rhythm classifications are described herein including at least with respect to FIG. 1A.

It should be appreciated that aspects of the technology described herein may include performing (e.g., by at least one processor) any combination of the processes 400, 410, and 420 shown in FIGS. 4A-4C.

Figure 4D:
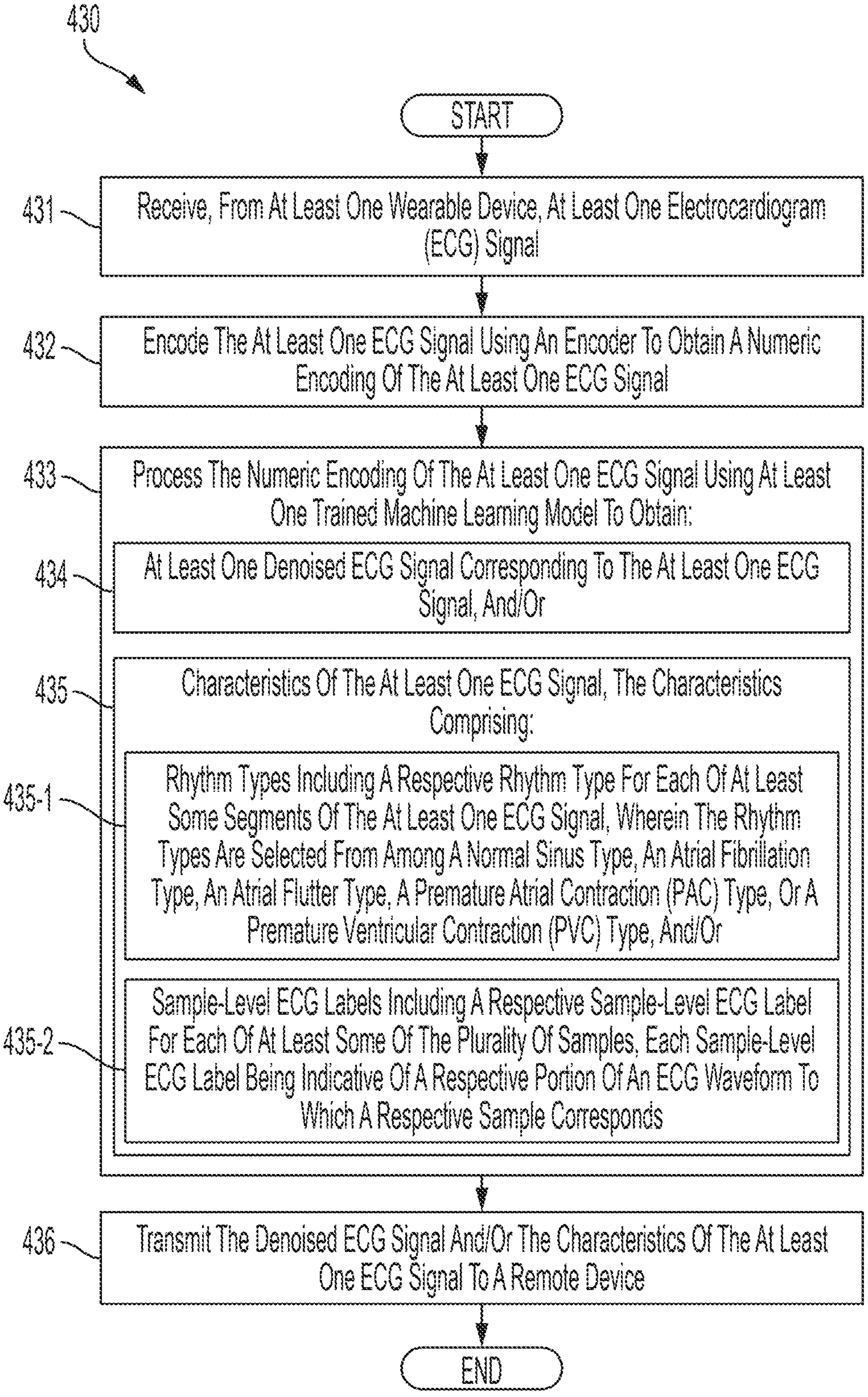
FIG. 4D is a flowchart of an illustrative process for analyzing at least one ECG signal on a server, according to some embodiments of the technology described herein.

Aspects of the technology described herein relate to communications between at least one wearable device and a server. FIG. 4D is a flowchart of an illustrative process 430 for analyzing at least one ECG signal on a server, according to some embodiments of the technology described herein. One or more of the acts of process 430 may be performed automatically by at least one wearable device, such as wearable device 104 described herein with respect to FIG. 1A. Additionally or alternatively, one or more of the acts of process 430 may be performed using any suitable computing device(s) such as, for example, a laptop computer, a desktop computer, a server, in a cloud computing environment, computing device(s) 110 described herein with respect to FIG. 1A, computing device(s) 310 described herein with respect to FIG. 3A, computing system 900 described herein with respect to FIG. 9, and/or in any other suitable way, as aspects of the technology described herein are not limited in this respect.

At act 431, at least one ECG signal is received from a wearable device. In some embodiments, the at least one ECG signal was previously measured using ECG sensors on the wearable device. Example techniques for measuring and receiving at least one ECG signal are described herein including at least with respect to FIG. 1A. For example, the at least one ECG signal may include ECG signal(s) 108 shown in FIG. 1A, and the wearable device may include wearable device 104 shown in FIG. 1A.

At act 432, the at least one ECG signal is encoded using an encoder to obtain a numeric encoding of the at least one ECG signal. Example techniques for encoding the at least one ECG signal are described herein including at least with respect to FIG. 1B and FIGS. 5A-5C. For example, the at least one ECG signal may be processed using encoder 122 shown in FIG. 1B and/or encoder 502 shown in FIG. 5A.

In some embodiments, encoding the at least one ECG signal at act 432 optionally includes quantizing the numeric encoding of the at least one ECG signal to obtain a quantized numeric encoding of the at least one ECG signal. Example techniques Example techniques for quantizing a numeric encoding of at least one ECG signal are described herein including at least with respect to FIG. 1B and FIG. 5D. For example, the numeric encoding may be quantized using the RVQ 126 shown in FIG. 1B and/or the grouped RVQ 506 shown in FIG. 5D.

At act 433, the numeric encoding of the at least one ECG signal is processed using at least one trained machine learning model to obtain (i) at least one denoised ECG signal 434 corresponding to the at least one ECG signal, and/or (ii) characteristics 435 of the at least one ECG signal. In some embodiments, the characteristics 435 comprise: (i) rhythm types 435-1 indicating a respective rhythm type for each of at least some segments of the at least one ECG signal, and/or (ii) sample-level ECG labels 435-2 including a respective sample-level ECG label for each of at least some of the plurality of samples.

At act 436, the denoised ECG signal and/or the characteristics of the at least one ECG signal are transmitted to a remote device. For example, the at denoised ECG signal and/or characteristics may be transmitted to the wearable device so that they can be viewed by a wearer of the wearable device. Additionally or alternatively, the denoised ECG signal and/or characteristics may be transmitted to any other suitable device such as, for example, the device of a technician who reviews (e.g., validates and/or edits) the denoised ECG signal and/or characteristics.

It should be appreciated that aspects of process 430 may include performing (e.g., by at least one processor) any combination of the processes 400, 410, and 420 shown in FIGS. 4A-4C. For example, any combination of processes 400, 410, and 420 may be performed, and the result(s) of processing may be transmitted to the remote device at act 436. Additionally or alternatively, the remote device may be configured to perform any combination of processes 400, 410, and 420.

Figure 4E:
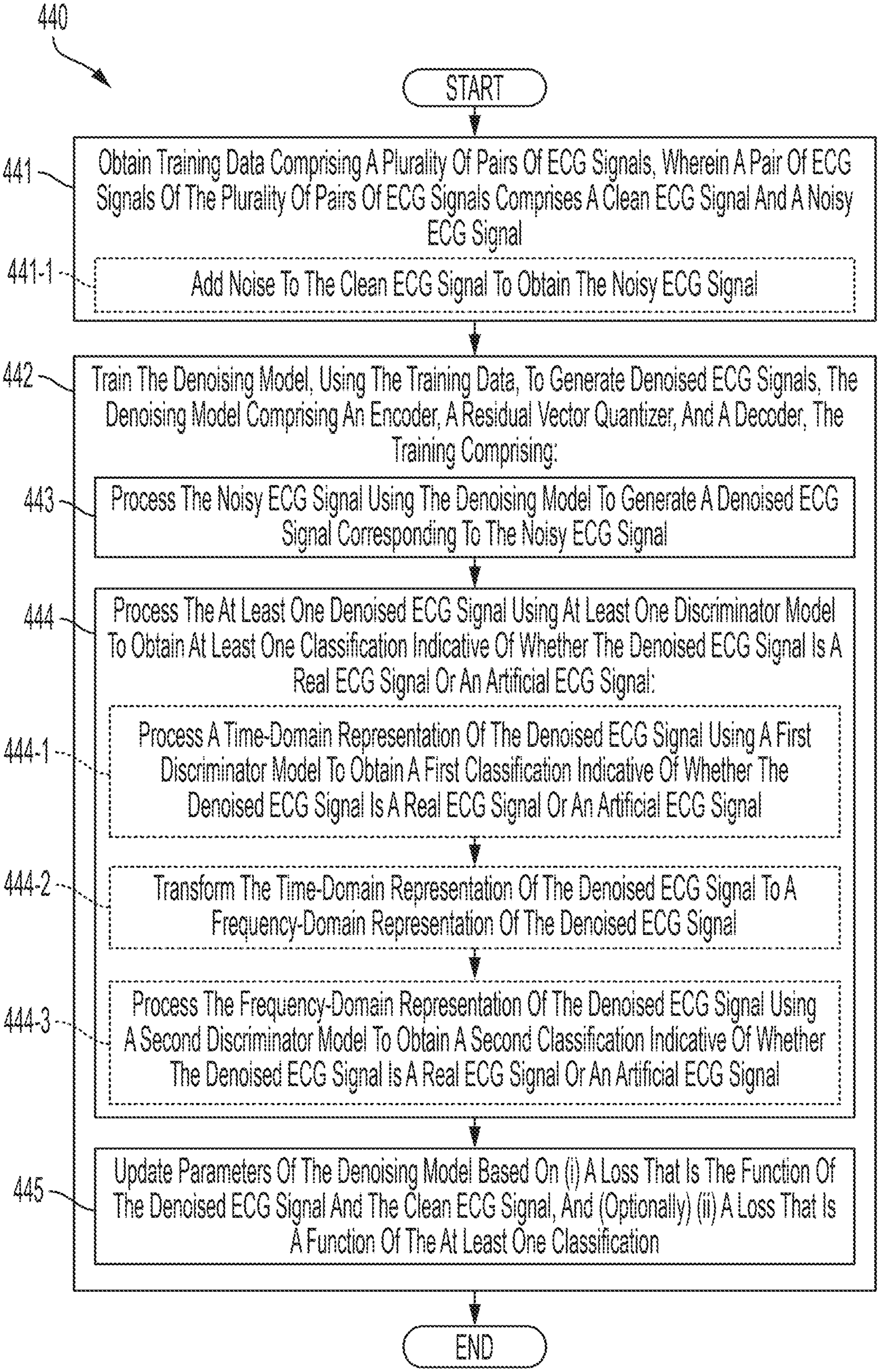
FIG. 4E is a flowchart of an illustrative process for training a denoising model to denoise at least one ECG signal, according to some embodiments of the technology described herein.

Aspects of the technology described herein relate to training at least one denoising model to denoise at least one ECG signal. FIG. 4E is a flowchart of an illustrative process 440 for training a denoising model to denoise at least one ECG signal, according to some embodiments of the technology described herein. One or more of the acts of process 440 may be performed automatically by at least one wearable device, such as wearable device 104 described herein with respect to FIG. 1A. Additionally or alternatively, one or more of the acts of process 440 may be performed using any suitable computing device(s) such as, for example, a laptop computer, a desktop computer, a server, in a cloud computing environment, computing device(s) 110 described herein with respect to FIG. 1A, computing device(s) 310 described herein with respect to FIG. 3A, computing system 900 described herein with respect to FIG. 9, and/or in any other suitable way, as aspects of the technology described herein are not limited in this respect.

At act 441, training data comprising a plurality of pairs of ECG signals is obtained. In some embodiments, a pair of ECG signals of the plurality of pairs of ECG signals comprises a clean ECG signal and a noisy ECG signal. Example techniques for obtaining and pre-processing training data are described herein including at least with respect to FIG. 2. For example, as shown in FIG. 2, clean ECG signals 202 may be obtained and pre-processed at act 204 to obtain training data 206 comprising a plurality of pairs of ECG signals.

In some embodiments, act 441 includes act 441-1. At act 441-1, noise is added to the clean ECG signal to obtain the noisy ECG signal. For example, the noise may be added as part of pre-processing clean ECG signals to obtain training data. Example techniques for pre-processing clean ECG signals are described herein including at least with respect to act 204 shown in FIG. 2.

At act 442, the denoising model is trained using the training data to generate denoised ECG signals. In some embodiments, the denoising model comprises an encoder, an RVQ, and a decoder. In some embodiments, act 442 includes acts 443, 444, and 445.

At act 443, the noisy ECG signal is processed using the denoising model to generate a denoised ECG signal corresponding to the noisy ECG signal. Example techniques for processing a noisy ECG signal using a denoising model are described herein including at least with respect to FIG. 2. For example, as shown in FIG. 2, a noisy ECG signal 210 may be processed using denoising model 212 to obtain denoised ECG signal 220.

At act 444, the at least one denoised ECG signal is processed using at least one discriminator model to obtain at least one classification indicative of whether the denoised ECG signal is a real ECG signal or an artificial ECG signal. In some embodiments, act 444 includes acts 444-1, 444-2, and 444-3.

At act 444-1, a time-domain representation of the denoised ECG signal is processed using a first discriminator model to obtain a first classification indicative of whether the denoised ECG signal is a real ECG signal or an artificial ECG signal. Example techniques for processing a time-domain representation of a denoised ECG signal using a first discriminator model are described herein including at least with respect to FIG. 2, FIG. 5I-1, and FIG. 5I-2. For example, a time-domain representation of a denoised ECG signal may be processed using the first discriminator model 222 shown in FIG. 2 and/or the discriminator 521 shown in FIG. 5I-1 and FIG. 5I-2.

At act 444-2, the time-domain representation of the denoised ECG signal is transformed to a frequency-domain representation of the denoised ECG signal. Example techniques for transforming a time-domain representation to a frequency-domain representation are described herein including at least with respect to act 228 shown in FIG. 2. For example, the time-domain representation may be transformed to a frequency-domain representation by determining the short-time Fourier transform of the time-domain representation.

At act 444-3, the frequency-domain representation of the denoised ECG signal is processed using a second discriminator model to obtain a second classification indicative of whether the denoised ECG signal is a real ECG signal or an artificial ECG signal. Example techniques for processing a frequency-domain representation of a denoised ECG signal using a second discriminator model are described herein including at least with respect to FIG. 2 and FIGS. 5J-5K. For example, a frequency-domain representation of a denoised ECG signal may be processed using the second discriminator model 232 shown in FIG. 2 and/or the STFT discriminator 525 shown in FIG. 5J.

At act 445, parameters of the denoising model are updated based on (i) a loss that is the function of the denoised ECG signal and the clean ECG signal, and (ii) a loss that is a function of the at least one classification. Example techniques for determining loss are described herein including at least with respect to acts 226 and 236 shown in FIG. 2. Example techniques for updating parameters of at least on denoising model are described herein including at least with respect to act 238 shown in FIG. 2.

Additionally or alternatively, parameters of the first discriminator model are updated based on the first classification indicative of whether the denoised ECG signal is a real ECG signal or an artificial ECG signal, as determined at act 444-1. Example techniques for training the first discriminator model (e.g., updating parameters of the first discriminator model) are described herein including at least with respect to FIG. 2.

Additionally or alternatively, parameters of the second discriminator model are updated based on the second classification indicative of whether the denoised ECG signal is a real ECG signal or an artificial ECG signal, as determined at act 444-3. Example techniques for training the second discriminator model (e.g., updating parameters of the second discriminator model) are described herein including at least with respect to FIG. 2.

Figure 5A:
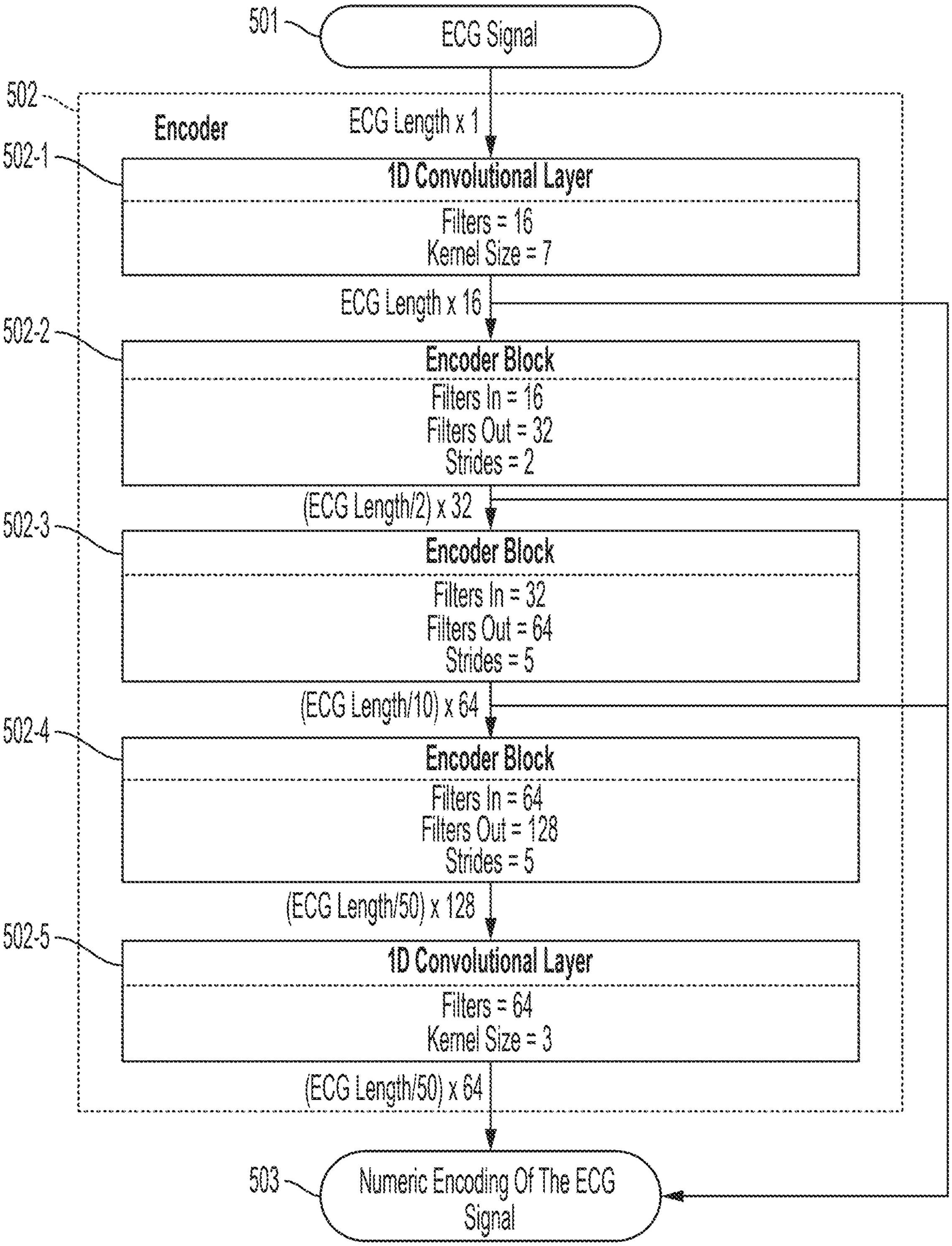
FIG. 5A shows an example architecture of an encoder (e.g., encoder 122 shown in FIG. 1B) used to obtain a numeric encoding of an ECG signal, according to some embodiments of the technology described herein.

FIG. 5A shows an example architecture of an encoder 502 used to obtain a numeric encoding of an ECG signal, according to some embodiments of the technology described herein. As shown in FIG. 5A, the encoder 502 comprises encodings from multiple layers, including one or more convolutional layers and/or one or more encoder layers. The encoder 502 includes multiple encoder layers (e.g., encoder blocks 502-2, 502-3, 502-4) at different resolutions. For example, the encoder 502 includes multiple encoder layers at progressively increased resolutions. The encoder 502 includes skip connections such that the numeric encoding 503 receives inputs from layers at resolutions that are not the final resolution.

The encoder 502 receives ECG signal 501 and processes the ECG signal 501 using the layers shown in FIG. 5A to obtain a numeric encoding 503 of the ECG signal 501. In some embodiments, the encoder 502 includes at least 100, 000 parameters, at least 150,000 parameters, at least 200,000 parameters, at least 250,000 parameters, at least 300,000 parameters, at least 350,000 parameters, at least 400,000 parameters, at least 450,000 parameters, at least 500,000 parameters, or at least any other suitable number of parameters. In some embodiments, the encoder 502 includes at most 1 million parameters, at most 950,000 parameters, at most 900,000 parameters, at most 850,000 parameters, at most 800,000 parameters, at most 750,000 parameters, at most 700,000 parameters, at most 650,000 parameters, at most 600,000 parameters, at most 550,000 parameters, at most 500,000 parameters, at most 450,000 parameters, at most 400,000 parameters, or at most any other suitable number of parameters. For example, the encoder 502 may have 456,416 trainable parameters and 672 non-trainable parameters. It should be appreciated that any of the above-listed upper bounds may be coupled with any of the above-listed lower bounds. In some embodiments, a hyperparameter of the encoder 502 includes the learning rate for the denoising model of which the encoder 502 is part.

As shown in FIG. 5A, the encoder 502 is configured to receive an ECG signal 501 as input. For example, the ECG signal 501 may include a plurality of samples that may have been obtained by digitizing the ECG signal. The ECG signal 501 may be a vector comprising the plurality of samples. In some embodiments, the ECG signal 501 is resampled prior to processing using the encoder 502. For example, the ECG signal 501 may be resampled to a sampling rate of 250 Hz. Example techniques for resampling an ECG signal are described herein including at least with respect to FIG. 1B.

The length of the ECG signal 501 may vary depending on the duration over which the ECG signal 501 was measured. For example, an ECG signal measured over a duration of a few seconds will be shorter than an ECG signal measured over a duration of multiple days. If the ECG signal 501 is shorter than a threshold length, then the end of the ECG signal 501 may be padded with zeros. In some embodiments, the ECG signal 501 represents a segment of a longer ECG signal that has been divided into multiple segments. For example, the longer ECG signal may have been divided into segments of equal length, and each of the segments may be separately processed using the encoder 502.

In some embodiments, the ECG signal 501 is provided as input to a 1D convolutional layer 502-1. As an example, the 1D convolutional layer 502-1 may have 16 filters, a kernel size of 7, and a padding of "same." The 1D convolutional layer 502-1 may use any suitable activation function such as, for example, exponential linear unit (ELU).

The output of the 1D convolutional layer 502-1 may be coupled to a series of three encoder blocks 502-2, 502-3, and 502-4. As an example, the first encoder block 502-2 may have 16 filters, 32 filters out, and a stride of 2. The first encoder block 502-2 may be coupled to the second encoder block 502-3. As an example, the second encoder block 502-3 may have 32 filters in, 64 filters out, and a stride of 5. The second encoder block 502-3 may be coupled to the third encoder block 502-4. As an example, the third encoder block 502-4 may have 64 filters in, 128 filters out, and a stride of 5. An example implementation of an encoder block 504 is described herein including at least with respect to FIG. 5B.

The output of the third encoder block 502-4 may be coupled to a 1D convolutional layer 502-5. As an example, the 1D convolutional layer 502-5 may have 64 filters, a kernel size of 3, and a padding of "same."

The output of the encoder 502 may include a numeric encoding 503 of the ECG signal. For example, the numeric encoding 503 may include a list of outputs from each of the layers 502-1, 502-2, 502-3, 502-4, and 502-5. For example, the outputs may be listed in the order that they were created.

It should be appreciated that there may be variations of the architecture of the encoder 502 shown in FIG. 5A. For example, in a first variation, the encoder 502 may include two encoder blocks, instead of three encoder blocks, and the dimensions of the output of the 1D convolutional layer 502-5 may be (ECG Length/10)×64.

In a second variation, the encoder 502 may include four encoder blocks (e.g., encoder blocks 502-2, 502-3, 502-4 plus an additional encoder block). As an example, the fourth encoder block may have a stride of 5 and output dimensions of (ECG length/250)×256, and the output dimensions of the 1D convolutional layer 502-5 may be (ECG Length/250)×256.

In a third variation, the number of filters for each encoder block may be varied. For example, the encoder block 502-2 may have 8 filters in and 16 filters out, the encoder block 502-3 may have 16 filters in and 32 filters out, and the encoder block 502-4 may have 32 filters in and 64 filters out. Alternatively, the encoder block 502-2 may have 32 filters in and 64 filters out, the encoder block 502-3 may have 64 filters in and 128 filters out, and the encoder block 502-4 may have 128 filters in and 256 filters out.

In a fourth variation, the number of strides of the encoder blocks may be varied. For example, the encoder blocks 502-2, 502-3, and 502-4 may have strides of 2, 4, or 5.

Figure 5B:
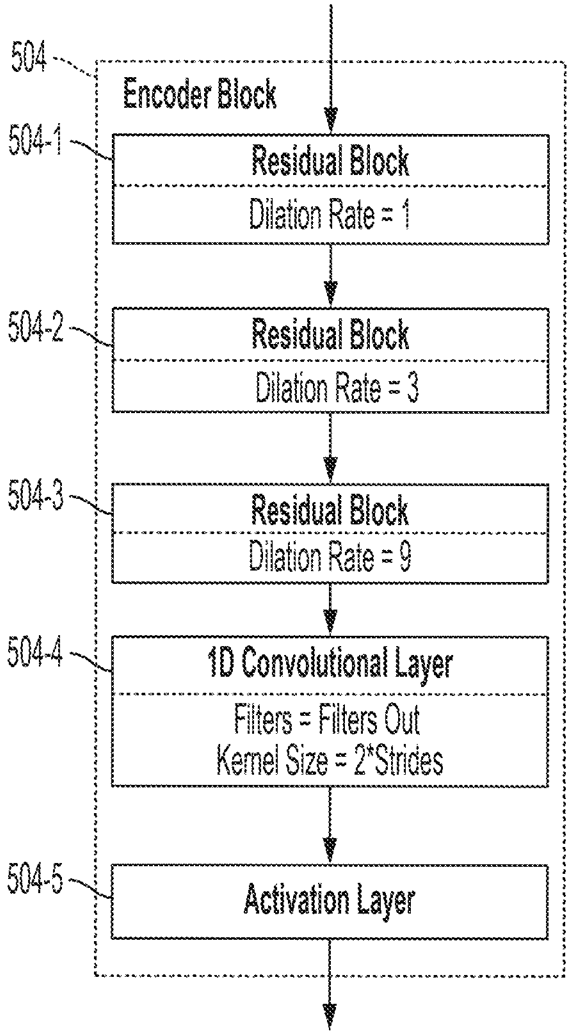
FIG. 5B shows an example architecture of an encoder block of the encoder shown in FIG. 5A, according to some embodiments of the technology described herein.

FIG. 5B shows an example architecture of an encoder block 504 of the encoder 502 shown in FIG. 5A, according to some embodiments of the technology described herein. For example, each of the encoder blocks 502-2, 502-3, and 502-4, shown in FIG. 5A, may be implemented as encoder block 504. Additionally or alternatively, the encoder block 513-8, shown in FIG. 5E, may be implemented as encoder block 504. Additionally or alternatively, the encoder block 516-3, shown in FIG. 5G, may be implemented as encoder block 504. Additionally or alternatively, the encoder block 518-8, shown in FIG. 5H, may be implemented as encoder block 504. Thus, the value of the variable "filters in," may depend on the value of the "filters in" for the specific encoder block being implemented.

As shown in FIG. 5B, the input to the encoder block is processed using a series of residual blocks 504-1, 504-2, and 504-3. As an example, the first residual block 504-1 may have a dilation rate of 1, a number of filters equal to "filters in," and a kernel size of 7. The first residual block 504-1 may be coupled to the second residual block 504-2. As an example, the second residual block 504-2 may have a dilation rate of 3, a number of filters equal to "filters in," and a kernel size of 7. The second residual block 504-2 may be coupled to the third residual block 504-3. As an example, the third residual block 504-3 may have a dilation rate of 9, a number of filters equal to "filters in," and a kernel size of 7. An example implementation of a residual block 505 is described herein including at least with respect to FIG. 5C.

The output of the third residual block 504-3 may be coupled to 1D convolutional layer 504-4. As an example, the 1D convolutional layer 504-4 may have a kernel size of (2*strides), a number of filters equal to "filters out," a number of strides equal to "strides," and a padding equal to "same." The 1D convolutional layer 504-4 may use any suitable activation function such as, for example, ELU.

The output of the 1D convolutional layer 504-4 may be coupled to an activation layer 504-5. The activation layer 504-5 may use any suitable activation function (e.g., ELU, sigmoid linear unit (SiLU), rectified linear unit (ReLU), leaky ReLU, hyperbolic tangent, softmax, etc.).

Figure 5C:
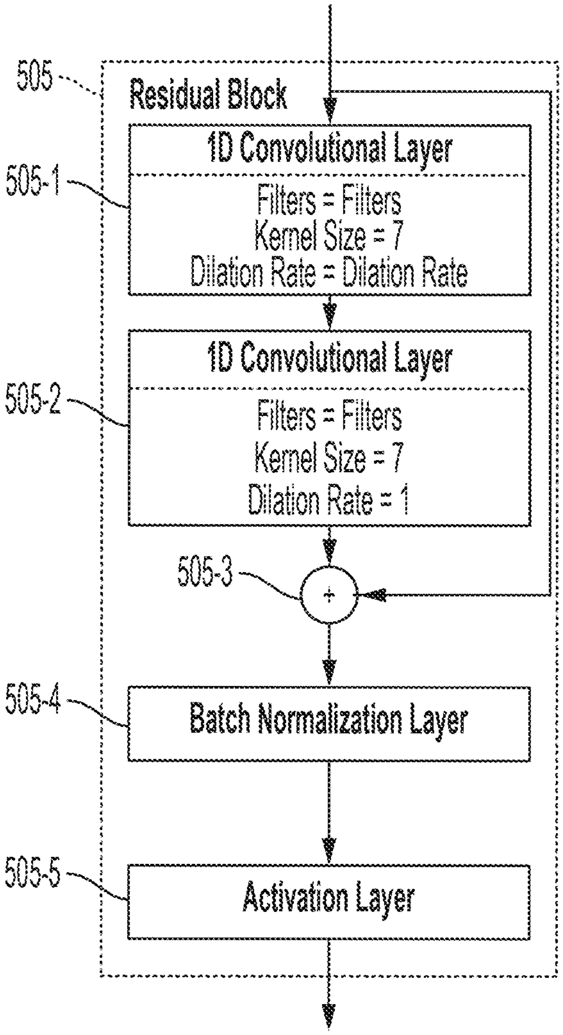
FIG. 5C shows an example architecture of a residual block of the encoder shown in FIG. 5A, according to some embodiments of the technology described herein.
Figure 5D:
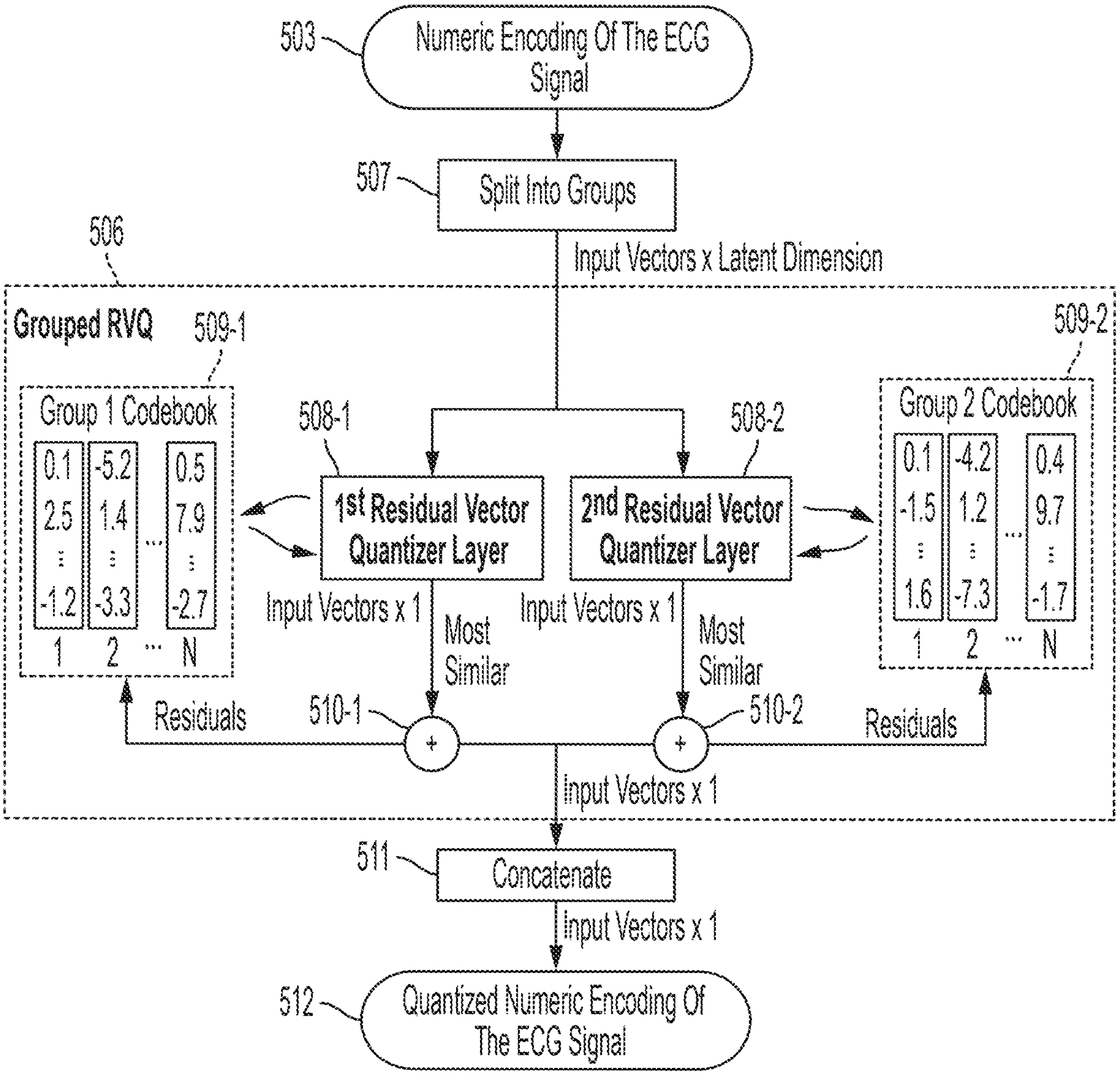
FIG. 5D shows an example architecture of a grouped residual vector quantizer (RVQ) (e.g., RVQ 126 shown in FIG. 1B) used to obtain a quantized numeric encoding of an ECG signal, according to some embodiments of the technology described herein.
Figure 5E:
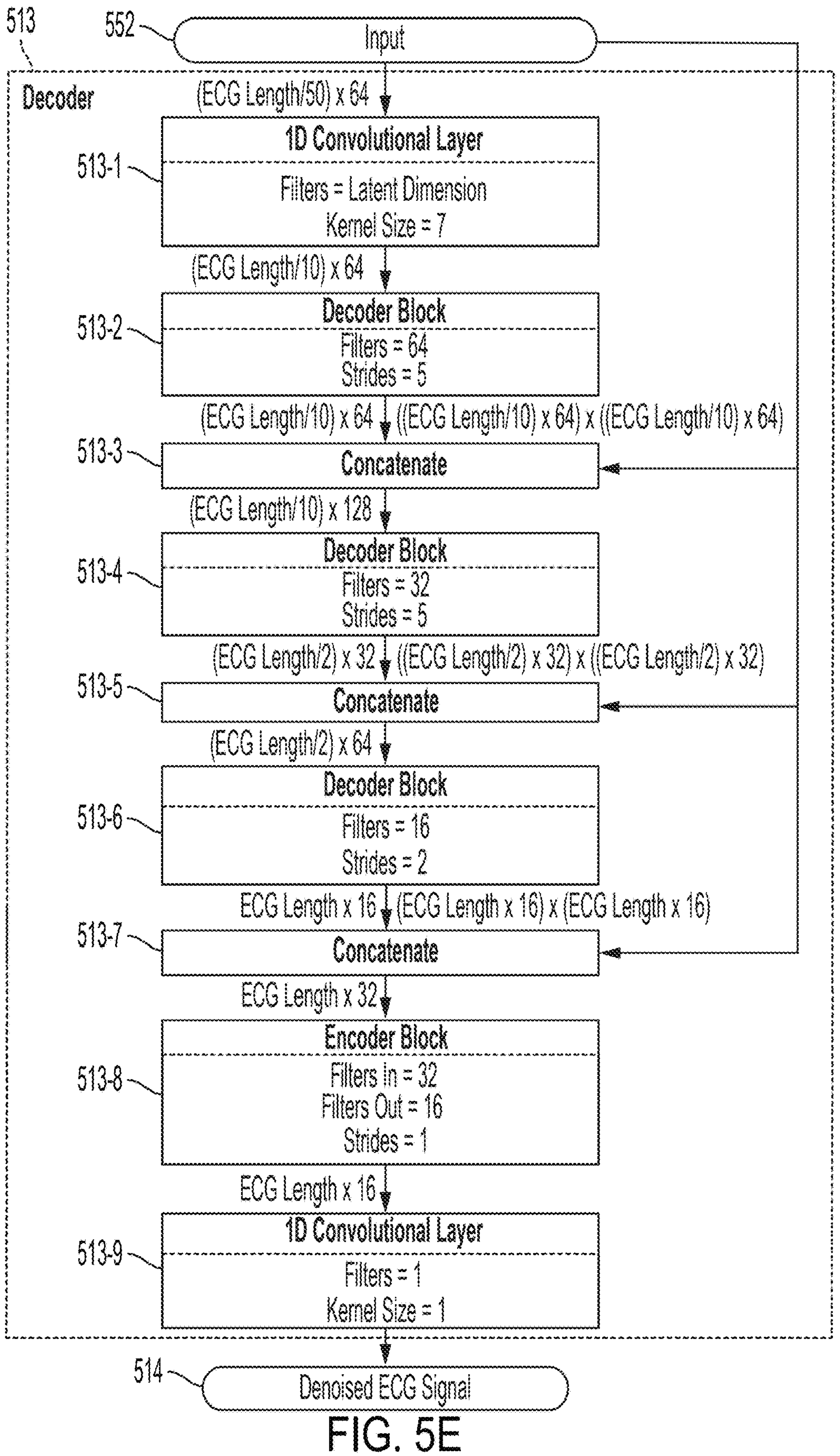
FIG. 5E shows an example architecture of a decoder (e.g., decoder 130 shown in FIG. 1B) used to obtain a denoised ECG signal, according to some embodiments of the technology described herein.
Figure 5F:
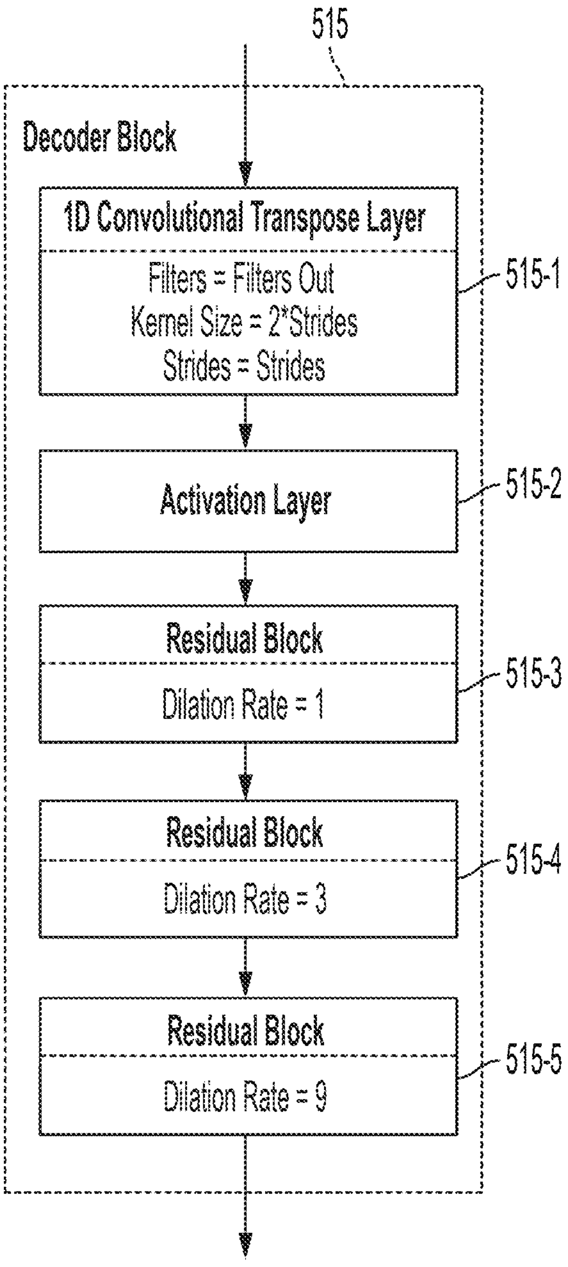
FIG. 5F shows an example architecture of a decoder block of the decoder shown in FIG. 5E, according to some embodiments of the technology described herein.

FIG. 5C shows an example architecture of a residual block 505 of the encoder 502 shown in FIG. 5A and the decoder block 515 shown in FIG. 5F, according to some embodiments of the technology described herein. For example, each of the residual blocks 504-1, 504-2, and 504-3 shown in FIG. 5A may be implemented as residual block 505. Additionally or alternatively, each of the residual blocks 515-3, 515-4, 515-5 shown in FIG. 5F. Thus, the values of the variables "kernel size," "filters," and "dilation rate," may depend on the values of variables of the specific residual block being implemented.

As shown in FIG. 5C, the input to the residual block 505 is processed using a 1D convolutional layer 505-1. As an example, the 1D convolutional layer 505-1 may have a kernel size equal to "kernel size," a number of filters equal to "filters," a dilation rate equal to "dilation rate," and a padding of "same." The 1D convolutional layer 505-1 may use any suitable activation function such as, for example, ELU.

The output of the 1D convolutional layer 505-1 may be coupled to the 1D convolutional layer 505-2. As an example, the 1D convolutional layer 505-2 may have a kernel size of 1, a number of filters equal to "filters," and a padding of "same." The 1D convolutional layer 505-2 may use a dilation rate of 1, by default.

The output of the 1D convolutional layer 505-2 may be coupled to an add layer 505-3. The add layer may add the input of the residual block 505 to the output of the 1D convolutional layer 505-2.

The output of the add layer 505-3 may be coupled to a batch normalization layer 505-4, which may be coupled to activation layer 505-5. The activation layer 505-5 may use any suitable activation function (e.g., ELU, SiLU, ReLU, leaky ReLU, hyperbolic, softmax, etc.).

FIG. 5D shows an example architecture of a grouped RVQ 506 used to obtain a quantized numeric encoding 512 of an ECG signal, according to some embodiments of the technology described herein. As shown in FIG. 5D, the grouped RVQ 506 comprises residual vector quantizer layers. The residual vector quantizer layers use (e.g., access) respective codebooks) for performing the quantization.

The grouped RVQ 506 receives numeric encoding 503 and processes the numeric encoding 503 using the acts (e.g., 507 and 511) and layers shown in FIG. 5D to obtain the quantized numeric encoding 512 of the ECG signal. For example, the output of the encoder 502 shown in FIG. 5A may be coupled to the grouped RVQ 506. The example grouped RVQ 506 uses five parameters: groups, number of vector quantizer layers (nq), number of embeddings, embedding dimensions, and beta. The values for the parameters are passed on to each vector quantizer layer used in the grouped RVQ. Examples of parameter values include nq=12 and number of embeddings=256. The parameter beta is a parameter that is used for training RVQs and represents the weight of commitment loss during training.

The grouped RVQ 506 performs grouped residual vector quantization using residual vector quantizer layer 508-1 and residual vector quantizer layer 508-2. Each of the residual vector quantizer layers 508-1, 508-2 processes a respective group of embeddings derived from the numeric encoding 503 of the ECG signal. The groups of embeddings may be obtained, at act 507, by splitting input vectors vertically into evenly sized groups, and performing residual vector quantization on each group. For example, the vectors may be split evenly according to the number of groups (e.g., using 64 dimensional vectors and 2 groups, the size of each of the groups is 64/2=32).

The residual vector quantizer layers 508-1, 508-2 use parameters: nq, number of embeddings, embedding dimensions, and beta. Each of the residual vector quantizer layers 508-1, 508-2 also uses a list of vector quantizer layers. A residual vector quantizer layer may take vectors as input (e.g., vectors from a respective group embeddings) and perform residual vector quantization on the vectors using the embeddings of its associated vector quantizer layers.

In some embodiments, when a vector quantizer layer is called, the vector quantizer layer returns the embedding(s) that most closely match the input vector(s). For example, the embedding(s) may be selected from a respective codebook 509-1, 509-2 of embeddings. As described herein, the codebooks 509-1, 509-2 are obtained during training of the denoising model. The selected embeddings may be added. For example, add layer 510-1 may add the selected embeddings output by the first residual vector quantizer layer 508-1, and add layer 510-2 may add the selected embeddings output by the second residual vector quantizer layer 508-2. The resulting embeddings (e.g., the summed embeddings) may be concatenated at act 511 to obtain the quantized numeric encoding 512.

Each vector quantizer layer (e.g., included in residual vector quantizer layer) uses parameters: number of embeddings, embedding dimensions, and beta. The weights of each vector quantizer layer are an (embedding dimensions×number of embeddings) matrix. The weights may be initialized by generating a tensor with a uniform distribution. For example, the tensor may be generated using the function tensorflow.random_uniform_initializero with dtype="float32". The loss function for a vector quantizer may be: commitment loss*beta+codebook loss.

In alternative embodiments, the grouped RVQ 506 may be modified such that it is not grouped. This would mean that the entire vector is quantized using a single codebook. Thus, the architecture shown in FIG. 5D would omit the step of splitting the vector into groups, and there would be a single residual vector quantizer layer that uses a single codebook (instead of a first and second residual vector quantizer layer and a group 1 codebook and group 2 codebook). Using a grouped RVQ allows the denoising model to represent a much larger number of vectors without significantly increasing the size of the codebook. This improves the efficiency of the RVQ without sacrificing the quality of the reconstruction during inference.

FIG. 5E shows an example architecture of a decoder 513 used to obtain a denoised ECG signal, according to some embodiments of the technology described herein. As shown in FIG. 5E, the decoder 513 comprises decoder layers and 1D convolutional layers. The decoder layers are at different resolutions. For example, the decoder layers are at progressively decreased resolutions. The decoder 513 also includes an encoder layer (e.g., encoder block 513-8). The decoder 513 also includes skip connections.

The decoder 513 receives input 552 and processes the input 552 using the layers shown in FIG. 5E to obtain the denoised ECG signal 514. In some embodiments, the decoder 513 includes at least 100,000 parameters, at least 150,000 parameters, at least 200,000 parameters, at least 250,000 parameters, at least 300,000 parameters, at least 350,000 parameters, at least 400,000 parameters, at least 450,000 parameters, at least 500,000 parameters, or at least any other suitable number of parameters. In some embodiments, the decoder 513 includes at most 1 million parameters, at most 950,000 parameters, at most 900,000 parameters, at most 850,000 parameters, at most 800,000 parameters, at most 750,000 parameters, at most 700,000 parameters, at most 650,000 parameters, at most 600,000 parameters, at most 550,000 parameters, at most 500,000 parameters, at most 450,000 parameters, at most 400,000 parameters, or at most any other suitable number of parameters. For example, the decoder 513 may have 271,249 trainable parameters and 864 non-trainable parameters. It should be appreciated that any of the above-listed upper bounds may be coupled with any of the above-listed lower bounds. In some embodiments, a hyperparameter of the decoder 513 includes the learning rate for the denoising model of which the decoder 513 is part.

As shown in FIG. 5E, the decoder 513 is configured to receive input 552. In some embodiments, the input 552 includes a list containing the outputs of the encoder 502 and/or the grouped RVQ 506. For example, the input 552 may include the numeric encoding 503 of the ECG signal 501 and/or the quantized numeric encoding 512.

In some embodiments, the input 552 is provided as input to a 1D convolutional layer 513-1. As an example, the 1D convolutional layer 513-1 may have filters equal to the latent dimension, a kernel size of 7, and a padding of "same."

The output of the 1D convolutional layer 513-1 may be coupled to decoder block 513-2. As an example, the decoder block 513-2 may have 64 filters and a stride of 5. An example implementation of a decoder block 515 is described herein including at least with respect to FIG. 5F.

The output of the decoder block 513-2 may be coupled to a concatenate layer 513-3. The concatenate layer 513-3 may concatenate the output of the decoder block 513-2 with the third output of the encoder 502. For example, the third output of the encoder 502 may include the output of the encoder block 502-3 shown in FIG. 5A.

The output of the concatenate layer 513-3 may be coupled to decoder block 513-4. As an example, the decoder block 513-4 may have 32 filters and a stride of 5. An example implementation of a decoder block 515 is described herein including at least with respect to FIG. 5F.

The output of the decoder block 513-4 may be coupled to a concatenate layer 513-5. The concatenate layer 513-5 may concatenate the output of the decoder block 513-4 with the second output of the encoder 502. For example, the second output of the encoder 502 may include the output of the encoder block 502-2 shown in FIG. 5A.

The output of the concatenate layer 513-5 may be coupled to a decoder block 513-6. As an example, the decoder block 513-6 may have 16 filters and a stride of 2. An example implementation of a decoder block 515 is described herein including at least with respect to FIG. 5F.

The output of the decoder block 513-6 may be coupled to a concatenate layer 513-7. The concatenate layer 513-7 may concatenate the output of the decoder block 513-6 with the first output of the encoder 502. For example, the first output of the encoder 502 may include the output of the 1D convolutional layer 502-1 shown in FIG. 5A.

The output of the concatenate layer 513-7 may be coupled to an encoder block 513-8. As an example, the encoder block 513-8 may have 32 filters in, 16 filters out, and a stride of 1. An example implementation of an encoder block 504 is described herein including at least with respect to FIG. 5B.

The output of the encoder block 513-8 may be coupled to a 1D convolutional layer 513-9. As an example, the 1D convolutional layer 513-9 may have 1 filter, a kernel size of 1, and a padding of "same." The output of the 1D convolutional layer 513-9 may be the denoised ECG signal 514.

FIG. 5F shows an example architecture of a decoder block 515 of the decoder shown in FIG. 5E, according to some embodiments of the technology described herein. For example, each of the decoder blocks 513-2, 513-4, and 513-6, shown in FIG. 5D, may be implemented as decoder block 515. Additionally or alternatively, the decoder blocks 518-2, 518-4, and 518-6, shown in FIG. 5H, may be implemented as decoder block 515. Thus, the values of variables "filters," "kernel size," and "strides" may depend on the values of variables of the specific decoder blocks being implemented.

As shown in FIG. 5F, the input to the decoder block 515 is provided as input to a 1D convolutional transpose layer 515-1. As an example, the 1D convolutional transpose layer 515-1 has a kernel size of (2*"strides"), a number of filters equal to "filters," a number of strides equal to "strides," and a padding of "same." The 1D convolutional transpose layer 515-1 may use any suitable activation function such as, for example, ELU.

The output of the 1D convolutional transpose layer 515-1 may be coupled to activation layer 515-2. The activation layer 515-2 may use any suitable activation function (e.g., ELU, sigmoid linear unit (SiLU), rectified linear unit (ReLU), leaky ReLU, hyperbolic, softmax, etc.).

The output of the activation layer 515-2 may be coupled to a series of residual blocks 515-3, 515-4, 515-5. As an example, the first residual block 515-3 may have a dilation rate of 1, a number of filters equal to "filters," and a kernel size of 7. The first residual block 515-3 may be coupled to the second residual block 515-4. As an example, the second residual block 515-4 may have a dilation rate of 3, a number of filters equal to "filters," and a kernel size of 7. The second residual block 515-4 may be coupled to the third residual block 515-5. As an example, the third residual block 515-5 may have a dilation rate of 9, a number of filters equal to "filters," and a kernel size of 7. An example implementation of a residual block 505 is described herein including at least with respect to FIG. 5C.

Figure 5G:
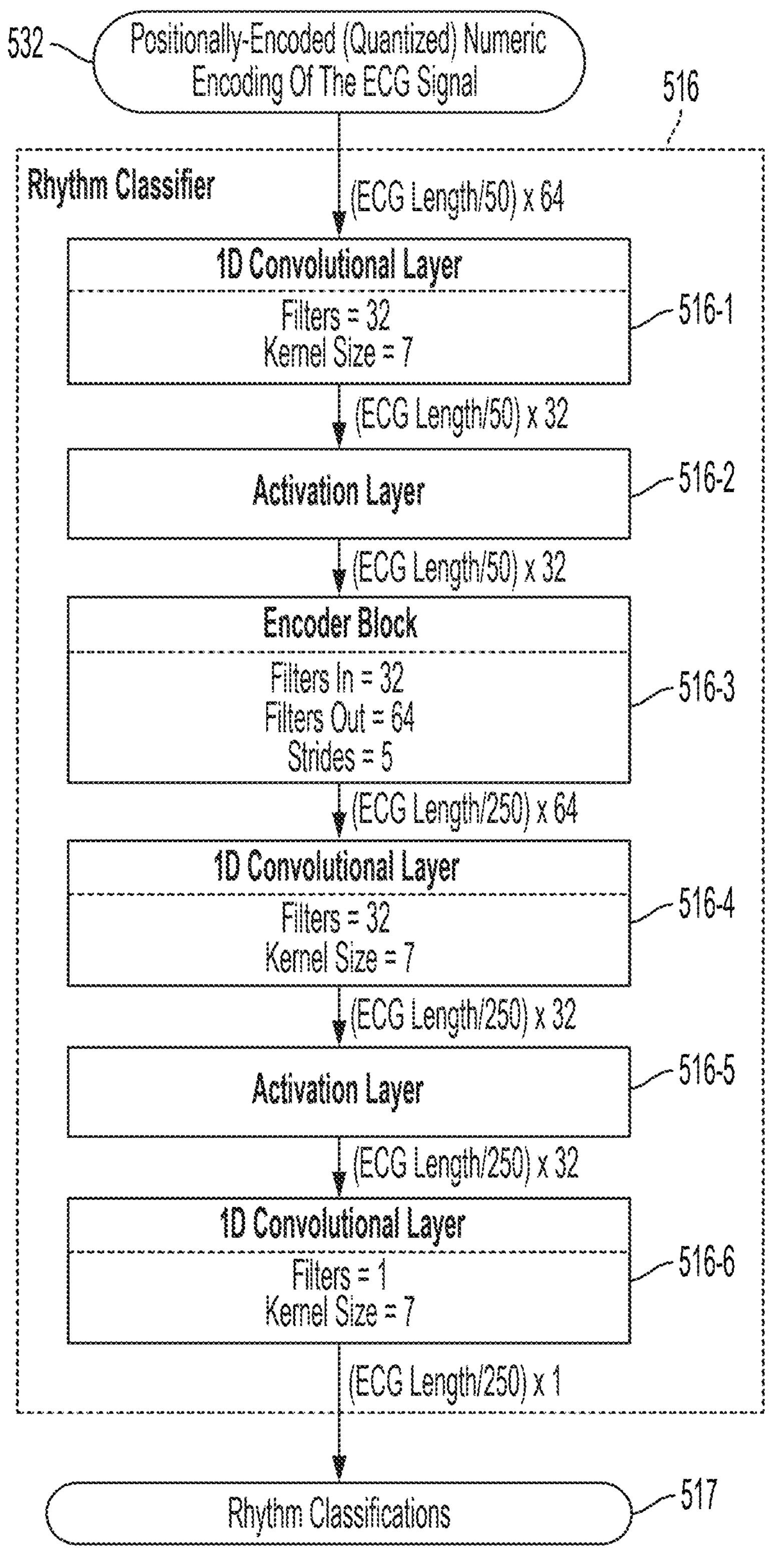
FIG. 5G shows an example architecture of a rhythm classifier (e.g., rhythm classifier 136 shown in FIG. 1B), according to some embodiments of the technology described herein.

FIG. 5G shows an example architecture of a rhythm classifier 516, according to some embodiments of the technology described herein. In some embodiments, the rhythm classifier 516 is a classification head that comprises one or more convolutional layers. In some embodiments, the classification head is a deep neural network comprising one or more convolutional layers, one or more activation layers, and one or more encoder blocks.

The rhythm classifier 516 receives a positionally-encoded (optionally, quantized) numeric encoding 532 of an ECG signal and processes the positionally-encoded numeric encoding 532 using the layers shown in FIG. 5G to obtain rhythm classifications 517. In some embodiments, the rhythm classifier 516 includes at least 100,000 parameters, at least 150,000 parameters, at least 200,000 parameters, at least 250,000 parameters, at least 300,000 parameters, at least 350,000 parameters, at least 400,000 parameters, at least 450,000 parameters, at least 500,000 parameters, or at least any other suitable number of parameters. In some embodiments, the rhythm classifier 516 includes at most 1 million parameters, at most 950,000 parameters, at most 900,000 parameters, at most 850,000 parameters, at most 800,000 parameters, at most 750,000 parameters, at most 700,000 parameters, at most 650,000 parameters, at most 600,000 parameters, at most 550,000 parameters, at most 500,000 parameters, at most 450,000 parameters, at most 400,000 parameters, or at most any other suitable number of parameters. For example, the rhythm classifier 516 may have 306,659 trainable parameters and 864 non-trainable parameters. It should be appreciated that any of the above-listed upper bounds may be coupled with any of the above-listed lower bounds. In some embodiments, a hyperparameter of the rhythm classifier 516 includes the learning rate used for training the rhythm classifier.

As shown in FIG. 5G, the rhythm classifier 516 is configured to receive a positionally-encoded (optionally, quantized) numeric encoding 532 of an ECG signal. In some embodiments, obtaining a positionally-encoded numeric encoding 532 of an ECG signal includes positionally encoding the numeric encoding 503 output by the encoder 502 shown in FIG. 5A. In some embodiments, obtaining a positionally-encoded quantized numeric encoding 532 of an ECG signal includes positionally encoding the quantized numeric encoding 512 output by the grouped RVQ 506 shown in FIG. 5D. Example techniques for positionally encoding a numeric encoding are described herein including at least with respect to FIG. 1B.

In some embodiments, the positionally-encoded (optionally, quantized) numeric encoding 532 is provided as input to a 1D convolutional layer 516-1 of the rhythm classifier 516. As an example, the 1D convolutional layer 516-1 may have 32 filters, a kernel size of 7, and a padding of "same." The 1D convolutional layer 516-1 may use any suitable activation function such as, for example, exponential linear unit (ELU).

The output of the 1D convolutional layer 516-1 may be coupled to activation layer 516-2. The activation layer 516-2 may use any suitable activation function (e.g., ELU, sigmoid linear unit (SiLU), rectified linear unit (ReLU), leaky ReLU, hyperbolic tangent, softmax, etc.).

The output of the activation layer 516-2 may be coupled to encoder block 516-3. As an example, the encoder block may have 32 filters in, 64 filters out, and a stride of 5. An example implementation of an encoder block 504 is described herein including at least with respect to FIG. 5B.

The output of the encoder block 516-3 may be coupled to 1D convolutional layer 516-4. As an example, the 1D convolutional layer 516-4 may have 32 filters, a kernel size of 7, and a padding of "same." The 1D convolutional layer 516-4 may use any suitable activation function such as, for example, exponential linear unit (ELU).

The output of the 1D convolutional layer 516-4 may be coupled to activation layer 516-5. The activation layer 516-5 may use any suitable activation function (e.g., ELU, sigmoid linear unit (SiLU), rectified linear unit (ReLU), leaky ReLU, hyperbolic, softmax, etc.).

The output of the activation layer 516-5 may be coupled to 1D convolutional layer 516-6. As an example, the 1D convolutional layer 516-6 may have 1 filter, a kernel size of 7, and a padding of "same." The 1D convolutional layer 516-6 may use any suitable activation function such as, for example, exponential linear unit (ELU).

In some embodiments, the output of the 1D convolutional layer 516-6 is rhythm classifications 517. For example, rhythm classifications 517 may be formatted as a tensor having a size: (ECG length/250)×1. Rows of the tensor may represent segments of the ECG signal. For example, each segment may be a one second segment of the ECG signal. The tensor values may be indicative of the probability that a particular segment has an arrhythmia. For example, the tensor values may range from 0 to 1, with 1 corresponding to the highest probability and 0 corresponding to the lowest probability, or vice versa. Alternatively, the tensor values may include a binary indication of whether the particular segment has an arrhythmia. For example, the tensor values may be 0 or 1, with 1 corresponding to an arrhythmia and 0 corresponding to no arrhythmia (e.g., a normal sinus rhythm), or vice versa.

In alternative embodiments, the rhythm classifications 517 may include classifications for multiple classes. For example, the multiple classes may include a respective class for each rhythm type of multiple rhythm types. The multiple rhythm types may include, for example, a normal sinus rhythm type, an atrial fibrillation type, and/or an atrial flutter type. Additionally or alternatively, the multiple rhythm types may include a PAC type and/or a PVC type. The classifications 517 may include a respective value (e.g., a binary value, a value indicative of likelihood, etc.) for each rhythm type, where a particular value is indicative of whether or not the segment represents the particular rhythm type. For example, the classifications 517 may include, for each segment, values indicating the probability that the segment has the multiple rhythm types. Alternatively, the classifications 517 may include, for each segment, values indicating whether or not the segment has the multiple rhythm types.

Figure 5H:
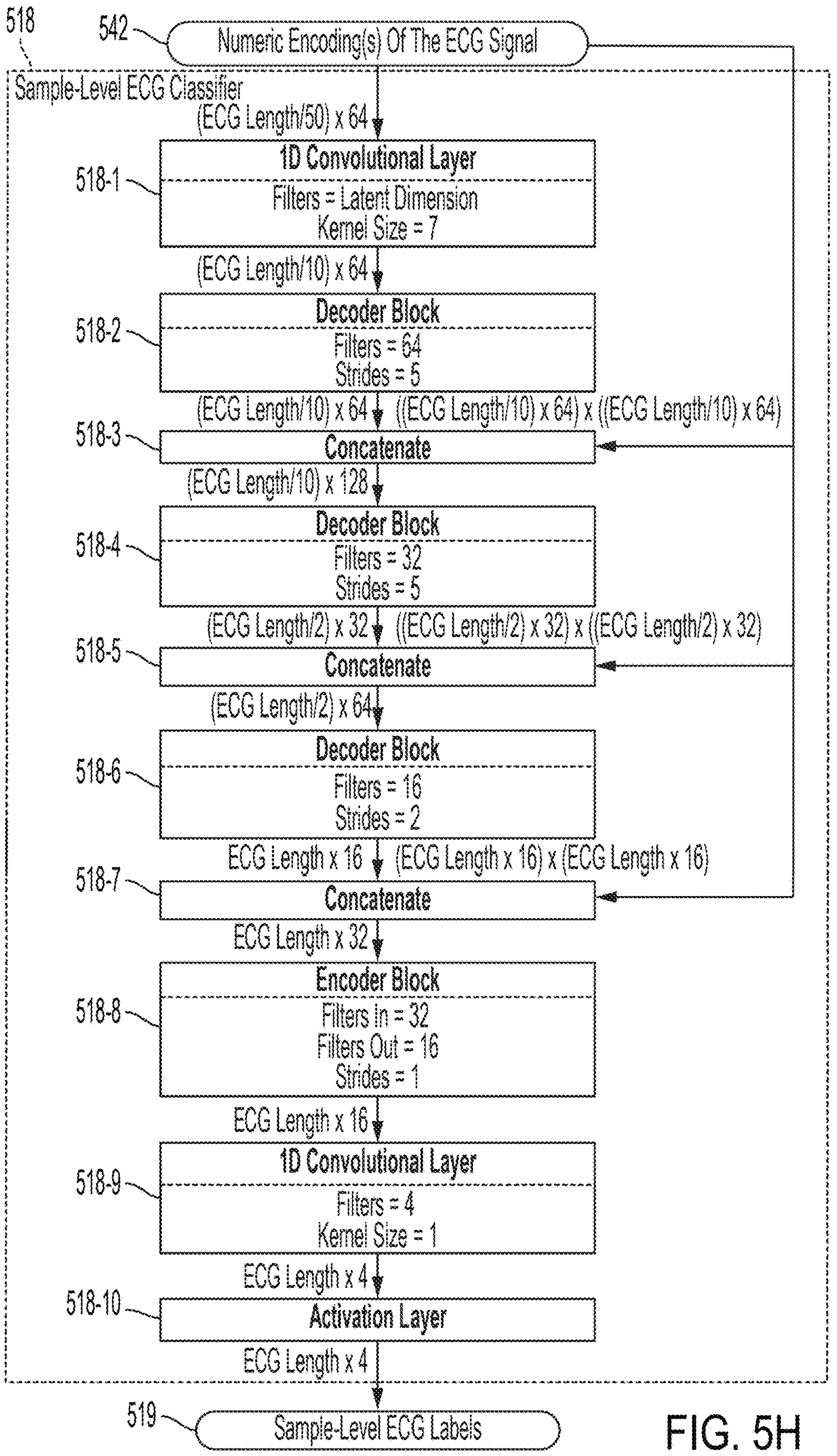
FIG. 5H shows an example architecture of a sample-level ECG classifier (e.g., sample-level ECG classifier 138 shown in FIG. 1B), according to some embodiments of the technology described herein.
Figures 1, 5I:
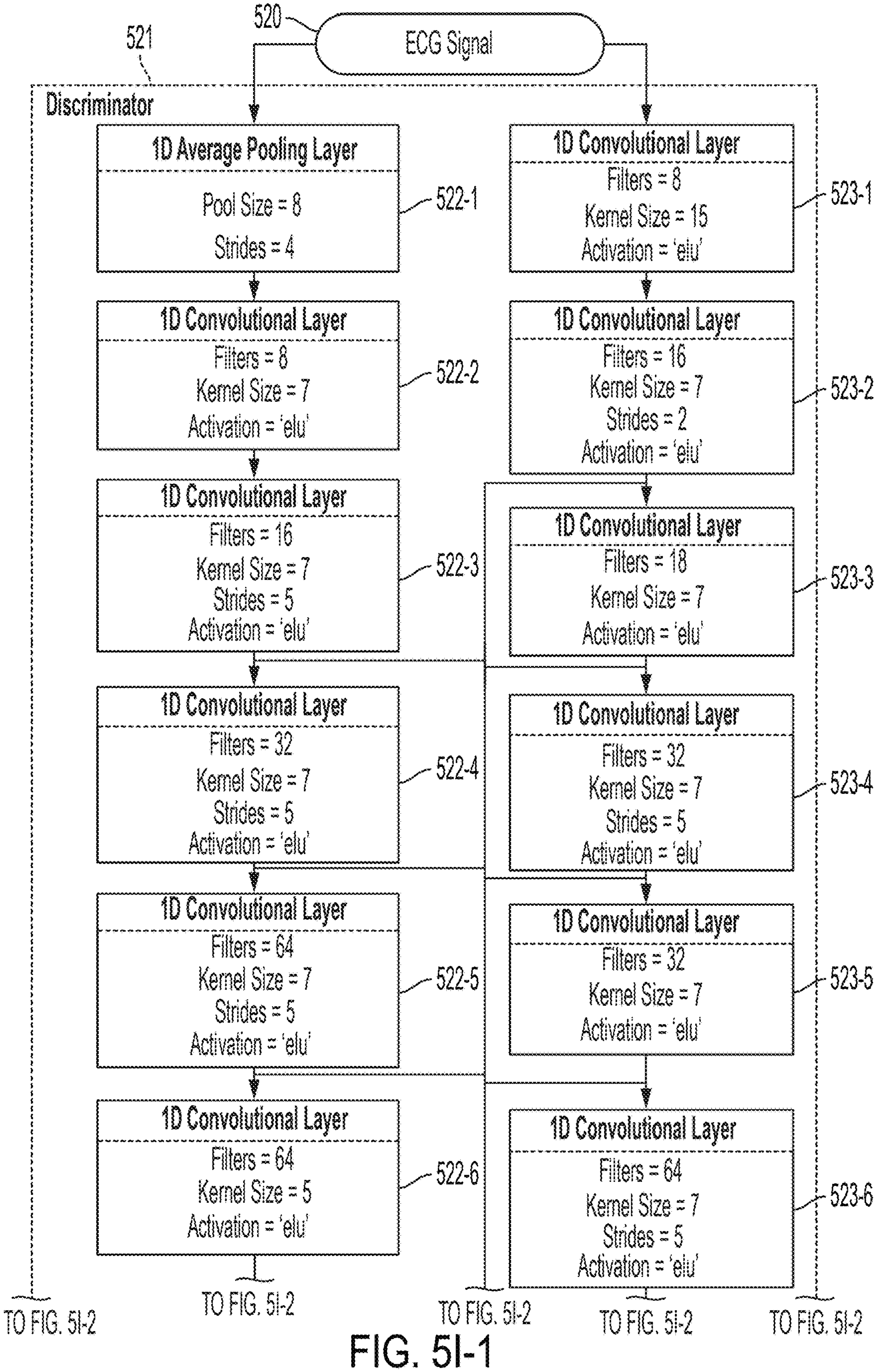
Figures 2, 5I:
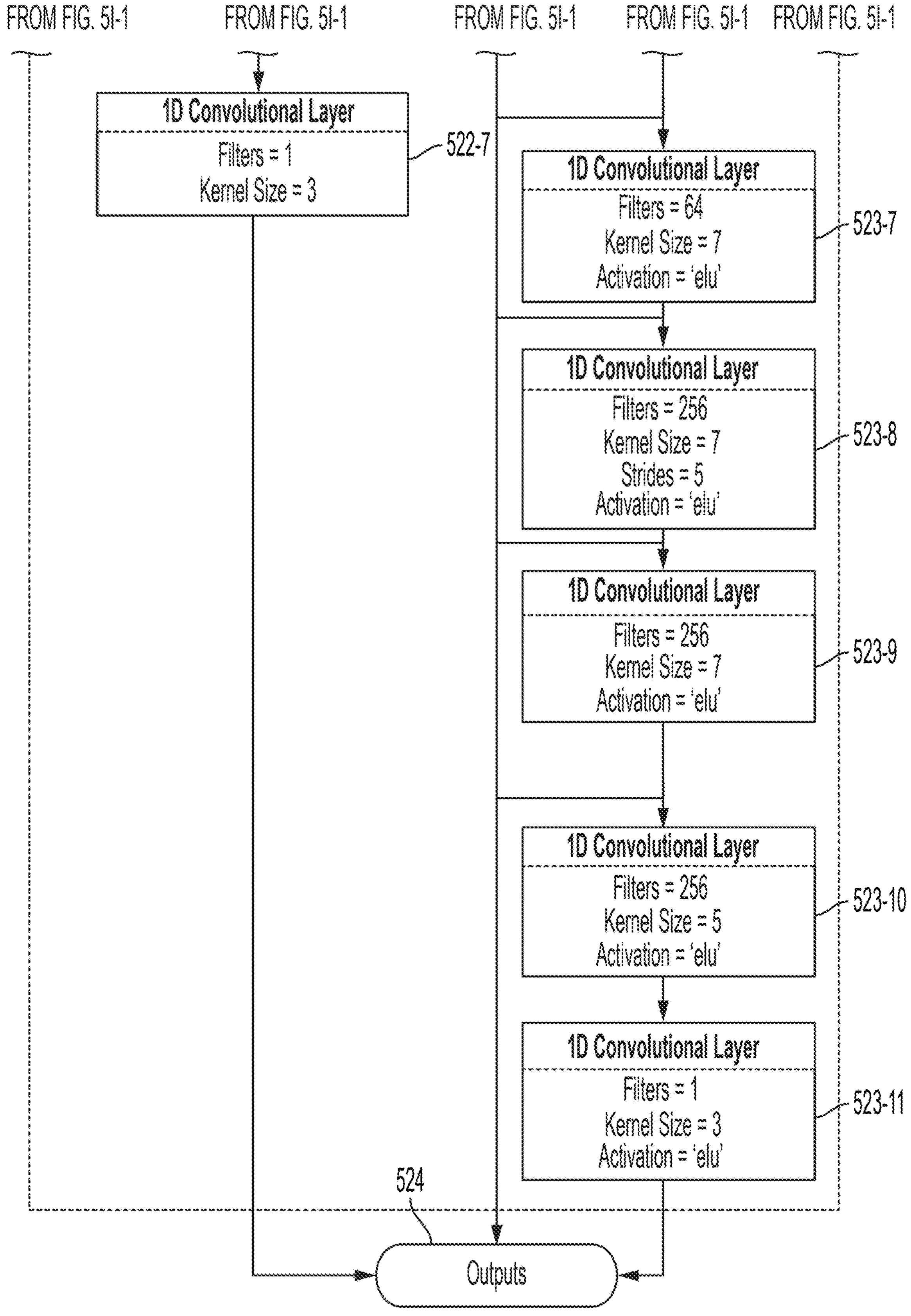
Figure 5J:
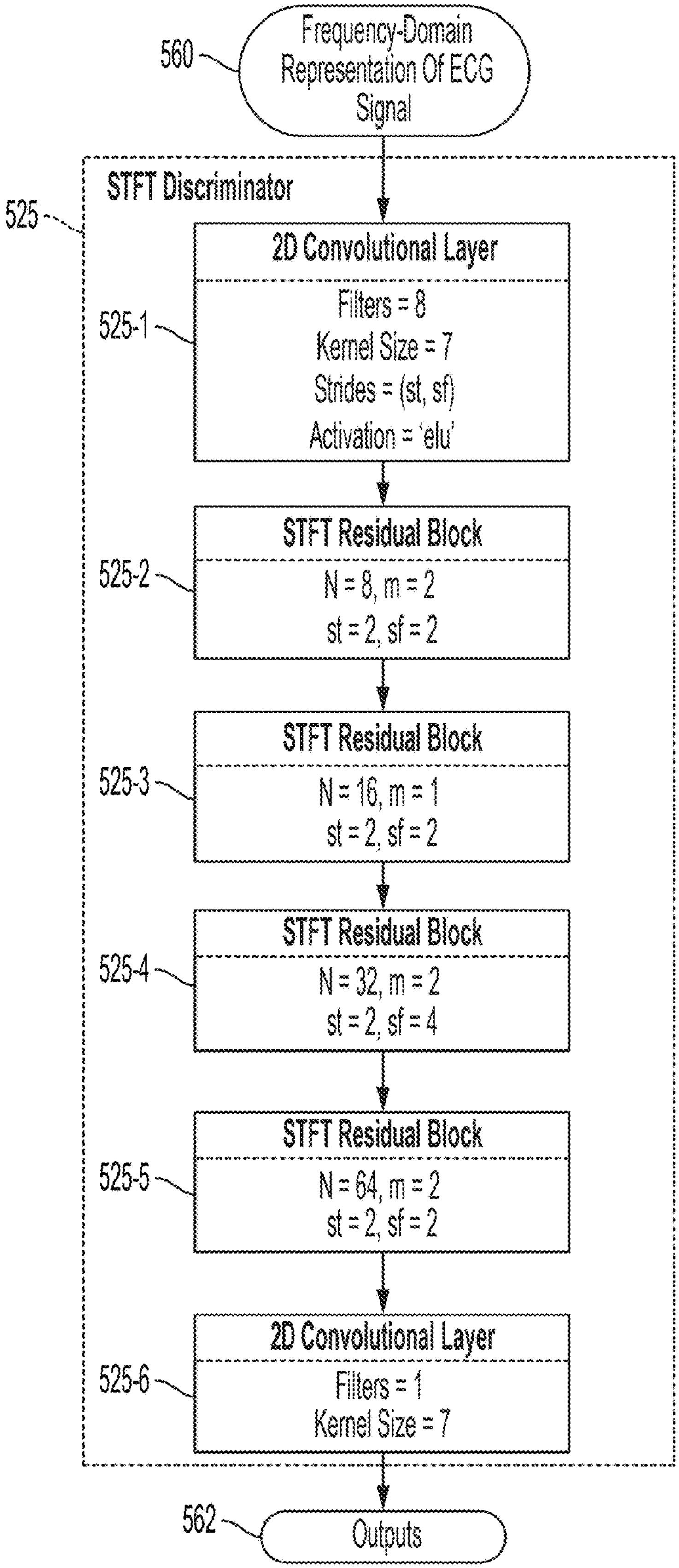
FIG. 5J shows an example architecture of a short-time Fourier transform (STFT) discriminator (e.g., discriminator 232 shown in FIG. 2) used to train a denoising model, according to some embodiments of the technology described herein.
Figure 5K:
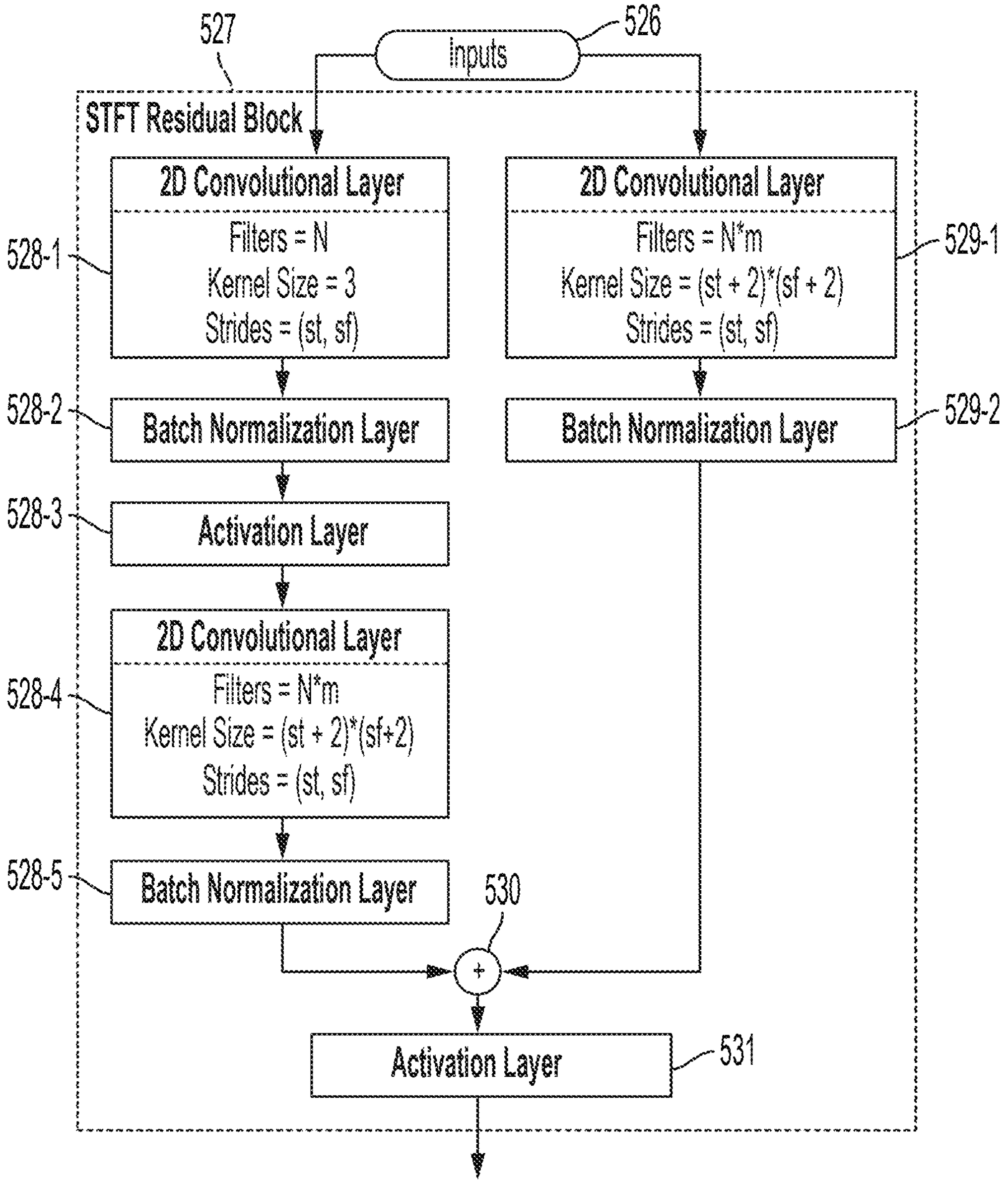
FIG. 5K shows an example architecture of a short-time FT (STFT) residual block of the FT discriminator shown in FIG. 5J, according to some embodiments of the technology described herein.

FIG. 5H shows an example architecture of a sample-level ECG classifier 518, according to some embodiments of the technology described herein. In some embodiments, the sample-level ECG classifier 518 is a classification head that comprises one or more convolutional layers. In some embodiments, the classification head is a deep neural network comprising one or more convolutional layers, one or more encoder blocks, and one or more decoder blocks.

The sample-level ECG classifier 518 receives numeric encoding(s) 542 of the ECG signal and processes the numeric encoding(s) 542 using the layers shown in FIG. 5H to obtain sample-level ECG labels 519. In some embodiments, the sample-level ECG classifier 518 includes at least 100,000 parameters, at least 150,000 parameters, at least 200,000 parameters, at least 250,000 parameters, at least 300,000 parameters, at least 350,000 parameters, at least 400,000 parameters, at least 450,000 parameters, at least 500,000 parameters, or at least any other suitable number of parameters. In some embodiments, the sample-level ECG classifier 518 includes at most 1 million parameters, at most 950,000 parameters, at most 900,000 parameters, at most 850,000 parameters, at most 800,000 parameters, at most 750,000 parameters, at most 700,000 parameters, at most 650,000 parameters, at most 600,000 parameters, at most 550,000 parameters, at most 500,000 parameters, at most 450,000 parameters, at most 400,000 parameters, or at most any other suitable number of parameters. It should be appreciated that any of the above-listed upper bounds may be coupled with any of the above-listed lower bounds. For example, the sample-level ECG classifier may include 272,164 trainable parameters and 864 non-trainable parameters. In some embodiments, a hyperparameter of the sample-level ECG classifier 518 includes the learning rate for the sample-level ECG classifier.

As shown in FIG. 5H, the sample-level ECG classifier 518 is configured to receive numeric encoding(s) 542 as input. For example, the numeric encoding(s) 542 may include the numeric encoding 503 output by the encoder 502 shown in FIG. 5A. Additionally or alternatively, the numeric encoding(s) 542 may include the quantized numeric encoding 512 output by the grouped RVQ 506 shown in FIG. 5D.

In some embodiments, the numeric encoding(s) 542 are provided as input to the 1D convolutional layer 518-1 of the sample-level ECG classifier 518. As an example, the 1D convolutional layer 518-1 may have a number of filters equal to the latent dimension, a kernel size of 7, and a padding of "same."

The output of the 1D convolutional layer 518-1 may be coupled to the decoder block 518-2. As an example, the decoder block 518-2 may have 64 filters and a stride of 5. An example implementation of a decoder block 515 is described herein including at least with respect to FIG. 5F.

The output of the decoder block 518-2 may be coupled to the concatenate layer 518-3. The concatenate layer 518-3 may concatenate the output of the decoder block 518-2 with the third output of the encoder 502 shown in FIG. 5A. For example, the third output of the encoder 502 may include the output of encoder block 502-3.

The output of the concatenate layer 518-3 may be coupled to decoder block 518-4. As an example, the decoder block 518-4 may have 32 filters and a stride of 5. An example implementation of a decoder block 515 is described herein including at least with respect to FIG. 5F.

The output of the decoder block 518-4 may be coupled to the concatenate layer 518-5. The concatenate layer 518-5 may concatenate the output of the decoder block 518-4 with the second output of the encoder 502 shown in FIG. 5A. For example, the second output of the encoder 502 may include the output of encoder block 502-2.

The output of the concatenate layer 518-5 may be coupled to decoder block 518-6. As an example, the decoder block 518-6 may have 16 filters and a stride of 2. An example implementation of a decoder block 515 is described herein including at least with respect to FIG. 5F.

The output of the decoder block 518-6 may be coupled to the concatenate layer 518-7. The concatenate layer 518-7 may concatenate the output of the decoder block 518-6 with the first output of the encoder 502 shown in FIG. 5A. For example, the first output of the encoder 502 may include the output of 1D convolutional layer 502-1.

The output of the concatenate layer 518-7 may be coupled to encoder block 518-8. As an example, the encoder block 518-8 may have 32 filters in, 16 filters out, and a stride of 1. An example implementation of an encoder block 504 is described herein including at least with respect to FIG. 5B.

The output of the encoder block 518-8 may be coupled to 1D convolutional layer 518-9. As an example, the 1D convolutional layer 518-9 may have 4 filters, a kernel size of 1, and a padding of "same." The 1D convolutional layer 518-9 may use any suitable activation function such as, for example, exponential linear unit (ELU)

The output of the 1D convolutional layer 518-9 may be coupled to activation layer 518-10. The activation layer 518-10 may use any suitable activation function (e.g., ELU, sigmoid linear unit (SiLU), rectified linear unit (ReLU), leaky ReLU, hyperbolic, softmax, etc.).

In some embodiments, the output of the activation layer 518-10 is sample-level ECG labels 519. For example, the sample-level ECG labels 519 may be formatted as a tensor having a size: ECG length×4. Rows of the tensor may correspond to the part of the ECG that is being labeled. The columns of the tensor may correspond to the label of that part of the ECG. For example, the first column may correspond to no wave, the second column may correspond to the P-wave, the third column may correspond to the QRS complex, and the fourth column may correspond to the T-wave. The tensor values may indicate the probabilities for each label. Alternatively, the tensor values may indicate binary values for each label. For example, the binary values corresponding to a particular label may indicate, for each sample, whether or not the label is applicable (e.g., whether or not the sample corresponds to a P-wave and thus should be labelled as corresponding to a P-wave, etc.).

FIG. 5I-1 and FIG. 5I-2 show an example architecture of a discriminator 521 used to train a denoising model, according to some embodiments of the technology described herein. The discriminator 521 comprises multiple convolutional layers. Additionally, the discriminator 521 comprises one or more pooling layers (e.g., an average pooling layer). The discriminator 521 may include skip connections.

As shown in FIG. 5I-1 and FIG. 5I-2, the discriminator 521 may be composed of two smaller discriminator models, each of which takes the ECG signal 520 as input. For example, the first discriminator includes layers 523-1-523-11, and the second discriminator includes layers 522-1-522-7. The discriminator 521 may process the ECG signal 520 using the layers of the first and second discriminator models to obtain outputs 524.

Referring to first to the first discriminator model having layers 523-1-523-11, the ECG signal 520 may be provided as input to the 1D convolutional layer 523-1. As an example, the 1D convolutional layer 523-1 may have 8 filters, a kernel size of 15, and a padding of "same." The 1D convolutional layer 523-1 may use any suitable activation function such as, for example, ELU.

The output of the 1D convolutional layer 523-1 may be coupled to 1D convolutional layer 523-2. As an example, the 1D convolutional layer 523-2 may have 16 filters, a kernel size of 7, a stride of 2, and a padding of "same." The 1D convolutional layer 523-2 may use any suitable activation function such as, for example, ELU.

The output of the 1D convolutional layer 523-2 may be coupled to 1D convolutional layer 523-3. As an example, the 1D convolutional layer 523-3 may have 16 filters, a kernel size of 7, and a padding of "same." The 1D convolutional layer 523-3 may use any suitable activation function such as, for example, ELU.

The output of the 1D convolutional layer 523-3 may be coupled to 1D convolutional layer 523-4. As an example, the 1D convolutional layer 523-4 may have 32 filters, a kernel size of 7, a stride of 5, and a padding of "same." The 1D convolutional layer 523-4 may use any suitable activation function such as, for example, ELU.

The output of the 1D convolutional layer 523-4 may be coupled to 1D convolutional layer 523-5. As an example, the 1D convolutional layer 523-5 may have 32 filters, a kernel size of 7, a stride of 2, and a padding of "same." The 1D convolutional layer 523-5 may use any suitable activation function such as, for example, ELU.

The output of the 1D convolutional layer 523-5 may be coupled to 1D convolutional layer 523-6. As an example, the 1D convolutional layer 523-6 may have 64 filters, a kernel size of 7, a stride of 5, and a padding of "same." The 1D convolutional layer 523-6 may use any suitable activation function such as, for example, ELU.

The output of the 1D convolutional layer 523-6 may be coupled to 1D convolutional layer 523-7. As an example, the 1D convolutional layer 523-7 may have 64 filters, a kernel size of 7, and a padding of "same." The 1D convolutional layer 523-7 may use any suitable activation function such as, for example, ELU.

The output of the 1D convolutional layer 523-7 may be coupled to 1D convolutional layer 523-8. As an example, the 1D convolutional layer 523-8 may have 256 filters, a kernel size of 7, a stride of 5, and a padding of "same." The 1D convolutional layer 523-8 may use any suitable activation function such as, for example, ELU.

The output of the 1D convolutional layer 523-8 may be coupled to 1D convolutional layer 523-9. As an example, the 1D convolutional layer 523-9 may have 256 filters, a kernel size of 7, and a padding of "same." The 1D convolutional layer 523-9 may use any suitable activation function such as, for example, ELU.

The output of the 1D convolutional layer 523-9 may be coupled to 1D convolutional layer 523-10. As an example, the 1D convolutional layer 523-10 may have 256 filters, a kernel size of 5, and a padding of "same." The 1D convolutional layer 523-10 may use any suitable activation function such as, for example, ELU.

The output of the 1D convolutional layer 523-10 may be coupled to 1D convolutional layer 523-11. As an example, the 1D convolutional layer 523-11 may have 1 filter, a kernel size of 3, and a padding of "same."

Referring now to the second discriminator having layers 522-1-522-7, the ECG signal 520 may be provided as input to the 1D average pooling layer 522-1. As an example, the 1D average pooling layer 522-1 may have a pool size of 8, a stride of 4, and a padding of "same."

The output of the 1D average pooling layer 522-1 may be coupled to 1D convolutional layer 522-2. As an example, the 1D convolutional layer 522-2 may have 8 filters, a kernel size of 7, and a padding of "same." The 1D convolutional layer 522-2 may use any suitable activation function such as, for example, ELU.

The output of the 1D convolutional layer 522-2 may be coupled to the 1D convolutional layer 522-3. As an example, the 1D convolutional layer 522-3 may have 16 filters, a kernel size of 7, a stride of 5, and a padding of "same." The 1D convolutional layer 522-3 may use any suitable activation function such as, for example, ELU.

The output of the 1D convolutional layer 522-3 may be coupled to the 1D convolutional layer 522-4. As an example, the 1D convolutional layer 522-4 may have 32 filters, a kernel size of 7, a stride of 5, and a padding of "same." The 1D convolutional layer 522-4 may use any suitable activation function such as, for example, ELU.

The output of the 1D convolutional layer 522-4 may be coupled to the 1D convolutional layer 522-5. As an example, the 1D convolutional layer 522-5 may have 64 filters, a kernel size of 7, a stride of 5, and a padding of "same." The 1D convolutional layer 522-5 may use any suitable activation function such as, for example, ELU.

The output of the 1D convolutional layer 522-5 may be coupled to the 1D convolutional layer 522-6. As an example, the 1D convolutional layer 522-6 may have 64 filters, a kernel size of 5, and a padding of "same." The 1D convolutional layer 522-6 may use any suitable activation function such as, for example, ELU.

The output of the 1D convolutional layer 522-6 may be coupled to the 1D convolutional layer 522-7. As an example, the 1D convolutional layer 522-7 may have 1 filter, a kernel size of 3, and a padding of "same."

In some embodiments, the outputs 524 include a list of outputs of at least some of the layers of the first discriminator and outputs of at least some of the layers of the second discriminator. For example, the outputs 524 may include outputs from layers 522-3, 522-4, 522-5, 522-7, 523-2, 523-3, 523-4, 523-5, 523-6, 523-7, 523-8, 523-9, and 523-11.

FIG. 5J shows an example architecture of a short-time Fourier transform (STFT) discriminator 525 used to train a denoising model, according to some embodiments of the technology described herein. As shown in FIG. 5J, the STFT discriminator 525 comprises multiple STFT residual blocks. The STFT discriminator 525 additionally comprises one or more convolutional layers.

The STFT discriminator 525 may process the frequency-domain representation 560 of an ECG signal using the layers shown in FIG. 5J to obtain outputs 562. In some embodiments, the STFT discriminator 525 uses the variables "N," "m," "st," and "sf."

In some embodiments, the frequency-domain representation 560 is provided as input to 2D convolutional layer 525-1 of the STFT discriminator 525. As an example, the 2D convolutional layer may have 8 filters, a kernel size of 7, and (st, sf) strides. The 2D convolutional layer 525-1 may use any suitable activation function such as, for example, ELU.

The output of the 2D convolutional layer 525-1 may be coupled to a series of STFT residual blocks 525-2, 525-3, 525-4, and 525-5. As an example, the first STFT residual block 525-2 may have N equal to 8, m equal to 2, st equal to 2, and sf equal to 2. The first STFT residual block 525-2 may be coupled to the second STFT residual block 525-3. As an example, the second STFT residual block 525-3 may have N equal to 16, m equal to 1, st equal to 2, and sf equal to 2. The second STFT residual block 525-3 may be coupled to the third STFT residual block 525-4. As an example, the third STFT residual block 525-4 may have N equal to 32, m equal to 2, st equal to 2, and sf equal to 4. The third STFT residual block 525-4 may be coupled to the fourth STFT residual block 525-5. As an example, the fourth STFT residual block 525-5 may have N equal to 64, m equal to 1, st equal to 2, and sf equal to 2. An example implementation of an STFT residual block 527 is described herein including at least with respect to FIG. 5K.

The output of the fourth STFT residual block 525-5 may be coupled to 2D convolutional layer 525-6. As an example, the 2D convolutional layer 525-6 may have a kernel size of 7, 1 filter, and a padding of "same."

The outputs 562 of the STFT discriminator 525 may include a list of outputs from each of at least some of the layers 525-1-525-6. For example, the outputs 562 may include the output from each layer except layer 525-1.

FIG. 5K shows an example architecture of a STFT residual block 527 of the STFT discriminator 525 shown in FIG. 5J, according to some embodiments of the technology described herein. For example, each of the STFT residual blocks 525-2, 525-3, 525-4, and 525-5, shown in FIG. 5J, may be implemented as STFT residual block 527.

The STFT residual block 527 runs two different sets of layers on the inputs 526, then adds them. The two different sets of layers include layers 528-1-528-5 and layers 529-1-529-2.

Referring to the first set of layers 528-1-528-5, the inputs 526 are provided as input to a 2D convolutional layer 528-1. As an example, the 2D convolutional layer 528-1 may have N filters, a kernel size of 3, and a padding of "same."

The 2D convolutional layer 528-1 may be coupled to a batch normalization layer 528-2, which may be coupled to an activation layer 528-3. The activation layer 528-3 The activation layer 528-3 may use any suitable activation function (e.g., ELU, sigmoid linear unit (SiLU), rectified linear unit (ReLU), leaky ReLU, hyperbolic, softmax, etc.).

The activation layer 528-3 may be coupled to a 2D convolutional layer 528-4. As an example, the 2D convolutional layer 528-4 may have N*m filters, a kernel size of (st+2)*(sf+2), a stride of (st, sf), and a padding of "same." The 2D convolutional layer 528-4 may be coupled to a batch normalization layer 528-5.

Referring now to the set of layers 529-1-529-2, the inputs 526 are provided as input to a 2D convolutional layer 529-1. As an example, the 2D convolutional layer 529-1 may have N*m filters, a kernel size of (st+2)*(sf+2), a stride of (st, sf), and a padding of "same." The 2D convolutional layer 529-1 may be coupled to batch normalization layer 529-2.

The addition layer 530 may be configured to add the outputs of the batch normalization layer 528-5 and the batch normalization layer 529-2.

The addition layer 530 may be coupled to activation layer 531. The activation layer 531 may use any suitable activation function (e.g., ELU, sigmoid linear unit (SiLU), rectified linear unit (ReLU), leaky ReLU, hyperbolic, softmax, etc.).

Figure 6A:
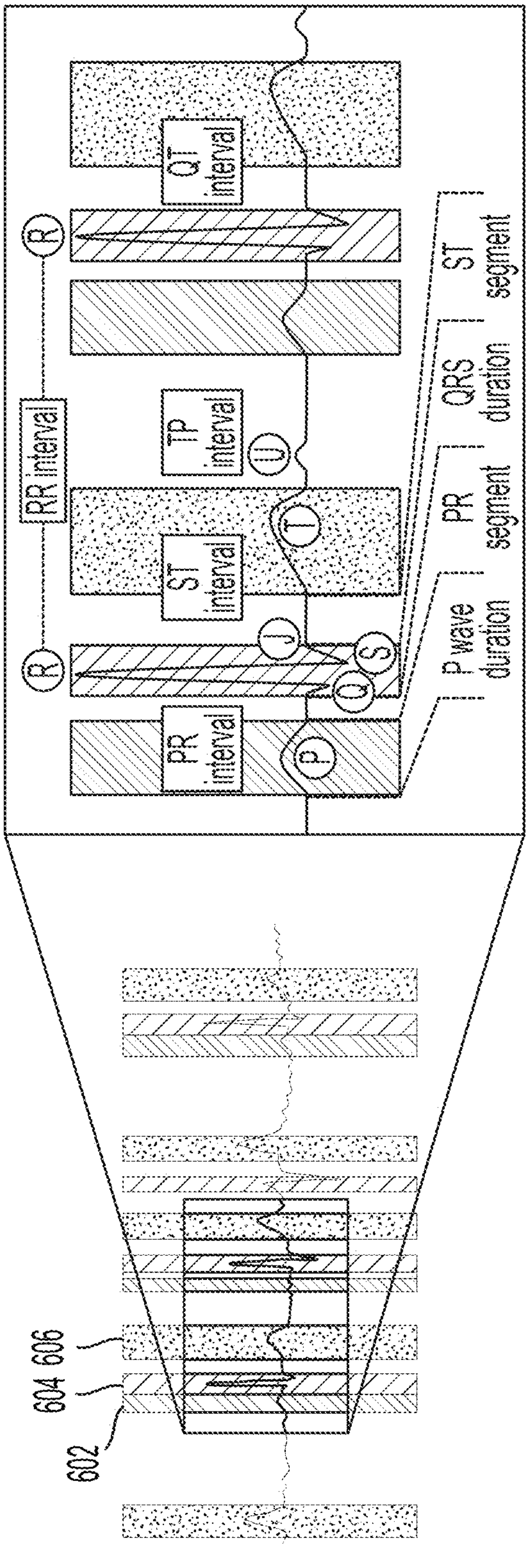
FIG. 6A shows an example of a labeled ECG signal, according to some embodiments of the technology described herein.

FIG. 6A shows an example of a labeled ECG signal, according to some embodiments of the technology described herein. In FIG. 6A, ECG portions (e.g., P-waves, QRS-complexes, and T-waves) are labeled using patterned blocks. Pattern 602 represents labelled P-waves, pattern 604 represents labelled QRS-complexes, and pattern 606 represented labelled T waves. The patterns 602, 604, and 606 are used in FIGS. 6B-6K and FIGS. 7D-7H and represent the same ECG portions in each of the figures. The labeled ECG portions are determined by determining sample-level ECG labels. Example techniques for determining sample-level ECG labels are described herein including at least with respect to FIG. 1B, 1D, and FIG. 4B. For example, the sample-level ECG labels may be obtained by processing an ECG signal with an encoder, an optional RVQ, and a sample-level ECG classifier.

The example also includes labels for waveform metrics that can be determined for the ECG signal. The waveform metrics include P-wave duration, PR interval, PR segment, ST interval, QRS duration, ST segment, TP interval, RR interval, and QT interval. As described herein, the waveform metrics can be obtained by (i) determining sample-level ECG labels for the ECG signal, and (ii) determining the waveform metrics using the sample-level ECG labels. For example, the sample-level ECG labels can be used to determine the onsets and offsets (e.g., the beginning and ending) of the ECG waves, which can then be used to determine the metrics. The onset and offset of a particular wave type may be determined by identifying a segment of multiple samples labeled as corresponding to the particular wave type. The onset and offset may be considered to be the first sample and the last sample of the identified segment, respectively.

For example, the sample-level ECG labels can be used to determine the onset and offset of the P-wave, which can be used to determine the P-wave duration. The sample-level ECG labels can be used to determine the P-wave onset and offset and the QRS-complex onset, which can be used to determine the PR interval and the PR segment. The sample-level ECG labels can be used to determine the QRS-complex onset and offset, which can be used to determine the QRS duration. The sample-level ECG labels can be used to determine the offset of the QRS-complex and the onset and offset of the T wave, which can be used to determine the ST segment and the ST interval. The sample-level ECG labels can be used to determine the offset of the QRS-complex and the onset of the T wave, which can be used to determine the QT interval.

Figure 6B:
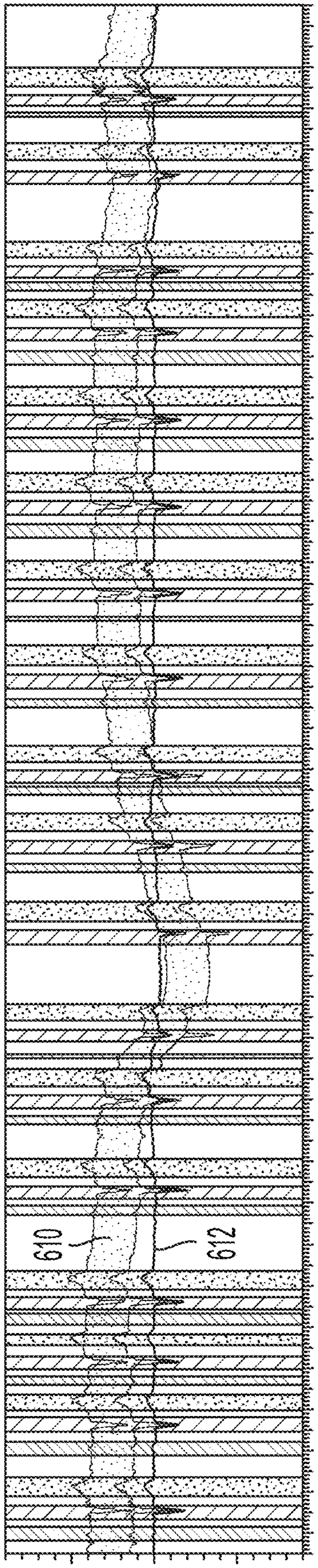
FIGS. 6B-6K show examples of denoised ECG signals compared to the measured ECG signals, according to some embodiments of the technology described herein.

FIGS. 6B-6K show examples of denoised ECG signals compared to the measured ECG signals, according to some embodiments of the technology described herein. In FIG. 6B, pattern 610 indicates the ECG signal before it is denoised and is used in each of FIGS. 6C-6K to represent respective ECG signals before they are denoised. The solid black line 612 represents the denoised ECG signal. A black solid line is similarly used in each of FIGS. 6C-6K to represent respective denoised ECG signals. For each of FIGS. 6C-6K, the denoised ECG signal was obtained by processing the ECG signal using a trained denoising model. The trained denoising model included an encoder, a residual vector quantizer, and a decoder. The encoder had the architecture shown in FIG. 5A, the residual vector quantizer had the architecture shown in FIG. 5D, and the decoder had the architecture shown in FIG. 5E.

Figure 6C:
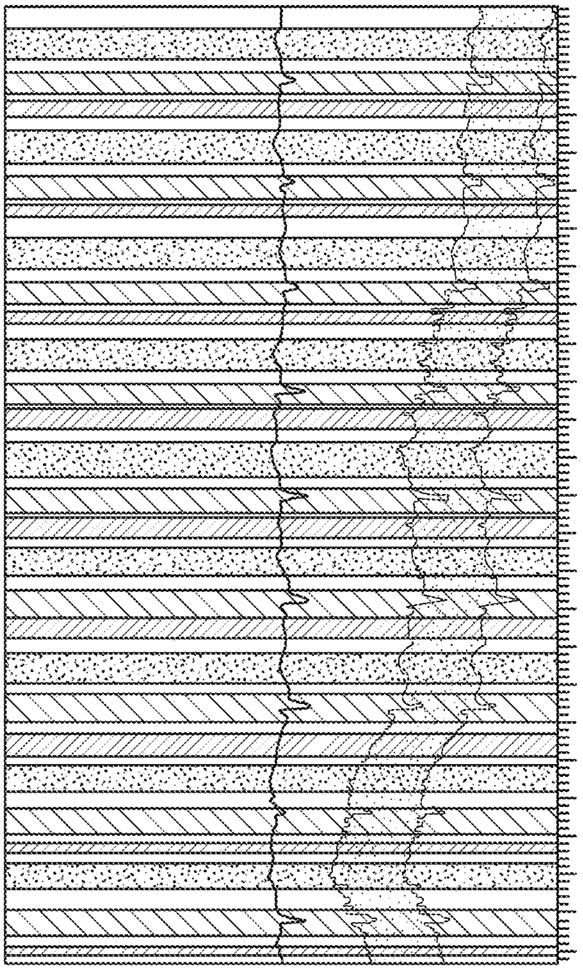

FIG. 6B and FIG. 6C shows that embodiments of the technology described by the inventors can be used to denoise an ECG signal to remove baseline wander. Centering wandering baselines on strips helps maintain a stable reference point, making it easier to analyze cardiac events. This ensures reliable measurements as wandering baselines can produce false rates on current systems.

Figure 6D:
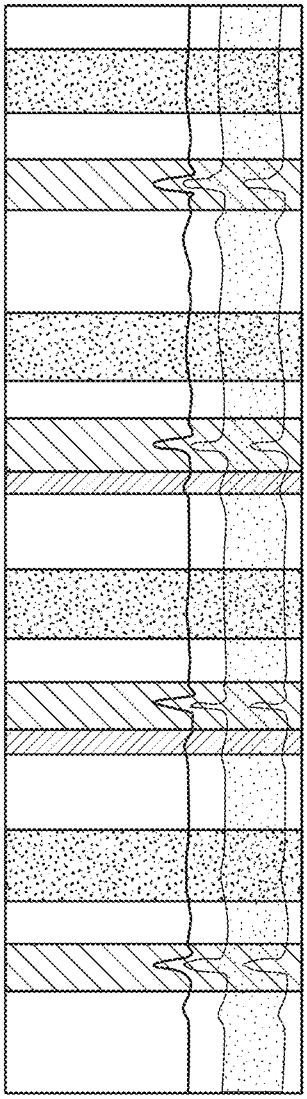

FIG. 6D show that embodiments of the technology described herein can be used to detect P-waves, even when the P-waves have low amplitudes. Detecting the P-wave on an ECG provides valuable insights into atrial electrical activity and can help identify several abnormalities. Additionally, detecting P-waves is important for determining the PR interval, which measures the time between the P-wave and the QRS complex. The PR interval can be used to detect conditions such as Wolff-Parkinson-White syndrome and AV block, for example.

Figure 6E:
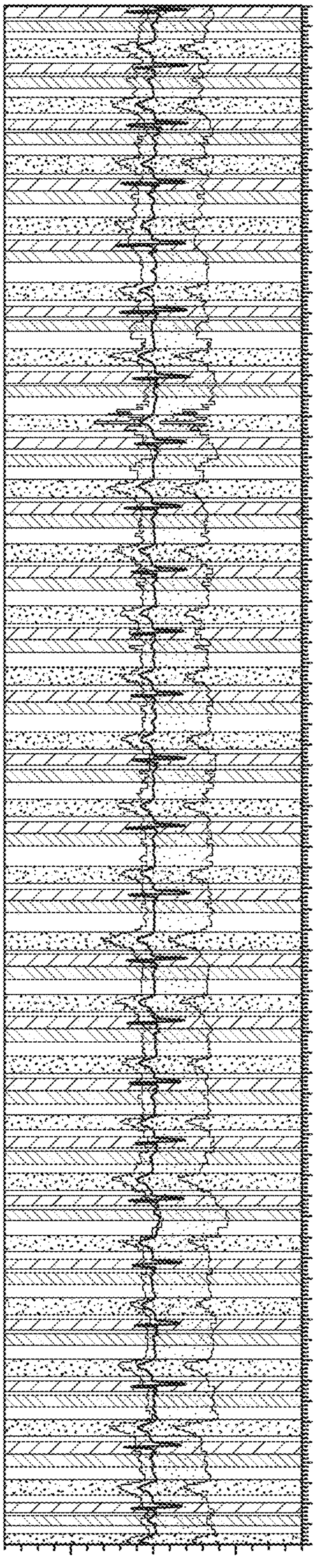
Figure 6F:
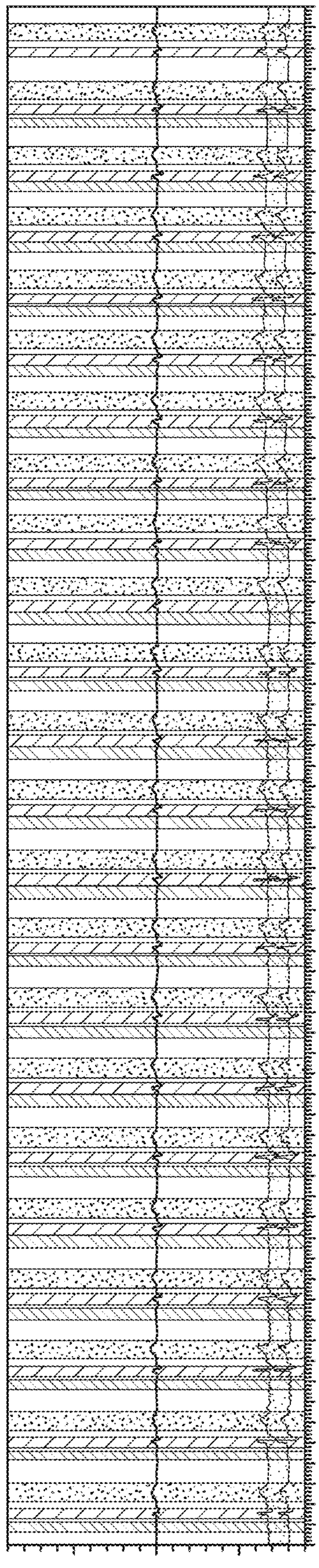
Figure 6G:
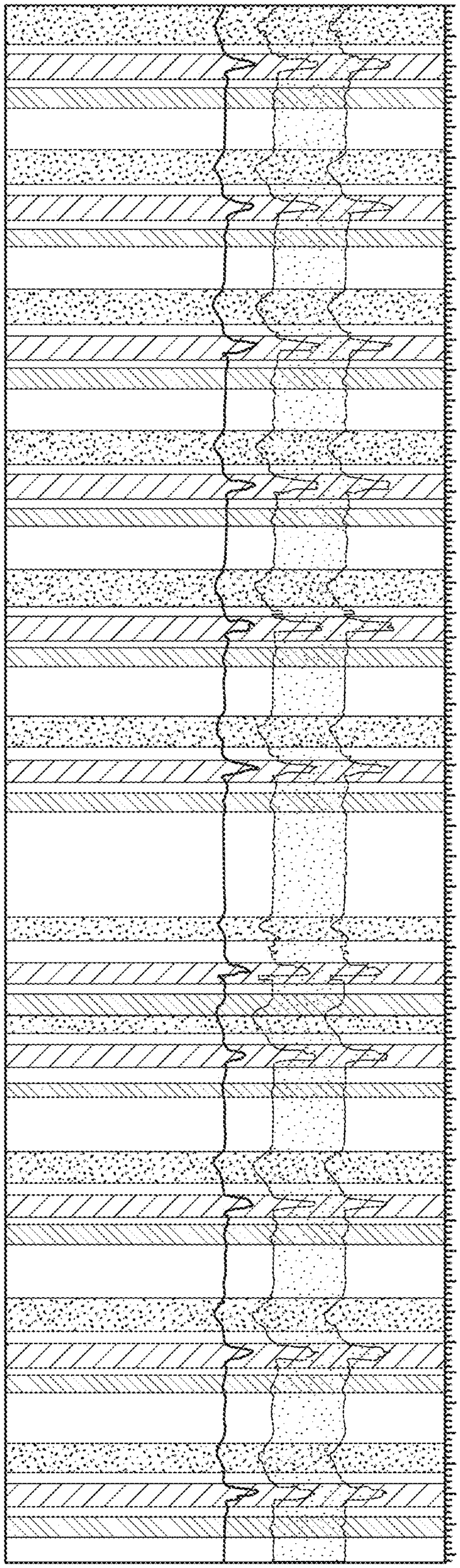

FIG. 6F and FIG. 6G show examples of low amplitude ECG signals compared to that shown in FIG. 6E. FIG. 6F and FIG. 6G also shows that embodiments of the technology described herein can be used to identify parts (e.g., waves) of the ECG waveform, even in low amplitude ECG signals.

Figure 6H:
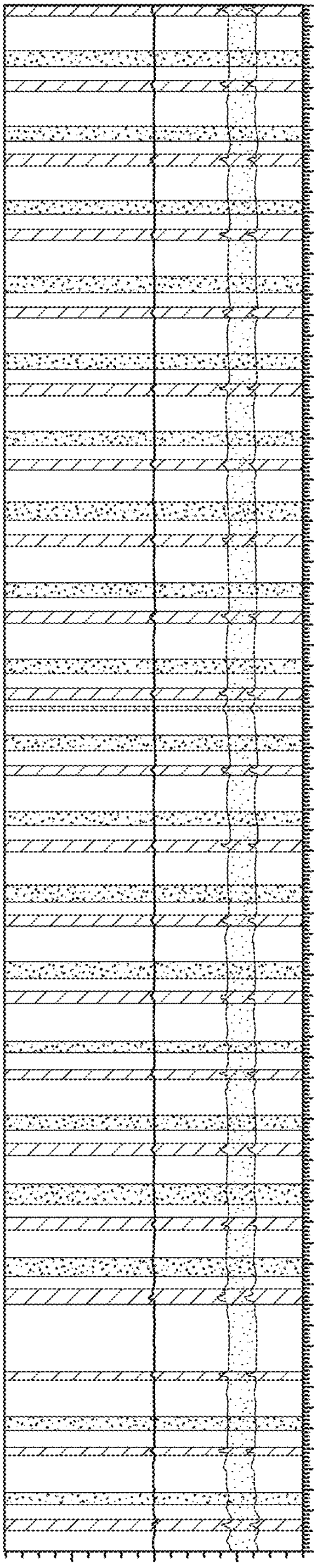

FIG. 6H shows that even when P-waves are difficult to detect in low amplitude ECG signals, embodiments of the technology described herein can be used to denoise the low amplitude ECG signal to produce valuable data by revealing clear QRS and T-waves, which can help identify arrhythmias, measure QRS width, and detect ventricular ectopy.

Figure 6I:
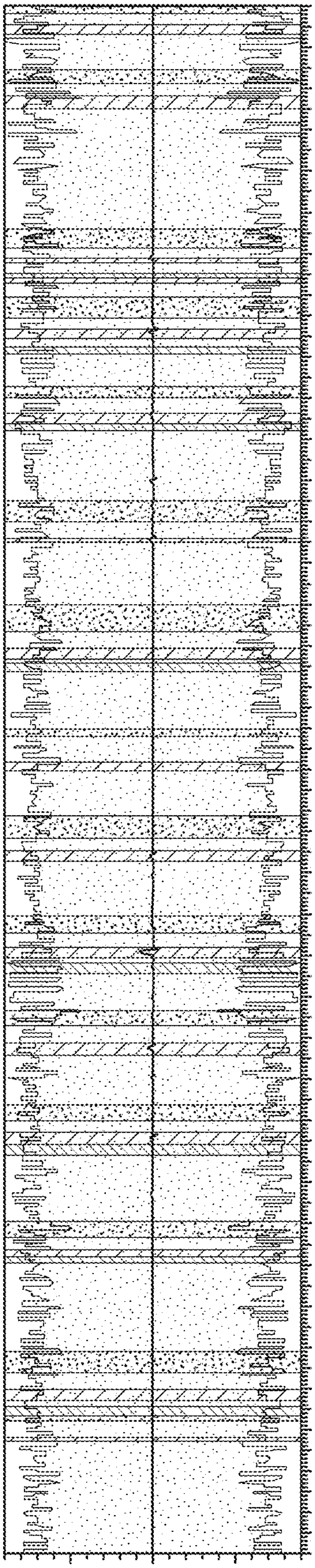

FIG. 6I shows that embodiments of the technology described herein can be used to denoise an ECG signal having excessive noise. Salvaging even a small amount of data from the poor quality ECG tracings can provide important insights into cardiac events.

Figure 6J:
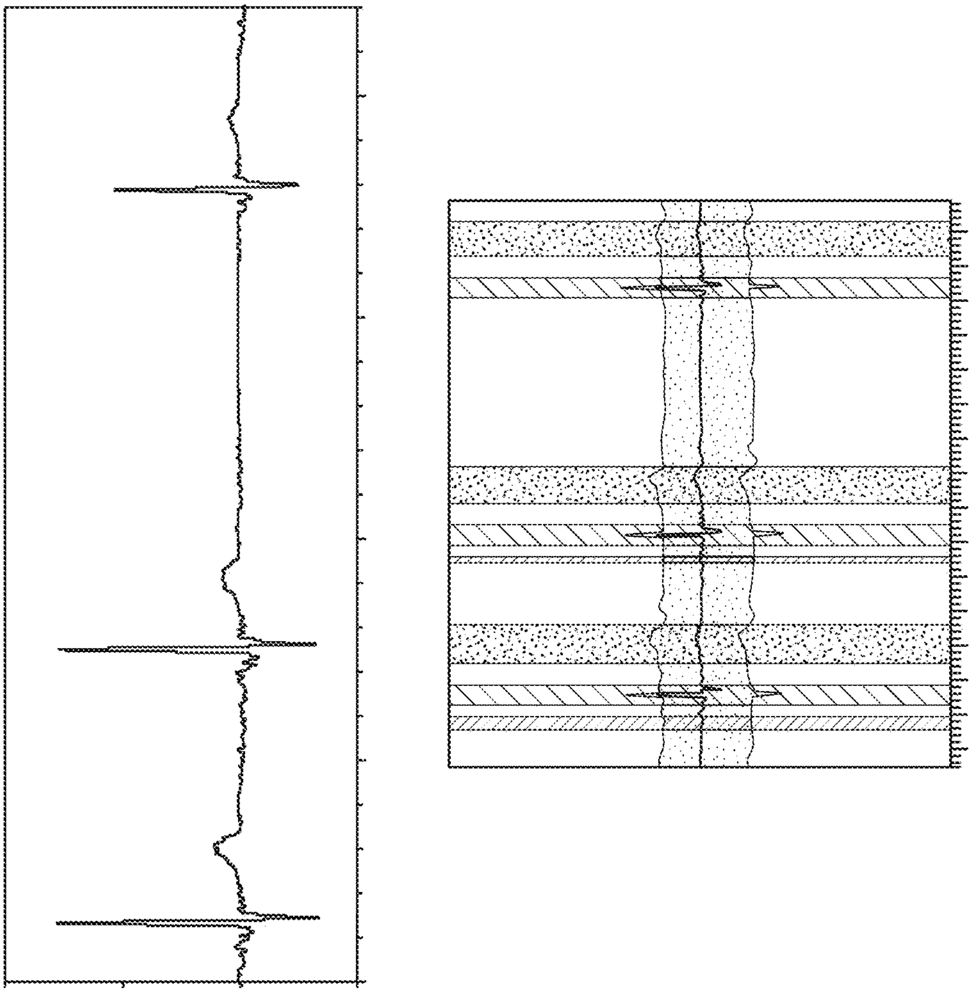

FIG. 6J shows that embodiments of the technology described herein can be used to denoise an ECG signal to accurately distinguish between low amplitude P-waves and a junctional escape (no P-wave).

Figure 6K:
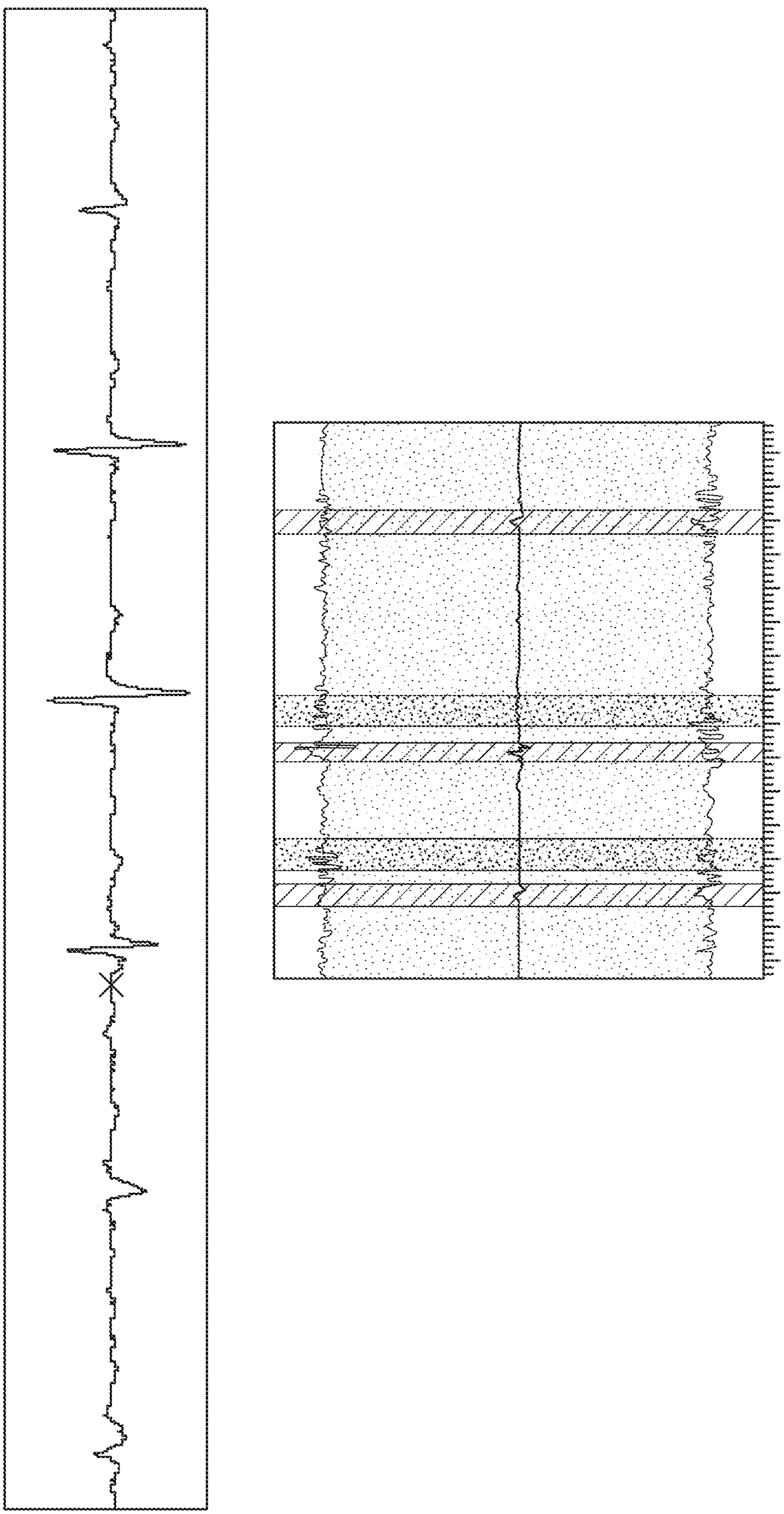

FIG. 6K shows that embodiments of the technology described herein can be used to denoise an ECG signal that has ECG signal loss, yet still identify QRS complexes despite the low amplitude.

Example Interactive Graphical User Interface (GUI)

As described herein, aspects of the technology described herein include generating an interactive graphical user interface (GUI) through which user(s) may interact with software that performs analysis of ECG signals as described herein. For example, the interactive GUI may be used to upload files, view ECG signals (e.g., raw ECG signals, denoised ECG signals, annotated ECG signals, etc.), provide input specifying processing of ECG signals, view results of processing ECG signals, and/or provide feedback about the results of processing the ECG signals, among other functions. FIGS. 7A-7M show examples of an interactive GUI through which user(s) may interact.

Figure 7A:
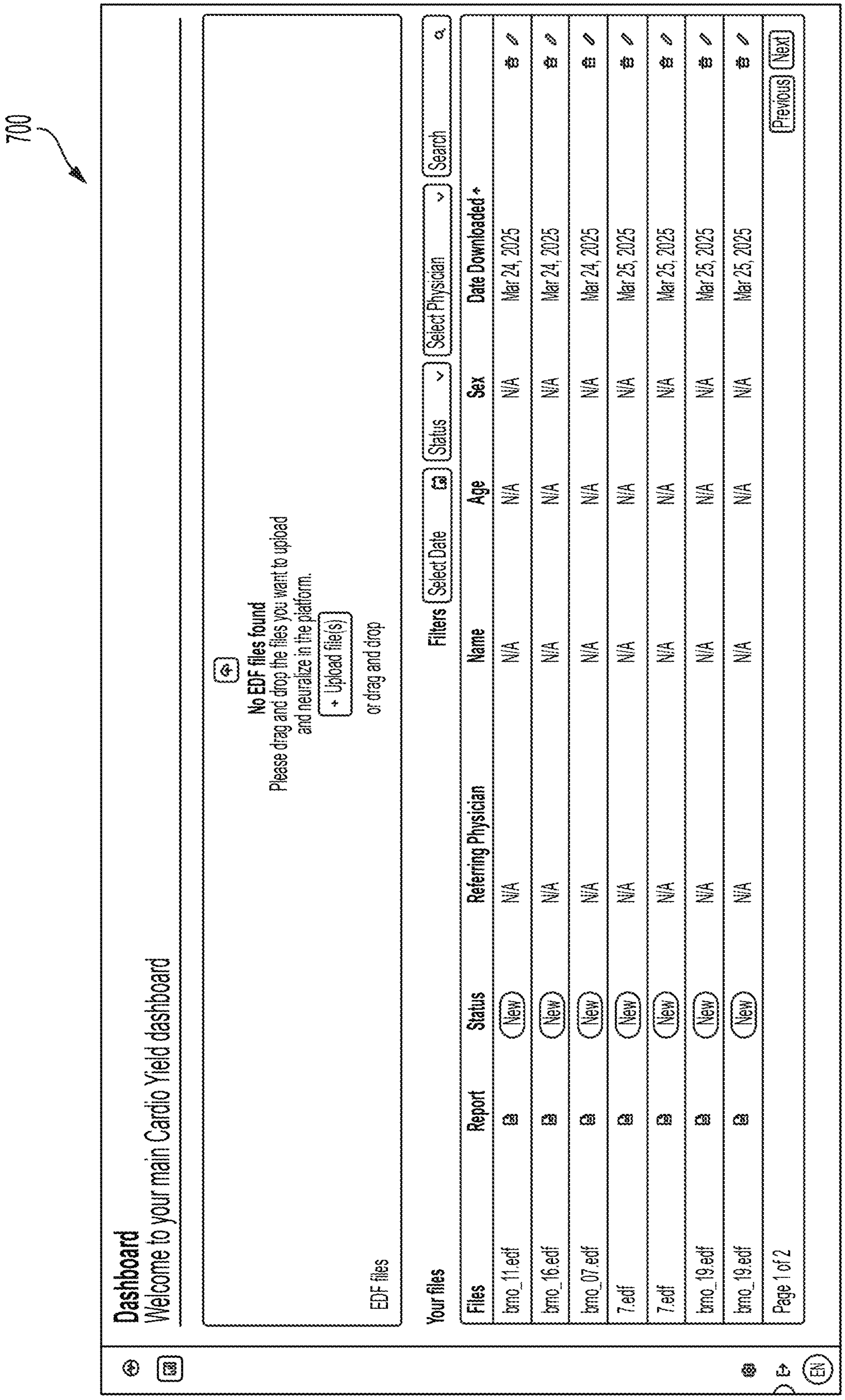
FIGS. 7A-7M are examples of an interactive graphical user interface (GUI), according to some embodiments of the technology described herein.
Figure 7B:

FIG. 7A shows an example of a portion 700 of an interactive GUI through which user(s) may upload and/or access ECG files. For example, previously-uploaded files may be listed in the table labeled "Your files." The list of files may include information about the files and the subjects for which the files were obtained. FIG. 7B shows an example of a portion of a interactive GUI through which user(s) may enter such information. For example, the information may include the referring physician, the name of the subject, the age of the subject, the sex of the subject, the date the file was downloaded, and/or the status. Additionally or alternatively, the list of files may include links to reports generated for respective files. For example, the reports may include results of processing ECG signals included in the files. Additionally or alternatively, the example interactive GUI may include tools for deleting previously-uploaded files and/or editing information about one or more previously-uploaded files.

Figure 7C:
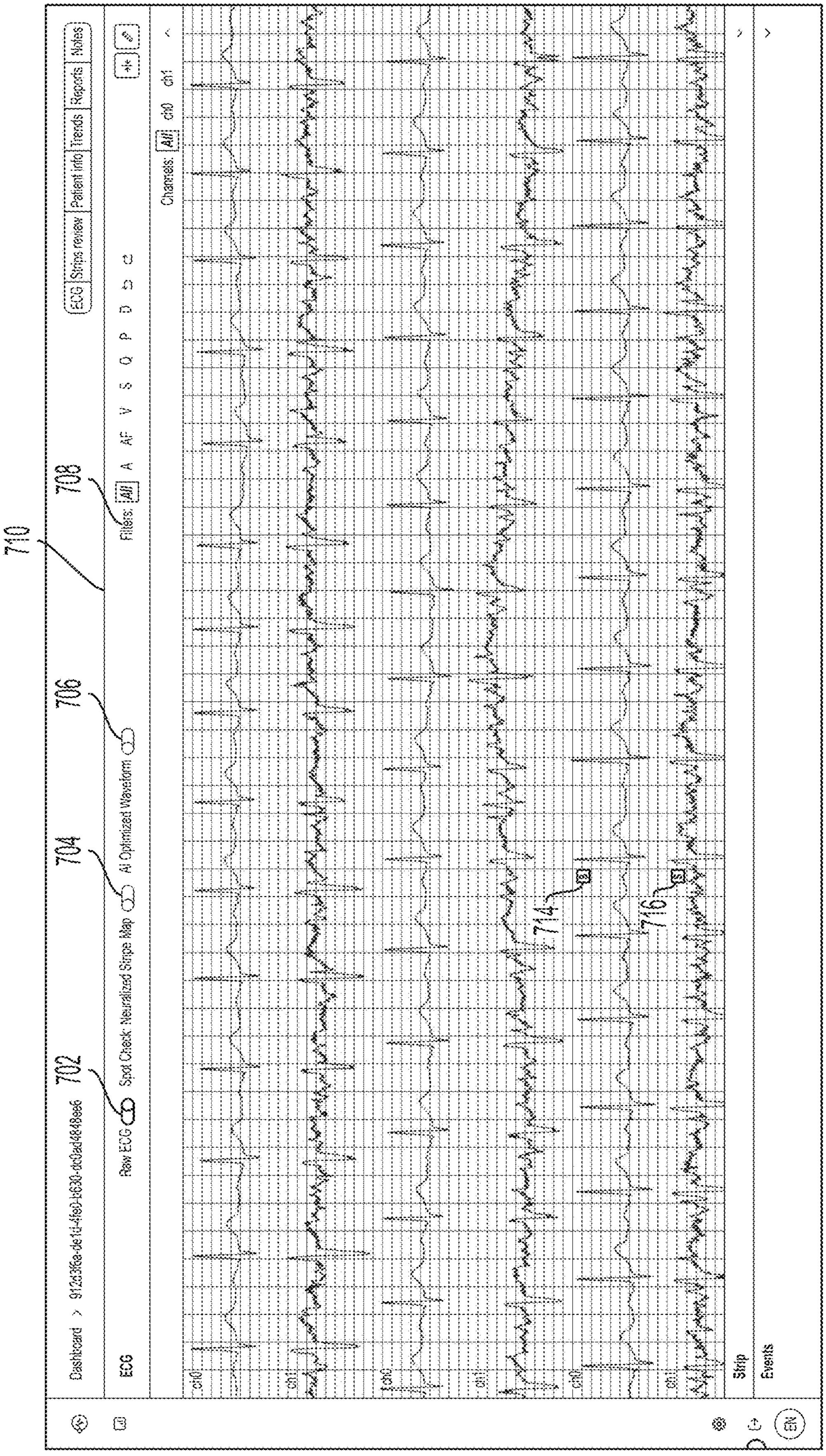

In some embodiments, by selecting a file listed in the GUI shown in FIG. 7A, user(s) can view ECG signals and/or results of processing ECG signals contained in the selected file. FIG. 7C shows an example of a portion 710 of the interactive GUI used to display strips of raw (e.g., unprocessed) ECG signals included in a selected file. As shown, the interactive GUI can be used to display strips of ECG signals obtained from multiple channels (e.g., leads). Additionally or alternatively, the interactive GUI can be used to display multiple ECG strips corresponding to different intervals of time.

As shown in FIG. 7C, the displayed ECG strips may be annotated with one or more types of labels. The labels may be generated as a result of processing the ECG strips according to embodiments of the technology described herein. For example, the labels may include labels indicating rhythm types, ECG metrics, and/or conditions/abnormalities. For example, the labels indicating rhythm types may be generated using the rhythm classification techniques described herein including at least with respect to FIG. 1B, FIG. 1C, and FIG. 4C. The labels indicating the ECG metrics, conditions, and/or abnormalities may be determined using the rhythm classifications and sample-level ECG labels, as described herein including at least with respect to FIG. 1B and Tables 1 and 2.

As shown in FIG. 7C, labels 714 and 716 are used to annotate the displayed ECG strips. User(s) may optionally interact with filter buttons 708 to cause different labels or combinations of labels to be displayed. In the example of FIG. 7C, the filters are set such that all of the types of applicable labels are displayed.

The interactive GUI portion 710 may include one or more selectable elements with which the user(s) may interact to change the type(s) of information that may be displayed. For example, as shown in FIG. 7C, the GUI may include selectable element 702 which, when selected (as shown), causes the raw ECG strips to be displayed. The interactive GUI portion 710 also includes selectable elements 704 and 706.

Figure 7D:
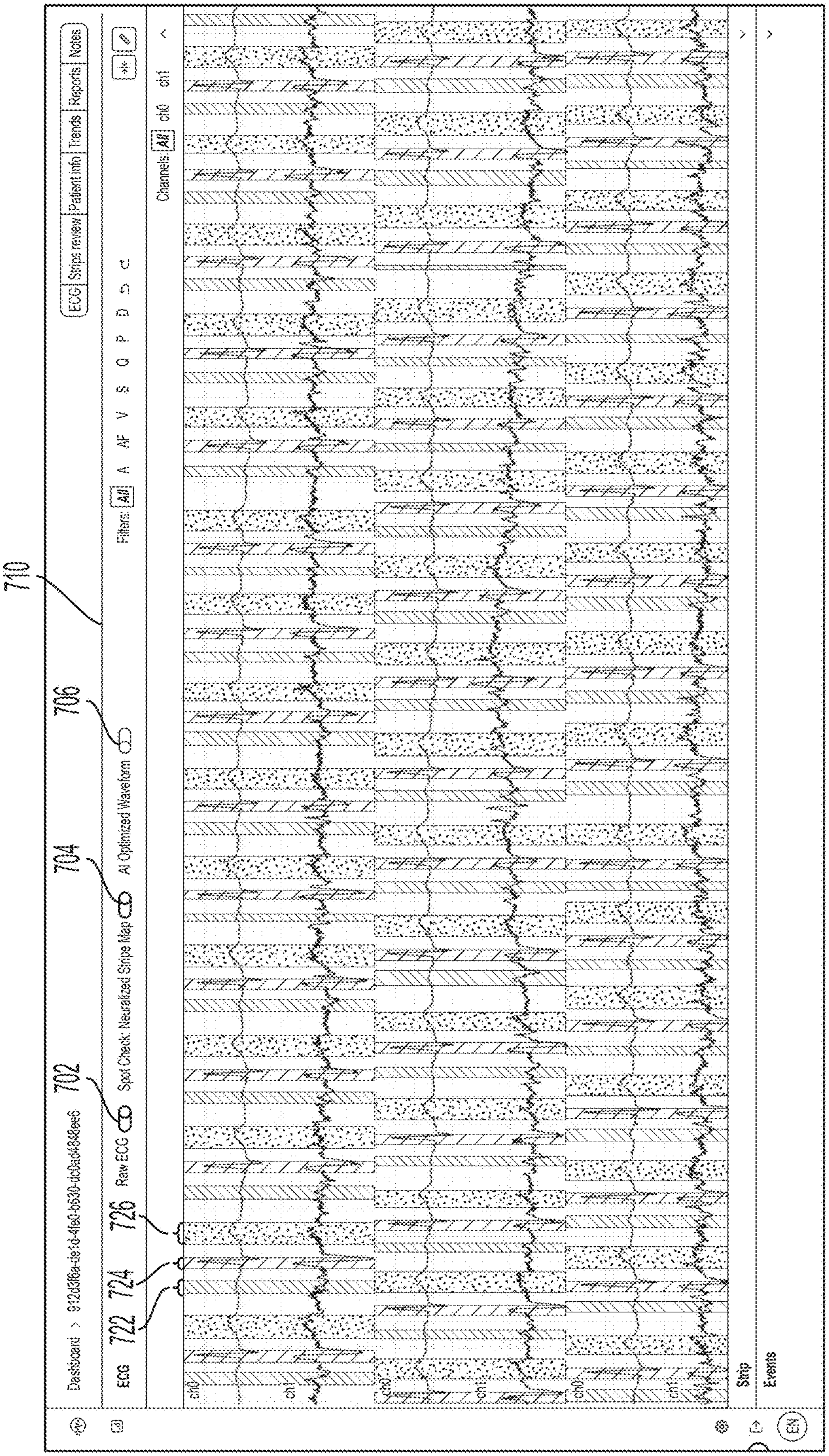

Selectable element 704 ("Spot Check: Neuralized Stripe Map) is used to display an indication of the onsets and offsets of different ECG waves, as determined according to embodiments of the technology described herein. For example, the onsets and offsets may be derived from sample-level ECG labels obtained using a sample-level ECG classifier (e.g., sample-level ECG classifier 138 shown in FIG. 1B). FIG. 7D shows an example of the information displayed when selectable element 704 is selected. In this example, shaded stripes are used to identify different ECG waves that have been detected, as well as their onsets and offsets. For example, shaded stripe 722 indicates a P-wave, shaded stripe 724 indicates a QRS complex, and shaded stripe 726 indicates a T-wave.

Figure 7E:
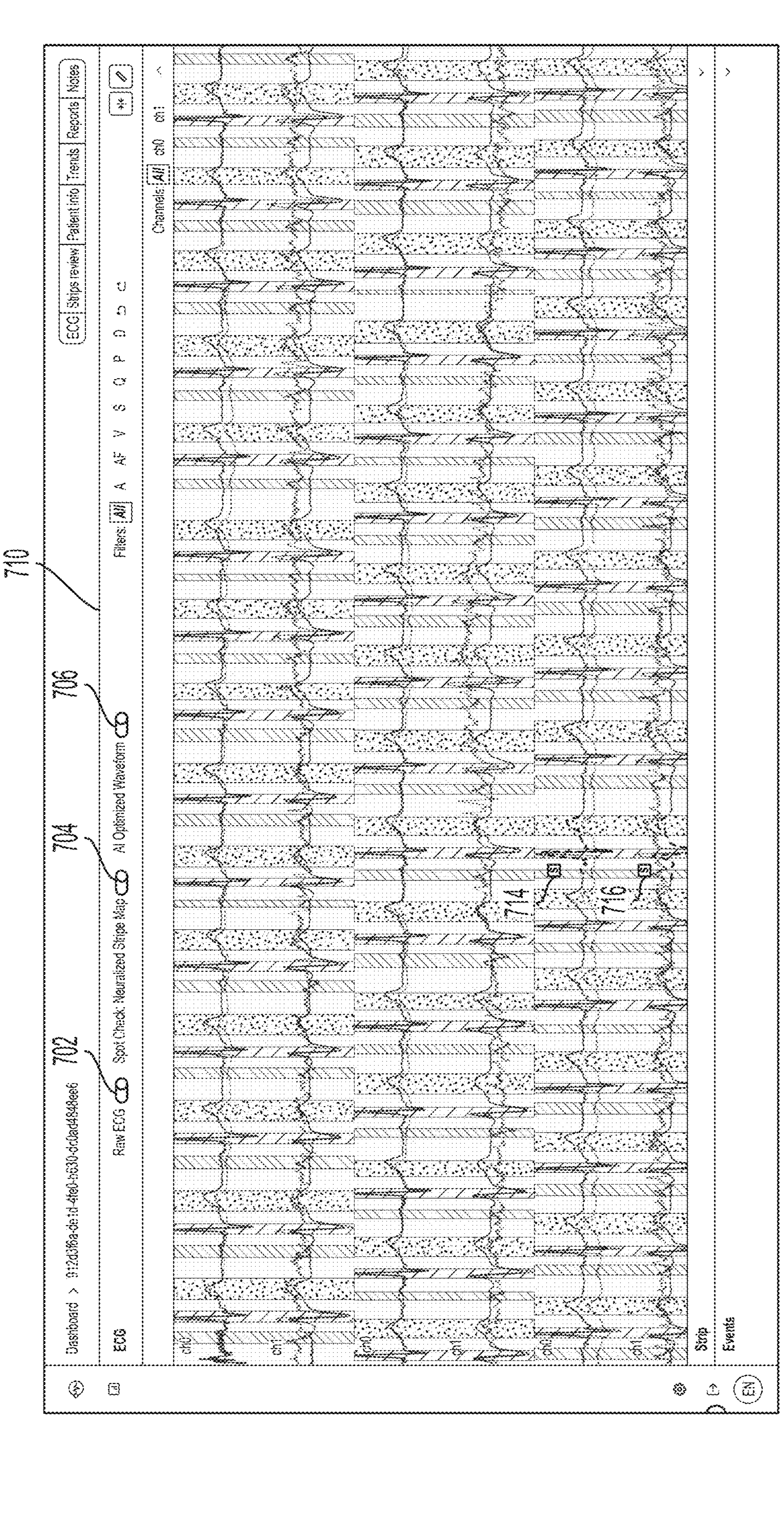

Selectable element 706 ("AI Optimized Waveform") is used to display the denoised version of the raw ECG signal included in the file. For example, the denoised version may have been obtained according to embodiments of the technology described herein, such as by using a trained denoising model (e.g., trained denoising model 120 shown in FIG. 1B). FIG. 7E shows an example of the information displayed when selectable element 706 is selected. In this example, the raw ECG signal is overlaid with the denoised ECG signal, though the raw ECG signal may be removed from the display by deselecting selectable element 702. As shown in FIG. 7E, the denoised ECG signal may also be labeled (e.g., using labels 714 and 716).

Figure 7F:
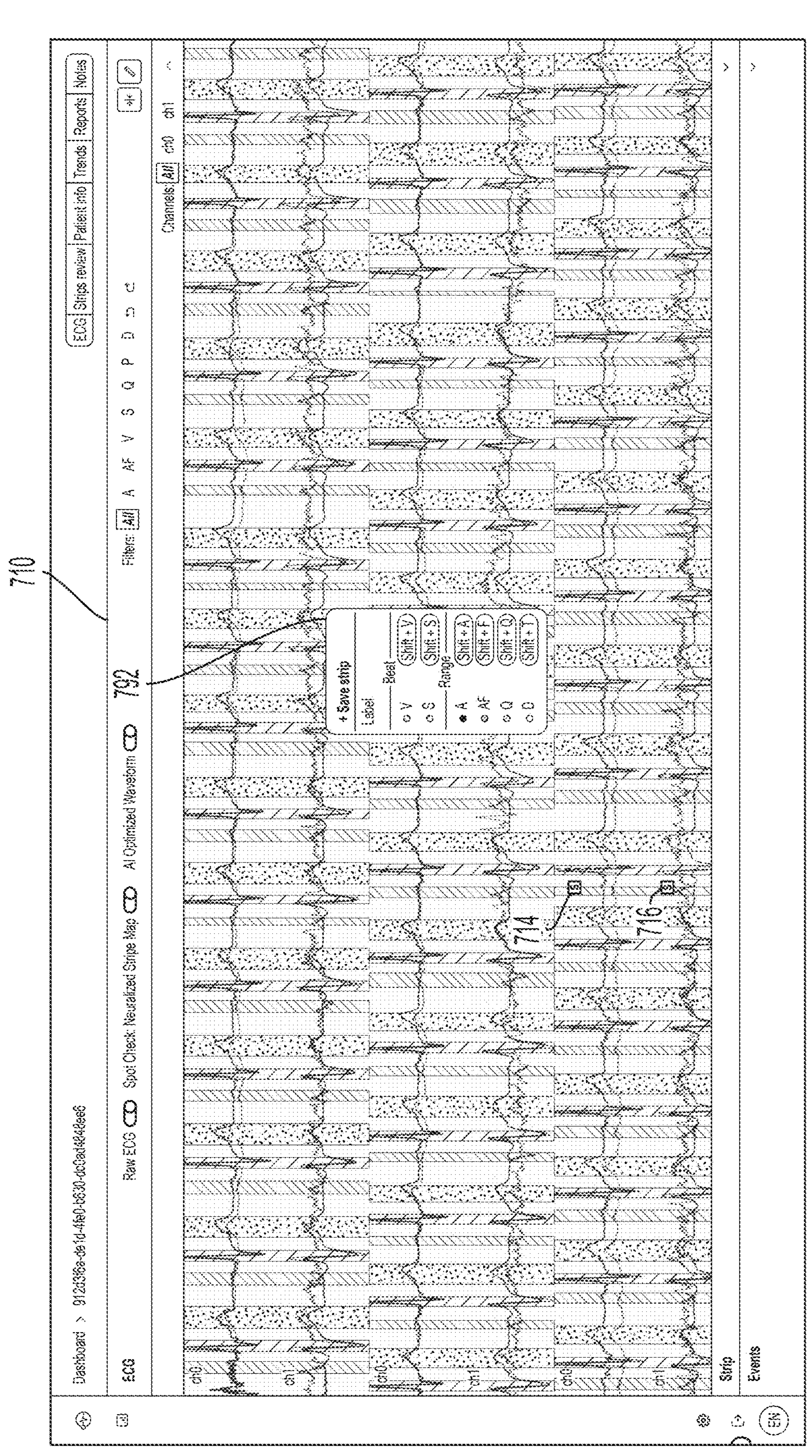
Figure 7G:
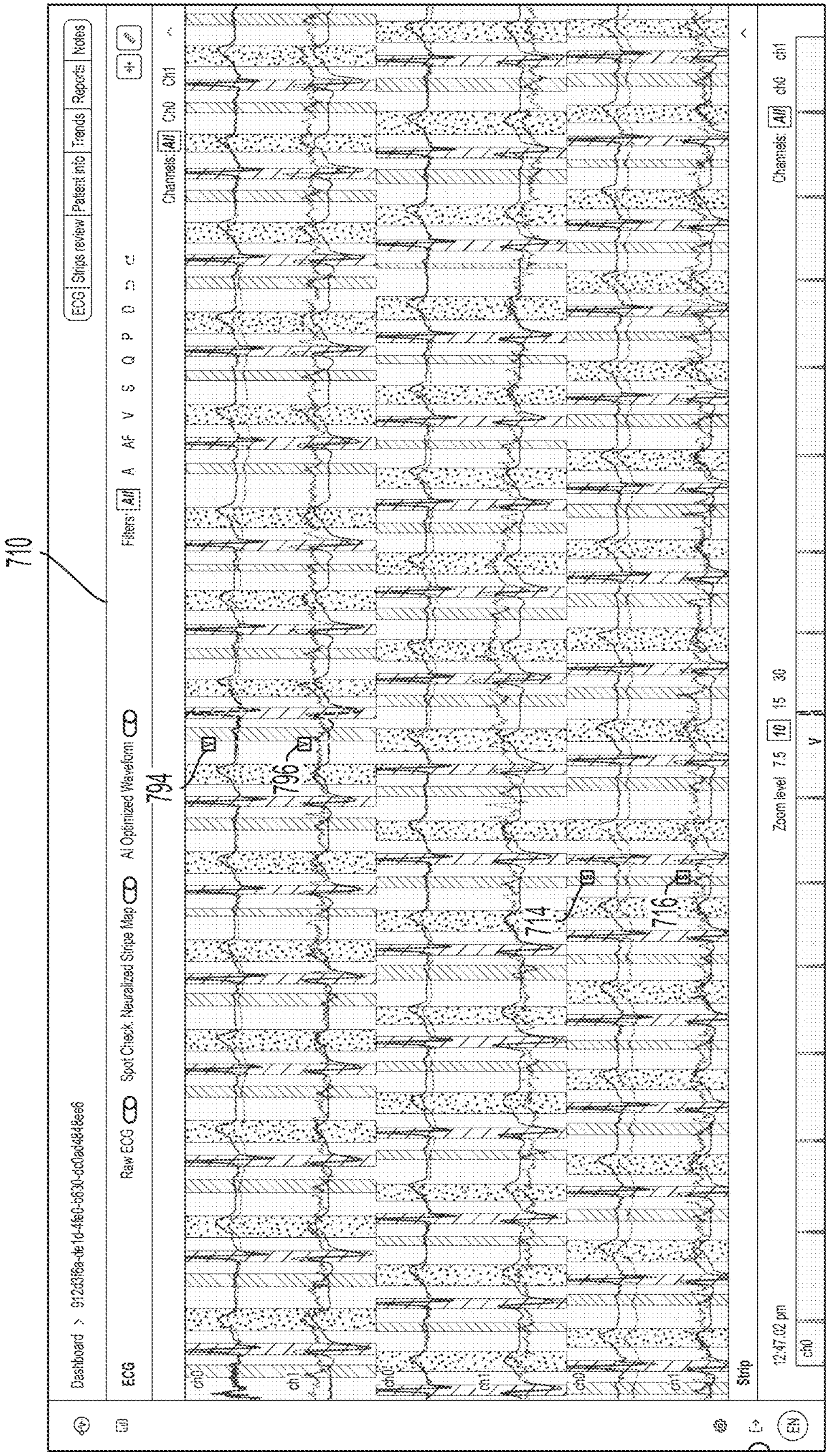
Figure 7H:
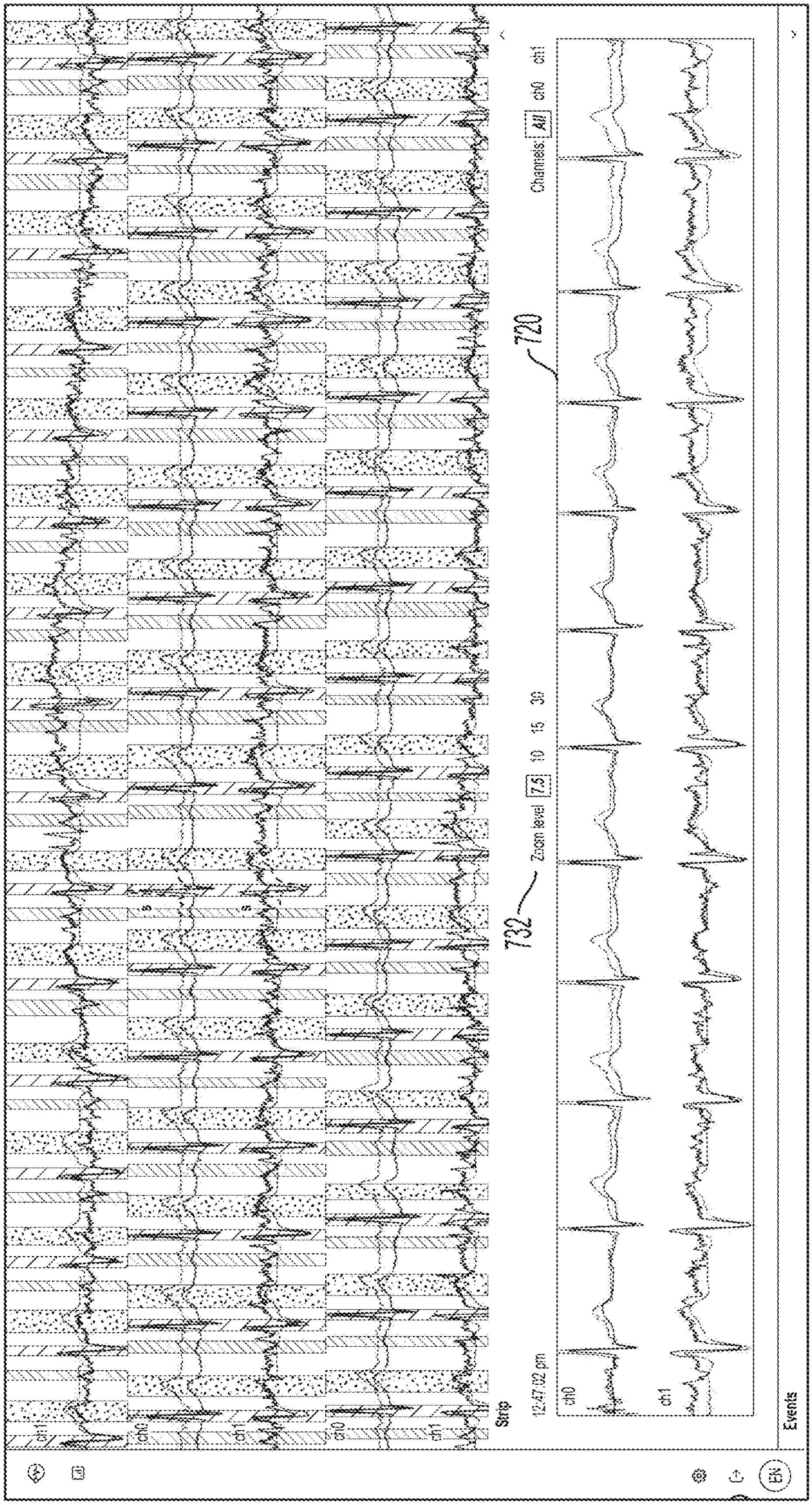

In some embodiments, user(s) can interact with the interactive GUI to add, remove, and/or edit labels used to annotate the raw and/or denoised ECG signals. For example, as shown in FIG. 7F, the interactive GUI portion 710 may include tool menu 792, which may include tools for saving and/or labeling ECG strips. For example, as shown in FIG. 7G, by interacting with the tools shown in the tool menu 792 (FIG. 7F), the user(s) added labels 794 and 796. The interactive GUI may include one or more features that enable user(s) to closely examine the raw and/or denoised ECG signals. For example, as shown in FIG. 7H, the interactive GUI may include a portion 720 that displays zoomed in versions of one or more of the strips shown in the portion 710. User(s) may interact with buttons 732 to adjust the factor by which to zoom in on the displayed ECG strips. For example, as shown in FIG. 7H, the displayed ECG strips may be zoomed in by a factor of 7.5, 10, 15, or 30.

Figure 7I:
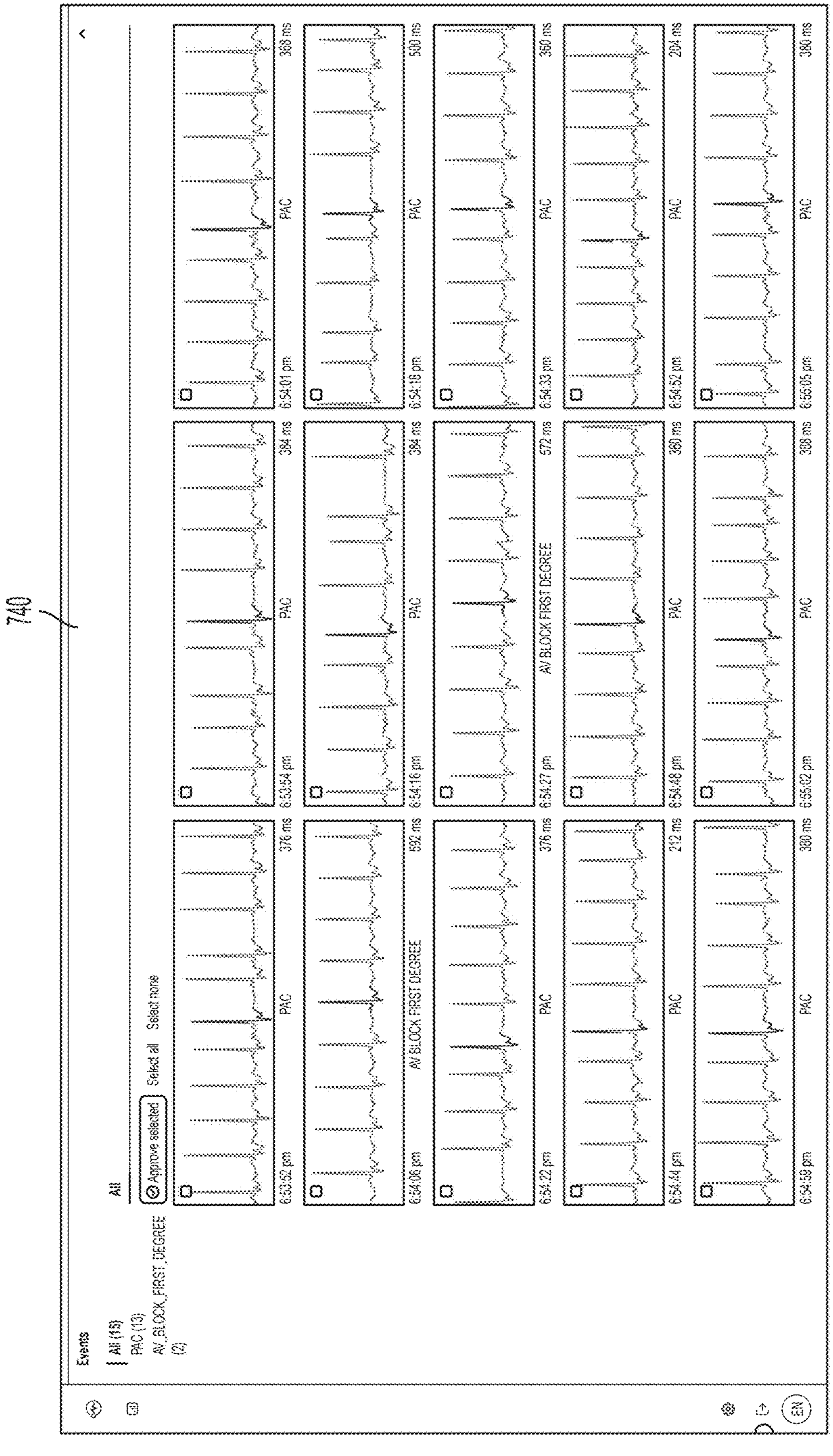
Figure 7J:
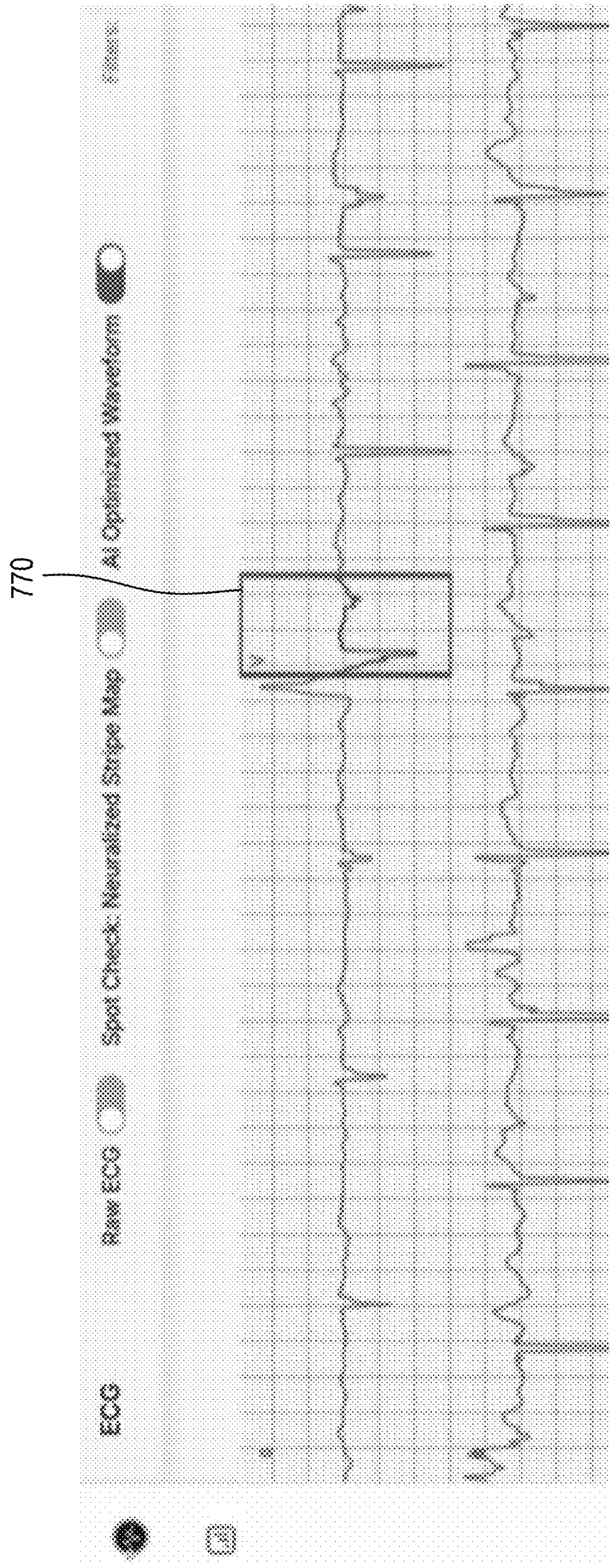

In some embodiments, the techniques described herein include identifying one or more conditions and/or abnormalities ("events") associated with an ECG signal and/or individual waveforms of an ECG signal. As shown in FIG. 7I, the interactive GUI may additionally or alternatively include a portion 740 used to view ECG waveforms that have been labelled as indicating a particular event. For example, the portion 740 includes a respective window for each premature atrial contraction (PAC) and atrioventricular block (AV) event. The particular events may include the rhythm types, ECG metrics, conditions, and/or abnormalities for which the labels 792 (FIG. 7F) are available.

Figure 7K:
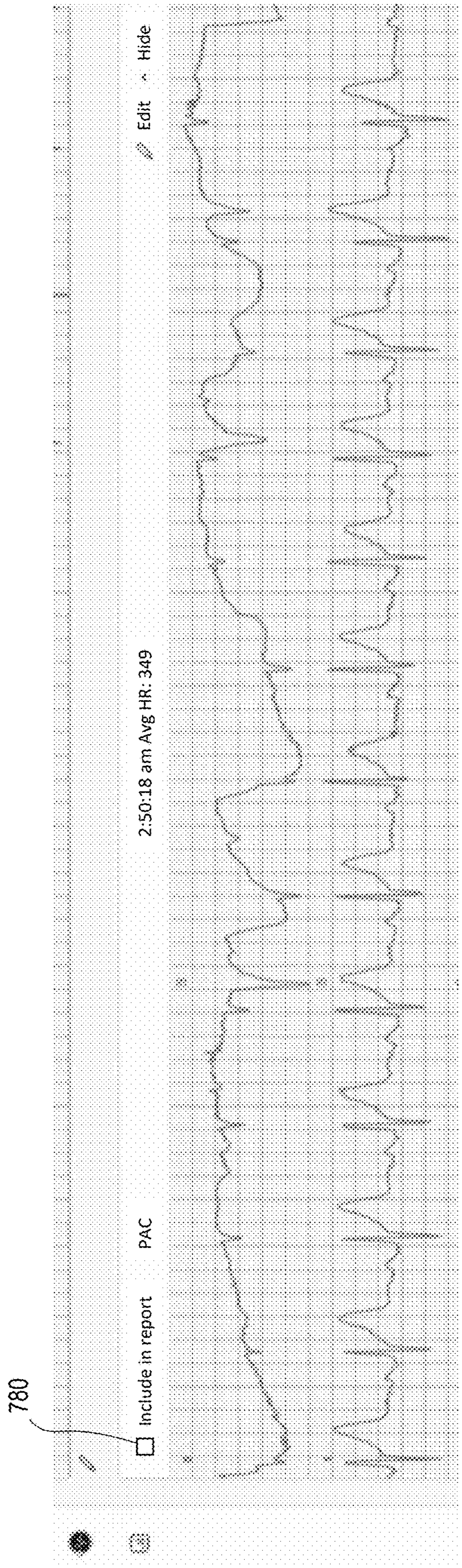

Each window includes the ECG waveform labeled as indicating the particular event, as well as the surrounding ECG waveforms. Accordingly, a user may quickly and easily review the labeled ECG waveforms and confirm whether they have been accurately labeled as indicating the particular event. The portion 740 may include checkboxes for selecting particular windows to confirm or revise the label, to select the portion of the ECG signal for additional processing, and/or to efficiently include the events in a report. For example, when a user selects the portion of the ECG signal, the event may be indicated in the interactive GUI portion 710, as shown by the box 770 displayed in FIG. 7J. Additionally, as shown in FIG. 7K, a user may select an event using checkbox 780 to be added to a report.

Figure 7L:
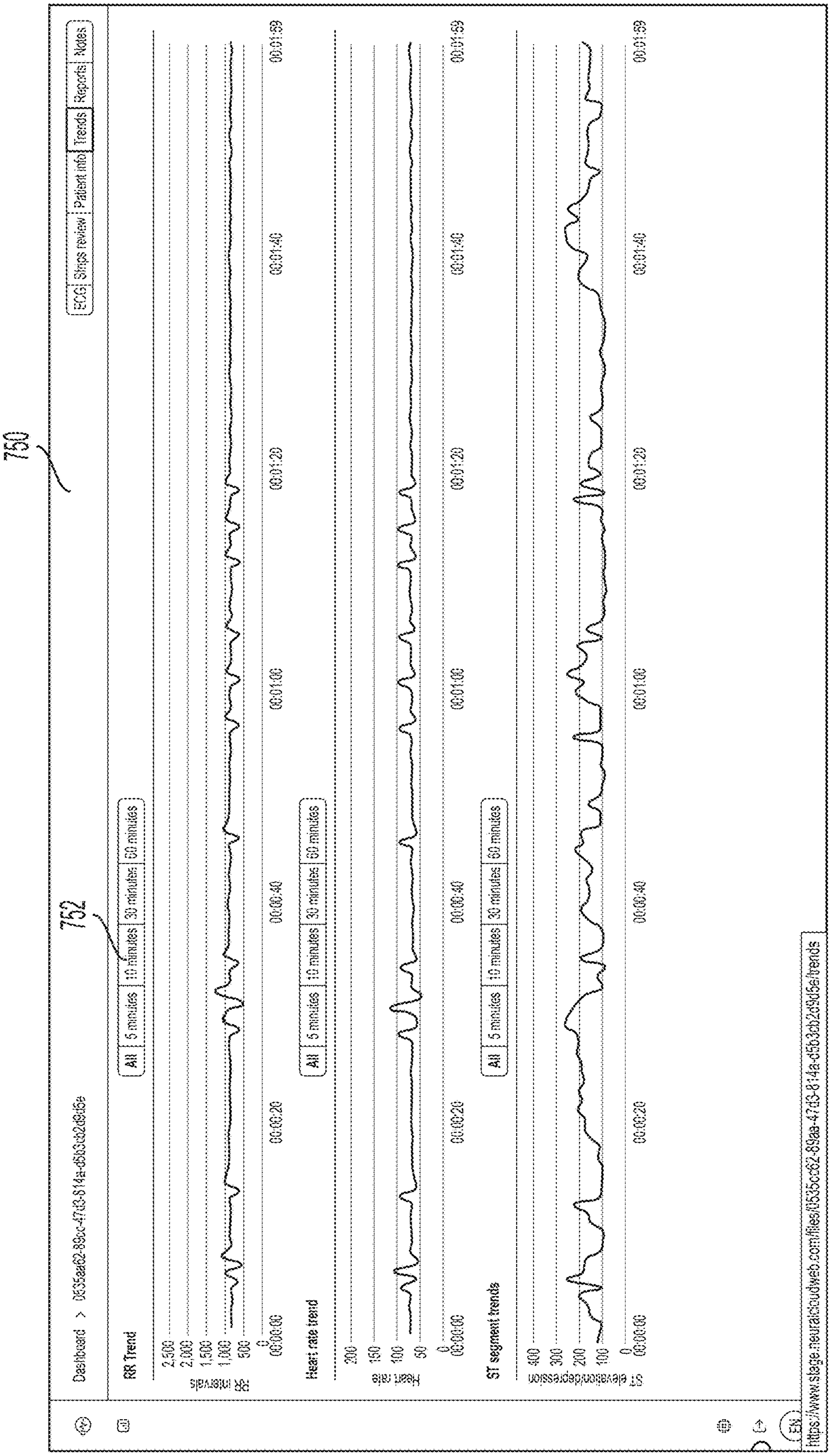

In some embodiments, the techniques described herein may additionally or alternatively be used to determine one or more ECG metrics. Accordingly, the interactive GUI may include one or more portions used to display said metrics. For example, as shown in FIG. 7L, the portion 750 is used to display metrics related to the RR interval, heart rate, and ST segments. Specifically, the portion 750 includes graphs showing the trends in RR interval, heart rate, and ST segments over time. Each graph may include elements, such as buttons 752, that allow user(s) to adjust the time axis.

Figure 7M:
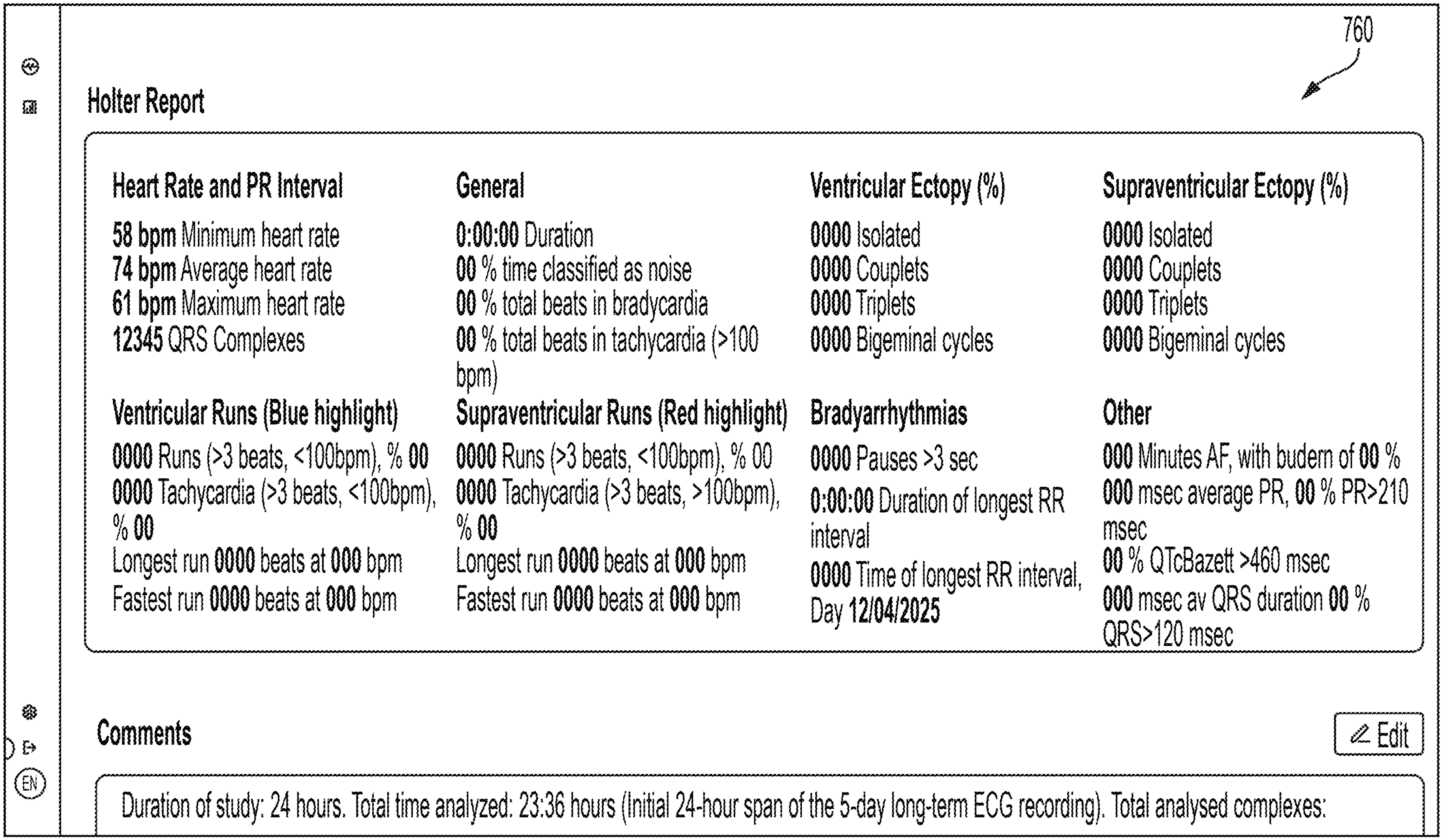

The interactive GUI may additionally or alternatively include one or more portions used to generate and/or display a report that indicates raw ECG signal(s), denoised ECG signal(s), and/or results of processing the ECG signal(s). For example, as shown in FIG. 7M, the interactive GUI may include a portion 760 used to display a Holter report that is generated for ECG signals obtained using a Holter monitor.

EXAMPLES

Example 1: Denoising Model Training

The following examples (Examples 2-5) demonstrate the performance of embodiments of the technology developed by the inventors. Specifically, the following examples demonstrate use of a trained denoising model that includes a trained encoder, trained RVQ, and trained decoder. The trained encoder was implemented as the encoder 502 shown in FIG. 5A, with encoder blocks implemented as shown in FIG. 5B and residual blocks implemented as shown in FIG. 5C. The trained RVQ was implemented as the grouped RVQ 506 shown in FIG. 5D. The trained decoder was implemented as the decoder 513 shown in FIG. 5E, with decoder blocks implemented as shown in FIG. 5F, an encoder block implemented as shown in FIG. 5B, and residual blocks implemented as shown in FIG. 5C.

The denoising model (e.g., the encoder, RVQ, and decoder) were trained using pairs of ECG signals. Each pair of ECG signals included a clean ECG signal and a corresponding noisy ECG signal. A total of 257,342 clean ECG signals were obtained from the following public datasets: the Icentia11k Single Lead Continuous Raw Electrocardiogram Dataset, CODE-15%, Brno University of Technology ECG Quality Database, and the Lobachevsky University Electrocardiography Database.

The 257,342 clean ECG signals were pre-processed to obtain corresponding noisy ECG signals. The clean ECG signals were resampled to a random value, generated by 250+random.randint(−80, 80). After resampling, amplitude noise was added to the ECG signals. Amplitude noise was added by multiplying each ECG signal by a respective factor of random.random( )+0.5. ECG signals shorter than 60 seconds were padded with zeroes. 1 in 3 ECG signals had neurokit2.ecg_clean applied to them, using the "neurokit" method. 4 in 5 of the ECG signals had additional noise added to them.

The additional noise includes white noise, intense sectional white noise, signal distortion noise, artifacts with random amplitude, linear drift, random jump, wander, and/or powerline noise. As described below, linear drift, random jump, wander, and powerline noise were not added to all ECG signals to which additional noise was added.

White noise was generated from a random normal distribution with a mean of 0 and a standard deviation equal to the standard deviation of the signal, multiplied by a number chosen from a random uniform distribution from 0.001 to 1.001. White noise was then added to the ECG signals.

Intense sectional white noise is white noise that is generated for only a part of the signal. It was generated the same way as ordinary white noise was generated. Intense sectional white noise was only added to random parts of the signal. The start point of a section of white noise was chosen from a uniform distribution from 0 to the length of the signal, and the length of the section was chosen from a uniform distribution from 10 to 500. The number of white noise sections was a random number chosen from a uniform distribution from 0 to 3.

Noise was also added using neurokit2.signal_distort. A list of 1 to 4 frequencies called noise_frequency was randomly generated. The frequencies were generated using int(10.0*random.random( )+5). signal_distort uses the parameters: noise_amplitude=random.randint(0, 4)*0.5*random.random( ), noise_frequency=noise_frequency.

Artifacts with random amplitude were added using neurokit2.signal_distort. A random number, 'artifacts', was generated with random.randint(0, 2). Then the parameters for signal_distort were: artifacts_amplitude= artifacts*2.0*random.random( ), artifacts_frequency=random.randint(5, 25), artifacts_number=artifacts*random.randint(1, 20).

There was a 1 in 4 chance that linear drift was added. Linear drift was generated with the following algorithm:

$$\text{drift\_start} = 2.0 * \text{random} \cdot \text{random}\ ( ) - 1.0$$

$$\text{drift\_end} = 2.0 * \text{random} \cdot \text{random}\ ( ) - 1.0$$

$$\text{drift} = \textit{numpy} \cdot \textit{linspace}\ (\text{drift\_start}, \text{drift\_end}, \textit{len}\ (\text{signal})$$

$$\text{baseline} = 10.0 * \text{random} \cdot \text{random}\ ( ) - 5.0$$

$$\text{distorted} = \text{distorted} + \text{drift} + \text{baseline}$$

There was a 1 in 6 chance a random jump was added. A random jump was added with the following algorithm:

$$\text{baseline} = 2.0 * \text{random} \cdot \text{random}\ ( ) - 1.0$$

$$s = \text{random} \cdot \text{randint}\ (0, \textit{len}\ (\text{signal}) - 1)$$

$$e = \text{random} \cdot \text{randint}\ (s, \textit{len}\ (\text{signal}) - 1)$$

$$\text{signal}\ [s{:}e] \mathrel{+}= \text{baseline}$$

There was a 1 in 4 chance wander was added. Wander was added by repeating the following algorithm 4 times:

$$fs = 1.0 * \text{random} \cdot \text{random}\ ( ) + 0.001$$

$$\text{time} = \textit{numpy} \cdot \textit{linspace}\ (0, \textit{len}\ (\text{signal}) * \text{sampling\_rate}, \textit{len}\ (\text{signal})) + fs * \text{random} \cdot \text{random}\ ( )$$

$$\text{wave} = (3 * \text{random} \cdot \text{random}\ ( ) + 0.2) * \textit{numpy} \cdot \sin\ (\textit{time} * 2 * \textit{numpy} \cdot \textit{pi} * fs)$$

$$\text{distorted} = \text{distorted} + \text{wave}$$

There was a 1 in 6 chance of powerline noise being added. Powerline noise was added by the following algorithm:

$$fs = 5 * \text{random} \cdot \text{random}\ ( ) + 60$$

$$\text{time} = \textit{numpy} \cdot \textit{linspace}\ (0, \textit{len}\ (\text{signal}) * \text{sampling\_rate}, \textit{len}\ (\text{signal})) + fs * \text{random} \cdot \text{random}\ ( )$$

$$\text{wave} = (0.5 * \text{random} \cdot \text{random}\ ( ) + 0.02) * \textit{np} \cdot \sin\ (\textit{time} * 2 * \textit{np} \cdot \textit{pi} * fs)$$

$$\text{distorted} = \text{distorted} + \text{wave}.$$

The resulting pairs of ECG signals were used to train the denoising model. The denoising model was trained by (a) processing the noisy ECG signals using the denoising model, and (b) updating parameters of the denoising model based on results of processing the noisy ECG signals using the denoising model. Specifically, the parameters of the denoising model (e.g., the parameters of the encoder, the codebooks of the RVQ, and the parameters of the decoder) were updated based on (a) a first loss that was determined as a function of the denoised ECG signal and the clean ECG signal, and (b) a second loss that was determined as a function of first and second outputs of first and second discriminator models, respectively.

The first loss was reconstruction loss calculated using Equations 24 and 25. The second loss included (i) generator loss (based on outputs of a first discriminator model) and (ii) STFT generator loss (based on outputs of a second discriminator model). The first discriminator model was implemented as the discriminator model shown in FIG. 5I-1 and FIG. 5I-2, and the second discriminator model was implemented as the discriminator model shown in FIG. 5J. The generator loss was calculated using Equation 26 and the STFT generator loss was calculated using Equation 27.

The first and second discriminator models were trained together with the denoising model. The first discriminator model was trained to predict whether the denoised ECG signal output by the denoising model was real or artificial. The parameters of the first discriminator model were updated using the loss functions of Equations 28-30. The second discriminator model was trained to predict whether a frequency-domain representation of a denoised ECG signal output by the denoising model was real or artificial. The parameters of the second discriminator model were updated using the loss functions of Equations 31-33.

Example 2: Sample-Level ECG Classifier

In this example, the sample-level ECG classification techniques developed by the inventors were used to label samples of ECG signals. The results demonstrate that the techniques developed by the inventors are able to accurately and consistently identify parts of an ECG waveform, including the P-wave.

The sample-level ECG classifier of this example was implemented as the sample-level ECG classifier 518 shown in FIG. 5H. The sample-level ECG classifier was a classification head added to the RVQ of the denoising model described in Example 1. Specifically, the sample-level ECG classifier received, as input, the quantized numeric encodings output by the RVQ.

The sample-level ECG classifier was trained simultaneously with the denoising model described in Example 1. The training data described in Example 1 included ground truth labels for the samples of the clean ECG signals. A ground truth label indicated a class to which a respective sample belonged, where the class was selected from among: a P-wave class, a QRS-complex class, a T-wave class, and a no wave class. The sample-level ECG classifier was initialized using randomly generated weights. The output of the sample-level ECG classifier and the ground truth labels were used to compute a loss, which was used to update the weights of the sample-level ECG classifier.

The test set included 398 segments of ECG signals. Each ECG segment has a sampling rate of 250 Hz and is 10 seconds long. There were 4,449 ECG waveforms (e.g., heartbeats) represented across the test set. The ECG signals were obtained from public datasets of ECG signals. ECG signals came from the CODE-15% dataset (Ribeiro, Antônio H., et al. "CODE-15%: A large-scale annotated dataset of 12-lead ECGs." Zenodo, Jun. 9 (2021): 10-5281) and the Icentia11k Single Lead Continuous Raw Electrocardiogram Dataset (Tan, Shawn, et al. "Icentia11k: An unsupervised representation learning dataset for arrhythmia subtype discovery." arXiv preprint arXiv:1910.09570 (2019)).

The ECG segments were processed using the sample-level ECG classifier to obtain outputs indicating predicted labels for samples (e.g., timestamps). Specifically, the ECG segments were processed by: (a) encoding the ECG segments using the trained encoder (described in Example 1) to obtain numeric encodings of the ECG segments, (b) quantizing the numeric encodings using the trained RVQ (described in Example 1) to obtain quantized numeric encodings of the ECG segments, and (c) processing the quantized numeric encodings of the ECG segments using the trained sample-level ECG classifier to obtain the sample-level ECG labels.

Prior to determining onsets and offsets, the sample-level ECG labels were pre-processed. First, the sample-level ECG labels were used to identify short (e.g., less than or equal to a threshold) segments of the ECG signal. In this context, a segment of the ECG signal refers to one or more consecutive samples sharing the same label. For example, a P-wave segment includes one or more consecutive samples labeled as a corresponding to a P-wave, a QRS-complex segment includes one or more consecutive samples labeled as corresponding to a QRS-complex, and a T-wave segment includes one or more samples labeled as corresponding to a T-wave. The ECG segments were compared to respective thresholds to determine whether further pre-processing should be applied. Specifically, P-wave segments were compared to a threshold of 16 ms to determine whether they were shorter than the threshold. QRS-complex segments were compared to a threshold of 12 ms to determine whether they were shorter than the threshold. T-wave segments were compared to a threshold of 24 ms to determine whether they were shorter than the threshold. If a segment was shorter than its respective threshold and it occurred immediately before or after another longer segment, then the labels of samples in the shorter segment were changed to match the labels of the samples in the longer segment. Otherwise, the short segment was removed. Additionally, where two segments sharing the same label were separated by a gap shorter than or equal to 32 ms, then the samples in the gap were labeled to match the labels of the abutting segments.

The sample-level ECG labels were used to determine the onsets and offsets of the P-waves, QRS-complexes, and T-waves. The onsets and offsets were validated against the ground truth labels. The ground truth labels were generated by ECG technicians and others trained in labeling ECG signals. Specifically, the labelers labeled the onsets and offsets of P-wave, QRS-complexes, and T-waves.

The results show that, on the test set of 4,499 ECG waveforms, the trained sample-level ECG classification techniques correctly identify 3,122 out of 3,311 P-waves (94.3%) and correctly identify 1,018 out of 1,188 missing P-waves (85.7%). A P-wave is considered correctly identified if an ECG waveform has an associated P-wave labeled in the data and the techniques predict a P-wave to exist immediately before the associated ECG waveform. Likewise, a missing P-wave is considered correctly identified if an ECG waveform does not have an associated P-wave labeled in the data and the techniques do not predict a P-wave to exist immediately before the associated ECG waveform.

FIG. 8A shows histograms for the errors for the calculated P-wave onsets and offsets. The reported error is the difference between the time when the wave onset/offset is predicted to happen and the time when the onset/offset is labeled to happen. As shown, the predicted P-wave onsets and offsets are usually very close to their true values. The techniques find P-wave onsets with an average error of 0 ms and a standard deviation of 15 ms. The techniques find P-wave offsets with an average error of 0 ms and a standard deviation of 16 ms.

In this example, the above-described techniques were also used to identify QRS-complex onsets. The P-wave onsets and QRS-complex onsets can then be used to find the P-R interval, which is defined as the time from the onset of the P-wave to the onset of the QRS-complex. As indicated above, the techniques find P-wave onsets with an average error of 0 ms and a standard deviation of 15 ms. Additionally, the techniques find QRS-complex onsets with an average error of 1 ms and a standard deviation of 9 ms, indicating low error. FIG. 8B and FIG. 8C are histograms for the errors calculated for the calculated P-wave onsets and QRS-complex onsets, respectively.

As described herein, the techniques developed by the inventors enable the accurate and precise identification of the P-waves and QRS-complexes, and their onsets and offsets. First, because the sample-level ECG classifier takes, as input, the quantized numeric encodings output by the RVQ, the sample-level ECG classifier accounts for the noise present in the original (i.e., not denoised) ECG signals. Thus, the trained sample-level ECG makes predictions using complete and comprehensive information that captures detailed information that might have otherwise been filtered out or ignored using conventional techniques for analyzing ECG signals. This in turn enables the sample-level ECG classifier to make nuanced distinctions between noise and the ECG signal, thereby enabling the accurate P-wave (94.3%) and missing P-wave (85.7%) identifications.

Second, by generating sample-level ECG labels, the sample-level ECG classifier enables the identification of the precise boundaries of the P-waves and QRS-complexes, as evidenced by the low errors shown in FIGS. 8A-8C. By contrast, conventional techniques for analyzing ECG signals are less precise because they involve merely detecting waveform peaks and estimating onsets and offsets based on the detected peaks and the average width of the wave or complex.

Example 3: Rhythm Classifier

In this example, the rhythm classification techniques developed by the inventors were used to classify ECG segments as representing a normal sinus rhythm or an arrhythmia. The results demonstrate that the techniques developed by the inventors are able to accurately identify rhythm types of segments of ECG signals.

The rhythm classifier of this example was implemented as the rhythm classifier 516 shown in FIG. 5G. The rhythm classifier was a classification head added to the RVQ of the denoising model described in Example 1. Specifically, the rhythm classifier received, as input, the quantized numeric encodings output by the RVQ.

The rhythm classifier was trained simultaneously with the denoising model described in Example 1. The training data described in Example 1 included ground truth labels for the one second segments of the clean ECG signals (the ECG signals were divided into one second segments). A ground truth label indicated a class to which a respective segment belonged, where the class was selected from among: a first class corresponding to a normal sinus rhythm and a second class corresponding to an arrhythmia. The rhythm classifier was initialized using randomly generated weights. The output of the rhythm classifier and the ground truth labels were used to compute a loss, which was used to update the weights of the rhythm classifier.

The test set included 25,136 ECG signals. Each signal is 60 seconds long and is split up into 60 segments, each 1 second long.

The ECG signals were processed using the trained rhythm classifier to obtain outputs indicating predicted classes (i.e., normal sinus rhythm or an arrhythmia) for respective segments of the ECG signals. Specifically, the ECG segments were processed by: (a) encoding the ECG segments using the trained encoder (described in Example 1) to obtain numeric encodings of the ECG segments, (b) quantizing the numeric encodings using the trained RVQ (described in Example 1) to obtain quantized numeric encodings of the ECG segments, and (c) processing the quantized numeric encodings of the ECG segments using the trained rhythm classifier to obtain the predicted classes.

The predicted rhythm classifications were validated against the ground truth rhythm classifications. Specifically, each segment was labeled based on whether it represents a heartbeat that is labeled as being part of a run of atrial fibrillation or atrial flutter. In some cases, segments of the ECG signals were not labeled. Segments that were not labeled were removed from the final results. Segments that were labeled as containing arrhythmia made up 7.3% of the test set.

Table 3 is a confusion matrix showing the performance of the techniques developed by the inventors in classifying rhythms of segments (e.g., of heartbeats represented in the segments) of the ECG signals in the test set.

TABLE 3

Performance of rhythm classifier in classifying rhythms of heartbeats in ECG signals.

| | Predicted Normal | Predicted Arrhythmia |
|---|---|---|
| True Normal | 170,679 | 6,137 |
| True Arrhythmia | 234 | 13,551 |

Table 4 lists the performance metrics of the techniques developed by the inventors when used to classify the rhythms of the segments of the ECG signals in the test set. Precision is likely low because individual symptoms of atrial fibrillation and atrial flutter can appear. Performance is also shown by the receiver operating characteristic curve (ROC) of FIG. 8D.

TABLE 4

Performance metrics of classifying rhythms of segments of ECG signals.

| Performance Metrics | Values |
|---|---|
| Accuracy | 0.9666 |
| Precision | 0.6883 |
| Sensitivity | 0.9830 |
| Specificity | 0.9653 |
| F1 Score | 0.8097 |

As described herein, because the rhythm classifier takes, as input, the quantized numeric encodings output by the RVQ, the rhythm classifier accounts for the noise present in the original (i.e., not denoised) ECG signals. Thus, the trained sample-level ECG makes predictions using complete and comprehensive information that captures detailed information that might have otherwise been filtered out or ignored using conventional techniques for analyzing ECG signals. This in turn enables the rhythm classifier to make nuanced distinctions between noise and the ECG signal, thereby enabling the accurate predictions evidenced in Tables 3 and 4.

Example 4: Denoising Model

As described herein, the inventors have developed techniques for denoising ECG signals using a trained denoising model. This example shows the performance of different aspects of a trained denoising model used to denoise ECG signals.

First, the trained denoising model, described in Example 1, was used to denoise ECG signals having varying lengths ranging from 0 to 6 days. FIG. 8E is a graph showing that the trained denoising model can be used to denoise, in mere minutes, ECG signals having durations on the order of multiple days. For example, as shown in FIG. 8E, a 6-day ECG file takes approximately 13 minutes and 16 seconds to process. Processing time with respect to the ECG input duration is linear. Every additional day of ECG input adds approximately 2 minutes and 13 seconds of processing time. These results indicate that the techniques developed by the inventors are an improvement over the conventional automated techniques for denoising and analyzing ECG signals because, due to their ability to denoise a days-long ECG signal in a matter of minutes, they enable near-real-time analysis of ECG signals of relatively long durations.

Second, two versions of a trained denoising model were used to denoise ECG signals: (a) the version of a trained denoising model including a residual vector quantizer, as described in Example 1, and (b) a version of the trained denoising model excluding an RVQ. The version of trained denoising model excluding the RVQ was trained as described in Example 1, except the denoising model excluded the RVQ.

Table 5 shows that using an RVQ improves the performance of the trained denoising model in denoising ECG signals, compared to denoising ECG signals using a denoising model that excludes an RVQ. Specifically, Table 5 lists the errors in detecting the offsets and onsets of the P-wave, QRS complex, and T-wave. When using the version of the trained denoising model with the RVQ, the standard deviations of errors in detecting the onsets and offsets of all wave types are smaller compared to those obtained when using the version of the trained denoising model without the RVQ. This indicates that the RVQ helps the denoising model to produce results that are closer to the true value more often. For example, the P-wave onsets and offsets, QRS complex onsets and offsets, and the T-wave onsets are all closer to zero. This shows that the RVQ reduces the bias of the denoising model. Thus, denoising ECG signals using a denoising model that includes an RVQ represents an improvement over conventional denoising techniques that do not use an RVQ. Specifically, as described herein and as demonstrated by the results, quantizing the numeric encodings using the RVQ helps the denoising model to become less sensitive and more robust to environmental differences, thereby producing denoised ECG signals that are closer to the true ECG signals.

TABLE 5

Performance of a trained denoising model, with and without an RVQ, in detecting ECG waveform offsets and onsets. Results are given in milliseconds.

| | Mean with RVQ | Standard Deviation with RVQ | Mean without RVQ | Standard Deviation without RVQ |
|---|---|---|---|---|
| P Onsets | 0 | 15 | −5 | 17 |
| P Offsets | 0 | 16 | 5 | 18 |
| QRS Onsets | 1 | 9 | 3 | 9 |
| QRS Offsets | −2 | 11 | −1 | 12 |
| T Onsets | 0 | 15 | 5 | 18 |
| T Offsets | −2 | 11 | −1 | 12 |

Third, the trained denoising model was used to denoise 100 ECG signals, each having a duration of 10 seconds. The ECG signals were randomly selected from multiple databases with a wide range of demographics, conditions, and arrhythmias, capturing real-world ECG signals and events.

Noise was added to each ECG signal to obtain pairs of ECG signals including the original signal and a corresponding noisy signal. Noise was added to the ECG signals according to the techniques for adding noise to pre-processing techniques described in Example 1.

The trained denoising model, described in Example 1, was used to denoise the noisy ECG signals to obtained corresponding cleaned ECG signals. This results in multiple groups of ECG signals, each of which includes the original ECG signal and the corresponding noisy and cleaned ECG signals.

For each group of ECG signals, the Pearson correlation was computed between the original signal and either the noisy ECG signal or the cleaned ECG signal. Additionally, the signal-to-noise ratio (SNR) was computed between the original signal and either the noisy ECG signal or the cleaned ECG signal. The correlation and SNR were computed for each of the 100 ECG signals, then the mean and standard deviation were computed. Table 6 shows the results.

TABLE 6

Performance of a trained denoising model in denoising ECG signals.

| | Mean | Standard Deviation |
|---|---|---|
| Noise & Original Correlation | 0.738830 | 0.307031 |
| Clean & Original Correlation | 0.815936 | 0.197782 |
| Noise & Original SNR | 1165.398349 | 10008.402716 |
| Clean & Original SNR | 0.427139 | 0.17575 |

As demonstrated in Table 6, there is an improvement in correlation between the original signal and the cleaned signal, as compared to the correlation between the original signal and the noisy signal. When correlation improves, this indicates that more of the original signal is captured by the cleaned trace. A higher correlation shows a preserved morphology instead of artifact, so the P, QRS, and T align with the source rather than with noise patterns.

This is not just "cleaner looking" ECG—it's statistically more consistent. Noise can mimic or mask the signs of various heart problems. This is especially challenging when the ECG signals being monitored have a low amplitude or when there is significant baseline wander, which can hide subtle but critical changes. For example, muscle tremors can create artifacts that resemble life-threatening arrhythmias, while baseline wander could obscure signs of a heart attack.

A clear signal allows for precise measurement of ECG waveforms and confident identification of abnormalities. It will also enable reviewers to identify areas of concern quickly, without having to second-guess what is signal and what is noise.

This results in higher confidence in measurements, greater throughput from reduced adjudication, and better accuracy in downstream analysis.

Example 5: Sample-Level ECG Classifier and RVQ

As described herein, the inventors have developed techniques for predicting sample-level ECG labels for ECG signals using a sample-level ECG classifier. In some embodiments, the sample-level ECG classifier takes, as input, a numeric encoding output by a trained encoder of a trained denoising model. In some embodiments, the sample-level ECG classifier takes, as input, a quantized numeric encoding output by a trained RVQ of a trained denoising model. This example shows that the performance of the sample-level ECG classifier is improved when it is trained to take, as input, a quantized numeric encoding from a trained RVQ, rather than a numeric encoding from a trained encoder.

In this example, two versions of a sample-level ECG classifier were used to process ECG signals to predict sample-level ECG labels. The first version of the sample-level ECG classifier was trained to take, as input, a quantized numeric encoding from a trained RVQ of a denoising model, as described in Example 2.

The second version of the sample-level ECG classifier was trained to take, as input, a numeric encoding from a trained encoder of a denoising model. The second version was trained as described in Example 2, except the sample-level ECG classifier was added as a classification head to the trained encoder of the denoising model, as described in Example 1.

Each of the trained classifiers was used to classify samples of ECG signals as corresponding to a P-wave, a QRS-complex, a T-wave, or no wave. The sample-level ECG labels were used to determine the onsets and offsets of the P-wave, QRS-complex, and the T-wave. Example techniques for determining onsets and offsets are described herein including at least with respect to FIG. 1A.

For all wave types, errors for onsets and offsets have a smaller standard deviation when using the RVQ. This indicates that the RVQ helps the model give results that are close to the true value more often. With the exception of T offsets, the mean error is closer to zero. This shows that the RVQ reduces the bias of the model. The results are listed in Table 7. Thus, predicting sample-level ECG labels using quantized numeric encodings output by an RVQ represents an improvement over ECG analysis techniques that do not utilize an RVQ. Specifically, as described herein and as demonstrated by the results, using the RVQ enables the generation of quantized numeric encodings that are more robust to environmental differences, which can in turn be used to make more accurate and precise predictions of ECG sample-level labels.

TABLE 7

Performance of a trained sample-level ECG model in processing numeric encodings ("without RVQ") versus quantized numeric encodings, in detecting ECG waveform offsets and onsets. Results are given in milliseconds.

| | Mean | Std | Mean without RVQ | Std without RVQ |
|---|---|---|---|---|
| P onsets | 0 | 15 | −5 | 17 |
| P offsets | 0 | 16 | 5 | 18 |
| QRS onsets | 1 | 9 | 3 | 9 |
| QRS offsets | −2 | 11 | −1 | 12 |
| T onsets | 0 | 15 | 5 | 18 |
| T offsets | −2 | 11 | −1 | 12 |

Computer Implementation

Figure 9:
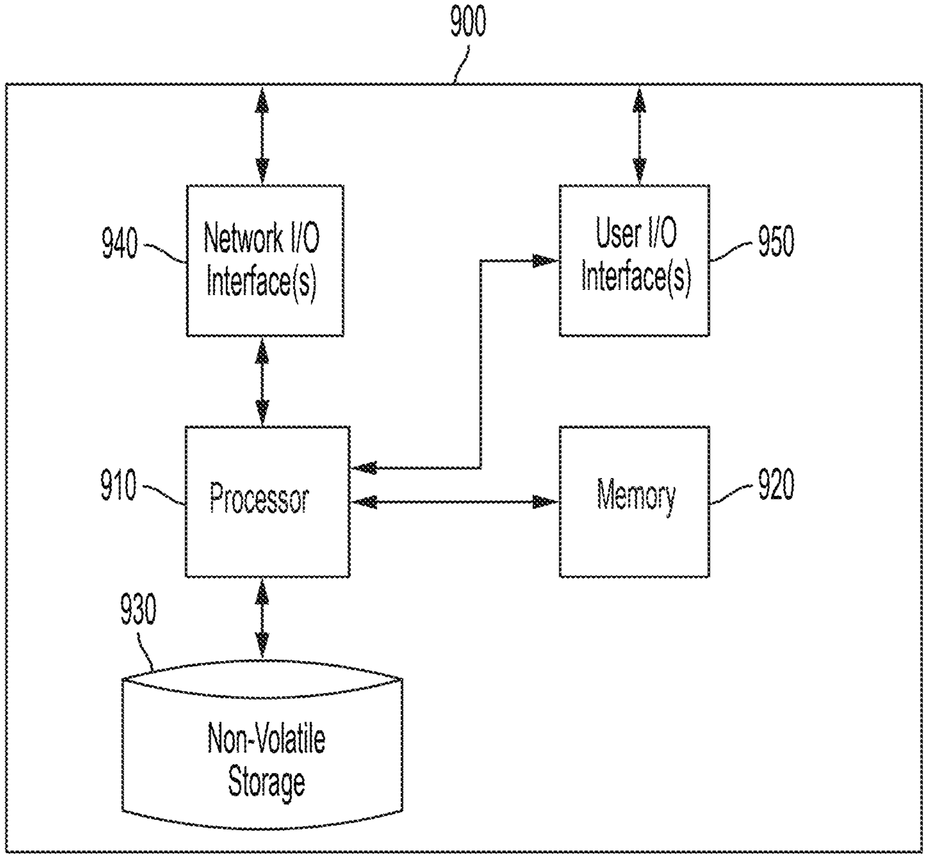
FIG. 9 is a schematic diagram of an illustrative computing device with which aspects described herein may be implemented.

An illustrative implementation of a computer system 900 that may be used in connection with any of the embodiments of the technology described herein (e.g., such as the processes of FIG. 4A, FIG. 4B, FIG. 4C, FIG. 4D, and FIG. 4E) is shown in FIG. 9. The computer system 900 includes one or more processors 910 and one or more articles of manufacture that comprise non-transitory computer-readable storage media (e.g., memory 920 and one or more non-volatile storage media 930). The processor 910 may control writing data to and reading data from the memory 920 and the non-volatile storage media 930 in any suitable manner, as the aspects of the technology described herein are not limited to any particular techniques for writing or reading data. To perform any of the functionality described herein, the processor 910 may execute one or more processor-executable instructions stored in one or more non-transitory computer-readable storage media (e.g., the memory 920), which may serve as non-transitory computer-readable storage media storing processor-executable instructions for execution by the processor 910.

Computing system 900 may include a network input/output (I/O) interface 940 via which the computing device may communicate with other computing devices. Such computing devices may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Computing system 900 may also include one or more user I/O interfaces 950, via which the computing device may provide output to and receive input from a user. The user I/O interfaces may include devices such as a keyboard, a mouse, a microphone, a display device (e.g., a monitor or touch screen), speakers, a camera, and/or various other types of I/O devices.

Further, it should be appreciated that a computer may be embodied in any of a number of forms, such as a rack-mounted computer, a desktop computer, a laptop computer, or a tablet computer, as examples. Additionally, a computer may be embedded in a device not generally regarded as a computer but with suitable processing capabilities, including a Personal Digital Assistant (PDA), a smartphone, a tablet, or any other suitable portable or fixed electronic device.

The above-described embodiments can be implemented in any of numerous ways. For example, the embodiments may be implemented using hardware, software, or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-described functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other tangible, non-transitory computer-readable storage medium) encoded with a computer program (i.e., a plurality of executable instructions) that, when executed on one or more processors, performs the above-described functions of one or more embodiments. The computer-readable medium may be transportable such that the program stored thereon can be loaded onto any computing device to implement aspects of the techniques described herein. In addition, it should be appreciated that the reference to a computer program which, when executed, performs any of the above-described functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques described herein.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

The foregoing description of implementations provides illustration and description but is not intended to be exhaustive or to limit the implementations to the precise form disclosed. Modifications and variations are possible in light of the above teachings or may be acquired from practice of the implementations. In other implementations the methods depicted in these figures may include fewer operations, different operations, differently ordered operations, and/or additional operations. Further, non-dependent blocks may be performed in parallel.

It will be apparent that example aspects, as described above, may be implemented in many different forms of software, firmware, and hardware in the implementations illustrated in the figures.

Example Aspects

Some aspects provide for a method for denoising at least one electrocardiogram (ECG) signal. The method comprises: using at least one processor to perform: obtaining the at least one ECG signal, the at least one ECG signal having been previously measured using ECG sensors; processing the at least one ECG signal using a trained denoising model to obtain at least one denoised ECG signal, the trained denoising model comprising an encoder, a residual vector quantizer, and a decoder, the processing comprising: encoding the at least one ECG signal using the encoder to obtain a numeric encoding of the at least one ECG signal; quantizing the numeric encoding of the at least one ECG signal using the residual vector quantizer to obtain a quantized numeric encoding of the at least one ECG signal; and decoding the quantized numeric encoding of the at least one ECG signal using the decoder to obtain the at least one denoised ECG signal; and outputting the at least one denoised ECG signal.

Some aspects provide for at least one non-transitory computer-readable storage medium storing processor-executable instructions that, when executed by at least one processor, cause the at least one processor to perform a method for denoising at least one electrocardiogram (ECG) signal. The method comprises: obtaining the at least one ECG signal, the at least one ECG signal having been previously measured using ECG sensors; processing the at least one ECG signal using a trained denoising model to obtain at least one denoised ECG signal, the trained denoising model comprising an encoder, a residual vector quantizer, and a decoder, the processing comprising: encoding the at least one ECG signal using the encoder to obtain a numeric encoding of the at least one ECG signal; quantizing the numeric encoding of the at least one ECG signal using the residual vector quantizer to obtain a quantized numeric encoding of the at least one ECG signal; and decoding the quantized numeric encoding of the at least one ECG signal using the decoder to obtain the at least one denoised ECG signal; and outputting the at least one denoised ECG signal.

Some aspects provide for a system comprising: at least one processor; and at least one non-transitory computer-readable storage medium storing processor-executable instructions that, when executed by the at least one processor, cause the at least one processor to perform a method for denoising at least one electrocardiogram (ECG) signal. The method comprises: obtaining the at least one ECG signal, the at least one ECG signal having been previously measured using ECG sensors; processing the at least one ECG signal using a trained denoising model to obtain at least one denoised ECG signal, the trained denoising model comprising an encoder, a residual vector quantizer, and a decoder, the processing comprising: encoding the at least one ECG signal using the encoder to obtain a numeric encoding of the at least one ECG signal; quantizing the numeric encoding of the at least one ECG signal using the residual vector quantizer to obtain a quantized numeric encoding of the at least one ECG signal; and decoding the quantized numeric encoding of the at least one ECG signal using the decoder to obtain the at least one denoised ECG signal; and outputting the at least one denoised ECG signal.

Embodiments of any of the above aspects may have one or more of the following features.

Some embodiments further comprise generating a graphical user interface (GUI) displaying the at least one denoised ECG signal.

In some embodiments, the at least one ECG signal comprises a first ECG signal and a second ECG signal. In some embodiments, processing the at least one ECG signal using the trained denoising model to obtain the at least one denoised ECG signal comprises: processing the first ECG signal using the trained denoising model to obtain a first denoised ECG signal; and processing the second ECG signal using the trained denoising model to obtain a second denoised ECG signal.

Some embodiments further comprise measuring the at least one ECG signal using the ECG sensors.

In some embodiments, the ECG sensors comprise at least two ECG sensors.

In some embodiments, measuring the at least one ECG signal using the ECG sensors comprises measuring the at least one ECG signal using a wearable device.

In some embodiments, the wearable device is a Holter monitor, a smartwatch, or a chest strap.

In some embodiments, measuring the at least one ECG signal using the ECG sensors comprises: measuring the at least one ECG signal, using a Holter monitor comprising at least three ECG leads, at a sampling rate of between 128 Hz and 256 Hz and for a duration of between one and fourteen days.

In some embodiments, measuring the at least one ECG signal using the ECG sensors comprises: measuring the at least one ECG signal, using a smartwatch comprising one ECG lead, at a sampling rate of between 128 Hz and 256 Hz and for a duration of between 10 seconds and 24 hours.

In some embodiments, the at least one ECG signal comprises a plurality of segments, the method further comprising classifying a respective rhythm of each of at least some of the segments between a plurality of classes to obtain a plurality of rhythm classifications, the classifying comprising: classifying a respective rhythm of each of at least some of the segments between a plurality of classes to obtain a plurality of rhythm classifications, the classifying comprising: positionally encoding the quantized numeric encoding of the at least one ECG signal to obtain a positionally encoded quantized numeric encoding of the at least one ECG signal; and processing the positionally encoded quantized numeric encoding of the at least one ECG signal using a trained rhythm classifier to obtain, for each of the at least some of the plurality of segments, a respective output indicative of a respective class of the plurality of classes.

In some embodiments, the plurality of classes comprise a normal sinus type, an atrial fibrillation type, an atrial flutter type, a premature atrial contraction (PAC) type, or a premature ventricular contraction (PVC) type.

In some embodiments, the at least one ECG signal comprises a plurality of samples, wherein a sample is an ECG measurement corresponding to a single time point, the method further comprising predicting sample-level ECG labels for at least some of the plurality of samples, wherein a sample-level ECG label for a particular sample of the at least some of the plurality of samples is indicative of a respective portion of an ECG waveform to which the particular sample corresponds, the predicting comprising: processing the quantized numeric encoding of the at least one ECG signal using a trained sample-level ECG classifier to obtain a respective sample-level ECG label for each of the at least some of the plurality of samples.

In some embodiments, the respective sample-level ECG label for each of the at least some of the plurality of samples is selected from among: a P-wave label, a QRS complex label, and/or a T-wave label.

In some embodiments, the at least one ECG signal comprises a plurality of ECG waves, the method further comprising deriving boundaries of each of at least some of the plurality of ECG waves using the sample-level ECG labels, wherein the plurality of ECG waves comprise one or more P-waves, one or more Q-waves, one or more R-waves, one or more S-waves, and/or one or more T-waves.

In some embodiments, the encoder comprises: a first 1D convolutional layer; a plurality of encoder blocks following the first 1D convolutional layer; and a second 1D convolutional layer following the plurality of encoder blocks.

In some embodiments, an encoder block of the plurality of encoder blocks comprises: a plurality of residual units comprising dilated convolutions; and a down-sampling layer following the plurality of residual units.

Some embodiments provide for a method for labelling at least one electrocardiogram (ECG) signal comprising a plurality of samples, wherein a sample is an ECG measurement corresponding to a single time point, the method comprising: using at least one processor to perform: obtaining the at least one ECG signal, the at least one ECG signal having been previously measured using ECG sensors; encoding the at least one ECG signal using a trained encoder to obtain a numeric encoding of the at least one ECG signal; quantizing the numeric encoding of the at least one ECG signal using a trained residual vector quantizer to obtain a quantized numeric encoding of the at least one ECG signal; and processing the quantized numeric encoding of the at least one ECG signal using a trained sample-level ECG classifier to obtain sample-level ECG labels for at least some of the plurality of samples of the at least one ECG signal, wherein a sample-level ECG label for a particular sample of the at least some of the plurality of samples is indicative of a respective portion of an ECG waveform to which the particular sample corresponds; and outputting the sample-level ECG labels.

Some embodiments provide for at least one non-transitory computer-readable storage medium storing processor-executable instructions that, when executed by at least one processor, cause the at least one processor to perform a method for labelling at least one electrocardiogram (ECG) signal comprising a plurality of samples, wherein a sample is an ECG measurement corresponding to a single time point, the method comprising: obtaining the at least one ECG signal, the at least one ECG signal having been previously measured using ECG sensors; encoding the at least one ECG signal using a trained encoder to obtain a numeric encoding of the at least one ECG signal; quantizing the numeric encoding of the at least one ECG signal using a trained residual vector quantizer to obtain a quantized numeric encoding of the at least one ECG signal; and processing the quantized numeric encoding of the at least one ECG signal using a trained sample-level ECG classifier to obtain sample-level ECG labels for at least some of the plurality of samples of the at least one ECG signal, wherein a sample-level ECG label for a particular sample of the at least some of the plurality of samples is indicative of a respective portion of an ECG waveform to which the particular sample corresponds; and outputting the sample-level ECG labels.

Some embodiments provide for a system comprising: at least one processor; and at least one non-transitory computer-readable storage medium storing processor-executable instructions that, when executed by the at least one processor, cause the at least one processor to perform a method for labelling at least one electrocardiogram (ECG) signal comprising a plurality of samples, wherein a sample is an ECG measurement corresponding to a single time point, the method comprising: obtaining the at least one ECG signal, the at least one ECG signal having been previously measured using ECG sensors; encoding the at least one ECG signal using a trained encoder to obtain a numeric encoding of the at least one ECG signal; quantizing the numeric encoding of the at least one ECG signal using a trained residual vector quantizer to obtain a quantized numeric encoding of the at least one ECG signal; and processing the quantized numeric encoding of the at least one ECG signal using a trained sample-level ECG classifier to obtain sample-level ECG labels for at least some of the plurality of samples of the at least one ECG signal, wherein a sample-level ECG label for a particular sample of the at least some of the plurality of samples is indicative of a respective portion of an ECG waveform to which the particular sample corresponds; and outputting the sample-level ECG labels.

Embodiments of any of the above aspects may have one or more of the following features.

In some embodiments, each of at least some of the sample-level ECG labels is selected from among: a P-wave label, a QRS complex label, and/or a T-wave label.

Some embodiments further comprise: determining one or more metrics using the sample-level ECG labels, the one or more metrics comprising a P-wave peak, a Q-wave peak, an R-wave peak, an S-wave peak, a T-wave peak, an RR interval, a PR segment, a PR interval, a QRS interval, a QT interval, an ST segment, a P-wave duration, a T-wave duration, a QT corrected (QTc) interval, a P-wave amplitude, a T-wave amplitude, a P-wave absence, and/or a T-wave absence.

In some embodiments, the at least one ECG signal comprises a plurality of ECG waves, the method further comprising deriving boundaries of each of at least some of the plurality of ECG waves using the sample-level ECG labels, wherein the plurality of ECG waves comprise one or more P-waves, one or more Q-waves, one or more R-waves, one or more S-waves, and/or one or more T-waves.

In some embodiments, the trained sample-level ECG classifier is a classification head comprising one or more convolutional layers, one or more encoder layers, and one or more decoder layers.

In some embodiments, outputting the sample-level ECG labels comprises generating an interactive graphical user interface (GUI) indicating the predicted sample-level ECG labels.

Some embodiments further comprise: annotating the at least one ECG signal using the sample-level ECG labels, wherein the interactive GUI indicating the sample-level ECG labels comprises a display indicating the at least one annotated ECG signal.

Some embodiments further comprise: measuring the at least one ECG signal using the ECG sensors.

In some embodiments, the ECG sensors comprise between at least two ECG sensors.

In some embodiments, measuring the at least one ECG signal using the ECG sensors comprises measuring the at least one ECG signal using a wearable device.

In some embodiments, the wearable device is a Holter monitor, a smartwatch, or a chest strap.

In some embodiments, measuring the at least one ECG signal using the ECG sensors comprises measuring the at least one ECG signal for a duration of between five seconds and fourteen days.

Some aspects provide for a method for labelling at least one electrocardiogram (ECG) signal comprising a plurality of samples, wherein a sample is an ECG measurement at a single time point, the method comprising: using at least one processor to perform: obtaining the at least one ECG signal, the at least one ECG signal having been previously measured using ECG sensors; encoding the at least one ECG signal to obtain a numeric encoding of the at least one ECG signal; processing the numeric encoding of the at least one ECG signal using a trained sample-level ECG classifier to obtain sample-level ECG labels for at least some of the plurality of samples, wherein a sample-level ECG label for a particular sample of the at least some of the plurality of samples is indicative of a respective portion of an ECG waveform to which the particular sample corresponds; generating an interactive graphical user interface (GUI) indicating the sample-level ECG labels for the at least some of the plurality of samples; and receiving user input via the interactive GUI, wherein the user input is indicative of a verification or a modification of a sample-level ECG label of the sample-level ECG labels.

Some aspects provide for at least one non-transitory computer-readable storage medium storing processor-executable instructions that, when executed by at least one processor, cause the at least one processor to perform a method for labelling at least one electrocardiogram (ECG) signal comprising a plurality of samples, wherein a sample is an ECG measurement at a single time point, the method comprising: obtaining the at least one ECG signal, the at least one ECG signal having been previously measured using ECG sensors; encoding the at least one ECG signal to obtain a numeric encoding of the at least one ECG signal; processing the numeric encoding of the at least one ECG signal using a trained sample-level ECG classifier to obtain sample-level ECG labels for at least some of the plurality of samples, wherein a sample-level ECG label for a particular sample of the at least some of the plurality of samples is indicative of a respective portion of an ECG waveform to which the particular sample corresponds; generating an interactive graphical user interface (GUI) indicating the sample-level ECG labels for the at least some of the plurality of samples; and receiving user input via the interactive GUI, wherein the user input is indicative of a verification or a modification of a sample-level ECG label of the sample-level ECG labels.

Some aspects provide for a system comprising: at least one processor; and at least one non-transitory computer-readable storage medium storing processor-executable instructions that, when executed by the at least one processor, cause the at least one processor to perform a method for labelling at least one electrocardiogram (ECG) signal comprising a plurality of samples, wherein a sample is an ECG measurement at a single time point, the method comprising: obtaining the at least one ECG signal, the at least one ECG signal having been previously measured using ECG sensors; encoding the at least one ECG signal to obtain a numeric encoding of the at least one ECG signal; processing the numeric encoding of the at least one ECG signal using a trained sample-level ECG classifier to obtain sample-level ECG labels for at least some of the plurality of samples, wherein a sample-level ECG label for a particular sample of the at least some of the plurality of samples is indicative of a respective portion of an ECG waveform to which the particular sample corresponds; generating an interactive graphical user interface (GUI) indicating the sample-level ECG labels for the at least some of the plurality of samples; and receiving user input via the interactive GUI, wherein the user input is indicative of a verification or a modification of a sample-level ECG label of the sample-level ECG labels.

Embodiments of any of the above aspects may have one or more of the following features.

In some embodiments, the at least one ECG signal was previously measured at a sampling rate of between 128 Hz and 256 Hz and for a duration of between 10 seconds and fourteen days.

Some embodiments further comprise when the user input is indicative of the modification of the sample-level ECG label, modifying the sample-level ECG label based on the user input.

Some embodiments further comprise after receiving the user input, generating a report indicating the sample-level ECG labels.

Some embodiments further comprise annotating the at least one ECG signal using the sample-level ECG labels, wherein the interactive GUI indicating the sample-level ECG labels comprises a display indicating the at least one annotated ECG signal.

Some embodiments further comprise processing the numeric encoding of the at least one ECG signal using a trained decoder to obtain at least one denoised ECG signal.

In some embodiments, annotating the at least one ECG signal using the sample-level ECG labels comprises annotating the at least one denoised ECG signal.

In some embodiments, each of at least some of the sample-level ECG labels is selected from among: a P-wave label, a QRS complex label, and/or a T-wave label.

Some embodiments further comprise determining one or more metrics using the sample-level ECG labels, the one or more metrics comprising a P-wave peak, a Q-wave peak, an R-wave peak, an S-wave peak, a T-wave peak, an RR interval, a PR segment, a PR interval, a QRS interval, a QT interval, an ST segment, a P-wave duration, a T-wave duration, a QT corrected (QTc) interval, a P-wave amplitude, a T-wave amplitude, a P-wave absence, and/or a T-wave absence.

In some embodiments, the interactive GUI further indicates the one or more metrics.

Some embodiments further comprise receiving user input via the interactive GUI, wherein the user input is indicative of a verification or a modification of a metric of the one or more metrics.

In some embodiments, the at least one ECG signal comprises a plurality of ECG waves, the method further comprising deriving boundaries of at least some of the plurality of ECG waves using the sample-level ECG labels, wherein the plurality of ECG waves comprise one or more P-waves, one or more Q-waves, one or more R-waves, one or more S-waves, and/or one or more T-waves.

In some embodiments, the interactive GUI further indicates the boundaries of the at least some of the plurality of ECG waves.

Some embodiments further comprise receiving user input via the interactive GUI, wherein the user input is indicative of a verification or a modification of one or more of the boundaries of the at least some of the plurality of ECG waves.

In some embodiments, the trained sample-level ECG classifier is a classification head comprising one or more convolutional layers, one or more encoder layers, and one or more decoder layers.

Some embodiments further comprise measuring the at least one ECG signal using the ECG sensors.

In some embodiments, measuring the at least one ECG signal using the ECG sensors comprises measuring the at least one ECG signal using a wearable device comprising the ECG sensors.

In some embodiments, measuring the at least one ECG signal using the wearable device comprises: measuring the at least one ECG signal using a Holter monitor comprising at least three ECG leads, at a sampling rate of between 128 Hz and 256 Hz, and for a duration of between one and fourteen days.

In some embodiments measuring the at least one ECG signal using the wearable device comprises: measuring the at least one ECG signal using a smartwatch comprising one ECG lead, at a sampling rate of between 128 Hz and 256 Hz, and for a duration of between 10 seconds and 24 hours.

In some embodiments, encoding the at least one ECG signal to obtain a numeric encoding of the at least one ECG signal comprises encoding the at least one ECG signal using an encoder, wherein the encoder is a convolutional neural network.

In some embodiments, the encoder is configured to map an input ECG signal from a high-dimensional space into a lower-dimensional latent representation, using multiple convolutional layers with non-linear activation functions.

Some aspects provide for a method for classifying rhythms of segments of at least one ECG signal, the method comprising: using at least one processor to perform: obtaining the at least one ECG signal, the at least one ECG signal comprising segments and having been previously measured using ECG sensors; encoding the at least one ECG signal to obtain a numeric encoding of the at least one ECG signal; positionally encoding the numeric encoding of the at least one ECG signal to obtain a positionally encoded numeric encoding of the at least one ECG signal; and classifying a respective rhythm of each of at least some of the segments between a plurality of classes to obtain a plurality of rhythm classifications, the classifying comprising: processing the positionally encoded numeric encoding of the at least one ECG signal using a trained rhythm classifier to obtain, for each of the at least some of the segments, a respective output indicative of a respective class of the plurality of classes; and outputting the plurality of rhythm classifications.

Some aspects provide for at least one non-transitory computer-readable storage medium storing processor-executable instructions that, when executed by at least one processor, cause the at least one processor to perform a method for classifying rhythms of segments of at least one ECG signal, the method comprising: obtaining the at least one ECG signal, the at least one ECG signal comprising segments and having been previously measured using ECG sensors; encoding the at least one ECG signal to obtain a numeric encoding of the at least one ECG signal; positionally encoding the numeric encoding of the at least one ECG signal to obtain a positionally encoded numeric encoding of the at least one ECG signal; and classifying a respective rhythm of each of at least some of the segments between a plurality of classes to obtain a plurality of rhythm classifications, the classifying comprising: processing the positionally encoded numeric encoding of the at least one ECG signal using a trained rhythm classifier to obtain, for each of the at least some of the segments, a respective output indicative of a respective class of the plurality of classes; and outputting the plurality of rhythm classifications.

Some aspects provide for a system comprising: at least one processor; and at least one non-transitory computer-readable storage medium storing processor-executable instructions that, when executed by the at least one processor, cause the at least one processor to perform a method for classifying rhythms of segments of at least one ECG signal, the method comprising: obtaining the at least one ECG signal, the at least one ECG signal comprising segments and having been previously measured using ECG sensors; encoding the at least one ECG signal to obtain a numeric encoding of the at least one ECG signal; positionally encoding the numeric encoding of the at least one ECG signal to obtain a positionally encoded numeric encoding of the at least one ECG signal; and classifying a respective rhythm of each of at least some of the segments between a plurality of classes to obtain a plurality of rhythm classifications, the classifying comprising: processing the positionally encoded numeric encoding of the at least one ECG signal using a trained rhythm classifier to obtain, for each of the at least some of the segments, a respective output indicative of a respective class of the plurality of classes; and outputting the plurality of rhythm classifications.

Embodiments of any of the above aspects may have one or more of the following features.

In some embodiments, each of the plurality of classes corresponds to a respective rhythm type of the plurality of rhythm types, wherein the plurality of rhythm types are selected from: a normal sinus type, an atrial fibrillation type, an atrial flutter type, a premature atrial contraction (PAC) type, and a premature ventricular contraction (PVC) type.

In some embodiments, the plurality of classes comprises a first class corresponding to a normal sinus type and a second class corresponding to an arrhythmia type, wherein the arrhythmia type includes one or more of an atrial fibrillation type, an atrial flutter type, a premature atrial contraction (PAC) type, and a premature ventricular contraction (PVC) type.

In some embodiments, the plurality of classes comprises a first class corresponding to a first rhythm type and a second class corresponding to any rhythm type that is not the first rhythm type, wherein the first rhythm type is selected from: a normal sinus type, an atrial fibrillation type, an atrial flutter type, a premature atrial contraction (PAC) type, and a premature ventricular contraction (PVC) type.

In some embodiments, the segments have a specified duration.

Some embodiments further comprise generating a notification when a rhythm of a segment of the at least some of the segments is classified as an atrial fibrillation type, an atrial flutter type, a PAC type, or a PVC type.

In some embodiments, the trained rhythm classifier comprises a transformer encoder and a classification layer.

In some embodiments, each of the segments represents one or more heartbeats.

Some aspects provide for a method of training a denoising model to denoise at least one electrocardiogram (ECG) signal, the method comprising: using at least one processor to perform: obtaining training data comprising a plurality of pairs of ECG signals, wherein a pair of ECG signals of the plurality of pairs of ECG signals comprises a clean ECG signal and a noisy ECG signal; training the denoising model, using the training data, to generate denoised ECG signals, the denoising model comprising an encoder, a residual vector quantizer, and a decoder, the training comprising: processing the noisy ECG signal using the denoising model to generate a denoised ECG signal corresponding to the noisy ECG signal; processing the denoised ECG signal using at least one discriminator model to obtain at least one classification indicative of whether the denoised ECG signal is a real ECG signal or an artificial ECG signal; and updating parameters of the denoising model based on (i) a loss that is a function of the denoised ECG signal and the clean ECG signal and (ii) a loss that is a function of the at least one classification.

Some aspects provide for at least one non-transitory computer-readable storage medium storing processor-executable instructions that, when executed by at least one processor, cause the at least one processor to perform a method of training a denoising model to denoise at least one electrocardiogram (ECG) signal, the method comprising: obtaining training data comprising a plurality of pairs of ECG signals, wherein a pair of ECG signals of the plurality of pairs of ECG signals comprises a clean ECG signal and a noisy ECG signal; training the denoising model, using the training data, to generate denoised ECG signals, the denoising model comprising an encoder, a residual vector quantizer, and a decoder, the training comprising: processing the noisy ECG signal using the denoising model to generate a denoised ECG signal corresponding to the noisy ECG signal; processing the denoised ECG signal using at least one discriminator model to obtain at least one classification indicative of whether the denoised ECG signal is a real ECG signal or an artificial ECG signal; and updating parameters of the denoising model based on (i) a loss that is a function of the denoised ECG signal and the clean ECG signal and (ii) a loss that is a function of the at least one classification.

Some aspects provide for a system comprising: at least one processor; and at least one non-transitory computer-readable storage medium storing processor-executable instructions that, when executed by the at least one processor, cause the at least one processor to perform a method of training a denoising model to denoise at least one electrocardiogram (ECG) signal, the method comprising: obtaining training data comprising a plurality of pairs of ECG signals, wherein a pair of ECG signals of the plurality of pairs of ECG signals comprises a clean ECG signal and a noisy ECG signal; training the denoising model, using the training data, to generate denoised ECG signals, the denoising model comprising an encoder, a residual vector quantizer, and a decoder, the training comprising: processing the noisy ECG signal using the denoising model to generate a denoised ECG signal corresponding to the noisy ECG signal; processing the denoised ECG signal using at least one discriminator model to obtain at least one classification indicative of whether the denoised ECG signal is a real ECG signal or an artificial ECG signal; and updating parameters of the denoising model based on (i) a loss that is a function of the denoised ECG signal and the clean ECG signal and (ii) a loss that is a function of the at least one classification.

Embodiments of any of the above aspects may have one or more of the following features.

Some embodiments further comprise prior to training the denoising model, adding noise to the clean ECG signal to obtain the noisy ECG signal.

In some embodiments, the noise comprises one or more types of noise selected from: white noise, artifacts, linear drift, random jumps in baseline, wander, and powerline noise.

In some embodiments, processing the denoised ECG signal using the at least one discriminator model comprises: processing a time-domain representation of the denoised ECG signal using a first discriminator model to obtain a first classification indicative of whether the denoised ECG signal is a real ECG signal or an artificial ECG signal; transforming the time-domain representation of the denoised ECG signal to a frequency-domain representation of the denoised ECG signal; and processing the frequency-domain representation of the denoised ECG signal using a second discriminator model to obtain a second classification indicative of whether the denoised ECG signal is a real ECG signal or an artificial ECG signal.

Some aspects provide for a Holter monitor, comprising: electrocardiogram (ECG) leads comprising at least three ECG leads; at least one processor; and at least one non-transitory computer-readable storage medium storing processor-executable instructions that, when executed by the at least one processor, cause the at least one processor to perform a method comprising: measuring at least one ECG signal using the ECG leads at a sampling rate of between 128 Hz and 256 Hz and for a duration of between one and fourteen days, the at least one ECG signal comprising a plurality of segments and a plurality of samples, wherein a sample is an ECG measurement at a single time point, and wherein a segment comprises at least some samples of the plurality of samples; encoding the at least one ECG signal to obtain a numeric encoding of the at least one ECG signal; processing the numeric encoding of the at least one ECG signal using at least one trained machine learning model to obtain one or more characteristics of the at least one ECG signal, the one or more characteristics comprising: (i) rhythm types including a respective rhythm type for each of at least some of the plurality of segments, wherein the rhythm types are selected from among a normal sinus type, an atrial fibrillation type, an atrial flutter type, a premature atrial contraction (PAC) type, or a premature ventricular contraction (PVC) type, and/or (ii) sample-level ECG labels including a respective sample-level ECG label for each of at least some of the plurality of samples, each sample-level ECG label being indicative of a respective portion of an ECG waveform to which a respective sample corresponds; and outputting the one or more characteristics of the at least one ECG signal.

Embodiments of any of the above aspects may have one or more of the following features.

Some embodiments further comprise a user interface, and the method further comprises: generating an indication of the one or more characteristics of the at least one ECG signal, wherein outputting the one or more characteristics of the at least one ECG signal comprises outputting the indication via the user interface.

In some embodiments, the one or more characteristics comprise the rhythm types, and processing the numeric encoding of the at least one ECG signal using the at least one trained machine learning model to obtain the one or more characteristics of the at least one ECG signal comprises: positionally encoding the numeric encoding of the at least one ECG signal to obtain a positionally encoded numeric encoding of the at least one ECG signal; and processing the positionally encoded numeric encoding of the at least one ECG signal using a trained rhythm classifier to obtain, for each of the at least some of the plurality of segments, a respective output indicative of a respective rhythm type.

In some embodiments, the trained rhythm classifier is a classification head comprising one or more convolutional layers.

In some embodiments, the one or more characteristics comprise the sample-level ECG labels, and processing the numeric encoding of the at least one ECG signal using the at least one trained machine learning model to obtain the one or more characteristics of the at least one ECG signal comprises: processing the numeric encoding of the at least one ECG signal using a trained sample-level ECG classifier to obtain a respective sample-level ECG label for each of the at least some of the plurality of samples.

In some embodiments, the trained sample-level ECG classifier is a classification head comprising one or more convolutional layers, one or more encoder layers, and one or more decoder layers.

Some embodiments further comprise: quantizing the numeric encoding of the at least one ECG signal using a residual vector quantizer to obtain a quantized numeric encoding of the at least one ECG signal; and processing the quantized numeric encoding of the at least one ECG signal using the at least one trained machine learning model to obtain the one or more characteristics of the at least one ECG signal.

In some embodiments, the residual vector quantizer is a grouped residual vector quantizer.

Some embodiments further comprise: decoding the quantized numeric encoding of the at least one ECG signal using a decoder to obtain at least one denoised ECG signal.

Some embodiments further comprise: transmitting, to at least one remote device, an indication of the one or more characteristics of the at least one ECG signal and/or the at least one denoised ECG signal.

In some embodiments, encoding the at least one ECG signal to obtain the numeric encoding of the at least one ECG signal comprises encoding the at least one ECG signal using an encoder, wherein the encoder in a convolutional neural network.

Some aspects provide for a smartwatch, comprising: an electrocardiogram (ECG) lead; at least one processor; and at least one non-transitory computer-readable storage medium storing processor-executable instructions that, when executed by the at least one processor, cause the at least one processor to perform a method, comprising: measuring the at least one ECG signal using the ECG lead at a sampling rate of between 128 Hz and 256 Hz and for a duration of between 10 seconds and 24 hours, the at least one ECG signal comprising a plurality of segments and a plurality of samples, wherein a sample is an ECG measurement at a single time point, and wherein a segment comprises at least some samples of the plurality of samples; encoding the at least one ECG signal to obtain a numeric encoding of the at least one ECG signal; processing the numeric encoding of the at least one ECG signal using at least one trained machine learning model to obtain one or more characteristics of the at least one ECG signal, the characteristics comprising: (i) rhythm types including a respective rhythm type for each of at least some of the plurality of segments, wherein the rhythm types are selected from among a normal sinus type, an atrial fibrillation type, an atrial flutter type, a premature atrial contraction (PAC) type, or a premature ventricular contraction (PVC) type, and/or (ii) sample-level ECG labels including a respective sample-level ECG label for each of at least some of the plurality of samples, each sample-level ECG label being indicative of a respective portion of an ECG waveform to which a respective sample corresponds; and outputting the one or more characteristics of the at least one ECG signal via a graphical user interface (GUI) of the smartwatch.

Embodiments of any of the above aspects may have one or more of the following features.

In some embodiments, the one or more characteristics comprise the rhythm types, and processing the numeric encoding of the at least one ECG signal using the at least one trained machine learning model to obtain the one or more characteristics of the at least one ECG signal comprises: positionally encoding the numeric encoding of the at least one ECG signal to obtain a positionally encoded numeric encoding of the at least one ECG signal; and processing the positionally encoded numeric encoding of the at least one ECG signal using a trained rhythm classifier to obtain, for each of the at least some of the plurality of segments, a respective output indicative of a respective rhythm type.

Some embodiments further comprise: a user interface, and the method further comprises: generating an alert when one or more of the rhythm types include the atrial fibrillation type, the atrial flutter type, the PAC type, or the PVC type; and outputting the alert via the user interface.

In some embodiments, the trained rhythm classifier is a classification head comprising one or more convolutional layers.

In some embodiments, the one or more characteristics comprise the sample-level ECG labels, and processing the numeric encoding of the at least one ECG signal using the at least one trained machine learning model to obtain the one or more characteristics of the at least one ECG signal comprises: processing the quantized numeric encoding of the at least one ECG signal using a trained sample-level ECG classifier to obtain a respective sample-level ECG label for each of the at least some of the plurality of samples.

In some embodiments, the trained sample-level ECG classifier is a classification head comprising one or more convolutional layers, one or more encoder layers, and one or more decoder layers.

Some embodiments further comprise: quantizing the numeric encoding of the at least one ECG signal using a residual vector quantizer to obtain a quantized numeric encoding of the at least one ECG signal; and processing the quantized numeric encoding of the at least one ECG signal using the at least one trained machine learning model to obtain the one or more characteristics of the at least one ECG signal.

Some embodiments further comprise: decoding the quantized numeric encoding of the at least one ECG signal using a decoder to obtain at least one denoised ECG signal.

In some embodiments, encoding the at least one ECG signal to obtain the numeric encoding of the at least one ECG signal comprises encoding the at least one ECG signal using an encoder, wherein the encoder in a convolutional neural network.

Some aspects provide for a method comprising: using at least one processor to perform: receiving, from at least one wearable device, at least one electrocardiogram (ECG) signal comprising a plurality of samples, wherein a sample is an ECG measurement corresponding to a single time point, and comprising segments; encoding the at least one ECG signal using an encoder to obtain a numeric encoding of the at least one ECG signal; processing the numeric encoding of the at least one ECG signal using at least one trained machine learning model to obtain: (i) at least one denoised ECG signal corresponding to the at least one ECG signal, and/or (ii) characteristics of the at least one ECG signal, the characteristics comprising: (i) rhythm types including a respective rhythm type for each of at least some of the segments, wherein the rhythm types are selected from among a normal sinus type, an atrial fibrillation type, an atrial flutter type, a premature atrial contraction (PAC) type, or a premature ventricular contraction (PVC) type, and/or (ii) sample-level ECG labels including a respective sample-level ECG label for each of at least some of the plurality of samples, each sample-level ECG label being indicative of a respective portion of an ECG waveform to which a respective sample corresponds; and transmitting the denoised ECG signal and/or the characteristics of the at least one ECG signal to a remote device.

Some aspects provide for a distributed electrocardiogram (ECG) system comprising: at least one wearable device configured to: measure at least one ECG signal at a sampling rate of between 128 Hz and 256 Hz and for a duration of between one and fourteen days, the at least one ECG signal comprising a plurality of samples, wherein a sample is an ECG measurement at a single time point; encode the at least one ECG signal using an encoder to obtain a numeric encoding of the at least one ECG signal; and quantize the numeric encoding of the at least one ECG signal using a residual vector quantizer to obtain a quantized numeric encoding of the at least one ECG signal; and at least one processor coupled to the at least one wearable device and configured to: receive the quantized numeric encoding of the at least one ECG signal from the at least one wearable device; and process the quantized numeric encoding of the at least one ECG signal using at least one trained machine learning model to obtain: (i) at least one denoised ECG signal corresponding to the at least one ECG signal, and/or (ii) at least one characteristic of the at least one ECG signal, the at least one characteristic comprising: (i) rhythm types including a respective rhythm type for each of at least some segments of the at least one ECG signal, wherein the rhythm types are selected from among a normal sinus type, an atrial fibrillation type, an atrial flutter type, a premature atrial contraction (PAC) type, or a premature ventricular contraction (PVC) type, and/or (ii) sample-level ECG labels including a respective sample-level ECG label for each of at least some of the plurality of samples, each sample-level ECG label being indicative of a respective portion of an ECG waveform to which a respective sample corresponds.

Embodiments of any of the above aspects may have one or more of the following features.

In some embodiments, the at least one processor is configured to process the quantized numeric encoding of the at least one ECG signal using the at least one trained machine learning model to obtain the at least one denoised ECG signal, and processing the quantized numeric encoding of the at least one ECG signal using the at least one trained machine learning model to obtain the at least one denoised ECG signal comprises decoding the quantized numeric encoding of the at least one ECG signal using a decoder to obtain the at least one denoised ECG signal.

In some embodiments, the at least one processor is configured to process the quantized numeric encoding of the at least one ECG signal using the at least one trained machine learning model to obtain the at least one characteristic of the at least one ECG signal, the at least one characteristic comprising the rhythm types, and processing the quantized numeric encoding of the at least one ECG signal using the at least one trained machine learning model to obtain the rhythm types comprises: positionally encoding the quantized numeric encoding of the at least one ECG signal to obtain a positionally-encoded quantized numeric encoding of the at least one ECG signal; and processing the positionally-encoded quantized numeric encoding of the at least one ECG signal using a trained rhythm classifier to obtain, for each of the at least some segments of the at least one ECG signal, a respective output indicative of a respective rhythm type.

In some embodiments, the at least one processor is configured to process the quantized numeric encoding of the at least one ECG signal using the at least one trained machine learning model to obtain the at least one characteristic of the at least one ECG signal, the at least one characteristic comprising the sample-level ECG labels, and processing the quantized numeric encoding of the at least one ECG signal using the at least one trained machine learning model to obtain the sample-level ECG labels comprises processing the quantized numeric encoding of the at least one ECG signal using a trained sample-level ECG classifier to obtain a respective sample-level ECG label for each of the at least some of the plurality of samples.

In some embodiments, the at least one wearable device comprises a Holter monitor, a smartwatch, or a chest strap.

In some embodiments, the at least one wearable device comprises a plurality of wearable devices, and wherein each of the plurality of wearable devices is configured to measure a respective ECG signal.

In some embodiments, the at least one processor is further configured to generate a report indicating (i) the at least one denoised ECG signal corresponding to the at least one ECG signal, and/or (ii) the at least one characteristic of the at least one ECG signal.

Some aspects provide for a distributed electrocardiogram (ECG) system, comprising: at least one wearable device configured to: measure at least one ECG signal at a sampling rate of between 128 Hz and 256 Hz and for a duration of between one and fourteen days, the at least one ECG signal comprising a plurality of samples, wherein a sample is an ECG measurement at a single time point; and segment the at least one ECG signal to obtain a plurality of ECG segments; and at least one processor coupled to the at least one wearable device and configured to: receive at least one ECG segment of the plurality of ECG segments from the at least one wearable device; encode the at least one ECG segment using an encoder to obtain a numeric encoding of the at least one ECG segment; quantize the numeric encoding of the at least one ECG segment using a residual vector quantizer to obtain a quantized numeric encoding of the at least one ECG segment; and process the quantized numeric encoding of the at least one ECG segment using at least one trained machine learning model to obtain: (i) at least one denoised ECG segment corresponding to the at least one ECG segment, and/or (ii) at least one characteristic of the at least one ECG segment, the at least one characteristic comprising: (i) at least one rhythm type for the at least one ECG segment, wherein the at least one rhythm type is selected from among a normal sinus type, an atrial fibrillation type, an atrial flutter type, a premature atrial contraction (PAC) type, or a premature ventricular contraction (PVC) type, and/or (ii) sample-level ECG labels including a respective sample-level ECG label for each of at least some of the plurality of samples, each sample-level ECG label being indicative of a respective portion of an ECG waveform to which a respective sample corresponds.

Embodiments of any of the above aspects may have one or more of the following features.

In some embodiments, the at least one processor is configured to process the quantized numeric encoding of the at least one ECG segment using the at least one trained machine learning model to obtain the at least one denoised ECG segment, and processing the quantized numeric encoding of the at least one ECG segment using the at least one trained machine learning model to obtain the at least one denoised ECG segment comprises decoding the quantized numeric encoding of the at least one ECG segment using a decoder to obtain the at least one denoised ECG segment.

In some embodiments, the at least one processor is configured to process the quantized numeric encoding of the at least one ECG segment using the at least one trained machine learning model to obtain the at least one characteristic of the at least one ECG segment, the at least one characteristic comprising the at least one rhythm type, and processing the quantized numeric encoding of the at least one ECG segment using the at least one trained machine learning model to obtain at least one rhythm type comprises: positionally encoding the quantized numeric encoding of the at least one ECG segment to obtain a positionally-encoded quantized numeric encoding of the at least one ECG segment; and processing the positionally-encoded quantized numeric encoding of the at least one ECG segment using a trained rhythm classifier to obtain an output indicative of at least one rhythm type.

In some embodiments, the at least one processor is configured to process the quantized numeric encoding of the at least one ECG segment using the at least one trained machine learning model to obtain the at least one characteristic of the at least one ECG segment, the at least one characteristic comprising the sample-level ECG labels, and processing the quantized numeric encoding of the at least one ECG segment using the at least one trained machine learning model to obtain the sample-level ECG labels comprises processing the quantized numeric encoding of the at least one ECG segment using a trained sample-level ECG classifier to obtain a respective sample-level ECG label for each of the at least some of the plurality of samples.

In some embodiments, the at least one wearable device comprises a Holter monitor, a smartwatch, or a chest strap.

In some embodiments, the at least one wearable device comprises a plurality of wearable devices, and wherein each of the plurality of wearable devices is configured to measure a respective ECG signal.

Some aspects provide for a distributed electrocardiogram (ECG) system, comprising: at least one wearable device configured to: measure at least one ECG signal at a sampling rate of between 128 Hz and 256 Hz and for a duration of between one and fourteen days, the at least one ECG signal comprising a plurality of samples, wherein a sample is an ECG measurement at a single time point; and at least one processor coupled to the at least one wearable device and configured to: receive the at least one ECG signal from the at least one wearable device; encode the at least one ECG signal using an encoder to obtain a numeric encoding of the at least one ECG signal; quantize the numeric encoding of the at least one ECG signal using a residual vector quantizer to obtain a quantized numeric encoding of the at least one ECG signal; and process the quantized numeric encoding of the at least one ECG signal using at least one trained machine learning model to obtain: (i) at least one denoised ECG signal corresponding to the at least one ECG signal, and/or (ii) at least one characteristic of the at least one ECG signal, the at least one characteristic comprising: (i) rhythm types including a respective rhythm type for each of at least some segments of the at least one ECG signal, wherein the rhythm types are selected from among a normal sinus type, an atrial fibrillation type, an atrial flutter type, a premature atrial contraction (PAC) type, or a premature ventricular contraction (PVC) type, and/or (ii) sample-level ECG labels including a respective sample-level ECG label for each of at least some of the plurality of samples, each sample-level ECG label being indicative of a respective portion of an ECG waveform to which a respective sample corresponds.

Embodiments of any of the above aspects may have one or more of the following features.

In some embodiments, the at least one processor is configured to process the quantized numeric encoding of the at least one ECG signal using the at least one trained machine learning model to obtain the at least one denoised ECG signal, and processing the quantized numeric encoding of the at least one ECG signal using the at least one trained machine learning model to obtain the at least one denoised ECG signal comprises decoding the quantized numeric encoding of the at least one ECG signal using a decoder to obtain the at least one denoised ECG signal.

In some embodiments, the at least one processor is configured to process the quantized numeric encoding of the at least one ECG signal using the at least one trained machine learning model to obtain the at least one characteristic of the at least one ECG signal, the at least one characteristic comprising the rhythm types, and processing the quantized numeric encoding of the at least one ECG signal using the at least one trained machine learning model to obtain the rhythm types comprises: positionally encoding the quantized numeric encoding of the at least one ECG signal to obtain a positionally-encoded quantized numeric encoding of the at least one ECG signal; and processing the positionally-encoded quantized numeric encoding of the at least one ECG signal using a trained rhythm classifier to obtain, for each of the at least some segments of the at least one ECG signal, a respective output indicative of a respective rhythm type.

In some embodiments, the at least one processor is configured to process the quantized numeric encoding of the at least one ECG signal using the at least one trained machine learning model to obtain the at least one characteristic of the at least one ECG signal, the at least one characteristic comprising the sample-level ECG labels, and processing the quantized numeric encoding of the at least one ECG signal using the at least one trained machine learning model to obtain the sample-level ECG labels comprises processing the quantized numeric encoding of the at least one ECG signal using a trained sample-level ECG classifier to obtain a respective sample-level ECG label for each of the at least some of the plurality of samples.

In some embodiments, the at least one wearable device comprises a Holter monitor, a smartwatch, or a chest strap.

In some embodiments, the at least one wearable device comprises a plurality of wearable devices, and wherein each of the plurality of wearable devices is configured to measure a respective ECG signal.

In some embodiments, the at least one processor is further configured to generate a report indicating (i) the at least one denoised ECG signal corresponding to the at least one ECG signal, and/or (ii) the at least one characteristic of the at least one ECG signal.

Some aspects provide for a method comprising using at least one processor to perform: receiving at least one ECG signal, the at least one ECG signal having been previously measured using ECG sensors; processing the at least one ECG signal using a trained machine learning model to obtain at least one denoised ECG signal, wherein the trained machine learning model comprises an encoder, a residual vector quantizer, and a decoder, and has been trained to take as input at least one ECG signal and produce as output a corresponding denoised ECG signal using training data comprising pairs of noisy ECG signals and corresponding clean ECG signals, the processing comprising: encoding the at least one ECG signal using the encoder to obtain a numeric encoding of the at least one ECG signal; quantizing the numeric encoding of the at least one ECG signal using the residual vector quantizer to obtain a quantized numeric encoding of the at least one ECG signal; and decoding the quantized numeric encoding of the at least one ECG signal using the decoder to obtain at least one denoised ECG signal.

Some aspects provide for at least one non-transitory computer-readable storage medium storing processor-executable instructions that, when executed by at least one processor, cause the at least one processor to perform a method comprising receiving at least one ECG signal, the at least one ECG signal having been previously measured using ECG sensors; processing the at least one ECG signal using a trained machine learning model to obtain at least one denoised ECG signal, wherein the trained machine learning model comprises an encoder, a residual vector quantizer, and a decoder, and has been trained to take as input at least one ECG signal and produce as output a corresponding denoised ECG signal using training data comprising pairs of noisy ECG signals and corresponding clean ECG signals, the processing comprising: encoding the at least one ECG signal using the encoder to obtain a numeric encoding of the at least one ECG signal; quantizing the numeric encoding of the at least one ECG signal using the residual vector quantizer to obtain a quantized numeric encoding of the at least one ECG signal; and decoding the quantized numeric encoding of the at least one ECG signal using the decoder to obtain at least one denoised ECG signal.

Some aspects provide for a system comprising: at least one processor; and at least one non-transitory computer-readable storage medium storing processor-executable instructions that, when executed by the at least one processor, cause the at least one processor to perform a method comprising receiving at least one ECG signal, the at least one ECG signal having been previously measured using ECG sensors; processing the at least one ECG signal using a trained machine learning model to obtain at least one denoised ECG signal, wherein the trained machine learning model comprises an encoder, a residual vector quantizer, and a decoder, and has been trained to take as input at least one ECG signal and produce as output a corresponding denoised ECG signal using training data comprising pairs of noisy ECG signals and corresponding clean ECG signals, the processing comprising: encoding the at least one ECG signal using the encoder to obtain a numeric encoding of the at least one ECG signal; quantizing the numeric encoding of the at least one ECG signal using the residual vector quantizer to obtain a quantized numeric encoding of the at least one ECG signal; and decoding the quantized numeric encoding of the at least one ECG signal using the decoder to obtain at least one denoised ECG signal.

Embodiments of any of the above aspects may have one or more of the following features.

In some embodiments, the trained machine learning model has been trained as a generator of a generative adversarial network further comprising one or more discriminators trained to distinguish between a real ECG signal and an ECG signal that has been generated by the generator.

In some embodiments, the at least one ECG signal corresponds to a single heartbeat.

Some embodiments further comprise performing beat segmentation on the received at least one ECG signal to obtain one or more segmented ECG signals corresponding to individual heartbeats, and processing one or more of the segmented ECG signals using the trained machine learning model.

In some embodiments, the ECG signal is an ECG signal that has been measured using a wearable device.

In some embodiments, the wearable device is a Holter monitor or an ECG patch.

In some embodiments, the at least one ECG signal has been measured using the Holter monitor, the Holter monitor comprising at least three ECG leads, at a sampling rate of between 128 Hz and 256 Hz and for a duration of between one and fourteen days.

In some embodiments, the at least one ECG signal comprises a plurality of segments, optionally wherein each segment has a predetermined length or each representing a heartbeat in a sequence of heartbeats, the method further comprising classifying each of at least some of the segments as comprising ECG signal associated with one of a plurality of rhythm types, the classifying comprising: positionally encoding the numeric encoding or the quantized numeric encoding of the at least one ECG signal to obtain a positionally encoded numeric encoding or quantized numeric encoding of the at least one ECG signal; and processing the positionally encoded numeric encoding or quantized numeric encoding of the at least one ECG signal using a trained rhythm classifier to obtain, for each of the at least some of the segments, a respective output indicative of a respective rhythm type of the plurality of rhythm types, wherein the trained rhythm classifier has been trained to take as input a positionally encoded numeric encoding or quantized numeric encoding of the at least one ECG signal produced as output of the encoder or residual vector quantizer, and produce an output indicative of a respective rhythm type of the plurality of rhythm types associated with the at least one ECG signal using training data comprising training ECG signals and associated with ground truth rhythm type labels.

In some embodiments, the plurality of rhythm types comprise a normal sinus type, an atrial fibrillation type, an atrial flutter type, a premature atrial contraction (PAC) type, a premature ventricular contraction (PVC) type, or a combination thereof, optionally wherein: (i) the trained rhythm classifier is trained to classify a segment of an ECG signal between a plurality of classes each corresponding to a different rhythm type selected from: a normal sinus type, an atrial fibrillation type, an atrial flutter type, a premature atrial contraction (PAC) type, a premature ventricular contraction (PVC) type; or (ii) the trained rhythm classifier is trained to classify a segment of an ECG signal between a first class corresponding to a normal sinus type, and a second class corresponding to an arrhythmia rhythm type, optionally wherein arrhythmia includes one or more or all of: an atrial fibrillation type, an atrial flutter type, a premature atrial contraction (PAC) type, a premature ventricular contraction (PVC) type; or (iii) the trained rhythm classifier is trained to classify a segment of an ECG signal between a first class corresponding to a first rhythm type and a second class corresponding to any rhythm type that is not the first rhythm type, optionally wherein the first rhythm type is selected from: a normal sinus type, an atrial fibrillation type, an atrial flutter type, a premature atrial contraction (PAC) type, and a premature ventricular contraction (PVC) type.

In some embodiments, the plurality of rhythm types comprises a normal sinus type, an atrial fibrillation type, and an atrial flutter type.

In some embodiments, the trained rhythm classifier comprises a transformer-based model.

In some embodiments, the at least one ECG signal corresponds to a single heartbeat and the method comprises processing the quantized numeric encoding of the at least one ECG signal using a trained beat classifier trained to label an input ECG signal with labels corresponding to a P wave, a Q wave, a R wave, a Q wave, a S wave, and a T wave, optionally wherein the beat classifier has been trained in a supervised manner using labelled ECG signals.

In some embodiments, the at least one ECG signal comprises a plurality of samples, wherein a sample is an ECG measurement corresponding to a single time point, the method further comprising predicting labels for at least some of the plurality of samples, wherein a label for a particular sample of the at least some of the plurality of samples is indicative of a respective portion of an ECG waveform to which the particular sample corresponds, the predicting comprising: processing the numeric encoding or the quantized numeric encoding of the at least one ECG signal using a trained beat classifier to obtain a respective label for each of the at least some of the plurality of samples, wherein the trained beat classifier has been trained to take as input a numeric encoding of the at least one ECG signal produced as output of the encoder or a quantized numeric encoding of the at least one ECG signal produced as output of the residual vector quantizer, and produce an output indicative of a respective portion of an ECG waveform to which the sample corresponds to, using training data comprising training ECG signals and associated ground truth labels indicating for each of a plurality of samples of the training ECG signals, a respective portion of an ECG waveform to which the particular sample corresponds.

In some embodiments, the respective portions are selected from: a P wave, a Q wave, a R wave, a S wave, and a T wave.

In some embodiments, the respective label for each of the at least some of the plurality of samples is selected from: a P-wave label, a QRS complex label, and/or a T-wave label; and/or wherein the trained beat classifier has been trained to classify samples of ECG signals between a plurality of classes comprising: a class associated with P waves, one or more classes associated with QRS complexes, and a class associated with T waves; and/or wherein the trained beat classifier has been trained to classify samples of ECG signals between a first class corresponding to P waves, QRS complexes or T waves, and a second class corresponding to signal other than the signal associated with the first class.

Some embodiments further comprise determining one or more PQRST intervals using results of processing by the beat classifier.

In some embodiments, the encoder is a deep neural network and/or wherein the encoder is a convolutional neural network, and/or wherein the encoder is configured to receive an input and map it into a latent space via a series of convolutional layers and nonlinear activation functions.

In some embodiments, the encoder is configured to map an input ECG signal from a high-dimensional space into a lower-dimensional latent representation, using multiple convolutional layers with non-linear activation functions.

In some embodiments, the encoder comprises: a plurality of encoder blocks at different resolutions; and skip connections such that the numeric encoding is obtained using direct outputs of the plurality of encoder blocks.

Some aspects provide for a method for labelling at least one electrocardiogram (ECG) signal corresponding to a single heartbeat, the method comprising: using at least one processor to perform: encoding the at least one ECG signal using a trained encoder to obtain a numeric encoding of the at least one ECG signal; quantizing the numeric encoding of the at least one ECG signal using a trained residual vector quantizer to obtain a quantized numeric encoding of the at least one ECG signal; and processing the quantized numeric encoding of the at least one ECG signal using a trained beat classifier trained to label an input ECG signal with labels corresponding to a P wave, a Q wave, a R wave, a S wave, and a T wave, optionally wherein the beat classifier has been trained in a supervised manner using labelled ECG signals, wherein the trained encoder and trained residual vector quantizer have been trained as part of a machine learning model comprising the encoder, the residual vector quantizer, and a decoder, to take as input the at least one ECG signal and produce as output a corresponding denoised ECG signal using training data comprising pairs of noisy ECG signals and corresponding clean ECG signals, and wherein the machine learning model has been trained as a generator of a generative adversarial network further comprising one or more discriminators trained to distinguish between a real ECG signal and an ECG signal that has been generated by the generator.

Some aspects provide for at least one non-transitory computer-readable storage medium storing processor-executable instructions that, when executed by at least one processor, cause the at least one processor to perform a method for labelling at least one electrocardiogram (ECG) signal corresponding to a single heartbeat, the method comprising: encoding the at least one ECG signal using a trained encoder to obtain a numeric encoding of the at least one ECG signal; quantizing the numeric encoding of the at least one ECG signal using a trained residual vector quantizer to obtain a quantized numeric encoding of the at least one ECG signal; and processing the quantized numeric encoding of the at least one ECG signal using a trained beat classifier trained to label an input ECG signal with labels corresponding to a P wave, a Q wave, a R wave, a S wave, and a T wave, optionally wherein the beat classifier has been trained in a supervised manner using labelled ECG signals, wherein the trained encoder and trained residual vector quantizer have been trained as part of a machine learning model comprising the encoder, the residual vector quantizer, and a decoder, to take as input the at least one ECG signal and produce as output a corresponding denoised ECG signal using training data comprising pairs of noisy ECG signals and corresponding clean ECG signals, and wherein the machine learning model has been trained as a generator of a generative adversarial network further comprising one or more discriminators trained to distinguish between a real ECG signal and an ECG signal that has been generated by the generator.

Some aspects provide for a system comprising: at least one processor; and at least one non-transitory computer-readable storage medium storing processor-executable instructions that, when executed by the at least one processor, cause the at least one processor to perform a method for labelling at least one electrocardiogram (ECG) signal corresponding to a single heartbeat, the method comprising: encoding the at least one ECG signal using a trained encoder to obtain a numeric encoding of the at least one ECG signal; quantizing the numeric encoding of the at least one ECG signal using a trained residual vector quantizer to obtain a quantized numeric encoding of the at least one ECG signal; and processing the quantized numeric encoding of the at least one ECG signal using a trained beat classifier trained to label an input ECG signal with labels corresponding to a P wave, a Q wave, a R wave, a S wave, and a T wave, optionally wherein the beat classifier has been trained in a supervised manner using labelled ECG signals, wherein the trained encoder and trained residual vector quantizer have been trained as part of a machine learning model comprising the encoder, the residual vector quantizer, and a decoder, to take as input the at least one ECG signal and produce as output a corresponding denoised ECG signal using training data comprising pairs of noisy ECG signals and corresponding clean ECG signals, and wherein the machine learning model has been trained as a generator of a generative adversarial network further comprising one or more discriminators trained to distinguish between a real ECG signal and an ECG signal that has been generated by the generator.

Embodiments of any of the above aspects may have one or more of the following features.

In some embodiments, each of at least some of the sample-level ECG labels is selected from: a P-wave label, a QRS complex label, and/or a T-wave label; and/or wherein the trained beat classifier has been trained to classify samples of ECG signals between a plurality of classes comprising: a class associated with P-waves, one or more classes associated with QRS complex, and a class associated with T-waves; and/or wherein the trained beat classifier has been trained to classify samples of ECG signals between a first class corresponding to P-waves, QRS complex or T-waves, and a second class corresponding to signal other than the signal associated with the first class.

Some embodiments further comprise determining one or more PQRST intervals using results of processing by the beat classifier.

Some embodiments further comprise determining one or more metrics using the one or more PQRST intervals determined using the results of the processing by the beat classifier, the one or more metrics comprising: a P-wave peak, a Q-wave peak, an R-wave peak, an S-wave peak, a T-wave peak, an RR interval, a PR segment, a PR interval, a QRS interval, a QT interval, an ST segment, a P-wave duration, a T-wave duration, a QT corrected (QTc) interval, and/or a P-wave amplitude.

In some embodiments, the trained beat classifier is a deep neural network, and/or wherein the trained beat classifier is a transformer-based deep neural network, and/or wherein the trained beat classifier comprises a transformer encoder and a classification layer, and/or wherein the trained beat classifier is a neural network.

In some embodiments, the at least one ECG signal is an ECG signal that has been measured using a wearable device.

In some embodiments, the wearable device is a Holter monitor or an ECG patch.

In some embodiments, the at least one ECG signal has been measured for a duration of between five seconds and fourteen days.

Some aspects provide for a method for classifying rhythms of segments of at least one ECG signal, the method comprising: using at least one processor to perform: receiving the at least one ECG signal, the at least one ECG signal comprising a plurality of segments, each segment representing a heartbeat in a sequence of heartbeats, the at least one ECG signal having been previously measured using ECG sensors; encoding the at least one ECG signal to obtain a numeric encoding of the at least one ECG signal using a trained encoder; optionally quantizing the numeric encoding of the at least one ECG signal to obtain a quantized numeric encoding of the at least one ECG signal using a trained residual vector quantizer; positionally encoding the optionally quantized numeric encoding of the at least one ECG signal, using a predetermined positional encoding scheme, to obtain a positionally encoded optionally quantized numeric encoding of the at least one ECG signal; and classifying a respective rhythm of each of at least some of the segments between a plurality of classes, each of the plurality of classes corresponding to a respective rhythm type of a plurality of rhythm types to obtain a plurality of rhythm classifications, the classifying comprising: processing the positionally encoded optionally quantized numeric encoding of the at least one ECG signal using a trained rhythm classifier to obtain, for each of the at least some of the segments, a respective output indicative of a class of the plurality of classes corresponding to a respective rhythm type of the plurality of rhythm types, wherein the trained rhythm classifier has been trained to take as input a positionally encoded numeric encoding or quantized numeric encoding of the at least one ECG signal produced as output of the trained encoder or trained residual vector quantizer, and produce an output indicative of the class of the plurality of classes using training data comprising training ECG signals and associated ground truth rhythm type labels, wherein the trained encoder and optional trained residual vector quantizer have been trained as part of a machine learning model comprising the encoder, the residual vector quantizer, and a decoder, to take as input at least one ECG signal and produce as output a corresponding denoised ECG signal using training data comprising pairs of noisy ECG signals and corresponding clean ECG signals, wherein the machine learning model has been trained as a generator of a generative adversarial network further comprising one or more discriminators trained to distinguish between a real ECG signal and an ECG signal has been generated by the generator.

Some aspects provide for at least one non-transitory computer-readable storage medium storing processor-executable instructions that, when executed by at least one processor, cause the at least one processor to perform a method for classifying rhythms of segments of at least one ECG signal, the method comprising: receiving the at least one ECG signal, the at least one ECG signal comprising a plurality of segments, each segment representing a heartbeat in a sequence of heartbeats, the at least one ECG signal having been previously measured using ECG sensors; encoding the at least one ECG signal to obtain a numeric encoding of the at least one ECG signal using a trained encoder; optionally quantizing the numeric encoding of the at least one ECG signal to obtain a quantized numeric encoding of the at least one ECG signal using a trained residual vector quantizer; positionally encoding the optionally quantized numeric encoding of the at least one ECG signal, using a predetermined positional encoding scheme, to obtain a positionally encoded optionally quantized numeric encoding of the at least one ECG signal; and classifying a respective rhythm of each of at least some of the segments between a plurality of classes, each of the plurality of classes corresponding to a respective rhythm type of a plurality of rhythm types to obtain a plurality of rhythm classifications, the classifying comprising: processing the positionally encoded optionally quantized numeric encoding of the at least one ECG signal using a trained rhythm classifier to obtain, for each of the at least some of the segments, a respective output indicative of a class of the plurality of classes corresponding to a respective rhythm type of the plurality of rhythm types, wherein the trained rhythm classifier has been trained to take as input a positionally encoded numeric encoding or quantized numeric encoding of the at least one ECG signal produced as output of the trained encoder or trained residual vector quantizer, and produce an output indicative of the class of the plurality of classes using training data comprising training ECG signals and associated ground truth rhythm type labels, wherein the trained encoder and optional trained residual vector quantizer have been trained as part of a machine learning model comprising the encoder, the residual vector quantizer, and a decoder, to take as input at least one ECG signal and produce as output a corresponding denoised ECG signal using training data comprising pairs of noisy ECG signals and corresponding clean ECG signals, wherein the machine learning model has been trained as a generator of a generative adversarial network further comprising one or more discriminators trained to distinguish between a real ECG signal and an ECG signal has been generated by the generator.

Some aspects provide for a system comprising: at least one processor; and at least one non-transitory computer-readable storage medium storing processor-executable instructions that, when executed by the at least one processor, cause the at least one processor to perform a method for classifying rhythms of segments of at least one ECG signal, the method comprising: receiving the at least one ECG signal, the at least one ECG signal comprising a plurality of segments, each segment representing a heartbeat in a sequence of heartbeats, the at least one ECG signal having been previously measured using ECG sensors; encoding the at least one ECG signal to obtain a numeric encoding of the at least one ECG signal using a trained encoder; optionally quantizing the numeric encoding of the at least one ECG signal to obtain a quantized numeric encoding of the at least one ECG signal using a trained residual vector quantizer; positionally encoding the optionally quantized numeric encoding of the at least one ECG signal, using a predetermined positional encoding scheme, to obtain a positionally encoded optionally quantized numeric encoding of the at least one ECG signal; and classifying a respective rhythm of each of at least some of the segments between a plurality of classes, each of the plurality of classes corresponding to a respective rhythm type of a plurality of rhythm types to obtain a plurality of rhythm classifications, the classifying comprising: processing the positionally encoded optionally quantized numeric encoding of the at least one ECG signal using a trained rhythm classifier to obtain, for each of the at least some of the segments, a respective output indicative of a class of the plurality of classes corresponding to a respective rhythm type of the plurality of rhythm types, wherein the trained rhythm classifier has been trained to take as input a positionally encoded numeric encoding or quantized numeric encoding of the at least one ECG signal produced as output of the trained encoder or trained residual vector quantizer, and produce an output indicative of the class of the plurality of classes using training data comprising training ECG signals and associated ground truth rhythm type labels, wherein the trained encoder and optional trained residual vector quantizer have been trained as part of a machine learning model comprising the encoder, the residual vector quantizer, and a decoder, to take as input at least one ECG signal and produce as output a corresponding denoised ECG signal using training data comprising pairs of noisy ECG signals and corresponding clean ECG signals, wherein the machine learning model has been trained as a generator of a generative adversarial network further comprising one or more discriminators trained to distinguish between a real ECG signal and an ECG signal has been generated by the generator.

Embodiments of any of the above aspects may have one or more of the following features.

In some embodiments, (i) the trained rhythm classifier is trained to classify a segment of the at least one ECG signal between the plurality of classes each corresponding to a different rhythm type selected from: a normal sinus type, an atrial fibrillation type, an atrial flutter type, a premature atrial contraction (PAC) type, a premature ventricular contraction (PVC) type; or (ii) the trained rhythm classifier is trained to classify a segment of the at least one ECG signal between a first class corresponding to a normal sinus type, and a second class corresponding to an arrhythmia rhythm type, optionally wherein arrhythmia includes one or more or all of: an atrial fibrillation type, an atrial flutter type, a premature atrial contraction (PAC) type, a premature ventricular contraction (PVC) type; or (iii) the trained rhythm classifier is trained to classify a segment of the at least one ECG signal between a first class corresponding to a first rhythm type and a second class corresponding to any rhythm type that is not the first rhythm type, optionally wherein the first rhythm type is selected from: a normal sinus type, an atrial fibrillation type, an atrial flutter type, a premature atrial contraction (PAC) type, and a premature ventricular contraction (PVC) type.

In some embodiments, the trained rhythm classifier is a transformer-based model.

In some embodiments, the trained rhythm classifier comprises a transformer encoder and a classification layer.

In some embodiments, the sequence of heartbeats comprises at least a threshold number of heartbeats.

In some embodiments, the threshold number of heartbeats is between 10 heartbeats and 100 heartbeats.

In some embodiments, the threshold number of heartbeats is 50 heartbeats.

In some embodiments, the ECG signal is an ECG signal that has been measured using a wearable device.

In some embodiments, the wearable device is a Holter monitor or an ECG patch.

In some embodiments, encoding the at least one ECG signal using the trained encoder to obtain the numeric encoding of the at least one ECG signal uses the trained encoder of the method as claimed in any of claims H1-H19; and/or wherein quantizing the numeric encoding of the at least one ECG signal using the trained residual vector quantizer to obtain the quantized numeric encoding of the at least one ECG signal uses the trained residual vector quantizer of the method as claimed in any of claims H1-H19.

Some aspects provide for a method of training a machine learning model to denoise at least one electrocardiogram (ECG) signal, the method comprising: using at least one processor to perform: obtaining training data comprising a plurality of pairs of ECG signals, wherein a pair of ECG signals of the plurality of pairs of ECG signals comprises a clean ECG signal and a noisy ECG signal; training the machine learning model, using the training data, to generate denoised ECG signals, the machine learning model comprising an encoder, a residual vector quantizer, and a decoder, the training comprising: processing the noisy ECG signal using the denoising model to generate a denoised ECG signal corresponding to the noisy ECG signal; processing the denoised ECG signal using at least one discriminator model to obtain at least one classification indicative of whether the denoised ECG signal is a real ECG signal or an artificial ECG signal; and updating parameters of the denoising model based on at least a loss that is a function of the at least one classification.

Some aspects provide for at least one non-transitory computer-readable storage medium storing processor-executable instructions that, when executed by at least one processor, cause the at least one processor to perform a method of training a machine learning model to denoise at least one electrocardiogram (ECG) signal, the method comprising: obtaining training data comprising a plurality of pairs of ECG signals, wherein a pair of ECG signals of the plurality of pairs of ECG signals comprises a clean ECG signal and a noisy ECG signal; training the machine learning model, using the training data, to generate denoised ECG signals, the machine learning model comprising an encoder, a residual vector quantizer, and a decoder, the training comprising: processing the noisy ECG signal using the denoising model to generate a denoised ECG signal corresponding to the noisy ECG signal; processing the denoised ECG signal using at least one discriminator model to obtain at least one classification indicative of whether the denoised ECG signal is a real ECG signal or an artificial ECG signal; and updating parameters of the denoising model based on at least a loss that is a function of the at least one classification.

Some aspects provide for a system comprising: at least one processor; and at least one non-transitory computer-readable storage medium storing processor-executable instructions that, when executed by the at least one processor, cause the at least one processor to perform a method of training a machine learning model to denoise at least one electrocardiogram (ECG) signal, the method comprising: obtaining training data comprising a plurality of pairs of ECG signals, wherein a pair of ECG signals of the plurality of pairs of ECG signals comprises a clean ECG signal and a noisy ECG signal; training the machine learning model, using the training data, to generate denoised ECG signals, the machine learning model comprising an encoder, a residual vector quantizer, and a decoder, the training comprising: processing the noisy ECG signal using the denoising model to generate a denoised ECG signal corresponding to the noisy ECG signal; processing the denoised ECG signal using at least one discriminator model to obtain at least one classification indicative of whether the denoised ECG signal is a real ECG signal or an artificial ECG signal; and updating parameters of the denoising model based on at least a loss that is a function of the at least one classification.

In some embodiments, the machine learning model is trained as a generator of a generative adversarial model comprising the at least one discriminator model, and/or wherein the method further comprises updating parameters of the at least one discriminator model.

In some embodiments, each of the ECG signals corresponds to a single heartbeat.

In some embodiments, obtaining the training data comprises receiving one or more clean ECG signals and adding noise to each of the one or more clean ECG signals to obtain one or more corresponding noisy ECG signals.

In some embodiments, the noise comprises one or more types of noise selected from: random noise, white noise, spikes, and drift.

In some embodiments, processing the denoised ECG signal using the at least one discriminator model comprises: processing a time-domain representation of the denoised ECG signal using a first discriminator model to obtain a first classification indicative of whether the denoised ECG signal is a real ECG signal or an artificial ECG signal; transforming the time-domain representation of the denoised ECG signal to a frequency-domain representation of the denoised ECG signal; and processing the frequency-domain representation of the denoised ECG signal using a second discriminator model to obtain a second classification indicative of whether the denoised ECG signal is a real ECG signal or an artificial ECG signal.

Some aspects provide for a Holter monitor, comprising: electrocardiogram (ECG) leads comprising at least three ECG leads; at least one processor; and at least one non-transitory computer-readable storage medium storing processor-executable instructions that, when executed by the at least one processor, cause the at least one processor to perform a method comprising: receiving at least one ECG signal from the ECG leads, the at least one ECG signal comprising a plurality of segments, each segment representing a heartbeat in a sequence of heartbeats; encoding the at least one ECG signal using a trained encoder to obtain a numeric encoding of the at least one ECG signal; optionally quantizing the numeric encoding of the at least one ECG signal to obtain a quantized numeric encoding of the at least one ECG signal using a trained residual vector quantizer; processing the numeric encoding or quantized numeric encoding of the at least one ECG signal using at least one trained classifier to obtain one or more characteristics of the at least one ECG signal, the characteristics comprising: (i) rhythm types including a respective rhythm type for each of at least some of the plurality of segments, wherein the rhythm types comprise a normal sinus type, an atrial fibrillation type, and an atrial flutter type, wherein the at least one classifier comprises a trained rhythm classifier, wherein the trained rhythm classifier has been trained to take as input a positionally encoded numeric encoding or quantized numeric encoding of the at least one ECG signal produced as output of the trained encoder or trained residual vector quantizer, and produce an output indicative of the class of the plurality of classes using training data comprising training ECG signals and associated ground truth rhythm type labels, and/or (ii) labels corresponding to a P wave, a Q wave, a R wave, a S wave, and a T wave, wherein the at least one classifier comprises a trained beat classifier that has been trained to take as input a numeric encoding of the at least one ECG signal produced as output of the encoder or a quantized numeric encoding of the at least one ECG signal produced as output of the residual vector quantizer, and produce an output indicative of a respective portion of an ECG waveform to which the sample corresponds to, wherein the trained encoder and optional trained residual vector quantizer have been trained as part of a machine learning model comprising the encoder, the residual vector quantizer, and a decoder, to take as input at least one ECG signal and produce as output a corresponding denoised ECG signal using training data comprising pairs of noisy ECG signals and corresponding clean ECG signals, wherein the machine learning model has been trained as a generator of a generative adversarial network further comprising one or more discriminators trained to distinguish between a real ECG signal and an ECG signal has been generated by the generator.

Some aspects provide for a wearable device, comprising: an electrocardiogram (ECG) lead; at least one processor; and at least one non-transitory computer-readable storage medium storing processor-executable instructions that, when executed by the at least one processor, cause the at least one processor to perform a method, comprising: receiving at least one ECG signal from the ECG lead, the at least one ECG signal comprising a plurality of segments, each segment representing a heartbeat in a sequence of heartbeats; encoding the at least one ECG signal using a trained encoder to obtain a numeric encoding of the at least one ECG signal; optionally quantizing the numeric encoding of the at least one ECG signal to obtain a quantized numeric encoding of the at least one ECG signal using a trained residual vector quantizer; processing the numeric encoding or the quantized numeric encoding of the at least one ECG signal using at least one trained classifier to obtain one or more characteristics of the at least one ECG signal, the characteristics comprising: (i) rhythm types including a respective rhythm type for each of at least some of the plurality of segments, wherein the rhythm types comprise a normal sinus type, an atrial fibrillation type, and an atrial flutter type, wherein the at least one classifier comprises a trained rhythm classifier, wherein the trained rhythm classifier has been trained to take as input a positionally encoded numeric encoding or quantized numeric encoding of the at least one ECG signal produced as output of the trained encoder or trained residual vector quantizer, and produce an output indicative of the class of the plurality of classes using training data comprising training ECG signals and associated ground truth rhythm type labels, and/or (ii) labels corresponding to a P wave, a Q wave, a R wave, a S wave, and a T wave, wherein the at least one classifier comprises a trained beat classifier that has been trained to take as input a numeric encoding of the at least one ECG signal produced as output of the encoder or a quantized numeric encoding of the at least one ECG signal produced as output of the residual vector quantizer, and produce an output indicative of a respective portion of an ECG waveform to which the sample corresponds to, wherein the trained encoder and optional trained residual vector quantizer have been trained as part of a machine learning model comprising the encoder, the residual vector quantizer, and a decoder, to take as input at least one ECG signal and produce as output a corresponding denoised ECG signal using training data comprising pairs of noisy ECG signals and corresponding clean ECG signals, wherein the machine learning model has been trained as a generator of a generative adversarial network further comprising one or more discriminators trained to distinguish between a real ECG signal and an ECG signal has been generated by the generator.

In some embodiments, the wearable device is a Holter monitor or an ECG patch.

Some aspects provide for a method, comprising: using at least one processor to perform: receiving, from at least one wearable device, at least one electrocardiogram (ECG) signal comprising a plurality of segments, each of the plurality of segments representing a heartbeat in a sequence of heartbeats; encoding the at least one ECG signal using a trained encoder to obtain a numeric encoding of the at least one ECG signal; optionally quantizing the numeric encoding of the at least one ECG signal to obtain a quantized numeric encoding of the at least one ECG signal using a trained residual vector quantizer; processing the numeric encoding of the at least one ECG signal using at least one trained machine learning model to obtain: (i) at least one denoised ECG signal corresponding to the at least one ECG signal, wherein the at least one trained machine learning model comprises a trained decoder, and/or (ii) characteristics of the at least one ECG signal, the characteristics comprising: (i) rhythm types including a respective rhythm type for each of at least some of the plurality of segments, wherein the rhythm types comprise a normal sinus type, an atrial fibrillation type, and an atrial flutter type, wherein the at least one trained machine learning model comprises a trained rhythm classifier, wherein the trained rhythm classifier has been trained to take as input a positionally encoded numeric encoding or quantized numeric encoding of the at least one ECG signal produced as output of the trained encoder or trained residual vector quantizer, and produce an output indicative of the class of the plurality of classes using training data comprising training ECG signals and associated ground truth rhythm type labels, and/or (ii) labels corresponding to a P wave, a Q wave, a R wave, a S wave, and a T wave, wherein the at least one trained machine learning model comprises a trained beat classifier that has been trained to take as input a numeric encoding of the at least one ECG signal produced as output of the encoder or a quantized numeric encoding of the at least one ECG signal produced as output of the residual vector quantizer, and produce an output indicative of a respective portion of an ECG waveform to which the sample corresponds to; and transmitting the denoised ECG signal and/or the characteristics of the at least one ECG signal to a remote device, wherein the trained encoder, optional trained residual vector quantizer, and trained decoder have been trained as part of a machine learning model comprising the encoder, the residual vector quantizer, and the decoder, to take as input at least one ECG signal and produce as output a corresponding denoised ECG signal using training data comprising pairs of noisy ECG signals and corresponding clean ECG signals, wherein the machine learning model has been trained as a generator of a generative adversarial network further comprising one or more discriminators trained to distinguish between a real ECG signal and an ECG signal has been generated by the generator.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize or be able to ascertain using no more than routine experimentation many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as an example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as an example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The terms "approximately," "substantially," and "about" may be used to mean within ±20% of a target value in some embodiments, within ±10% of a target value in some embodiments, within ±5% of a target value in some embodiments, within ±2% of a target value in some embodiments. The terms "approximately," "substantially," and "about" may include the target value.

What is claimed is:

1. A distributed electrocardiogram (ECG) system comprising:

at least one wearable device comprising a Holter monitor, a smart watch, or a chest strap and configured to:

measure at least one ECG signal at a sampling rate of between 128 Hz and 256 Hz and for a duration of between one and fourteen days, the at least one ECG signal comprising a plurality of samples, wherein a sample is an ECG measurement at a single time point;

encode the at least one ECG signal using an encoder to obtain a numeric encoding of the at least one ECG signal, wherein the encoder comprises a neural network encoder; and quantize the numeric encoding of the at least one ECG signal using a residual vector quantizer to obtain a quantized numeric encoding of the at least one ECG signal; and at least one processor coupled to the at least one wearable device and configured to:

receive the quantized numeric encoding of the at least one ECG signal from the at least one wearable device; and process the quantized numeric encoding of the at least one ECG signal using at least one trained machine learning model to obtain:

(i) at least one denoised ECG signal corresponding to the at least one ECG signal, and/or (ii) at least one characteristic of the at least one ECG signal, the at least one characteristic comprising:

(i) rhythm types including a respective rhythm type for each of at least some segments of the at least one ECG signal, wherein the rhythm types are selected from among a normal sinus type, an atrial fibrillation type, an atrial flutter type, a premature atrial contraction (PAC) type, or a premature ventricular contraction (PVC) type, and/or (ii) sample-level ECG labels including a respective sample-level ECG label for each of at least some of the plurality of samples, each sample-level ECG label being indicative of a respective portion of an ECG waveform to which a respective sample corresponds.

2. The distributed ECG system of claim 1, wherein the at least one processor is configured to process the quantized numeric encoding of the at least one ECG signal using the at least one trained machine learning model to obtain the at least one denoised ECG signal, and wherein processing the quantized numeric encoding of the at least one ECG signal using the at least one trained machine learning model to obtain the at least one denoised ECG signal comprises decoding the quantized numeric encoding of the at least one ECG signal using a decoder to obtain the at least one denoised ECG signal.

3. The distributed ECG system of claim 1, wherein the at least one processor is configured to process the quantized numeric encoding of the at least one ECG signal using the at least one trained machine learning model to obtain the at least one characteristic of the at least one ECG signal, the at least one characteristic comprising the rhythm types, and wherein processing the quantized numeric encoding of the at least one ECG signal using the at least one trained machine learning model to obtain the rhythm types comprises:

positionally encoding the quantized numeric encoding of the at least one ECG signal to obtain a positionally-encoded quantized numeric encoding of the at least one ECG signal; and processing the positionally-encoded quantized numeric encoding of the at least one ECG signal using a trained rhythm classifier to obtain, for each of the at least some segments of the at least one ECG signal, a respective output indicative of a respective rhythm type.

4. The distributed ECG system of claim 1, wherein the at least one processor is configured to process the quantized numeric encoding of the at least one ECG signal using the at least one trained machine learning model to obtain the at least one characteristic of the at least one ECG signal, the at least one characteristic comprising the sample-level ECG labels, and wherein processing the quantized numeric encoding of the at least one ECG signal using the at least one trained machine learning model to obtain the sample-level ECG labels comprises processing the quantized numeric encoding of the at least one ECG signal using a trained sample-level ECG classifier to obtain a respective sample-level ECG label for each of the at least some of the plurality of samples.

5. The distributed ECG system of claim 1, wherein the at least one wearable device comprises a plurality of wearable devices, and wherein each of the plurality of wearable devices is configured to measure a respective ECG signal.

6. The distributed ECG system of claim 1, wherein the at least one processor is further configured to generate a report indicating (i) the at least one denoised ECG signal corresponding to the at least one ECG signal, and/or (ii) the at least one characteristic of the at least one ECG signal.

7. The distributed ECG system of claim 1, wherein quantizing the numeric encoding comprises:

mapping the numeric encoding to a first closest vector in a first codebook of vectors, determining a first residual by determining a difference between the numeric encoding and the first closest vector, mapping the first residual to a second closest vector in a second codebook of vectors, and determining the quantized numeric encoding based at least in part on a sum of the first and second closest vectors.

8. A distributed electrocardiogram (ECG) system, comprising:

at least one wearable device comprising a Holter monitor, a smart watch, or a chest strap and configured to:

measure at least one ECG signal at a sampling rate of between 128 Hz and 256 Hz and for a duration of between one and fourteen days, the at least one ECG signal comprising a plurality of samples, wherein a sample is an ECG measurement at a single time point; and segment the at least one ECG signal to obtain a plurality of ECG segments; and at least one processor coupled to the at least one wearable device and configured to:

receive at least one ECG segment of the plurality of ECG segments from the at least one wearable device;

encode the at least one ECG segment using an encoder to obtain a numeric encoding of the at least one ECG segment, wherein the encoder comprises a neural network encoder;

quantize the numeric encoding of the at least one ECG segment using a residual vector quantizer to obtain a quantized numeric encoding of the at least one ECG segment; and process the quantized numeric encoding of the at least one ECG segment using at least one trained machine learning model to obtain:

(i) at least one denoised ECG segment corresponding to the at least one ECG segment, and/or (ii) at least one characteristic of the at least one ECG segment, the at least one characteristic comprising:

(i) at least one rhythm type for the at least one ECG segment, wherein the at least one rhythm type is selected from among a normal sinus type, an atrial fibrillation type, an atrial flutter type, a premature atrial contraction (PAC) type, or a premature ventricular contraction (PVC) type, and/or (ii) sample-level ECG labels including a respective sample-level ECG label for each of at least some of the plurality of samples, each sample-level ECG label being indicative of a respective portion of an ECG waveform to which a respective sample corresponds.

9. The distributed ECG system of claim 8, wherein the at least one processor is configured to process the quantized numeric encoding of the at least one ECG segment using the at least one trained machine learning model to obtain the at least one denoised ECG segment, and wherein processing the quantized numeric encoding of the at least one ECG segment using the at least one trained machine learning model to obtain the at least one denoised ECG segment comprises decoding the quantized numeric encoding of the at least one ECG segment using a decoder to obtain the at least one denoised ECG segment.

10. The distributed ECG system of claim 8, wherein the at least one processor is configured to process the quantized numeric encoding of the at least one ECG segment using the at least one trained machine learning model to obtain the at least one characteristic of the at least one ECG segment, the at least one characteristic comprising the at least one rhythm type, and wherein processing the quantized numeric encoding of the at least one ECG segment using the at least one trained machine learning model to obtain at least one rhythm type comprises:

positionally encoding the quantized numeric encoding of the at least one ECG segment to obtain a positionally-encoded quantized numeric encoding of the at least one ECG segment; and processing the positionally-encoded quantized numeric encoding of the at least one ECG segment using a trained rhythm classifier to obtain an output indicative of at least one rhythm type.

11. The distributed ECG system of claim 8, wherein the at least one processor is configured to process the quantized numeric encoding of the at least one ECG segment using the at least one trained machine learning model to obtain the at least one characteristic of the at least one ECG segment, the at least one characteristic comprising the sample-level ECG labels, and wherein processing the quantized numeric encoding of the at least one ECG segment using the at least one trained machine learning model to obtain the sample-level ECG labels comprises processing the quantized numeric encoding of the at least one ECG segment using a trained sample-level ECG classifier to obtain a respective sample-level ECG label for each of the at least some of the plurality of samples.

12. The distributed ECG system of claim 8, wherein the at least one wearable device comprises a plurality of wearable devices, and wherein each of the plurality of wearable devices is configured to measure a respective ECG signal.

13. The distributed ECG system of claim 8, wherein quantizing the numeric encoding comprises:

mapping the numeric encoding to a first closest vector in a first codebook of vectors, determining a first residual by determining a difference between the numeric encoding and the first closest vector, mapping the first residual to a second closest vector in a second codebook of vectors, and determining the quantized numeric encoding based at least in part on a sum of the first and second closest vectors.

14. A distributed electrocardiogram (ECG) system, comprising:

at least one wearable device comprising a Holter monitor, a smart watch, or a chest strap and configured to:

measure at least one ECG signal at a sampling rate of between 128 Hz and 256 Hz and for a duration of between one and fourteen days, the at least one ECG signal comprising a plurality of samples, wherein a sample is an ECG measurement at a single time point; and at least one processor coupled to the at least one wearable device and configured to:

receive the at least one ECG signal from the at least one wearable device;

encode the at least one ECG signal using an encoder to obtain a numeric encoding of the at least one ECG signal, wherein the encoder comprises a neural network encoder;

quantize the numeric encoding of the at least one ECG signal using a residual vector quantizer to obtain a quantized numeric encoding of the at least one ECG signal; and process the quantized numeric encoding of the at least one ECG signal using at least one trained machine learning model to obtain:

(i) at least one denoised ECG signal corresponding to the at least one ECG signal, and/or (ii) at least one characteristic of the at least one ECG signal, the at least one characteristic comprising:

(i) rhythm types including a respective rhythm type for each of at least some segments of the at least one ECG signal, wherein the rhythm types are selected from among a normal sinus type, an atrial fibrillation type, an atrial flutter type, a premature atrial contraction (PAC) type, or a premature ventricular contraction (PVC) type, and/or (ii) sample-level ECG labels including a respective sample-level ECG label for each of at least some of the plurality of samples, each sample-level ECG label being indicative of a respective portion of an ECG waveform to which a respective sample corresponds.

15. The distributed ECG system of claim 14, wherein the at least one processor is configured to process the quantized numeric encoding of the at least one ECG signal using the at least one trained machine learning model to obtain the at least one denoised ECG signal, and wherein processing the quantized numeric encoding of the at least one ECG signal using the at least one trained machine learning model to obtain the at least one denoised ECG signal comprises decoding the quantized numeric encoding of the at least one ECG signal using a decoder to obtain the at least one denoised ECG signal.

16. The distributed ECG system of claim 14, wherein the at least one processor is configured to process the quantized numeric encoding of the at least one ECG signal using the at least one trained machine learning model to obtain the at least one characteristic of the at least one ECG signal, the at least one characteristic comprising the rhythm types, and wherein processing the quantized numeric encoding of the at least one ECG signal using the at least one trained machine learning model to obtain the rhythm types comprises:

positionally encoding the quantized numeric encoding of the at least one ECG signal to obtain a positionally-encoded quantized numeric encoding of the at least one ECG signal; and processing the positionally-encoded quantized numeric encoding of the at least one ECG signal using a trained rhythm classifier to obtain, for each of the at least some segments of the at least one ECG signal, a respective output indicative of a respective rhythm type.

17. The distributed ECG system of claim 14, wherein the at least one processor is configured to process the quantized numeric encoding of the at least one ECG signal using the at least one trained machine learning model to obtain the at least one characteristic of the at least one ECG signal, the at least one characteristic comprising the sample-level ECG labels, and wherein processing the quantized numeric encoding of the at least one ECG signal using the at least one trained machine learning model to obtain the sample-level ECG labels comprises processing the quantized numeric encoding of the at least one ECG signal using a trained sample-level ECG classifier to obtain a respective sample-level ECG label for each of the at least some of the plurality of samples.

18. The distributed ECG system of claim 14, wherein the at least one wearable device comprises a plurality of wearable devices, and wherein each of the plurality of wearable devices is configured to measure a respective ECG signal.

19. The distributed ECG system of claim 14, wherein the at least one processor is further configured to generate a report indicating (i) the at least one denoised ECG signal corresponding to the at least one ECG signal, and/or (ii) the at least one characteristic of the at least one ECG signal.

20. The distributed ECG system of claim 14, wherein quantizing the numeric encoding comprises:

mapping the numeric encoding to a first closest vector in a first codebook of vectors, determining a first residual by determining a difference between the numeric encoding and the first closest vector, mapping the first residual to a second closest vector in a second codebook of vectors, and determining the quantized numeric encoding based at least in part on a sum of the first and second closest vectors.

* * * * *